United States Patent
Kym et al.

(10) Patent No.: US 6,818,772 B2
(45) Date of Patent: Nov. 16, 2004

(54) ANTAGONISTS OF MELANIN CONCENTRATING HORMONE EFFECTS ON THE MELANIN CONCENTRATING HORMONE RECEPTOR

(75) Inventors: Philip R. Kym, Grayslake, IL (US); Kresna Hartandi, Gurnee, IL (US); Ju Gao, Gurnee, IL (US); Kathleen M. Phelan, Gurnee, IL (US); Irini Akritopoulou-Zanze, Lake Bluff, IL (US); Christine A. Collins, Skokie, IL (US); Anil Vasudevan, Gurnee, IL (US); Mary K. Verzal, Burlington, WI (US)

(73) Assignee: Abbott Laboratories, Abbott Park, IL (US)

( * ) Notice: Subject to any disclaimer, the term of this patent is extended or adjusted under 35 U.S.C. 154(b) by 5 days.

(21) Appl. No.: 10/372,359

(22) Filed: Feb. 21, 2003

(65) Prior Publication Data

US 2003/0229119 A1 Dec. 11, 2003

Related U.S. Application Data

(60) Provisional application No. 60/359,081, filed on Feb. 22, 2002.

(51) Int. Cl.[7] .............. C07D 215/38; C07D 215/44; A61K 31/47
(52) U.S. Cl. ............... 546/160; 546/162; 514/313
(58) Field of Search ............... 546/160, 162; 514/313

(56) References Cited

U.S. PATENT DOCUMENTS 5,736,557 A * 4/1998 Hofheinz et al. ........... 514/313
5,948,791 A * 9/1999 Hofheinz et al. ........... 514/313
6,479,504 B1 * 11/2002 Macfarlane et al. ........ 514/297

FOREIGN PATENT DOCUMENTS

| EP | 045920 | | 6/2003 |
|---|---|---|---|
| WO | 9535287 | | 12/1995 |
| WO | WO 95/35287 | * | 12/1995 |
| WO | 9718193 | | 5/1997 |
| WO | WO 97/18193 | * | 5/1997 |
| WO | 0206245 | | 1/2002 |

OTHER PUBLICATIONS

Bass, J Med Chem, 1971, vol. 14, No. 4, pp275–283.*
Wang, Ind eng chem Res, 2000, vol 39, pp4487–4490.*
*Chemical Abstracts No.* 103:3537, abstract of Geary, J *protozoology*, 1985, vol. 32(1), pp65–69.*
Nahon, J–L., "The Melanin–Concentrating Hormone: From the Peptide to the Gene", *Critical Reviews in Neurobiology*, 8(4):221–262 (1994).
Bass, G. E., et al., "Mechanism of Antimalarial Activity of Chloroquine Analogs from Quantitative Structure–Activity Studies. Free Energy Rellated Model", *Journ. Of Medicinal Chem.*, 14(4):275–283.

* cited by examiner

Primary Examiner—D. Margaret Seaman
(74) Attorney, Agent, or Firm—Johanna M. Corbir

(57) ABSTRACT

The present invention relates to the antagonism of the effects of melanin-concentrating hormone (MCH) through the melanin concentrating hormone receptor which is useful for the prevention or treatment of eating disorders, weight gain, obesity, abnormalities in reproduction and sexual behavior, thyroid hormone secretion, diuresis and water/electrolyte homeostasis, sensory processing, memory, sleeping, arousal, anxiety, depression, seizures, neurodegeneration and psychiatric disorders.

35 Claims, No Drawings

ANTAGONISTS OF MELANIN CONCENTRATING HORMONE EFFECTS ON THE MELANIN CONCENTRATING HORMONE RECEPTOR

This application claims priority to the provisional application Ser. No. 60/359,081 filed on Feb. 22, 2002.

TECHNICAL FIELD

The present invention relates to the antagonism of the effects of melanin-concentrating hormone (MCH) through the melanin concentrating hormone receptor which is useful for the prevention or treatment of eating disorders, weight gain, obesity, abnormalities in reproduction and sexual behavior, thyroid hormone secretion, diuresis and water/electrolyte homeostasis, sensory processing, memory, sleeping, arousal, anxiety, depression, seizures, neurodegeneration and psychiatric disorders.

BACKGROUND OF THE INVENTION

Obesity is a major cause and contributor to health problems such as type II diabetes, coronary heart disease, increased incidence of certain forms of cancer, and respiratory complications. It is a disease that is increasing at an alarming rate due to increased availability of high-fat diets, genetic susceptibility, and a more sedentary way of life in modern society. Obesity can be defined as weight gain resulting from a mismatch of energy intake and energy expenditure. Food intake and energy metabolism are regulated, in part, by the interaction of neuropeptides and their receptors. Recently, the role that the hormone leptin plays in controlling appetite has been elucidated.

Leptin is a peptide hormone produced by fat cells, regulating both food intake and and metabolism by acting on leptin receptors in the hypothalamus. Increased fat stores leads to increased secretion of leptin, resulting in a signal to the hypothalamus to decrease food intake, whereas decreases in adiposity result in lower leptin levels and a stimulation of food intake. Melanin-concentrating hormone (MCH) has been identified as an orexigenic peptide that counterbalances the activity of leptin.

MCH is a cyclic 19 amino acid neuropeptide expressed in the zona incerta and lateral hypothalamus in response to both energy restriction and leptin deficiency. MCH is known to stimulate feeding when injected into the lateral ventricle of rats and the mRNA for MCH is upregulated in the hypothalamus of genetically obese mice (ob/ob) and in fasted control and ob/ob animals. Mice lacking MCH are hypophagic and lean with increased metabolic rate, whereas animals over-expressing MCH gain excess weight on both standard and high fat diets. MCH is thought to have effects on other nervous system functions as well (Nahon J L., The melanin-concentrating hormone: from the peptide to the gene. Crit Rev Neurobiol 8:221–262, 1994). An orphan G-protein coupled receptor (GPCR) was recently identified as a receptor for MCH.

Although there exists current pharmacologic therapies used to treat obesity, none of the current therapies achieve the U.S. Food and Drug Administration criteria for benefit measured by a 5% difference in mean weight loss, as weight loss efficacy is diminished by reduction of patient adherence to pharmacological therapy due to side effects of the drugs. Some of the side effects associated with current therapies include increased heart rate and blood pressure, and uncontrolled excretion of fat in stools. Thus, there exists a medical need for agents capable of preventing or treating eating disorders, weight gain and obesity, that at the same time, have improved efficacy and safety.

SUMMARY OF THE INVENTION

The present invention is directed to compounds of formula (I):

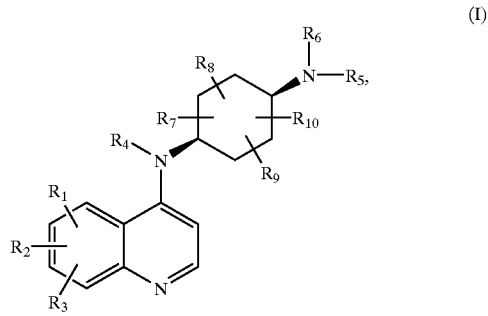

or a therapeutically suitable salts, ester, prodrug or zwitterion thereof, wherein $R_1$, $R_2$ and $R_3$ are independently a member selected from the group consisting of hydrogen, alkyl, alkoxy, halo, haloalkyl, haloalkoxy, hydroxy and $R_AR_BN$— wherein $R_A$ and $R_B$ are each independently a member selected from the group consisting of hydrogen and alkyl, alkylcarbonyl, alkylsulfonyl, arylcarbonyl, arylsulfonyl and $R_CR_DN$carbonyl, wherein $R_C$ and $R_D$ are independently a member selected from the group consisting of hydrogen, alkyl and aryl;

$R_4$ is a member selected from the group consisting of hydrogen and alkyl;

$R_5$ is —$(CH_2)_m$—Y-A-B;

m is from 0–6;

A is absent or is a member selected from the group consisting of alkoxyalkylene, alkylene and hydroxyalkylene;

B is a member selected from the group consisting of hydrogen, alkyl, aryl, arylC(O)—, arylS(O)$_2$—, arylalkenyl, aryloxyalkyl, biaryl, biarylalkyl, cycloalkyl, heterocycle, heterocycleC(O)—, heterocycleS(O)$_2$—, haloalkyl, $R_ER_FN$—, $R_ER_FNC(O)$—, $R_GS$— and $R_GO$—;

$R_E$ and $R_F$ are each independently a member selected from the group consisting of hydrogen, alkyl, alkylC(O)—, aryl, arylalkyl, heterocycle, heterocyclealkyl, arylC(O)— and arylS(O)$_2$—;

$R_G$ is a member selected from the group consisting of hydrogen, alkyl, aryl, arylalkyl and heterocycle;

Y is a member selected from the group consisting of —C(O)—, —S—, —S(O)— and —S(O)$_2$—, or is absent;

$R_6$ is a member selected from the group consisting of hydrogen, alkyl and arylcarboxyalkyl; and $R_7$, $R_8$, $R_9$, and $R_{10}$ are each independently a member selected from the group consisting of hydrogen, alkyl, alkoxy, halo, haloalkyl, haloalkoxy and hydroxy or $R_7$ and $R_8$ taken together with the carbon atom that they are attached form oxo;

with the following provisos $P_1$–$P_4$:

$P_1$ if Y is absent, m is 0 and if A is absent or is a member selected from the group consisting of alkoxyalkylene, alkylene and hydroxyalkylene,
then B is a member selected from the group consisting of hydrogen, alkyl, arylC(O)—, arylS(O)$_2$—, arylalkenyl, aryloxyalkyl, biarylalkyl, cycloalkyl, heterocycle, heterocycleC(O)—, heterocycleS(O)$_2$—, haloalkyl, R$_E$R$_F$N—, R$_E$R$_F$NC(O)—, R$_G$S— and R$_G$O—; or P$_2$ if Y is —C(O)—, m is 0 and A is absent,
then B is a member selected from the group consisting of hydrogen, alkyl, arylalkenyl, aryloxyalkyl, cycloalkyl, heterocycle, haloalkyl, and R$_E$R$_F$NC(O)—; or P$_3$ if Y is —C(O)—, A is absent and B is aryl or heterocycle, then m is 1–6; or P$_4$ if Y is —C(O)— and B is a member selected from the group consisting of arylC(O)—, arylS(O)$_2$—, heterocycleC(O)—, heterocycleS(O)$_2$—,
then A is a member selected from the group consisting of alkoxyalkylene, alkylene and hydroxyalkylene.

The present invention also provides a method of treating disorders mediated by MCH through the MCH receptor comprising administering a therapeutically effective amount of a compound of formula (II),

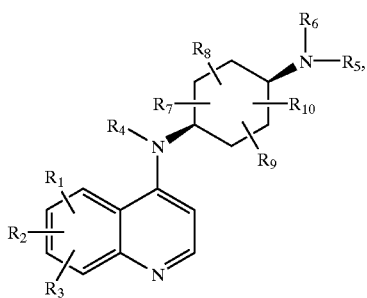

(II)

or a therapeutically suitable salts, ester, prodrug or zwitterion thereof, wherein R$_1$, R$_2$ and R$_3$ are independently a member selected from the group consisting of hydrogen, alkyl, alkoxy, halo, haloalkyl, haloalkoxy, hydroxy and R$_A$R$_B$N— wherein R$_A$ and R$_B$ are each independently a member selected from the group consisting of hydrogen and alkyl, alkylcarbonyl, alkylsulfonyl, arylcarbonyl, arylsulfonyl and R$_C$R$_D$Ncarbonyl, wherein R$_C$ and R$_D$ are independently a member selected from the group consisting of hydrogen, alkyl and aryl;

R$_4$ is a member selected from the group consisting of hydrogen and alkyl;

R$_5$ is —(CH$_2$)$_m$—Y-A-B;

m is from 0–6;

A is absent or is a member selected from the group consisting of alkoxyalkylene, alkylene and hydroxyalkylene;

B is a member selected from the group consisting of hydrogen, alkyl, aryl, arylC(O)—, arylS(O)$_2$—, arylalkenyl, aryloxyalkyl, biaryl, biarylalkyl, cycloalkyl, heterocycle, heterocycleC(O)—, heterocycleS(O)$_2$—, haloalkyl, R$_E$R$_F$N—, R$_E$R$_F$NC(O)—, R$_G$S— and R$_G$O—;

R$_E$ and R$_F$ are each independently a member selected from the group consisting of hydrogen, alkyl, alkylC(O)—, aryl, arylalkyl, heterocycle, heterocyclealkyl, arylC(O)— and arylS(O)$_2$—;

R$_G$ is a member selected from the group consisting of hydrogen, alkyl, aryl, arylalkyl and heterocycle;

Y is a member selected from the group consisting of —C(O)—, —S—, —S(O)— and —S(O)$_2$—, or is absent;

R$_6$ is a member selected from the group consisting of hydrogen, alkyl and arylcarboxyalkyl; and R$_7$, R$_8$, R$_9$, and R$_{10}$ are each independently a member selected from the group consisting of hydrogen, alkyl, alkoxy, halo, haloalkyl, haloalkoxy and hydroxy or R$_7$ and R$_8$ taken together with the carbon atom that they are attached form oxo.

In particular, one such disorder mediated by MCH through the MCH receptor is obesity. Other disorders that are mediated by MCH through the MCH receptor are abnormalities in reproduction and sexual behavior, thyroid hormone secretion, diuresis and water/electrolyte homeostasis, sensory processing, memory, sleeping and arousal, anxiety and depression, seizure and in treatment of neurodegeneration or psychiatric disorders. Therefore the compounds of the present invention are useful in treating disorder such as obesity, abnormalities in reproduction and sexual behavior, thyroid hormone secretion, diuresis and water/electrolyte homeostasis, sensory processing, memory, sleeping and arousal, anxiety and depression, seizure and in treatment of neurodegeneration or psychiatric disorders. Accordingly, the present invention provides a method for treating obesity, abnormalities in reproduction and sexual behavior, thyroid hormone secretion, diuresis and water/electrolyte homeostasis, sensory processing, memory, sleeping and arousal, anxiety and depression, seizure and in treatment of neurodegeneration and psychiatric disorders comprising administering a therapeutically effective amount of a compound of formula (II).

According to another embodiment, the present invention is directed to a pharmaceutical composition comprising a therapeutically effective amount of a compound of formula (II) in combination with a pharmaceutically suitable carrier.

DETAILED DESCRIPTION OF THE INVENTION

Definitions

As used throughout this specification and the appended claims, the following terms have the following meanings:

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkylene," as used herein, refers to an alkoxy group, as defined herein, appended to the parent molecular moiety through an alkylene atom, as defined herein. Representative examples of alkoxyalkylene include, but are not limited to, methoxypropyl, methoxybutyl, ethoxypropyl, ethoxypentyl, propoxybutyl and propoxypetyl.

The term "alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl," as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylene," denotes a divalent group derived from a straight or branched chain hydrocarbon of from 1 to 10 carbon atoms. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkylsulfonyl," as used herein, refers to an alkyl group, as defined herein, appended to the parent molecular moiety through a sulfonyl group, as defined herein. Representative examples of alkylsulfonyl include, but are not limited to, methylsulfonyl and ethylsulfonyl.

The term "aryl," as used herein, refers to a monocyclic-ring system, or a bicyclic- or a tricyclic-fused ring system wherein one or more of the fused rings are aromatic. Representative examples of aryl include, but are not limited to, anthracenyl, azulenyl, fluorenyl, indanyl, indenyl, naphthyl, phenyl, and tetrahydronaphthyl.

The aryl groups of this invention can be substituted with 0, 1, 2, or 3 substituents independently a member selected from alkenyl, alkoxy, alkoxycarbonyl, alkyl, alkylcarbonyl, alkylcarbonyloxy, alkynyl, aryloxy, arylalkenyl, carboxy, carboxyalkyl, cyano, cyanoalkyl, formyl, halogen, haloalkyl, heterocycle, hydroxy, hydroxyalkylene, nitro, —$NR_AR_B$, aryl and heterocycle, wherein aryl of said aryloxy, said aryl and said heterocycle can each be substituted with 0, 1, 2, or 3 substitutents selected from the group consisting of alkenyl, alkoxy, alkoxycarbonyl, alkyl, alkylcarbonyl, carboxy, carboxyalkyl, cyano, cyanoalkyl, halogen, haloalkyl, hydroxy, hydroxyalkyl and nitro.

The term "arylalkyl," as used herein, refers to an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "arylalkenyl," as used herein, refers to an aryl group, as defined herein, appended to the parent molecular moiety through an alkenyl group, as defined herein. Representative examples of arylalkenyl include, but are not limited to, prop-1-enylbenzene, 1-(prop-1-enyl)naphthalene and the like.

The term "arylcarbonyl," as used herein, refers to an aryl group, as defined herein, appended to the parent molecular moiety through a carbonyl group, as defined herein. Representative examples of arylcarbonyl include, but are not limited to, benzoyl and naphthoyl.

The term "arylcarbonylalkyl" as used herein, refers to an arylcarbonyl group, as defined herein, appended to the parent molecular moiety through a carbonyl group, as defined herein. Representative examples of arylcarbonylalkyl include, but are not limited to, propiophenone, 1-(1-naphthyl)propan-1-one and the like.

The term "aryloxy," as used herein, refers to an aryl group, as defined herein, appended to the parent molecular moiety through an oxygen atom. Representative examples of aryloxy include, but are not limited to, phenoxy, naphthyloxy, 3-bromophenoxy, 4-chlorophenoxy, 4-methylphenoxy, and 3,5-dimethoxyphenoxy.

The term "aryloxyalkyl," as used herein, refers to an aryloxy group, as defined herein, appended to the parent molecular moiety through an alkyl group, as defined herein. Representative examples of aryloxyalkyl include, but are not limited to, 2-phenoxyethyl, 3-naphth-2-yloxypropyl and 3-bromophenoxymethyl.

The term "arylsulfonyl," as used herein, refers to an aryl group, as defined herein, appended to the parent molecular moiety through a sulfonyl group, as defined herein. Representative examples of arylsulfonyl include but are not limited to (ethylsulfonyl)benzene, 1-(ethylsulfonyl)naphthalene and the like.

The term "biarylalkyl" as used herein, refers to two aryl groups, as defined herein, appended to the parent molecular moiety through an alkyl group, as defined herein. Representative examples of biarylalkyl include but are not limited to (1-phenylbutyl)benzene and the like.

The term "carbonyl," as used herein, refers to a —C(O)— group.

The term "cycloalkyl," as used herein, refers to a monocyclic, bicyclic, or tricyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl, and cyclooctyl. Bicyclic ring systems are exemplified by a bridged monocyclic ring system in which two non-adjacent carbon atoms of the monocyclic ring are linked by an alkylene bridge of between one and three additional carbon atoms. Representative examples of bicyclic ring systems include, but are not limited to, bicyclo(3.1.1)heptane, bicyclo(2.2.1)heptane, bicyclo(2.2.2)octane, bicyclo(3.2.2)nonane, bicyclo(3.3.1)nonane, and bicyclo(4.2.1)nonane. Tricyclic ring systems are exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo($3.3.1.0^{3,7}$)nonane and tricyclo($3.3.1.1^{3,7}$)decane (adamantane).

The cycloalkyl groups of this invention can be substituted with 0, 1, 2, or 3 substituents independently a member selected from alkenyl, alkoxy, alkoxycarbonyl, alkyl, alkylcarbonyl, alkylcarbonyloxy, alkynyl, aryl, aryloxy, arylalkenyl, carboxy, carboxyalkyl, cyano, cyanoalkyl, formyl, halogen, haloalkyl, heterocycle, hydroxy, hydroxyalkyl, nitro and —$NR_AR_B$ wherein $R_A$ and $R_B$ are each independently a member selected from the group consisting of hydrogen, alkyl, alkylcarbonyl and alkylformyl The term "halo" or "halogen," as used herein, refers to —Cl, —Br, —I or —F.

The term "haloalkoxy," as used herein, refers to at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heterocycle" or "heterocyclic," as used herein, refers to a monocyclic, bicyclic, or tricyclic ring system. Monocyclic ring systems are exemplified by any 3- or 4-membered ring containing a heteroatom independently a member selected from oxygen, nitrogen and sulfur; or a 5-, 6- or 7-membered ring containing one, two or three heteroatoms wherein the heteroatoms are independently a member selected from nitrogen, oxygen and sulfur. The 5-membered ring has from 0–2 double bonds and the 6- and 7-membered ring have from 0–3 double bonds. Representative examples of monocyclic ring systems include, but are not limited to, azetidinyl, azepanyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridinyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl (thiomorpholine sulfone), thiopyranyl, triazinyl, triazolyl, and trithianyl. Bicyclic ring systems are exemplified by any of the above monocyclic ring systems fused to an aryl group as defined herein, a cycloalkyl group as defined herein, or another monocyclic ring system. Representative examples of bicyclic ring systems include but are not limited to, for example, benzimidazolyl, benzodioxinyl, benzothiazolyl, benzothienyl, benzotriazolyl, benzoxazolyl, benzofuranyl, benzopyranyl, benzothiopyranyl, cinnolinyl, indazolyl, indolyl, 2,3-dihydroindolyl, indolizinyl, naphthyridinyl, isobenzofuranyl, isobenzothienyl, isoindolyl, isoquinolinyl, phthalazinyl, 4H-pyrido(1,2-a)pyrimidin-4-one, pyranopyridinyl, quinolinyl, quinolizinyl, quinoxalinyl, quinazolinyl, tetrahydroisoquinolinyl, tetrahydroquinolinyl, and thiopyranopyridinyl. Tricyclic rings systems are exemplified by any of the above bicyclic ring systems fused to an aryl group as defined herein, a cycloalkyl group as defined herein, or a monocyclic ring system. Representative examples of tricyclic ring systems include, but are not limited to, acridinyl, carbazolyl, carbolinyl, dibenzo(b,d)furanyl, dibenzo(b,d)thienyl, naphtho(2,3-b)furan, naphtho(2,3-b)thienyl, phenazinyl, phenothiazinyl, phenoxazinyl, thianthrenyl, thioxanthenyl and xanthenyl.

The heterocycles of this invention can be substituted with 0, 1, 2, or 3 substituents independently a member selected from alkenyl, alkoxy, alkoxycarbonyl, alkyl, alkylcarbonyl, alkylcarbonyloxy, alkynyl, aryl, aryloxy, arylalkenyl, carboxy, carboxyalkyl, cyano, cyanoalkyl, formyl, halogen, haloalkyl, heterocycle, hydroxy, hydroxyalkyl, nitro and —NR$_A$R$_B$, wherein aryl of said aryloxy, aryl of said arylalkenyl, said aryl and said heterocycle can be substituted with 0, 1, 2, or 3 substitutents selected from the group consisting of alkenyl, alkoxy, alkoxycarbonyl, alkyl, alkylcarbonyl, carboxy, carboxyalkyl, cyano, cyanoalkyl, halogen, haloalkyl, hydroxy, hydroxyalkyl and nitro.

The term "heterocyclealkyl," as used herein, refers to a heterocycle, as defined herein, appended to the parent molecular moiety through an alkyl group, as defined herein. Representative examples of heterocyclealkyl include, but are not limited to, pyridin-3-ylmethyl and 2-pyrimidin-2-ylpropyl.

The term "hydroxy," as used herein, refers to an —OH group.

The term "hydroxyalkylene," as used herein, refers to a hydroxy group, as defined herein, appended to the parent molecular moiety through an alkylene group, as defined herein. Representative examples of hydroxyalkylene include, but are not limited to, hydroxybutyl, hydroxypentyl and hydroxyhexyl.

The term "oxo," as used herein, refers to a =O moiety.

The term "sulfonyl," as used herein, refers to a —SO$_2$— group.

The present invention is directed to compounds of formula (I), wherein R$_1$, R$_2$, R$_3$, R$_4$, R$_5$, R$_6$, R$_7$, R$_8$, R$_9$, R$_{10}$, R$_A$, R$_B$, R$_C$, R$_D$, R$_E$, R$_F$, A, B, Y and m are defined herein.

The present invention is also directed to a method of treating disorders mediated by MCH through the MCH receptor.

As antagonists of MCH action upon the MCH receptor, therefore, the compounds of the present invention are useful in treating disorders that are mediated by MCH through the MCH receptor. Disorders that are mediated by MCH through the MCH receptor are obesity, abnormalities in reproduction and sexual behavior, thyroid hormone secretion, diuresis and water/electrolyte homeostasis, sensory processing, memory, sleeping and arousal, anxiety and depression, seizure and in treatment of neurodegeneration or psychiatric disorders. Therefore the compounds of the present invention are useful in treating obesity, abnormalities in reproduction and sexual behavior, thyroid hormone secretion, diuresis and water/electrolyte homeostasis, sensory processing, memory, sleeping and arousal, anxiety and depression, seizure and in treatment of neurodegeneration or psychiatric disorders.

In the principal embodiment of the present invention there is provided a method of treating disorders mediated by MCH through the MCH receptor comprising administration of a therapeutically effective amount of a compound of formula (I),

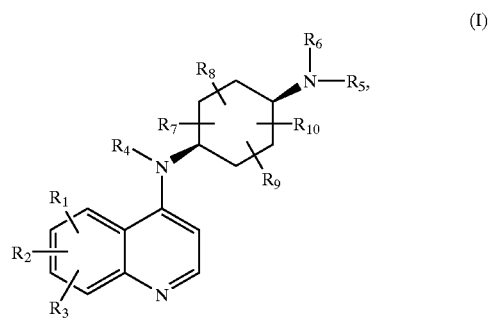

or a therapeutically suitable salts, ester, prodrug or zwitterion thereof, wherein R$_1$, R$_2$ and R$_3$ are each independently a member selected from the group consisting of hydrogen, alkyl, alkoxy, halo, haloalkyl, haloalkoxy, hydroxy and R$_A$R$_B$N— wherein R$_A$ and R$_B$ are selected from the group consisting of hydrogen and alkyl, alkylcarbonyl, alkylsulfonyl, arylcarbonyl, arylsulfonyl and R$_C$R$_D$Ncarbonyl, wherein R$_C$ and R$_D$ are independently a member selected from the group consisting of hydrogen, alkyl and aryl;

R$_4$ is a member selected from the group consisting of hydrogen and alkyl;

R$_5$ is —(CH$_2$)$_m$—Y-A-B;

m is 0–6;

A is absent or is a member selected from the group consisting of alkoxyalkylene, alkylene and hydroxyalkylene;

B is a member selected from the group consisting of hydrogen, alkyl, aryl, arylC(O)—, arylS(O)$_2$—, arylalkenyl, aryloxyalkyl, biaryl, biarylalkyl, cycloalkyl, heterocycle, heterocycleC(O)—, heterocycleS(O)$_2$—, haloalkyl, R$_E$R$_F$N—, R$_E$R$_F$NC(O)—, R$_G$S— and R$_G$O—;

R$_E$ and R$_F$ are independently a member selected from the group consisting of hydrogen, alkyl, alkylC(O)—, aryl, arylalkyl, heterocycle, heterocyclealkyl, arylC(O)— and arylS(O)$_2$—;

R$_G$ is a member selected from the group consisting of hydrogen, alkyl, aryl, arylalkyl and heterocycle;

Y is a member selected from the group consisting of —C(O)—, —S—, —S(O)— and —S(O)$_2$—, or is absent;

R$_6$ is a member selected from the group consisting of hydrogen, alkyl and arylcarboxyalkyl; and $R_7$, $R_8$, $R_9$, and $R_{10}$ are independently a member selected from the group consisting of hydrogen, alkyl, alkoxy, halo, haloalkyl, haloalkoxy and hydroxy or $R_7$ and $R_8$ taken together with the carbon atom that they are attached form oxo;

with the following provisos $P_1$–$P_4$:

$P_1$ if Y is absent, m is 0 and if A is absent or is a member selected from the group consisting of alkoxyalkylene, alkylene and hydroxyalkylene, then B is a member selected from the group consisting of hydrogen, alkyl, arylC(O)—, arylS(O)$_2$—, arylalkenyl, aryloxyalkyl, biarylalkyl, cycloalkyl, heterocycle, heterocycleC(O)—, heterocycleS(O)$_2$—, haloalkyl, $R_ER_FN$—, $R_ER_FNC(O)$—, $R_GS$— and $R_GO$—; or $P_2$ if Y is —C(O)—, m is 0 and A is absent, then B is a member selected from the group consisting of hydrogen, alkyl, arylalkenyl, aryloxyalkyl, cycloalkyl, heterocycle, haloalkyl, and $R_ER_FNC(O)$—; or $P_3$ if Y is —C(O)—, A is absent and B is aryl or heterocycle, then m is 1–6; or $P_4$ if Y is —C(O)— and B is a member selected from the group consisting of arylC(O)—, arylS(O)$_2$—, heterocycleC(O)—, heterocycleS(O)$_2$—, then A is a member selected from the group consisting of alkoxyalkylene, alkylene and hydroxyalkylene.

According to a further embodiment of the present invention there is provided a compound of formula (I) wherein $R_5$ is B and wherein B is heterocycle; and $R_1$, $R_2$, $R_3$, $R_4$, $R_6$, $R_7$, $R_8$, $R_9$, $R_{10}$, $R_A$, $R_B$, $R_C$, $R_D$, A and m are as defined in formula (I), which is useful for the treatment of obesity.

According to a further embodiment of the present invention there is provided a compound of formula (I) wherein $R_5$ is -A-B, A is a member selected from the group consisting of alkoxyalkylene, alkylene and hydroxyalkylene, B is heterocycle; and $R_1$, $R_2$, $R_3$, $R_4$, $R_6$, $R_7$, $R_8$, $R_9$, $R_{10}$, $R_A$, $R_B$, $R_C$, $R_D$ and m are as defined in formula (I) which is useful for the treatment of obesity.

According to a further embodiment of the present invention there is provided a compound of formula (I) wherein $R_5$ is —(CH$_2$)$_m$—C(O)-A-B, m is from 0–6, A is absent or is a member selected from the group consisting of alkoxyalkylene, alkylene and hydroxyalkylene, B is a member selected from the group consisting of hydrogen, alkyl, aryl, arylC(O)—, arylS(O)$_2$—, arylalkenyl, aryloxyalkyl, biaryl, biarylalkyl, cycloalkyl, heterocycle, heterocycleC(O)—, heterocycleS(O)$_2$—, haloalkyl, $R_ER_FN$—, $R_ER_FNC(O)$—, $R_GS$— and $R_GO$—, $R_E$ and $R_F$ are independently a member selected from the group consisting of hydrogen, alkyl, alkylC(O)—, aryl, arylalkyl, heterocycle, heterocyclealkyl, arylC(O)— and arylS(O)$_2$—; and $R_1$, $R_2$, $R_3$, $R_4$, $R_6$, $R_7$, $R_8$, $R_9$, $R_{10}$, $R_A$, $R_B$, $R_C$, $R_D$ $R_G$ are as defined in formula (I) which is useful for the treatment of obesity.

According to a further embodiment of the present invention there is provided a compound of formula (I) wherein $R_5$ is —(CH$_2$)$_m$—C(O)-A-B, m is from 3–6, A is absent or is a member selected from the group consisting of alkoxyalkylene, alkylene and hydroxyalkylene, B is a member selected from the group consisting of hydrogen, alkyl, aryl, arylC(O)—, arylS(O)$_2$—, arylalkenyl, aryloxyalkyl, biaryl, biarylalkyl, cycloalkyl, heterocycle, heterocycleC(O)—, heterocycleS(O)$_2$—, haloalkyl, $R_ER_FN$—, $R_ER_FNC(O)$—, $R_GS$— and $R_GO$—, $R_E$ and $R_F$ are independently a member selected from the group consisting of hydrogen, alkyl, alkylC(O)—, aryl, arylalkyl, heterocycle, heterocyclealkyl, arylC(O)— and arylS(O)$_2$—; and $R_1$, $R_2$, $R_3$, $R_4$, $R_6$, $R_7$, $R_8$, $R_9$, $R_{10}$, $R_A$, $R_B$, $R_C$, $R_D$ $R_G$ are as defined in formula (I) which is useful for the treatment of obesity.

According to a further embodiment of the present invention there is provided a compound of formula (I) wherein $R_5$ is —(CH$_2$)$_m$—C(O)-A-B, m is 0, A is absent, B is a member selected from the group consisting of of aryl, arylalkenyl, aryloxyalkyl, biaryl and heterocycle; and $R_1$, $R_2$, $R_3$, $R_4$, $R_6$, $R_7$, $R_8$, $R_9$, $R_{10}$, $R_A$, $R_B$, $R_C$, $R_D$ are as defined in formula (I) which is useful for the treatment of obesity.

According to a further embodiment of the present invention there is provided a compound of formula (I) wherein $R_5$ is —(CH$_2$)$_m$—C(O)-A-B, m is 0, A is a member selected from the group consisting of alkoxyalkylene, alkylene and hydroxyalkylene, B is a member selected from the group consisting of arylC(O)—, arylNC(O)—, arylS(O)$_2$—, heterocycleC(O)—, heterocycleNC(O)— and heterocycleS(O)$_2$—; and $R_1$, $R_2$, $R_3$, $R_4$, $R_5$, $R_6$, $R_A$, $R_B$, $R_C$ and $R_D$ are as defined in formula (I) which is useful for the treatment of obesity.

According to a further embodiment of the present invention there is provided a compound of formula (I) wherein $R_5$ is —(CH$_2$)$_m$—C(O)-A-B, m is from 1–6, A is absent, B is a member selected from the group consisting of aryl and heterocycle; and $R_1$, $R_2$, $R_3$, $R_4$, $R_5$, $R_6$, $R_7$, $R_8$, $R_9$, $R_{10}$, $R_A$, $R_B$, $R_C$ and $R_D$ are as defined in formula (I) which is useful for the treatment of obesity.

According to a further embodiment of the present invention there is provided a compound of formula (I) wherein $R_5$ is —(CH$_2$)$_m$—C(O)-A-B, m is from 3–6, A is absent, B is a member selected from the group consisting of aryl and heterocycle; and $R_1$, $R_2$, $R_3$, $R_4$, $R_5$, $R_6$, $R_7$, $R_8$, $R_9$, $R_{10}$, $R_A$, $R_B$, $R_C$ and $R_D$ are as defined in formula (I) which is useful for the treatment of obesity.

According to a further embodiment of the present invention there is provided a compound of formula (I) wherein $R_5$ is —(CH$_2$)$_m$—C(O)-A-B, m is 0, A is absent or is a member selected from the group consisting of alkoxyalkylene, alkylene and hydroxyalkylene, B is a member selected from the group consisting of aryl and heterocycle and $R_1$, $R_2$, $R_3$, $R_4$, $R_5$, $R_6$, $R_7$, $R_8$, $R_9$, $R_{10}$, $R_A$, $R_B$, $R_C$ and $R_D$ are as defined in formula (I) which is useful for the treatment of obesity.

According to a further embodiment of the present invention there is provided a compound of formula (I) wherein $R_5$ is —(CH$_2$)$_m$C(O)-A-B, m is from 0–6, A is absent or is a member selected from the group consisting of alkoxyalkylene, alkylene and hydroxyalkylene, B is $R_ER_FN$—, $R_E$ and $R_F$ are independently a member selected from the group consisting of hydrogen, alkyl, alkylC(O)—, aryl, arylalkyl, heterocycle, heterocyclealkyl, arylC(O)— and arylS(O)$_2$—; and $R_1$, $R_2$, $R_3$, $R_4$ $R_6$, $R_7$, $R_8$, $R_9$, $R_{10}$, $R_A$, $R_B$, $R_C$ and $R_D$ are as defined in formula (I) which is useful for the treatment of obesity.

According to a further embodiment of the present invention there is provided a compound of formula (I) wherein $R_5$ is —(CH$_2$)$_m$C(O)-A-B, B is $R_ER_FN$—, $R_E$ is a member selected from the group consisting of alkylC(O)—, arylC(O)— and arylS(O)$_2$—, m is 0, A is alkylene; and $R_1$, $R_2$, $R_3$, $R_4$, $R_5$, $R_6$, $R_7$, $R_8$, $R_9$, $R_{10}$, $R_A$, $R_B$, $R_C$ and $R_D$ are as defined in formula (I) which is useful for the treatment of obesity.

According to a further embodiment of the present invention there is provided a compound of formula (I) wherein $R_5$ is —(CH$_2$)$_m$C(O)-A-B, B is $R_ER_FN$—, $R_E$ is a member selected from the group consisting of aryl, arylalkyl, heterocycle and heterocyclealkyl, m is 0, A is absent; and $R_1$, $R_2$, $R_3$, $R_4$, $R_5$, $R_6$, $R_7$, $R_8$, $R_9$, $R_{10}$, $R_A$, $R_B$, $R_C$, $R_D$ are as defined in formula (I) which is useful for the treatment of obesity.

According to a further embodiment of the present invention there is provided a compound of formula (I) wherein $R_5$ is —(CH$_2$)$_m$—C(O)-A-B, m is from 0–6, A is absent or is a member selected from the group consisting of alkoxyalkylene, alkylene and hydroxyalkylene, B is R$_E$R$_F$NC(O)—, R$_E$ and R$_F$ are independently a member selected from the group consisting of hydrogen, alkyl, alkylC(O)—, aryl, arylalkyl, heterocycle, heterocyclealkyl, arylC(O)— and arylS(O)$_2$—; and R$_1$, R$_2$, R$_3$, R$_4$, R$_5$, R$_6$, R$_7$, R$_8$, R$_9$, R$_{10}$, R$_A$, R$_B$, R$_C$ and R$_D$ are as defined in formula (I) which is useful for the treatment of obesity.

According to a further embodiment of the present invention there is provided a compound of formula (I) wherein R$_5$ is —(CH$_2$)$_m$—C(O)-A-B, m is from 3–6, A is absent or is a member selected from the group consisting of alkoxyalkylene, alkylene and hydroxyalkylene, B is R$_E$R$_F$NC(O)—, R$_E$ and R$_F$ are independently a member selected from the group consisting of hydrogen, alkyl, alkylC(O)—, aryl, arylalkyl, heterocycle, heterocyclealkyl, arylC(O)— and arylS(O)$_2$—; and R$_1$, R$_2$, R$_3$, R$_4$, R$_5$, R$_6$, R$_7$, R$_8$, R$_9$, R$_{10}$, R$_A$, R$_B$, R$_C$ and R$_D$ are as defined in formula (I) which is useful for the treatment of obesity.

According to a further embodiment of the present invention there is provided a compound of formula (I) wherein R$_5$ is —(CH$_2$)$_m$—C(O)-A-B, m is 0, A is alkylene, B is R$_E$R$_F$NC(O)—, R$_E$ is a member selected from the group consisting of aryl, arylalkyl, heterocycle and heterocyclealkyl, and R$_1$, R$_2$, R$_3$, R$_4$, R$_5$, R$_6$, R$_7$, R$_8$, R$_9$, R$_{10}$, R$_A$, R$_B$, R$_C$ and R$_D$ are as defined in formula (I) which is useful for the treatment of obesity.

According to a further embodiment of the present invention there is provided a compound of formula (I) wherein R$_5$ is —(CH$_2$)$_m$—C(O)-A-B, m is from 0–6, A is absent or is a member selected from the group consisting of alkoxyalkylene, alkylene and hydroxyalkylene, B is a member selected from the group consisting of R$_G$S— and R$_G$O—, R$_G$ is a member selected from the group consisting of hydrogen, alkyl, aryl, arylalkyl and heterocycle; and R$_1$, R$_2$, R$_3$, R$_4$, R$_6$, R$_7$, R$_8$, R$_9$, R$_{10}$, R$_A$, R$_B$, R$_C$ and R$_D$ are as defined in formula (I) which is useful for the treatment of obesity.

According to a further embodiment of the present invention there is provided a compound of formula (I) wherein R$_5$ is —(CH$_2$)$_m$—C(O)-A-B, m is from 3–6, A is absent or is a member selected from the group consisting of alkoxyalkylene, alkylene and hydroxyalkylene, B is a member selected from the group consisting of R$_G$S— and R$_G$O—, R$_G$ is a member selected from the group consisting of hydrogen, alkyl, aryl, arylalkyl and heterocycle; and R$_1$, R$_2$, R$_3$, R$_4$, R$_6$, R$_7$, R$_8$, R$_9$, R$_{10}$, R$_A$, R$_B$, R$_C$ and R$_D$ are as defined in formula (I) which is useful for the treatment of obesity.

According to a further embodiment of the present invention there is provided a compound of formula (I) wherein R$_5$ is —(CH$_2$)$_m$—C(O)-A-B, m is 0, A is alkylene, B is a member selected from the group consisting of R$_G$S— and R$_G$O—, R$_G$ is a member selected from the group consisting of alkyl, aryl, arylalkyl, heterocycle and heterocyclealkyl; and R$_1$, R$_2$, R$_3$, R$_4$, R$_6$, R$_7$, R$_8$, R$_9$, R$_{10}$, R$_A$, R$_B$, R$_C$ and R$_D$ are as defined in formula (I) which is useful for the treatment of obesity.

According to a further embodiment of the present invention there is provided a compound of formula (I) wherein R$_5$ is —(CH$_2$)$_m$—C(O)-A-B, m is 0, A is absent or is a member selected from the group consisting of alkoxyalkylene, alkylene and hydroxyalkylene, B is a member selected from the group consisting of alkyl, cycloalkyl and haloalkyl; and R$_1$, R$_2$, R$_3$, R$_4$, R$_6$, R$_7$, R$_8$, R$_9$, R$_{10}$, R$_A$, R$_B$, R$_C$ and R$_D$ are as defined in formula (I) which is useful for the treatment of obesity.

According to a further embodiment of the present invention there is provided a compound of formula (I) wherein R$_5$ is —(CH$_2$)$_m$—S(O)$_2$-A-B, m is from 0–6, A is absent or is a member selected from the group consisting of alkoxyalkylene, alkylene and hydroxyalkylene, B is a member selected from the group consisting of alkyl, aryl, arylalkenyl, cycloalkyl and heterocycle; and R$_1$, R$_2$, R$_3$, R$_4$, R$_6$, R$_7$, R$_8$, R$_9$, R$_{10}$, R$_A$, R$_B$, R$_C$ and R$_D$ are as defined in formula (I) which is useful for the treatment of obesity.

According to a further embodiment of the present invention there is provided a compound of formula (I) wherein R$_5$ is —(CH$_2$)$_m$—S(O)$_2$-A-B, m is from 3–6, A is absent or is a member selected from the group consisting of alkoxyalkylene, alkylene and hydroxyalkylene, B is a member selected from the group consisting of alkyl, aryl, arylalkenyl, cycloalkyl and heterocycle; and R$_1$, R$_2$, R$_3$, R$_4$, R$_6$, R$_7$, R$_8$, R$_9$, R$_{10}$, R$_A$, R$_B$, R$_C$ and R$_D$ are as defined in formula (I) which is useful for the treatment of obesity.

According to a further embodiment of the present invention there is provided a compound of formula (I) wherein R$_5$ is —(CH$_2$)$_m$—S(O)$_2$-A-B, m is 0, A is absent, B is a member selected from the group consisting of aryl and heterocycle; and R$_1$, R$_2$, R$_3$, R$_4$, R$_6$, R$_7$, R$_8$, R$_9$, R$_{10}$, R$_A$, R$_B$, R$_C$ and R$_D$ are as defined in formula (I) which is useful for the treatment of obesity.

According to a further embodiment of the present invention there is provided a compound of formula (I) wherein R$_5$ is —(CH$_2$)$_m$—S(O)$_2$-A-B, m is 0, A is alkylene, B is a member selected from the group consisting of aryl and heterocycle; and R$_1$, R$_2$, R$_3$, R$_4$, R$_6$, R$_7$, R$_8$, R$_9$, R$_{10}$, R$_A$, R$_B$, R$_C$ and R$_D$ are as defined in formula (I) which is useful for the treatment of obesity.

According to a further embodiment of the present invention there is provided a compound of formula (I) wherein R$_5$ is —(CH$_2$)$_m$—S(O)$_2$-A-B, m is 0, A is alkylene, B is a member selected from the group consisting of alkyl and cycloalkyl; and R$_1$, R$_2$, R$_3$, R$_4$, R$_6$, R$_7$, R$_8$, R$_9$, R$_{10}$, R$_A$, R$_B$, R$_C$ and R$_D$ are as defined in formula (I) which is useful for the treatment of obesity.

The present invention provides a method of treating disorders mediated by MCH through the MCH receptor comprising administering a therapeutically effective amount of a compound of formula (II),

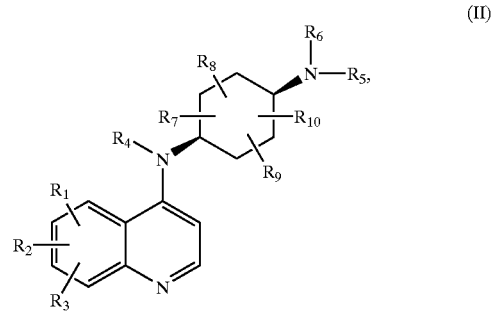

(II)

or a therapeutically suitable salts, ester, prodrug or zwitterion thereof, wherein R$_1$, R$_2$ and R$_3$ are each independently selected from the group consisting of hydrogen, alkyl, alkoxy, halo, haloalkyl, haloalkoxy, hydroxy and R$_A$R$_B$N— wherein R$_A$ and R$_B$ are selected from the group consisting of hydrogen and alkyl, alkylcarbonyl, alkylsulfonyl, arylcarbonyl, arylsulfonyl and R$_C$R$_D$Ncarbonyl, wherein R$_C$ and R$_D$ are independently a member selected from the group consisting of hydrogen, alkyl and aryl;

$R_4$ is a member selected from the group consisting of hydrogen and alkyl;

$R_5$ is —$(CH_2)_m$—Y-A-B;

m is from 0–6;

A is absent or is a member selected from the group consisting of alkoxyalkylene, alkylene and hydroxyalkylene;

B is a member selected from the group consisting of hydrogen, alkyl, aryl, arylC(O)—, arylS(O)$_2$—, arylalkenyl, aryloxyalkyl, biaryl, biarylalkyl, cycloalkyl, heterocycle, heterocycleC(O)—, heterocycleS(O)$_2$—, haloalkyl, $R_E R_F N$—, $R_E R_F NC(O)$—, $R_G S$— and $R_G O$—;

$R_E$ and $R_F$ are independently a member selected from the group consisting of hydrogen, alkyl, alkylC(O)—, aryl, arylalkyl, heterocycle, heterocyclealkyl, arylC(O)— and arylS(O)$_2$—;

$R_G$, is a member selected from the group consisting of hydrogen, alkyl, aryl, arylalkyl and heterocycle;

Y is a member selected from the group consisting of —C(O)—, —S—, —S(O)— and —S(O)$_2$—, or is absent;

$R_6$ is a member selected from the group consisting of hydrogen, alkyl and arylcarboxyalkyl; and $R_7$, $R_8$, $R_9$, and $R_{10}$ are independently a member selected from the group consisting of hydrogen, alkyl, alkoxy, halo, haloalkyl, haloalkoxy and hydroxy or $R_7$ and $R_8$ taken together with the carbon atom that they are attached form oxo.

In particular, one such disorder mediated by MCH through the MCH receptor is obesity. Accordingly, the present invention provides a method for treating obesity comprising administering a therapeutically effective amount of a compound of formula (II).

Other disorder mediated by MCH through the MCH receptor are abnormalities in reproduction and sexual behavior, thyroid hormone secretion, diuresis and water/electrolyte homeostasis, sensory processing, memory, sleeping and arousal, anxiety and depression, seizure and in treatment of neurodegeneration and psychiatric disorders. Accordingly, the present invention provides a method for treating abnormalities in reproduction and sexual behavior, thyroid hormone secretion, diuresis and water/electrolyte homeostasis, sensory processing, memory, sleeping and arousal, anxiety and depression, seizure and in treatment of neurodegeneration and psychiatric disorders by inhibiting the effects of melanin concentrating hormone (MCH) through the melanin concentrating hormone receptor, comprising administrering a therapeutically effective amount of a compound of formula (II).

According to another embodiment, the present invention is directed to a pharmaceutical composition comprising a therapeutically effective amount of a compound of formula (II) in combination with a pharmaceutically suitable carrier.

The present compounds can exist as therapeutically suitable salts. The term "therapeutically suitable salt," refers to salts or zwitterions of the compounds which are water or oil-soluble or dispersible, suitable for treatment of disorders without undue toxicity, irritation, and allergic response, commensurate with a reasonable benefit/risk ratio, and effective for their intended use. The salts can be prepared during the final isolation and purification of the compounds or separately by reacting an amino group of the compounds with a suitable acid. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetic, trifluoroacetic, glutamate, para-toluenesulfonate, undecanoate, hydrochloric, hydrobromic, sulfuric, phosphoric, and the like. The amino groups of the compounds can also be quaternized with alkyl chlorides, bromides, and iodides such as methyl, ethyl, propyl, isopropyl, butyl, lauryl, myristyl, stearyl, and the like.

Basic addition salts can be prepared during the final isolation and purification of the present compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethylamine, diethylamine, ethylamine, tributlyamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine, ethylenediamine, ethanolamine, diethanolamine, piperidine, piperazine, and the like, are contemplated as being within the scope of the present invention.

The present compounds can also exist as therapeutically suitable esters and prodrugs. The term "therapeutically suitable esters and prodrug," refers to those esters and prodrugs or zwitterions which are suitable for use in contact with the tissues of patients without undue toxicity, irritation, and allergic response, are commensurate with a reasonable benefit/risk ratio, and are effective for their intended use. The term "prodrug," refers to compounds which are rapidly transformed in vivo to the parent compounds of formula (I–II) for example, by hydrolysis in blood. The term "therapeutically suitable ester," refers to compounds which are rapidly transformed in vivo to the parent compounds of formula (I–II) for example, by hydrolysis in blood. The term "therapeutically suitable ester," refers to alkoxycarbonyl groups appended to the parent molecule on an available carbon atom. More specifically, a "therapeutically suitable ester," may exist on one or more available aryl, cycloalkyl and heterocycle group as defined herein.

Asymmetric centers can exist in the present compounds. Individual stereoisomers of the compounds are prepared by synthesis from chiral starting materials or by preparation of racemic mixtures and separation by conversion to a mixture of diastereomers followed by separation or recrystallization, chromatographic techniques, or direct separation of the enantiomers on chiral chromatographic columns. Starting materials of particular stereochemistry are either commercially available or are made by the methods described hereinbelow and resolved by techniques well-known in the art.

Geometric isomers can exist in the present compounds. The invention contemplates the various geometric isomers and mixtures thereof resulting from the disposal of substituents around a carbon-carbon double bond, a cycloalkyl group, or a heterocycloalkyl group. Substituents around a carbon-carbon double bond are designated as being of Z or E configuration and substituents around a cycloalkyl or heterocycloalkyl are designated as being of cis or trans configuration.

Therapeutic compositions of the present compounds comprise an effective amount of the same formulated with one or more therapeutically suitable excipients. The term "therapeutically suitable excipient," as used herein, represents a non-toxic, solid, semi-solid or liquid filler, diluent, encapsulating material, or formulation auxiliary of any type. Examples of therapeutically suitable excipients include sugars; cellulose and derivatives thereof; oils; glycols; solutions; buffering, coloring, releasing, coating, sweetening, flavoring, and perfuming agents; and the like. These therapeutic compositions can be administered parenterally, intracisternally, orally, rectally, or intraperitoneally.

Liquid dosage forms for oral administration of the present compounds comprise formulations of the same as emulsions, microemulsions, solutions, suspensions, syrups, and elixirs. In addition to the compounds, the liquid dosage forms can contain diluents and/or solubilizing or emulsifying agents. Besides inert diluents, the oral compositions can include wetting, emulsifying, sweetening, flavoring, and perfuming agents. Injectable preparations of the present compounds comprise sterile, injectable, aqueous and oleaginous solutions, suspensions or emulsions, any of which can be optionally formulated with parenterally suitable diluents, dispersing, wetting, or suspending agents. These injectable preparations can be sterilized by filtration through a bacterial-retaining filter or formulated with sterilizing agents which dissolve or disperse in the injectable media.

Antagonism of the effects of MCH through the MCH receptor by the compounds of the present invention can be delayed by using a liquid suspension of crystalline or amorphous material with poor water solubility. The rate of absorption of the compounds depends upon their rate of dissolution which, in turn, depends on their crystallinity. Delayed absorption of a parenterally administered compound can be accomplished by dissolving or suspending the compound in oil. Injectable depot forms of the compounds can also be prepared by microencapsulating the same in biodegradable polymers. Depending upon the ratio of compound to polymer and the nature of the polymer employed, the rate of release can be controlled. Depot injectable formulations are also prepared by entrapping the compounds in liposomes or microemulsions which are compatible with body tissues.

Solid dosage forms for oral administration of the present compounds include capsules, tablets, pills, powders, and granules. In such forms, the compound is mixed with at least one inert, therapeutically suitable excipient such as a carrier, filler, extender, disintegrating agent, solution retarding agent, wetting agent, absorbent, or lubricant. With capsules, tablets, and pills, the excipient can also contain buffering agents. Suppositories for rectal administration can be prepared by mixing the compounds with a suitable non-irritating excipient which is solid at ordinary temperature but fluid in the rectum.

The present compounds can be micro-encapsulated with one or more of the excipients discussed previously. The solid dosage forms of tablets, dragees, capsules, pills, and granules can be prepared with coatings and shells such as enteric and release-controlling. In these forms, the compounds can be mixed with at least one inert diluent and can optionally comprise tableting lubricants and aids. Capsules can also optionally contain opacifying agents which delay release of the compounds in a desired part of the intestinal tract.

Transdermal patches have the added advantage of providing controlled delivery of the present compounds to the body. Such dosage forms are prepared by dissolving or dispensing the compounds in the proper medium. Absorption enhancers can also be used to increase the flux of the compounds across the skin, and the rate of absorption can be controlled by providing a rate controlling membrane or by dispersing the compounds in a polymer matrix or gel.

Disorders caused or exacerbated by MCH are treated or prevented in a patient by administering to the patient, a therapeutically effective amount of compound of the present invention in such an amount and for such time as is necessary to achieve the desired result. The term "therapeutically effective amount," refers to a sufficient amount of a compound to effectively ameliorate disorders mediated by MCH, by antagonizing the effect of MCH through the MCH receptor at a reasonable benefit/risk ratio applicable to any medical treatment. The specific therapeutically effective dose level for any particular patient will depend upon a variety of factors including the disorder being treated and the severity of the disorder; the activity of the compound employed; the specific composition employed; the age, body weight, general health, sex, and diet of the patient; the time of administration, route of administration, rate of excretion; the duration of the treatment; and drugs used in combination or coincidental therapy.

The total daily dose of the present compounds in single or divided doses can be in amounts, for example, from 0.01 to 50 mg/kg body weight or more usually from 0.1 to 25 mg/kg body weight. In general, treatment regimens comprise administration to a patient in need of such treatment from about 10 mg to about 1000 mg of the compounds per day in single or multiple doses.

Specific compounds of formula (I) include, but are not limited to:

cis-N,N'-bis(7-chloroquinolin-4-yl)cyclohexane-1,4-diamine;

cis-N-(4-chlorophenyl)-N'-{4-((7-chloroquinolin-4-yl)amino)cyclohexyl}urea;

cis-N-(2,8-bis(trifluoromethyl)quinolin-4-yl)-N'-(7-chloroquinolin-4-yl)cyclohexane-1,4-diamine;

cis-N-(7-chloroquinolin-4-yl)-N'-(8-(trifluoromethyl)quinolin-4-yl)cyclohexane-1,4-diamine;

cis-N-(7-chloroquinolin-4-yl)-N'-(7-(trifluoromethyl)quinolin-4-yl)cyclohexane-1,4-diamine;

cis-N-(7-chloroquinolin-4-yl)-N'-(2-(trifluoromethyl)quinolin-4-yl)cyclohexane-1,4-diamine;

cis-N-(7-chloroquinolin-4-yl)-N'-(2-methylquinolin-4-yl)cyclohexane-4-diamine;

cis-N-(7-chloroquinolin-4-yl)-N'-(quinolin-3-ylmethyl)cyclohexane-1,4-diamine;

cis-N-(7-chloroquinolin-4-yl)-N'-(quinolin-4-ylmethyl)cyclohexane-1,4-diamine;

cis-N-(4-bromobenzyl)-N'-(7-chloroquinolin-4-yl)cyclohexane-1,4-diamine;

cis-N-(7-chloroquinolin-4-yl)-N'-(3,4-difluorobenzyl)cyclohexane-1,4-diamine;

cis-N-(3-bromobenzyl)-N'-(7-chloroquinolin-4-yl)cyclohexane-1,4-diamine;

cis-N-(7-chloroquinolin-4-yl)-N'-{(4-(dimethylamino)-1-naphthyl)methyl}cyclohexane-1,4-diamine;

cis-N-(7-chloroquinolin-4-yl)-N'-(4-pyridin-2-ylbenzyl)cyclohexane-1,4-diamine;

cis-4-chloro-N-{4-((7-chloroquinolin-4-yl)amino)cyclohexyl}benzenesulfonamide;

cis-N-(7-chloroquinolin-4-yl)-N'-(2-phenylquinolin-4-yl)cyclohexane-4-diamine;

cis-N-(7-chloroquinolin-4-yl)-N'-(6-(trifluoromethyl)quinolin-4-yl)cyclohexane-1,4-diamine;

cis-N-(7-chloroquinolin-4-yl)-N'-(6-methyl-2-(trifluoromethyl)quinolin-4-yl)cyclohexane-1,4-diamine;

cis-N-(7-chloroquinolin-4-yl)-N'-(6-fluoro-2-(trifluoromethyl)quinolin-4-yl)cyclohexane-1,4-diamine;

cis-N-(7-chloroquinolin-4-yl)-N'-(8-chloro-2-(trifluoromethyl)quinolin-4-yl)cyclohexane-1,4-diamine;

cis-N-(7-chloroquinolin-4-yl)-N'-quinolin-4-ylcyclohexane-1,4-diamine;
cis-N-(7-chloroquinolin-4-yl)-N'-(5,7-dichloro-2-(trifluoromethyl)quinolin-4-yl)cyclohexane-1,4-diamine;
cis-N-{4-((7-chloroquinolin-4-yl)amino)cyclohexyl}-1H-indole-6-carboxamide;
cis-N-{4-((7-chloroquinolin-4-yl)amino)cyclohexyl}-1-(3,4-dichlorophenyl)methanesulfonamide;
cis-N-(7-chloroquinolin-4-yl)-N'-(1H-indol-6-ylmethyl)cyclohexane-1,4-diamine;
cis-N-{4-((7-chloroquinolin-4-yl)amino)cyclohexyl}-1-(3,5-dichlorophenyl)methanesulfonamide;
cis-N-{4-((7-chloroquinolin-4-yl)amino)cyclohexyl}-N'-(3-(methylthio)phenyl)urea;
cis-N-(2-chlorophenyl)-N'-{4-((7-chloroquinolin-4-yl)amino)cyclohexyl}urea;
cis-N-{4-((7-chloroquinolin-4-yl)amino)cyclohexyl}-N'-(2-(trifluoromethyl)phenyl)urea;
cis-N-{4-((7-chloroquinolin-4-yl)amino)cyclohexyl}-N'-(3-(trifluoromethyl)phenyl)urea;
cis-N-{4-((7-chloroquinolin-4-yl)amino)cyclohexyl}-N'-(4-(trifluoromethyl)phenyl)urea;
cis-N-{4-((7-chloroquinolin-4-yl)amino)cyclohexyl}-N'-(4-(trifluoromethoxy)phenyl)urea;
cis-N-1,3-benzodioxol-5-yl-N'-{4-((7-chloroquinolin-4-yl)amino)cyclohexyl}urea;
cis-N-{4-((7-chloroquinolin-4-yl)amino)cyclohexyl}-N'-{3-((trifluoromethyl)thio)phenyl}urea;
cis-N-(3-bromophenyl)-N'-{4-((7-chloroquinolin-4-yl)amino)cyclohexyl}urea;
cis-N-(4-bromophenyl)-N'-{4-((7-chloroquinolin-4-yl)amino)cyclohexyl}urea;
cis-N-{4-((7-chloroquinolin-4-yl)amino)cyclohexyl}-N'-(3,4-dichlorophenyl)urea;
cis-N,N'-bis((4E)-7-chloro-1-methylquinolin-4(1H)-ylidene)cyclohexane-1,4-diamine;
cis-N-{4-((7-chloroquinolin-4-yl)amino)cyclohexyl}-N'-(2,4-dichlorophenyl)urea;
cis-N-{4-((7-chloroquinolin-4-yl)amino)cyclohexyl}-N'-(3,5-dichlorophenyl)urea;
cis-N-{4-((7-chloroquinolin-4-yl)amino)cyclohexyl}-N'-1-naphthylurea;
cis-N-{4-((7-chloroquinolin-4-yl)amino)cyclohexyl}-N'-2-naphthylurea;
cis-N-benzyl-N'-{4-((7-chloroquinolin-4-yl)amino)cyclohexyl}urea;
cis-N-(3-chlorophenyl)-N'-{4-((7-chloroquinolin-4-yl)amino)cyclohexyl}urea;
cis-N-{4-((7-chloroquinolin-4-yl)amino)cyclohexyl}-3-methylbenzamide;
cis-N-{4-((7-chloroquinolin-4-yl)amino)cyclohexyl}-4-methylbenzamide;
cis-2-amino-N-{4-((7-chloroquinolin-4-yl)amino)cyclohexyl}benzamide;
cis-N-{4-((7-chloroquinolin-4-yl)amino)cyclohexyl}-2-hydroxybenzamide;
cis-N-{4-((7-chloroquinolin-4-yl)amino)cyclohexyl}-3-hydroxybenzamide;
cis-N-{4-((7-chloroquinolin-4-yl)amino)cyclohexyl}-3-methoxybenzamide;
cis-N-{4-((7-chloroquinolin-4-yl)amino)cyclohexyl}-4-methoxybenzamide;
cis-N-{4-((7-chloroquinolin-4-yl)amino)cyclohexyl}-3-fluorobenzamide;
cis-N-{4-((7-chloroquinolin-4-yl)amino)cyclohexyl}-4-fluorobenzamide;
cis-4-chloro-N-{4-((7-chloroquinolin-4-yl)amino)cyclohexyl}benzamide;
cis-2-bromo-N-{4-((7-chloroquinolin-4-yl)amino)cyclohexyl}benzamide;
cis-3-bromo-N-{4-((7-chloroquinolin-4-yl)amino)cyclohexyl}benzamide;
cis-4-bromo-N-{4-((7-chloroquinolin-4-yl)amino)cyclohexyl}benzamide;
cis-N-{4-((7-chloroquinolin-4-yl)amino)cyclohexyl}-4-cyanobenzamide;
cis-N-{4-((7-chloroquinolin-4-yl)amino)cyclohexyl}-3-(dimethylamino)benzamide;
cis-N-{4-((7-chloroquinolin-4-yl)amino)cyclohexyl}-3-cyanobenzamide;
cis-N-{4-((7-chloroquinolin-4-yl)amino)cyclohexyl}-4-(dimethylamino)benzamide;
cis-N-{4-((7-chloroquinolin-4-yl)amino)cyclohexyl}-3-(trifluoromethyl)benzamide;
cis-N-{4-((7-chloroquinolin-4-yl)amino)cyclohexyl}-4-(trifluoromethyl)benzamide;
cis-N-{4-((7-chloroquinolin-4-yl)amino)cyclohexyl}-2,3-dimethylbenzamide;
cis-N-{4-((7-chloroquinolin-4-yl)amino)cyclohexyl}-2,4-dimethylbenzamide;
cis-N-{4-((7-chloroquinolin-4-yl)amino)cyclohexyl}-3-(trifluoromethoxy)benzamide;
cis-N-{4-((7-chloroquinolin-4-yl)amino)cyclohexyl}-2,5-dimethylbenzamide;
cis-N-{4-((7-chloroquinolin-4-yl)amino)cyclohexyl}-3,4-dimethylbenzamide;
cis-N-{4-((7-chloroquinolin-4-yl)amino)cyclohexyl}-2,4-dimethoxybenzamide;
cis-N-{4-((7-chloroquinolin-4-yl)amino)cyclohexyl}-3,4-dimethoxybenzamide;
cis-N-{4-((7-chloroquinolin-4-yl)amino)cyclohexyl}-3,5-dimethoxybenzamide;
cis-N-{4-((7-chloroquinolin-4-yl)amino)cyclohexyl}-1,3-benzodioxole-5-carboxamide;
cis-N-{4-((7-chloroquinolin-4-yl)amino)cyclohexyl}-3,4,5-trimethoxybenzamide;
cis-2,4-dichloro-N-{4-((7-chloroquinolin-4-yl)amino)cyclohexyl}benzamide;
cis-3,4-dichloro-N-{4-((7-chloroquinolin-4-yl)amino)cyclohexyl}benzamide;
cis-N-{4-((7-chloroquinolin-4-yl)amino)cyclohexyl}-2-furamide;
cis-N-{4-((7-chloroquinolin-4-yl)amino)cyclohexyl}-3-furamide;
cis-N-{4-((7-chloroquinolin-4-yl)amino)cyclohexyl}-2,5-dimethyl-3-furamide;
cis-N-{4-((7-chloroquinolin-4-yl)amino)cyclohexyl}thiophene-2-carboxamide;
cis-N-{4-((7-chloroquinolin-4-yl)amino)cyclohexyl}thiophene-3-carboxamide;
cis-N-{4-((7-chloroquinolin-4-yl)amino)cyclohexyl}-3-methylthiophene-2-carboxamide;
cis-N-{4-((7-chloroquinolin-4-yl)amino)cyclohexyl}-1H-pyrrole-2-carboxamide;
cis-N-{4-((7-chloroquinolin-4-yl)amino)cyclohexyl}-3,5-dimethylbenzamide;
cis-N-{4-((7-chloroquinolin-4-yl)amino)cyclohexyl}-5-methylthiophene-2-carboxamide;
cis-N-{4-((7-chloroquinolin-4-yl)amino)cyclohexyl}-2,5-dimethyl-1H-pyrrole-3-carboxamide;
cis-N-{4-((7-chloroquinolin-4-yl)amino)cyclohexyl}-1,2,5-trimethyl-1H-pyrrole-3-carboxamide;
cis-N-{4-((7-chloroquinolin-4-yl)amino)cyclohexyl}-1,3-thiazole-2-carboxamide;
cis-N-{4-((7-chloroquinolin-4-yl)amino)cyclohexyl}-1-methyl-1H-pyrrole-2-carboxamide;

cis-N-{4-((7-chloroquinolin-4-yl)amino)cyclohexyl}-1,3-thiazole-4-carboxamide;
cis-N-{4-((7-chloroquinolin-4-yl)amino)cyclohexyl}-1,3-thiazole-5-carboxamide;
cis-N-{4-((7-chloroquinolin-4-yl)amino)cyclohexyl}isoxazole-5-carboxamide;
cis-N-{4-((7-chloroquinolin-4-yl)amino)cyclohexyl}-5-methyl-3-phenylisoxazole-4-carboxamide;
cis-N-{4-((7-chloroquinolin-4-yl)amino)cyclohexyl}pyridine-2-carboxamide;
cis-N-{4-((7-chloroquinolin-4-yl)amino)cyclohexyl)-3-hydroxypyridine-2-carboxamide;
cis-N-{4-((7-chloroquinolin-4-yl)amino)cyclohexyl}-2-hydroxynicotinamide;
cis-N-{4-((7-chloroquinolin-4-yl)amino)cyclohexyl}-5-methylpyrazine-2-carboxamide;
cis-N-{4-((7-chloroquinolin-4-yl)amino)cyclohexyl}-1H-indole-3-carboxamide;
cis-N-{4-((7-chloroquinolin-4-yl)amino)cyclohexyl}-8-methyl-4-oxo-4H-pyrido(1,2-a)pyrimidine-3-carboxamide;
cis-N-{4-((7-chloroquinolin-4-yl)amino)cyclohexyl}-5-methyl-1-phenyl-1H-pyrazole-4-carboxamide;
cis-N-{4-((7-chloroquinolin-4-yl)amino)cyclohexyl}-4-oxo-4,5,6,7-tetrahydro-1-benzofuran-3-carboxamide;
cis-6-chloro-N-{4-((7-chloroquinolin-4-yl)amino)cyclohexyl}-2H-chromene-3-carboxamide;
cis-N-{4-((7-chloroquinolin-4-yl)amino)cyclohexyl}-4-ethylbenzamide;
cis-N-{4-((7-chloroquinolin-4-yl)amino)cyclohexyl}-2-hydroxy-4-methylbenzamide;
cis-N-{4-((7-chloroquinolin-4-yl)amino)cyclohexyl}-3-hydroxy-4-methylbenzamide;
cis-N-{4-((7-chloroquinolin-4-yl)amino)cyclohexyl}-5-fluoro-2-methylbenzamide;
cis-N-{4-((7-chloroquinolin-4-yl)amino)cyclohexyl}-3-fluoro-4-methylbenzamide;
cis-N-{4-((7-chloroquinolin-4-yl)amino)cyclohexyl}-2,3-difluorobenzamide;
cis-N-{4-((7-chloroquinolin-4-yl)amino)cyclohexyl}-2,4-difluorobenzamide;
cis-N-{4-((7-chloroquinolin-4-yl)amino)cyclohexyl}-2,5-difluorobenzamide;
cis-N-{4-((7-chloroquinolin-4-yl)amino)cyclohexyl}-3,5-difluorobenzamide;
cis-2-(N-{4-((7-chloroquinolin-4-yl)amino)cyclohexyl}glycyl)benzaldehyde;
cis-4-acetyl-N-{4-((7-chloroquinolin-4-yl)amino)cyclohexyl}benzamide;
cis-N-{4-((7-chloroquinolin-4-yl)amino)cyclohexyl}-3-methoxy-4-methylbenzamide;
cis-N-{4-((7-chloroquinolin-4-yl)amino)cyclohexyl}-2-ethoxybenzamide;
cis-N-{4-((7-chloroquinolin-4-yl)amino)cyclohexyl}-4-(methylthio)benzamide;
cis-N-{4-((7-chloroquinolin-4-yl)amino)cyclohexyl}-3-fluoro-4-methoxybenzamide;
cis-N-{4-((7-chloroquinolin-4-yl)amino)cyclohexyl}-2-naphthamide;
cis-N-{4-((7-chloroquinolin-4-yl)amino)cyclohexyl}-1-naphthamide;
cis-5-chloro-N-{4-((7-chloroquinolin-4-yl)amino)cyclohexyl}-2-hydroxybenzamide;
cis-2-(acetylamino)-N-{4-((7-chloroquinolin-4-yl)amino)cyclohexyl}benzamide;
cis-4-(acetylamino)-N-{4-((7-chloroquinolin-4-yl)amino)cyclohexyl}benzamide;
cis-N-{4-((7-chloroquinolin-4-yl)amino)cyclohexyl}-4-isopropoxybenzamide;
cis-5-chloro-N-{4-((7-chloroquinolin-4-yl)amino)cyclohexyl}-2-methoxybenzamide;
cis-N-{4-((7-chloroquinolin-4-yl)amino)cyclohexyl}-4-fluoro-1-naphthamide;
cis-N-{4-((7-chloroquinolin-4-yl)amino)cyclohexyl}-3,4-diethoxybenzamide;
cis-2-benzyl-N-{4-((7-chloroquinolin-4-yl)amino)cyclohexyl}benzamide;
cis-N-{4-((7-chloroquinolin-4-yl)amino)cyclohexyl}-2-(2-phenylethyl)benzamide;
cis-2-bromo-N-{4-((7-chloroquinolin-4-yl)amino)cyclohexyl}-5-methoxybenzamide;
cis-N-{4-((7-chloroquinolin-4-yl)amino)cyclohexyl}-2-(4-methylbenzoyl)benzamide;
cis-N-{4-((7-chloroquinolin-4-yl)amino)cyclohexyl}-2-iodobenzamide;
cis-N-{4-((7-chloroquinolin-4-yl)amino)cyclohexyl}-3-iodobenzamide;
cis-N-{4-((7-chloroquinolin-4-yl)amino)cyclohexyl}-4-iodobenzamide;
cis-N-{4-((7-chloroquinolin-4-yl)amino)cyclohexyl}-2-(4-fluorophenyl)acetamide;
cis-di-3-({4-((7-chloroquinolin-4-yl)amino)cyclohexyl}amino)-1-(4-fluorophenyl)propan-1-one;
cis-5-({4-((7-chloroquinolin-4-yl)amino)cyclohexyl}amino)-1-(4-fluorophenyl)pentan-1-one;
cis-N-(4,4-bis(4-fluorophenyl)butyl)-N'-(7-chloroquinolin-4-yl)cyclohexane-1,4-diamine;
cis-N-(7-chloroquinolin-4-yl)-N'-(4-phenylbutyl)cyclohexane-1,4-diamine;
cis-N-(7-chloroquinolin-4-yl)-N'-(5-phenylpentyl)cyclohexane-1,4-diamine;
cis-N-(7-chloroquinolin-4-yl)-N'-(3,5-difluorobenzyl)cyclohexane-1,4-diamine;
cis-N-(7-chloroquinolin-4-yl)-N'-(3,5-difluorophenyl)cyclohexane-1,4-diamine;
cis-N-(7-chloroquinolin-4-yl)-N'-(3-fluorobenzyl)cyclohexane-1,4-diamine;
cis-N-(3-chlorobenzyl)-N'-(7-chloroquinolin-4-yl)cyclohexane-1,4-diamine;
cis-N-(4-chlorobenzyl)-N'-(7-chloroquinolin-4-yl)cyclohexane-1,4-diamine;
cis-N-(7-chloroquinolin-4-yl)-N'-(3-(trifluoromethyl)benzyl)cyclohexane-1,4-diamine;
cis-N-(7-chloroquinolin-4-yl)-N'-(4-(trifluoromethyl)benzyl)cyclohexane-1,4-diamine;
cis-N-(7-chloroquinolin-4-yl)-N'-(4-phenoxybenzyl)cyclohexane-1,4-diamine;
cis-N-(4-(benzyloxy)benzyl)-N'-(7-chloroquinolin-4-yl)cyclohexane-1,4-diamine;
cis-N-(7-chloroquinolin-4-yl)-N'-(2,4-dimethylbenzyl)cyclohexane-1,4-diamine;
cis-N-(7-chloroquinolin-4-yl)-N'-(2,5-dimethylbenzyl)cyclohexane-1,4-diamine;
cis-N-(7-chloroquinolin-4-yl)-N'-(3,4-dimethylbenzyl)cyclohexane-1,4-diamine;
cis-N-(7-chloroquinolin-4-yl)-N'-(3,5-dimethylbenzyl)cyclohexane-1,4-diamine;
cis-N-(7-chloroquinolin-4-yl)-N'-(3,5-dimethoxybenzyl)cyclohexane-1,4-diamine;
cis-N-(1,3-benzodioxol-5-ylmethyl)-N'-(7-chloroquinolin-4-yl)cyclohexane-1,4-diamine;
cis-N-(7-chloroquinolin-4-yl)-N'-(3,4,5-trimethoxybenzyl)cyclohexane-1,4-diamine;
cis-N-(7-chloroquinolin-4-yl)-N'-(2,3-dichlorobenzyl)cyclohexane-1,4-diamine;
cis-N-(7-chloroquinolin-4-yl)-N'-(2,4-dichlorobenzyl)cyclohexane-1,4-diamine;

cis-N-(7-chloroquinolin-4-yl)-N'-(2,5-dichlorobenzyl) cyclohexane-1,4-diamine;
cis-N-(7-chloroquinolin-4-yl)-N'-(3,4-dichlorobenzyl) cyclohexane-1,4-diamine;
cis-N-(7-chloroquinolin-4-yl)-N'-(3,5-dichlorobenzyl) cyclohexane-1,4-diamine;
cis-N-(7-chloroquinolin-4-yl)-N'-phenylcyclohexane-1,4-diamine;
cis-N-{4-((7-chloroquinolin-4-yl)amino)cyclohexyl}propane-1-sulfonamide;
cis-N-{4-((7-chloroquinolin-4-yl)amino)cyclohexyl}butane-1-sulfonamide;
cis-N-{4-((7-chloroquinolin-4-yl)amino)cyclohexyl}benzenesulfonamide;
cis-2-chloro-N-{4-((7-chloroquinolin-4-yl)amino)cyclohexyl}-4-fluorobenzenesulfonamide;
cis-N-{4-((7-chloroquinolin-4-yl)amino)cyclohexyl}thiophene-2-sulfonamide;
cis-N-{4-((7-chloroquinolin-4-yl)amino)cyclohexyl}-2-(trifluoromethoxy)benzenesulfonamide;
cis-N-{4-((7-chloroquinolin-4-yl)amino)cyclohexyl}-3-methylbenzenesulfonamide;
cis-N-{4-((7-chloroquinolin-4-yl)amino)cyclohexyl}-4-methylbenzenesulfonamide;
cis-N-{4-((7-chloroquinolin-4-yl)amino)cyclohexyl}-2-fluorobenzenesulfonamide;
cis-N-{4-((7-chloroquinolin-4-yl)amino)cyclohexyl}-3-fluorobenzenesulfonamide;
cis-N-{4-((7-chloroquinolin-4-yl)amino)cyclohexyl}-4-fluorobenzenesulfonamide;
cis-N-{4-((7-chloroquinolin-4-yl)amino)cyclohexyl}-2-cyanobenzenesulfonamide;
cis-N-{4-((7-chloroquinolin-4-yl)amino)cyclohexyl}-3-cyanobenzenesulfonamide;
cis-N-{4-((7-chloroquinolin-4-yl)amino)cyclohexyl}-4-cyanobenzenesulfonamide;
cis-N-{4-((7-chloroquinolin-4-yl)amino)cyclohexyl}-2,5-dimethylbenzenesulfonamide;
cis-N-{4-((7-chloroquinolin-4-yl)amino)cyclohexyl}-3-methoxybenzenesulfonamide;
cis-N-{4-((7-chloroquinolin-4-yl)amino)cyclohexyl}-4-methoxybenzenesulfonamide;
cis-2-chloro-N-{4-((7-chloroquinolin-4-yl)amino)cyclohexyl}benzenesulfonamide;
cis-N-(7-chloroquinolin-4-yl)-N'-(3,5-dimethylphenyl)cyclohexane-1,4-diamine;
cis-N-(7-chloroquinolin-4-yl)-N'-(2-fluorophenyl)cyclohexane-1,4-diamine;
cis-N-(7-chloroquinolin-4-yl)-N'-(3-fluorophenyl)cyclohexane-1,4-diamine;
cis-N-(7-chloroquinolin-4-yl)-N'-2-naphthylcyclohexane-1,4-diamine;
cis-N-(7-chloroquinolin-4-yl)-N'-(3-fluoro-4-methylphenyl)cyclohexane-1,4-diamine;
cis-N-(7-chloroquinolin-4-yl)-N'-1-naphthylcyclohexane-1,4-diamine;
cis-3-chloro-N-{4-((7-chloroquinolin-4-yl)amino)cyclohexyl}benzenesulfonamide;
cis-4-(2-chloro-6-nitrophenoxy)-N-{4-((7-chloroquinolin-4-yl)amino)cyclohexyl}benzenesulfonamide;
cis-N-{4-((7-chloroquinolin-4-yl)amino)cyclohexyl}-2,4-difluorobenzenesulfonamide;
cis-N-{4-((7-chloroquinolin-4-yl)amino)cyclohexyl}-3,4-difluorobenzenesulfonamide;
cis-N-{4-((7-chloroquinolin-4-yl)amino)cyclohexyl}-4-propylbenzenesulfonamide;
cis-N-{4-((7-chloroquinolin-4-yl)amino)cyclohexyl}-4-isopropylbenzenesulfonamide;
cis-4-chloro-N-({5-(({4-((7-chloroquinolin-4-yl)amino)cyclohexyl}amino)sulfonyl)thien-2-yl}methyl)benzamide;
cis-5-bromo-6-chloro-N-{4-((7-chloroquinolin-4-yl)amino)cyclohexyl}pyridine-3-sulfonamide;
cis-4-tert-butyl-N-{4-((7-chloroquinolin-4-yl)amino)cyclohexyl}benzenesulfonamide;
cis-3-chloro-N-{4-((7-chloroquinolin-4-yl)amino)cyclohexyl}-4-fluorobenzenesulfonamide;
cis-N-{4-(({4-((7-chloroquinolin-4-yl)amino)cyclohexyl}amino)sulfonyl)phenyl}acetamide;
cis-N-{4-((7-chloroquinolin-4-yl)amino)cyclohexyl}-2,5-dimethoxybenzenesulfonamide;
cis-N-{4-((7-chloroquinolin-4-yl)amino)cyclohexyl}-3,4-dimethoxybenzenesulfonamide;
cis-N-{4-((7-chloroquinolin-4-yl)amino)cyclohexyl}-3-(trifluoromethyl)benzenesulfonamide;
cis-N-{4-((7-chloroquinolin-4-yl)amino)cyclohexyl}-4-(trifluoromethyl)benzenesulfonamide;
cis-2,3-dichloro-N-{4-((7-chloroquinolin-4-yl)amino)cyclohexyl}benzenesulfonamide;
cis-2,4-dichloro-N-{4-((7-chloroquinolin-4-yl)amino)cyclohexyl}benzenesulfonamide;
cis-2,5-dichloro-N-{4-((7-chloroquinolin-4-yl)amino)cyclohexyl}benzenesulfonamide;
cis-3,4-dichloro-N-{4-((7-chloroquinolin-4-yl)amino)cyclohexyl}benzenesulfonamide;
cis-3,5-dichloro-N-{4-((7-chloroquinolin-4-yl)amino)cyclohexyl}benzenesulfonamide;
cis-N-{4-((7-chloroquinolin-4-yl)amino)cyclohexyl}-1,1'-biphenyl-4-sulfonamide;
cis-2-bromo-N-{4-((7-chloroquinolin-4-yl)amino)cyclohexyl}benzenesulfonamide;
cis-3-bromo-N-{4-((7-chloroquinolin-4-yl)amino)cyclohexyl}benzenesulfonamide;
cis-4-bromo-N-{4-((7-chloroquinolin-4-yl)amino)cyclohexyl}benzenesulfonamide;
cis-N-{4-((7-chloroquinolin-4-yl)amino)cyclohexyl}-4-(trifluoromethoxy)benzenesulfonamide;
cis-N-{4-((7-chloroquinolin-4-yl)amino)cyclohexyl}-3,5-dimethylisoxazole-4-sulfonamide;
cis-(E)-N-{4-((7-chloroquinolin-4-yl)amino)cyclohexyl}-2-phenylethylenesulfonamide;
cis-N-{4-((7-chloroquinolin-4-yl)amino)cyclohexyl}-4-vinylbenzenesulfonamide;
cis-5-chloro-N-{4-((7-chloroquinolin-4-yl)amino)cyclohexyl}thiophene-2-sulfonamide;
cis-N-{4-((7-chloroquinolin-4-yl)amino)cyclohexyl}-2,1,3-benzoxadiazole-4-sulfonamide;
cis-N-{4-((7-chloroquinolin-4-yl)amino)cyclohexyl}-3-nitrobenzenesulfonamide;
cis-N-{4-((7-chloroquinolin-4-yl)amino)cyclohexyl}-4-nitrobenzenesulfonamide;
cis-3-chloro-N-{4-((7-chloroquinolin-4-yl)amino)cyclohexyl}-4-methylbenzenesulfonamide;
cis-N-{4-((7-chloroquinolin-4-yl)amino)cyclohexyl}quinoline-8-sulfonamide;
cis-5-chloro-N-{4-((7-chloroquinolin-4-yl)amino)cyclohexyl}-1,3-dimethyl-1H-pyrazole-4-sulfonamide;
cis-N-{4-((7-chloroquinolin-4-yl)amino)cyclohexyl}-2,1,3-benzothiadiazole-4-sulfonamide;
cis-N-{4-((7-chloroquinolin-4-yl)amino)cyclohexyl}-2-methyl-5-nitrobenzenesulfonamide;
cis-methyl 3-(({4-((7-chloroquinolin-4-yl)amino)cyclohexyl}amino)sulfonyl)thiophene-2-carboxylate;
cis-N-{4-((7-chloroquinolin-4-yl)amino)cyclohexyl}-4-(1,1-dimethylpropyl)benzenesulfonamide;

cis-4-butoxy-N-{4-((7-chloroquinolin-4-yl)amino)cyclohexyl}benzenesulfonamide;
cis-N-{4-((7-chloroquinolin-4-yl)amino)cyclohexyl}-5-isoxazol-3-ylthiophene-2-sulfonamide;
cis-N-{4-((7-chloroquinolin-4-yl)amino)cyclohexyl}-1-((1S,4R)-7,7-dimethyl-2-oxobicyclo(2.2.1)hept-1-yl)methanesulfonamide;
cis-2,5-dichloro-N-{4-((7-chloroquinolin-4-yl)amino)cyclohexyl}thiophene-3-sulfonamide;
cis-4,5-dichloro-N-{4-((7-chloroquinolin-4-yl)amino)cyclohexyl}thiophene-2-sulfonamide;
cis-7-chloro-N-{4-((7-chloroquinolin-4-yl)amino)cyclohexyl}-2,1,3-benzoxadiazole-4-sulfonamide;
cis-N-{4-((7-chloroquinolin-4-yl)amino)cyclohexyl}-4-(methylsulfonyl)benzenesulfonamide;
cis-4-chloro-N-{4-((7-chloroquinolin-4-yl)amino)cyclohexyl}-3-nitrobenzenesulfonamide;
cis-6-chloro-N-{4-((7-chloroquinolin-4-yl)amino)cyclohexyl}-3H-1 lambda-4-imidazo(2,1-b)(1,3)thiazole-5-sulfonamide;
cis-N-{4-((7-chloroquinolin-4-yl)amino)cyclohexyl}-2-(trifluoroacetyl)-1,2,3,4-tetrahydroisoquinoline-7-sulfonamide;
cis-N-{4-((7-chloroquinolin-4-yl)amino)cyclohexyl}-5-fluoro-2-methylbenzenesulfonamide;
cis-4-chloro-N-{4-((7-chloroquinolin-4-yl)amino)cyclohexyl}-3-(trifluoromethyl)benzenesulfonamide;
cis-2,4,5-trichloro-N-{4-((7-chloroquinolin-4-yl)amino)cyclohexyl}benzenesulfonamide;
cis-2,4,6-trichloro-N-{4-((7-chloroquinolin-4-yl)amino)cyclohexyl}benzenesulfonamide;
cis-2,3,4-trichloro-N-{4-((7-chloroquinolin-4-yl)amino)cyclohexyl}benzene sulfonamide;
cis-5-chloro-N-{4-((7-chloroquinolin-4-yl)amino)cyclohexyl}-3-methyl-1-benzothiophene-2-sulfonamide;
cis-5-bromo-N-{4-((7-chloroquinolin-4-yl)amino)cyclohexyl}-2-methoxybenzenesulfonamide;
cis-N-{4-((7-chloroquinolin-4-yl)amino)cyclohexyl}-2-nitro-4-(trifluoromethyl)benzenesulfonamide;
cis-N-({5-(({4-((7-chloroquinolin-4-yl)amino)cyclohexyl}amino)sulfonyl)thien-2-yl}methyl)benzamide;
cis-N-{4-((7-chloroquinolin-4-yl)amino)cyclohexyl}-5-(2-(methylthio)pyrimidin-4-yl)thiophene-2-sulfonamide;
cis-N-{4-((7-chloroquinolin-4-yl)amino)cyclohexyl}-3,5-bis(trifluoromethyl)benzenesulfonamide;
cis-2,6-dichloro-N-{4-((7-chloroquinolin-4-yl)amino)cyclohexyl}-4-(trifluoromethyl)benzenesulfonamide;
cis-2-butoxy-N-{4-((7-chloroquinolin-4-yl)amino)cyclohexyl}-5-(1,1-dimethylpropyl)benzenesulfonamide;
cis-N-{4-((7-chloroquinolin-4-yl)amino)cyclohexyl}-5-(phenylsulfonyl)thiophene-2-sulfonamide;
cis-4-(3-chloro-2-cyanophenoxy)-N-{4-((7-chloroquinolin-4-yl)amino)cyclohexyl}benzenesulfonamide;
cis-N-{4-((7-chloroquinolin-4-yl)amino)cyclohexyl}-4-ethylbenzenesulfonamide;
cis-4-bromo-2,5-dichloro-N-{4-((7-chloroquinolin-4-yl)amino)cyclohexyl}thiophene-3-sulfonamide;
cis-N-{4-((7-chloroquinolin-4-yl)amino)cyclohexyl}-2-methoxy-5-methylbenzenesulfonamide;
cis-N-{4-((7-chloroquinolin-4-yl)amino)cyclohexyl}-2-nitrobenzenesulfonamide;
cis-2-chloro-N-{4-((7-chloroquinolin-4-yl)amino)cyclohexyl}isonicotinamide;
cis-2-chloro-N-{4-((7-chloroquinolin-4-yl)amino)cyclohexyl}-6-methylisonicotinamide;
cis-2,6-dichloro-N-{4-((7-chloroquinolin-4-yl)amino)cyclohexyl}isonicotinamide;
cis-N-{4-((7-chloroquinolin-4-yl)amino)cyclohexyl}-5-phenylpentanamide;
cis-$N^2$-benzoyl-$N^1$-{4-((7-chloroquinolin-4-yl)amino)cyclohexyl}glycinamide;
cis-N-{4-((7-chloroquinolin-4-yl)amino)cyclohexyl}-4-phenoxybutanamide;
cis-N-{4-((7-chloroquinolin-4-yl)amino)cyclohexyl}-3-(3-methyl-1H-indol-1-yl)propanamide;
cis-N-{4-((7-chloroquinolin-4-yl)amino)cyclohexyl}-3-(1-methyl-1H-benzimidazol-2-yl)propanamide;
cis-N-{4-((7-chloroquinolin-4-yl)amino)cyclohexyl}-2-(6-methoxy-3-oxo-2,3-dihydro-1H-inden-1-yl)acetamide;
cis-1-benzoyl-N-{4-((7-chloroquinolin-4-yl)amino)cyclohexyl}piperidine-4-carboxamide;
cis-$N^1$-{4-((7-chloroquinolin-4-yl)amino)cyclohexyl}-$N^3$-(4-nitrobenzoyl)-β-alaninamide;
cis-$N^3$-benzoyl-$N^1$-{4-((7-chloroquinolin-4-yl)amino)cyclohexyl}-β-alaninamide;
cis-N-{4-((7-chloroquinolin-4-yl)amino)cyclohexyl}-N'-(4-propoxyphenyl)urea;
cis-N-(5-tert-butyl-2-methoxyphenyl)-N'-{4-((7-chloroquinolin-4-yl)amino)cyclohexyl}urea;
cis-N-{4-((7-chloroquinolin-4-yl)amino)cyclohexyl}-N'-(2-furylmethyl)urea;
cis-N-{4-((7-chloroquinolin-4-yl)amino)cyclohexyl}-N'-(3-furylmethyl)urea;
cis-N-{4-((7-chloroquinolin-4-yl)amino)cyclohexyl}-2-cyclohexylacetamide;
cis-N-{4-((7-chloroquinolin-4-yl)amino)cyclohexyl}-2-cycloheptylacetamide;
cis-2-((1R,4S)-bicyclo(2.2.1)hept-2-yl)-N-{4-((7-chloroquinolin-4-yl)amino)cyclohexyl}acetamide;
cis-2-(1-adamantyl)-N-{4-((7-chloroquinolin-4-yl)amino)cyclohexyl}acetamide;
cis-N-{4-((7-chloroquinolin-4-yl)amino)cyclohexyl}-2-(3-fluorophenyl)acetamide;
cis-N-{4-((7-chloroquinolin-4-yl)amino)cyclohexyl}-2-(3-(trifluoromethyl)phenyl)acetamide;
cis-N-{4-((7-chloroquinolin-4-yl)amino)cyclohexyl}-2-(4-(trifluoromethyl)phenyl)acetamide;
cis-3,5-difluoro-N-(4-{(6-fluoro-2-(trifluoromethyl)quinolin-4-yl)amino}cyclohexyl)benzamide;
cis-3,5-difluoro-N-(4-{(8-(trifluoromethoxy)-2-(trifluoromethyl)quinolin-4-yl)amino}cyclohexyl)benzamide;
cis-N-(4-{(5,7-dichloro-2-(trifluoromethyl)quinolin-4-yl)amino}cyclohexyl)-3,5-difluorobenzamide;
cis-3,5-difluoro-N-(4-{(6-methyl-2-(trifluoromethyl)quinolin-4-yl)amino}cyclohexyl)benzamide;
cis-N-(7-chloroquinolin-4-yl)-N'-(3,5-dichlorophenyl)cyclohexane-1,4-diamine;
cis-N-(7-chloroquinolin-4-yl)-N'-(3-methylphenyl)cyclohexane-1,4-diamine;
cis-N-(3,5-bis(trifluoromethyl)phenyl)-N'-(7-chloroquinolin-4-yl)cyclohexane-1,4-diamine;
cis-N-1,1'-biphenyl-3-yl-N'-(7-chloroquinolin-4-yl)cyclohexane-1,4-diamine;
cis-N-(7-chloroquinolin-4-yl)-N'-(3-(trifluoromethyl)phenyl)cyclohexane-1,4-diamine;
cis-4-({4-((7-chloroquinolin-4-yl)amino)cyclohexyl}amino)-2H-chromen-2-one;
cis-N,N'-bis(7-chloro-4-aminoquinolin-4-yl)cyclohexane-1,4-diamine;
cis-N-1,1'-biphenyl-3-yl-N'-(7-chloroquinolin-4-yl)cyclohexane-1,4-diamine;
cis-N-(7-chloroquinazolin-4-yl)-N'-(7-chloroquinolin-4-yl)cyclohexane-1,4-diamine;

cis-4-({4-((7-chloroquinolin-4-yl)amino)cyclohexyl}amino)-2H-chromen-2-one;
cis-N-{4-((2-amino-7-chloroquinolin-4-yl)amino)cyclohexyl}-3,5-difluorobenzamide;
cis-N-{4-((2-amino-7-chloroquinolin-4-yl)amino)cyclohexyl}-3,5-dichlorobenzamide;
cis-N-{4-((2-amino-7-chloroquinolin-4-yl)amino)cyclohexyl}-4-phenoxybutanamide;
cis-7-chloro-N-4-(4-{(3-(trifluoromethyl)benzyl)amino}cyclohexyl)quinoline-2,4-diamine;
cis-7-chloro-N-4-(4-{(3-(trifluoromethoxy)benzyl)amino}cyclohexyl)quinoline-2,4-diamine;
cis-7-chloro-N-4-{4-((3,5-dimethylbenzyl)amino)cyclohexyl}quinoline-2,4-diamine;
cis-7-chloro-N-4-{4-((3,5-dichlorobenzyl)amino)cyclohexyl}quinoline-2,4-diamine;
cis-N-(7-chloroquinolin-4-yl)-N'-pyridin-2-ylcyclohexane-1,4-diamine;
cis-N-(7-chloroquinolin-4-yl)-N'-isoquinolin-4-ylcyclohexane-1,4-diamine;
cis-N-(7-chloroquinolin-4-yl)-N'-quinolin-3-ylcyclohexane-1,4-diamine;
cis-N-(7-chloroquinolin-4-yl)-N'-{(5-(4-nitrophenyl)-2-furyl)methyl}cyclohexane-1,4-diamine;
cis-2-({4-((7-chloroquinolin-4-yl)amino)cyclohexyl}amino)-1,2-di-2-furylethanone;
cis-N-(7-chloroquinolin-4-yl)-N'-{((2R)-1-(4-nitrophenyl)pyrrolidin-2-yl)methyl}cyclohexane-1,4-diamine;
cis-3,5-difluoro-N-(4-(quinolin-4-ylamino)cyclohexyl)benzamide;
cis-tert-butyl (2R)-2-(({4-((7-chloroquinolin-4-yl)amino)cyclohexyl}amino)methyl)pyrrolidine-1-carboxylate;
cis-N-(7-chloroquinolin-4-yl)-N'-1,4-dithiaspiro(4.5)dec-8-ylcyclohexane-1,4-diamine;
cis-N-(7-chloroquinolin-4-yl)-N'-((6-methylpyridin-2-yl)methyl)cyclohexane-1,4-diamine;
cis-N-(7-chloroquinolin-4-yl)-N'-(2-thien-3-ylethyl)cyclohexane-1,4-diamine;
cis-N-(7-chloroquinolin-4-yl)-N'-{((2S)-1-(2-methoxybenzoyl)pyrrolidin-2-yl)methyl}cyclohexane-1,4-diamine;
cis-N-(7-chloroquinolin-4-yl)-N'-(thien-3-ylmethyl)cyclohexane-1,4-diamine;
cis-N-(7-chloroquinolin-4-yl)-N'-(2-thien-2-ylethyl)cyclohexane-1,4-diamine;
cis-N-(7-chloroquinolin-4-yl)-N'-(thien-2-ylmethyl)cyclohexane-1,4-diamine;
cis-6-({4-((7-chloroquinolin-4-yl)amino)cyclohexyl}amino)-1,3-dimethylpyrimidine-2,4(1H,3H)-dione;
cis-6-({4-((7-chloroquinolin-4-yl)amino)cyclohexyl}amino)pyrimidine-2,4(1H,3H)-dione;
cis-N-(7-chloroquinolin-4-yl)-N'-(3-(6-methylpyridin-2-yl)propyl)cyclohexane-1,4-diamine;
cis-N-(7-chloroquinolin-4-yl)-N'-(3-furylmethyl)cyclohexane-1,4-diamine;
cis-N-(7-chloroquinolin-4-yl)-N'-(3-pyridin-2-ylpropyl)cyclohexane-1,4-diamine;
cis-N-(7-chloroquinolin-4-yl)-N'-(2-(2-methyl-5-nitro-1H-imidazol-1-yl)ethyl)cyclohexane-1,4-diamine;
cis-N-(7-chloroquinolin-4-yl)-N'-(3-pyridin-3-ylpropyl)cyclohexane-1,4-diamine;
cis-N-(7-chloroquinolin-4-yl)-N'-{((4R,5 S)-2-methyl-5-phenyl-4,5-dihydro-1,3-oxazol-4-yl)methyl}cyclohexane-1,4-diamine;
cis-N-(7-chloroquinolin-4-yl)-N'-(2-(4-methyl-1,3-thiazol-5-yl)ethyl)cyclohexane-1,4-diamine;
cis-N-(7-chloroquinolin-4-yl)-N'-(tetrahydrofuran-2-ylmethyl)cyclohexane-1,4-diamine;
cis-N-(7-chloroquinolin-4-yl)-N'-(pyridin-3-ylmethyl)cyclohexane-1,4-diamine;
cis-N-(7-chloroquinolin-4-yl)-N'-{2-(3-(6-methylpyridin-2-yl)propoxy)ethyl}cyclohexane-1,4-diamine;
cis-N-(7-chloroquinolin-4-yl)-N'-{((2R)-1-(2-methoxybenzoyl)pyrrolidin-2-yl)methyl}cyclohexane-1,4-diamine;
cis-N-(7-chloroquinolin-4-yl)-N'-(tetrahydrofuran-3-ylmethyl)cyclohexane-1,4-diamine;
cis-N-(7-chloroquinolin-4-yl)-N'-(2-furylmethyl)cyclohexane-1,4-diamine;
cis-N-(7-chloroquinolin-4-yl)-N'-((3-methyloxetan-3-yl)methyl)cyclohexane-1,4-diamine;
cis-N-(7-chloroquinolin-4-yl)-N'-(3-pyridin-4-ylpropyl)cyclohexane-1,4-diamine;
cis-N-(7-chloroquinolin-4-yl)-N'-((3-ethyloxetan-3-yl)methyl)cyclohexane-1,4-diamine;
cis-N-(7-chloroquinolin-4-yl)-N'-(pyridin-2-ylmethyl)cyclohexane-1,4-diamine;
cis-N-(7-chloroquinolin-4-yl)-N'-(1H-imidazol-4-ylmethyl)cyclohexane-1,4-diamine;
cis-N-(7-chloroquinolin-4-yl)-N'-{((4S)-2,2-dimethyl-1,3-dioxolan-4-yl)methyl}cyclohexane-1,4-diamine;
cis-N-1,3-benzothiazol-2-yl-N'-(7-chloroquinolin-4-yl)cyclohexane-1,4-diamine;
cis-6-({4-((7-chloroquinolin-4-yl)amino)cyclohexyl}amino)-3-methylpyrimidine-2,4(1H,3H)-dione;
(1S,2R,4S,5R)-N,N'-bis(7-chloroquinolin-4-yl)-2,5-dimethylcyclohexane-1,4-diamine;
(1S,2R,4S,5R)-N-(7-chloroquinolin-4-yl)-N'-(3,5-dimethylphenyl)-2,5-dimethylcyclohexane-1,4-diamine;
N-((1S,2R,4S,5R)-4-((7-chloroquinolin-4-yl)amino)-2,5-dimethylcyclohexyl)-3,5-difluorobenzamide;
5-bromo-N-{4-((7-chloroquinolin-4-yl)amino)cyclohexyl}-2-hydroxybenzamide;
3-bromo-N-{4-((7-chloroquinolin-4-yl)amino)cyclohexyl}-5-fluorobenzamide;
(1S,2R,4S,5R)-N,N'-bis(7-chloroquinolin-4-yl)-2,5-dimethylcyclohexane-1,4-diamine;
4-({4-((7-chloroquinolin-4-yl)amino)cyclohexyl}amino)-6-methyl-2H-chromen-2-one;
N-{4-((7-chloroquinolin-4-yl)amino)cyclohexyl}-3-methyl-2-phenylpentanamide;
N-{4-((7-chloroquinolin-4-yl)amino)cyclohexyl}-2-hydroxy-5-methylbenzamide;
N-{4-((7-chloroquinolin-4-yl)amino)cyclohexyl}-2,2-diphenylacetamide;
N-{4-((7-chloroquinolin-4-yl)amino)cyclohexyl}-5-fluoro-2-hydroxybenzamide;
N-{(1S,2R,4S,5R)-4-((7-chloroquinolin-4-yl)amino)-2,5-dimethylcyclohexyl}-3,5-difluorobenzamide;
N-(7-chloroquinolin-4-yl)-N'-(2',5-dimethyl-1,1'-biphenyl-3-yl)cyclohexane-1,4-diamine;
3-(5-acetylthien-2-yl)-N-{4-((7-chloroquinolin-4-yl)amino)cyclohexyl}-5-fluorobenzamide;
(2R)-N-{4-((7-chloroquinolin-4-yl)amino)cyclohexyl}-2-methoxy-2-phenylacetamide;
N-{4-((7-chloroquinolin-4-yl)amino)cyclohexyl}-2-hydroxy-5-methoxybenzamide;
(2S)-N-{4-((7-chloroquinolin-4-yl)amino)cyclohexyl}-2-methoxy-2-phenylacetamide;
4-chloro-N-{4-((7-chloroquinolin-4-yl)amino)cyclohexyl}-2-hydroxybenzamide;
N-{4-((7-chloroquinolin-4-yl)amino)cyclohexyl}quinoline-3-carboxamide;

N-{4-((7-chloroquinolin-4-yl)amino)cyclohexyl}-2-hydroxy-3-methylbenzamide;
N-{4-((7-chloroquinolin-4-yl)amino)cyclohexyl}-2,6-dimethoxynicotinamide;
N-{4-((7-chloroquinolin-4-yl)amino)cyclohexyl}-4-methylpentanamide;
N-(2-({4-((7-chloroquinolin-4-yl)amino)cyclohexyl}amino)-2-oxo-1-ethyl)-2-hydroxybenzamide;
3-chloro-N-{4-((7-chloroquinolin-4-yl)amino)cyclohexyl}-5-fluorobenzamide;
N-{4-((7-chloroquinolin-4-yl)amino)cyclohexyl}pentanamide;
3'-amino-N-{4-((7-chloroquinolin-4-yl)amino)cyclohexyl}-5-fluoro-1,1'-biphenyl-3-carboxamide;
N-2-acetyl-N-1-{4-((7-chloroquinolin-4-yl)amino)cyclohexyl}-L-leucinamide;
N-{4-((7-chloroquinolin-4-yl)amino)cyclohexyl}-2-(3,5-difluorophenyl)acetamide;
N-{4-((7-chloroquinolin-4-yl)amino)cyclohexyl}-2-((4-methylpyrimidin-2-yl)thio)acetamide;
N-{4-((7-chloroquinolin-4-yl)amino)cyclohexyl}-5-fluoro-3'-hydroxy-1,1'-biphenyl-3-carboxamide;
N-{4-((7-chloroquinolin-4-yl)amino)cyclohexyl}-5-fluoro-3'-(hydroxymethyl)-1,1'-biphenyl-3-carboxamide;
3-(2-chlorophenyl)-N-{4-((7-chloroquinolin-4-yl)amino)cyclohexyl}propanamide;
N-{4-((7-chloroquinolin-4-yl)amino)cyclohexyl}-5-fluoro-4'-hydroxy-1,1'-biphenyl-3-carboxamide;
N-(5-bromopyridin-3-yl)-N'-(7-chloroquinolin-4-yl)cyclohexane-1,4-diamine;
N-{4-((7-chloroquinolin-4-yl)amino)cyclohexyl}-1H-indole-4-carboxamide;
N-{4-((7-chloroquinolin-4-yl)amino)cyclohexyl}hexanamide;
N-{4-((7-chloroquinolin-4-yl)amino)cyclohexyl}cyclopentanecarboxamide;
N-{4-((7-chloroquinolin-4-yl)amino)cyclohexyl}-2-(3-methoxyphenoxy)acetamide;
N-1-{4-((7-chloroquinolin-4-yl)amino)cyclohexyl}-N-2-((4-methylphenyl)sulfonyl)glycinamide;
N-{4-((7-chloroquinolin-4-yl)amino)cyclohexyl}quinoxaline-2-carboxamide;
N-{4-((7-chloroquinolin-4-yl)amino)cyclohexyl}-2-(3-methylphenoxy)acetamide;
N-{4-((7-chloroquinolin-4-yl)amino)cyclohexyl}-2-cyclopentylacetamide;
(2S)-N-{4-((7-chloroquinolin-4-yl)amino)cyclohexyl}-2-phenylbutanamide;
N-{4-((7-chloroquinolin-4-yl)amino)cyclohexyl}-2-methylcyclohexanecarboxamide;
N-{4-((7-chloroquinolin-4-yl)amino)cyclohexyl}-N'-phenylpentanediamide;
N-{4-((7-chloroquinolin-4-yl)amino)cyclohexyl}-3-phenylpropanamide;
3-(4-chlorophenyl)-N-{4-((7-chloroquinolin-4-yl)amino)cyclohexyl}propanamide;
4'-amino-N-{4-((7-chloroquinolin-4-yl)amino)cyclohexyl}-5-fluoro-1,1'-biphenyl-3-carboxamide;
N-{4-((7-chloroquinolin-4-yl)amino)cyclohexyl}cycloheptanecarboxamide;
N-{4-((7-chloroquinolin-4-yl)amino)cyclohexyl}-4-oxo-4-thien-2-ylbutanamide;
N-{4-((7-chloroquinolin-4-yl)amino)cyclohexyl}-3-methylcyclohexanecarboxamide;
N-{4-((7-chloroquinolin-4-yl)amino)cyclohexyl}-2-hydroxy-4-methoxybenzamide;
N-{4-((7-chloroquinolin-4-yl)amino)cyclohexyl}cinnoline-4-carboxamide;
N-{4-((7-chloroquinolin-4-yl)amino)cyclohexyl}-4-methylcyclohexanecarboxamide;
N-{4-((7-chloroquinolin-4-yl)amino)cyclohexyl}-2-(2-methylphenoxy)acetamide;
N-{4-((7-chloroquinolin-4-yl)amino)cyclohexyl}-3-methylbutanamide;
N-{4-((7-chloroquinolin-4-yl)amino)cyclohexyl}cyclohexanecarboxamide;
N-{4-((7-chloroquinolin-4-yl)amino)cyclohexyl}-3-(2,5-dimethoxyphenyl)propanamide;
N-{4-((7-chloroquinolin-4-yl)amino)cyclohexyl}-3-methylpentanamide;
N-{4-((7-chloroquinolin-4-yl)amino)cyclohexyl}-2-hydroxy-6-methoxybenzamide;
3'-acetyl-N-{4-((7-chloroquinolin-4-yl)amino)cyclohexyl}-5-fluoro-1,1'-biphenyl-3-carboxamide;
N-{4-((7-chloroquinolin-4-yl)amino)cyclohexyl}-4,4,4-trifluorobutanamide;
5-bromo-N-{4-((7-chloroquinolin-4-yl)amino)cyclohexyl}-2-hydroxy-3-methylbenzamide;
N-{4-((7-chloroquinolin-4-yl)amino)cyclohexyl}-3-(phenylsulfonyl)propanamide;
N-(7-chloroquinolin-4-yl)-N'-(4-methoxy-3,5-dimethylphenyl)cyclohexane-1,4-diamine;
N-{4-((7-chloroquinolin-4-yl)amino)cyclohexyl}-3-phenoxypropanamide;
N-{4-((7-chloroquinolin-4-yl)amino)cyclohexyl}-4-thien-2-ylbutanamide;
3-(1,3-benzodioxol-5-yl)-N-{4-((7-chloroquinolin-4-yl)amino)cyclohexyl}-5-fluorobenzamide;
N-{4-((7-chloroquinolin-4-yl)amino)cyclohexyl}-2-(3,4-dimethylphenoxy)acetamide;
2-(4-chloro-2-methylphenoxy)-N-{4-((7-chloroquinolin-4-yl)amino)cyclohexyl}acetamide;
N-{4-((7-chloroquinolin-4-yl)amino)cyclohexyl}-5-fluoro-2'-hydroxy-1,1'-biphenyl-3-carboxamide;
4'-acetyl-N-{4-((7-chloroquinolin-4-yl)amino)cyclohexyl}-5-fluoro-1,1'-biphenyl-3-carboxamide;
N-{4-((7-chloroquinolin-4-yl)amino)cyclohexyl}-6-methylnicotinamide;
N-{4-((7-chloroquinolin-4-yl)amino)cyclohexyl}-4-phenylbutanamide;
N-{4-((7-chloroquinolin-4-yl)amino)cyclohexyl}-3-(4-methoxyphenyl)propanamide;
N-{4-((7-chloroquinolin-4-yl)amino)cyclohexyl}-3-fluoro-5-pyridin-4-ylbenzamide;
N-{4-((7-chloroquinolin-4-yl)amino)cyclohexyl}heptanamide;
N-{4-((7-chloroquinolin-4-yl)amino)cyclohexyl}-4-(4-methoxyphenyl)-4-oxobutanamide;
2-chloro-N-{4-((7-chloroquinolin-4-yl)amino)cyclohexyl}nicotinamide;
N-{4-((7-chloroquinolin-4-yl)amino)cyclohexyl}-3-(3-methoxyphenyl)propanamide;
2-(benzyloxy)-N-{4-((7-chloroquinolin-4-yl)amino)cyclohexyl}acetamide;
N-(7-chloroquinolin-4-yl)-N'-(5-methyl-1,1'-biphenyl-3-yl)cyclohexane-1,4-diamine;
6-(2-({4-((7-chloroquinolin-4-yl)amino)cyclohexyl}amino)-1,3-thiazol-4-yl)-3,4-dihydroquinolin-2(1H)-one;
N-{4-((7-chloroquinolin-4-yl)amino)cyclohexyl}-2-hydroxy-5-iodobenzamide;
N-{4-((7-chloroquinolin-4-yl)amino)cyclohexyl}butanamide;
N-{4-((7-chloroquinolin-4-yl)amino)cyclohexyl}-2-(3-phenoxyphenyl)acetamide;

N-(3-bromo-5-methylphenyl)-N'-(7-chloroquinolin-4-yl)cyclohexane-1,4-diamine;
N-{4-((7-chloroquinolin-4-yl)amino)cyclohexyl}-2-cyclopropylacetamide;
N-{4-((7-chloroquinolin-4-yl)amino)cyclohexyl}-2,2-dimethylpropanamide;
N-{4-((7-chloroquinolin-4-yl)amino)cyclohexyl}-2-fluoro-6-hydroxybenzamide;
N-(7-chloroquinolin-4-yl)-N'-(3-methyl-5-pyridin-4-ylphenyl)cyclohexane-1,4-diamine;
N-{4-((7-chloroquinolin-4-yl)amino)cyclohexyl}-4-oxo-4-phenylbutanamide;
N-{4-((7-chloroquinolin-4-yl)amino)cyclohexyl}-3-fluoro-5-thien-3-ylbenzamide;
N-{4-((7-chloroquinolin-4-yl)amino)cyclohexyl}-3-fluoro-5-((E)-2, phenylvinyl)benzamide;
N-{4-((7-chloroquinolin-4-yl)amino)cyclohexyl}-2-ethoxyacetamide;
N-{4-((7-chloroquinolin-4-yl)amino)cyclohexyl}-2-ethylbutanamide;
N-{4-((7-chloroquinolin-4-yl)amino)cyclohexyl}-1-phenylcyclopropanecarboxamide;
3-chloro-N-{4-((7-chloroquinolin-4-yl)amino)cyclohexyl}-2-hydroxybenzamide;
N-(7-chloroquinolin-4-yl)-N'-(4',5-dimethyl-1,1'-biphenyl-3-yl)cyclohexane-1,4-diamine;
N-(7-chloroquinolin-4-yl)-N'-(3',5-dimethyl-1,1'-biphenyl-3-yl)cyclohexane-1,4-diamine;
N-{4-((7-chloroquinolin-4-yl)amino)cyclohexyl}-3-fluoro-5-thien-2-ylbenzamide;
N-(7-chloroquinolin-4-yl)-N'-(4-(3,4-dihydro-2H-1,5-benzodioxepin-7-yl)-1,3-thiazol-2-yl)cyclohexane-1,4-diamine;
N-(7-chloroquinolin-4-yl)-N'-(4-methyl-5-phenyl-1,3-thiazol-2-yl)cyclohexane-1,4-diamine;
N-{4-((7-chloroquinolin-4-yl)amino)cyclohexyl}-2-(4-(methylsulfonyl)phenyl)acetamide;
N-{4-((7-chloroquinolin-4-yl)amino)cyclohexyl}-8-hydroxyquinoline-7-carboxamide;
N-{4-((7-chloroquinolin-4-yl)amino)cyclohexyl}-2-(pyrimidin-2-ylthio)acetamide;
N-{4-((7-chloroquinolin-4-yl)amino)cyclohexyl}-2-hydroxy-1-naphthamide;
N-{4-((7-chloroquinolin-4-yl)amino)cyclohexyl}-3,3-dimethylbutanamide;
N-{4-((7-chloroquinolin-4-yl)amino)cyclohexyl}adamantane-1-carboxamide;
N-(7-chloroquinolin-4-yl)-N'-(5-phenylpyridin-3-yl)cyclohexane-1,4-diamine;
(2R)-N-{4-((7-chloroquinolin-4-yl)amino)cyclohexyl}-2-hydroxy-4-phenylbutanamide;
3'-({4-((7-chloroquinolin-4-yl)amino)cyclohexyl}amino)-5'-methyl-1,1'-biphenyl-4-ol;
N-{4-((7-chloroquinolin-4-yl)amino)cyclohexyl}-2-methylpentanamide;
N'-{4-((2-N-methylamino-7-chloroquinolin-4-yl)amino)cyclohexyl}-7-chloro-N-methylquinoline-2,4-diamine;
N-{4-((7-chloroquinolin-4-yl)amino)cyclohexyl}-1-methylcyclohexanecarboxamide;
N-{4-((7-chloroquinolin-4-yl)amino)cyclohexyl}-2-hydroxy-3-isopropylbenzamide;
N-{4-((7-chloroquinolin-4-yl)amino)cyclohexyl}-3-hydroxy-2-naphthamide;
N-{4-((7-chloroquinolin-4-yl)amino)cyclohexyl}tetrahydrofuran-2-carboxamide;
N-{4-((7-chloroquinolin-4-yl)amino)cyclohexyl}-2-(4-methylphenoxy)acetamide;
N-(7-chloroquinolin-4-yl)-N'-(4-(4-methoxyphenyl)-1,3-thiazol-2-yl)cyclohexane-1,4-diamine;
3'-(({4-((7-chloroquinolin-4-yl)amino)cyclohexyl}amino)carbonyl)-5'-fluoro-1,1'-biphenyl-3-carboxylic acid;
3'-(({4-((7-chloroquinolin-4-yl)amino)cyclohexyl}amino)carbonyl)-5'-fluoro-1,1'-biphenyl-4-carboxylic acid;
N-(7-chloroquinolin-4-yl)-N'-(4,5-dimethyl-1,3-thiazol-2-yl)cyclohexane-1,4-diamine; and
7-chloro-N-{4-((7-chloroquinolin-4-yl)amino)cyclohexyl}-4-hydroxyquinoline-3-carboxamide.

Determination of Biological Activity

Assay for Release of Intracellular Calcium:

Activation of the melanin concentrating hormone receptor (MCHR) by MCH induces the release of $Ca^{++}$ from intracellular stores. This intracellular calcium release is measured using a fluorometric imaging-plate reader (FLIPR™, Molecular Devices Corp.) in conjunction with the $Ca^{++}$-sensitive dye Fluo-4. Release of $Ca^{++}$ from intracellular stores causes an increase in fluorescence of the dye that is proportional to $Ca^{++}$ concentration. Briefly, the assays are performed as follows. HEK293 cells expressing the murine MCHR are plated overnight at 50,000 cells/well in 96-well plates. The following day, culture medium is removed and replaced with 100 µl/well of D-PBS (+glucose and sodium pyruvate) containing 2.5 µM Fluo-4AM (Molecular Probes), 0.01% Pluronic F-127 and 2.5 mM probenecid. Cells are loaded with the Fluo-4 dye for at least one hour at room temp. After loading, the cells are washed gently to remove extracellular dye and 100 µl of D-PBS (+glucose and sodium pyruvate) is added to each well. Test compounds are prepared at 40 µM in 4% DMSO. The cell plate is placed in the FLIPR™ and 50 µl/well of test compound is delivered. The calcium signal is followed for 3 minutes to assay for potential agonist activity by the test compounds. Then 50 µl/well of 12 nM human MCH (in D-PBS containing 0.1% BSA) is added and the ligand-induced calcium signal is followed for an additional 3 minutes. Antagonist activity as determined by the test compounds ability to inhibit MCH induced $Ca^{++}$ flux is calculated as % inhibition as described by the following formula:

$$\% \text{ inhibition} = (1 - ((fTC - fB) \div (fMCH - fB))) \times 100.$$

fTC=MCH-induced fluorescence in the presence of test compound;
fMCH=MCH-induced fluorescence in the absence of test compound;
fB=Baseline fluorescence.

MCH (3 nM) usually elicits a response of 30,000–40,000 relative fluorescence units (RFU) with a baseline of ~1000 RFU. Fluo-4 fluorescence is measured at 488 nm, with an exposure of 0.40 sec. and F-stop=2.0 and the laser set at 0.40–0.60 W constant light output.

The compounds of the present invention inhibit MCH induced fluorescence at a dose of 10 µM. In a preferred range, compounds of the present invention inhibit MCH induced fluorescence in a range of 75–100% inhibition of MCH at a dose of 10 µM. In a more preferred range, compounds of the present invention inhibit MCH induced fluorescence in a range of 90–100% inhibition of MCH at a dose of 10 µM.

Assay for the Inhibition of MCH Binding to MCHR:

1 µg per well of cell membrane preparations of CHO-K cells expressing the human MCHR1 is added to a v-bottom micro titer plate (Costar). The well volume is brought up to 89 μl using binding buffer (25 mM Hepes ph 7.4, 1 mM CaCl$_2$, 5 mM MgCl$_2$, 0.5% BSA). 1 μl of test compound, dissolved in 100% DMSO, is next added to the wells for a final concentration of 2 μM followed by 10 μl of $^{125}$I-MCH (NEN). The final concentration of $^{125}$I-MCH in each well is 50 pM. The plate is then placed on a titer plate shaker for 1 hour at room temperature. The samples are then transferred to a 0.1% PEI (Polyethylenimine, Sigma) treated glass fiber filter plate (Packard) using a Packard Filtermate Harvestor. The filter plate is washed three times using 200 μl wash buffer (Binding buffer without BSA and with 0.5M NaCl). Microscint 20 (Packard) is added to all wells and the plate is sealed with Topseal A (Packard). CPM is measured from the plate using a microplate scintillation counter (Topcount, Packard).

The compounds of the present invention inhibit binding of $^{125}$I-MCH to human MCHR1 at a dose of 2 μM. In a preferred range, compounds of the present invention inhibit binding of $^{125}$I-MCH to human MCHR1 in a range of 75–100% inhibition of $^{125}$I-MCH at a dose of 2 μM. In a more preferred range, compounds of the present invention inhibit binding of $^{125}$I-MCH to human MCHR1 in a range of 90–100% inhibition of $^{125}$I-MCH at a dose of 2 μM.

As antagonists of MCH action upon the MCH receptor, therefore, the compounds of the present invention are useful in treating disorders that are mediated by MCH through the MCH receptor. Disorders that are mediated by MCH through the MCH receptor are obesity, abnormalities in reproduction and sexual behavior, thyroid hormone secretion, diuresis and water/electrolyte homeostasis, sensory processing, memory, sleeping and arousal, anxiety and depression, seizure and in treatment of neurodegeneration or psychiatric disorders. Therefore the compounds of the present invention are useful in treating obesity, abnormalities in reproduction and sexual behavior, thyroid hormone secretion, diuresis and water/electrolyte homeostasis, sensory processing, memory, sleeping and arousal, anxiety and depression, seizure and in treatment of neurodegeneration or psychiatric disorders.

Therapeutic agents acting through MCH receptor may also be useful in treatment of abnormalities in reproduction and sexual behavior (Murray, J. F.; Mercer J. G., Adan R. A., Datta J. J., Aldairy C, Moar K M, Baker B I, Stock M J, Wilson, C. A.; The effect of leptin on luteinizing hormone release is exerted in the zona incerta and mediated by melanin-concentrating hormone. J Neuroendocrinol 12:1133–1139, 2000.; Gonzalez, M. I., Baker, B. I., Wilson, C. A.; Stimulatory effect of melanin-concentrating hormone on luteinising hormone release. Neuroendocrinology 66:254–262, 1997.; Murray, J. F., Adan, R. A., Walker, R., Baker, B. I., Thody, A. J., Nijenhuis, W. A., Yukitake, J., Wilson, C. A.; Melanin concentrating hormone, melanocortin receptors and regulation of luteinizing hormone release. J Neuroendocrinol 12:217–223, 2000.; Nahon, J. L.; The melanin-concentrating hormone: from the peptide to the gene. Crit Rev Neurobiol 8:221–262, 1994.)

Therapeutic agents acting through MCH receptor may also be useful in treatment of thyroid hormone secretion (Kennedy, A. R., Todd, J. F., Stanley, S. A., Abbott, C. R., Small, C. J., Ghatei, M. A., Bloom, S. R.; Melanin-concentrating hormone (MCH) suppresses thyroid stimulating hormone (TSH) release, in vivo and in vitro, via the hypothalamus and the pituitary. Endocrinology 142:3265–3268, 2001).

Therapeutic agents acting through MCH receptor may also be useful in treatment of diuresis and water/electrolyte homeostasis (Hervieu, G., Volant, K., Grishina, O., Descroix-Vagne, M., Nahon, J. L.; Similarities in cellular expression and functions of melanin-concentrating hormone and atrial natriuretic factor in the rat digestive tract. Endocrinology 137:561–571, 1996.; and Parkes, D. G.; Diuretic and natriuretic actions of melanin concentrating hormone in conscious sheep. J Neuroendocrinol 8:57–63, 1996).

Therapeutic agents acting through MCH receptor may also be useful in treatment of sensory processing (Miller, C. L., Hruby, V. J., Matsunaga, T. O., Bickford, P. C.; Alpha-MSH and MCH are functional antagonists in a CNS auditory gating paradigm. Peptides 14:431–440, 1993.; Kokkotou, E. G., Tritos, N. A., Mastaitis, J. W., Slieker, L., Maratos-Flier, E.; Melanin-concentrating hormone receptor is a target of leptin action in the mouse brain. Endocrinology 142:680–686, 2001).

Therapeutic agents acting through MCH receptor may also be useful in treatment of memory (Monzon, M. E., De Barioglio, S. R.; Response to novelty after i.c.v. injection of melanin-concentrating hormone (MCH) in rats. Physiol Behav 67:813–817, 1999).

Therapeutic agents acting through MCH receptor may also be useful in treatment of sleeping and arousal (Bittencourt, J. C., Presse, F., Arias, C., Peto, C., Vaughan, J., Nahon, J. L., Vale, W., Sawchenko, P. E.; The melanin-concentrating hormone system of the rat brain: an immuno- and hybridization histochemical characterization. J Comp Neurol 319:218–245, 1992.; Nahon, J. L.; The melanin-concentrating hormone: from the peptide to the gene. Crit Rev Neurobiol 8:221–262, 1994).

Therapeutic agents acting through MCH receptor may also be useful in treatment of anxiety and depression (Monzon, M. E., Varas, M. M., De Barioglio, S. R.; Anxiogenesis induced by nitric oxide synthase inhibition and anxiolytic effect of melanin-concentrating hormone (MCH) in rat brain. Peptides 22:1043–1047, 2001.; Monzon, M. E., De Barioglio, S. R.; Response to novelty after i.c.v. injection of melanin-concentrating hormone (MCH) in rats. Physiol Behav 67:813–817, 1999.; Borowsky, B., Durkin, M. M., Ogozalek, K., Marzabadi, M. R., DeLeon, J., Lagu, B., Heurich, R., Lichtblau, H., Shaposhnik, Z., Daniewska, I., Blackburn, T. P., Branchek, T. A., Gerald, C., Vaysse, P. J., Forray, C.; Antidepressant, anxiolytic and anorectic effects of a melanin-concentrating hormone-1 receptor antagonist. Nat. Med. 8:825–830, 2002).

Therapeutic agents acting through MCH receptor may also be useful in treatment of seizure (Knigge, K. M., Wagner, J. E; Melanin-concentrating hormone (MCH) involvement in pentylenetetrazole (PTZ)-induced seizure in rat and guinea pig. Peptides 18:1095–1097, 1997) and in treatment of neurodegeneration or psychiatric disorders (Nahon, J. L.; The melanin-concentrating hormone: from the peptide to the gene. Crit Rev Neurobiol 8:221–262, 1994).

Synthetic Methods

The compounds and processes of the present invention will be better understood in connection with the following synthetic schemes which together illustrate the methods by which the compounds of the invention may be prepared. The groups $R_1$, $R_2$, $R_3$, $R_4$, $R_5$, $R_6$, $R_7$, $R_8$, $R_9$, $R_{10}$ are as defined above unless otherwise noted below.

Scheme 1

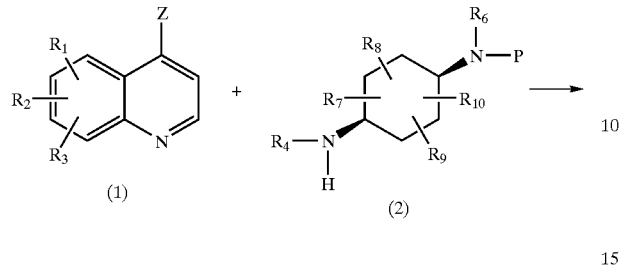

(1) + (2)

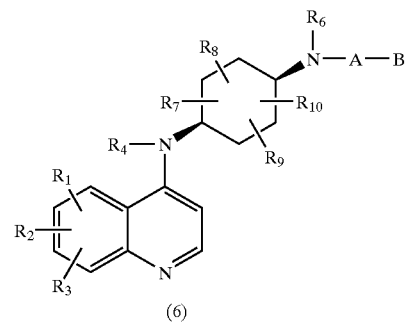

(6)

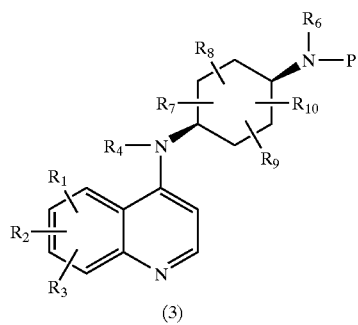

(3)

As shown in Scheme 1, compounds of formula (1) (Z is halogen) can be reacted under heated conditions with compounds of formula (2) (P is H or an optionally incorporated nitrogen protecting group such as but not limited to acetyl, tert-butoxycarbamate, benzylcarbamate and allylcarbamate), in the presence of base to form compounds of formula (3). Representative bases include but are not limited to triethylamine, diisopropylethylamine, N-methylmorpholine and sodium hydride. Examples of solvents used in these reactions include N-methylpyrrolidinone, N,N-dimethylformamide and dimethylsulfoxide. The reaction temperatures can range from between 60° C. to 230° C. and depends on the method and substrates chosen. Reaction times are typically between 10 minutes and 18 hours. When present, the optionally incorporated nitrogen protecting group can be removed to provide the amine (4) (Scheme 2), using standard conditions known to those skilled in the art.

As shown in Scheme 2, compounds of formula (4) can be reacted with compounds of formula (5) (wherein B is a member selected from the group consisting of aryl, arylalkenyl, aryloxyalkyl, biarylalkyl, cycloalkyl or heterocycle; A is absent or alkylene; Z is halide) in the presence of base under heated conditions to provide compounds of formula (6). Representative conditions including appropriate bases, solvents, reaction temperatures and reaction times that are used in Scheme 1, also are appropriate for the conversion of compounds of formula (4) to compounds of formula (6) in Scheme 2. Compounds of formula (4) and compounds of formula (5) (wherein A is absent) can also be reacted under heated conditions in the presence of palladium reagents such as but not limited to (1,1'bis (diphenylphosphino)ferrocene)dichloropalladium(II) complex with dichloromethane and the like in solvents such as tetrahydrofuran, dioxane or N,N-dimethylformamide to provide compounds of formula (6). In addition, compounds of formula (4) and compounds of formula (5) (wherein A is alkylene and Z is chloride) can be reacted under heated conditions in the presence of potassium carbonate and sodium iodide in solvents such as acetonitrile or N,N-dimethylformamide to provide compounds of formula (6).

Scheme 3

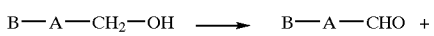

B—A—CH$_2$—OH ⟶ B—A—CHO +

(7)  (8)

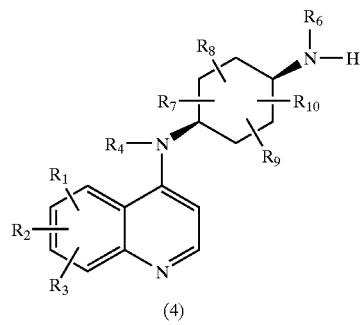

(4)

Scheme 2

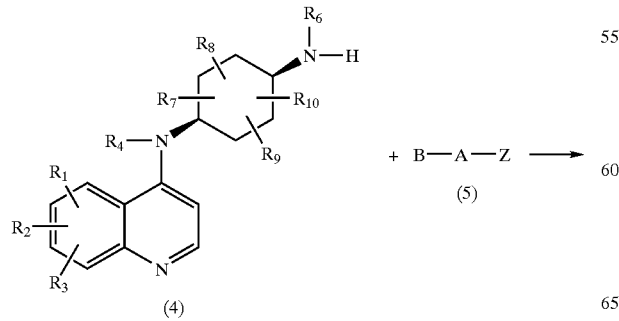

(4)  + B—A—Z ⟶

(5)

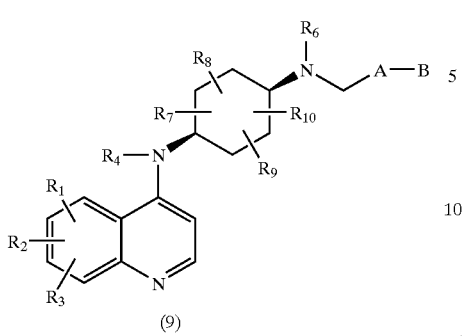

(9)

As shown in Scheme 3, the oxidation of compounds of formula (7) (wherein B is aryl, arylalkenyl, aryloxyalkyl, biarylalkyl, cycloalkyl or heterocycle; A is absent or alkylene) utilizing reagents such as Dess-Martin periodinane in dichloromethane, tetrapropylammonium perruthenate, the Swern oxidation or one of the other commonly utilized oxidation techniques known to those skilled in the art will provide compounds of formula (8). Compound of formula (8) can be reacted with compound of formula (4) in the presence of acetic acid and MP-sodium cyanoborohydride to provide compounds of formula (9). Typical solvents include but are not limited to tetrahydrofuran and dichloromethane. Alternatively, in the reaction of Scheme 3, reagents such as but not limited to sodium cyanoborohydride or borane THF complex can be substituted for MP-sodium cyanoborohydride.

Scheme 4

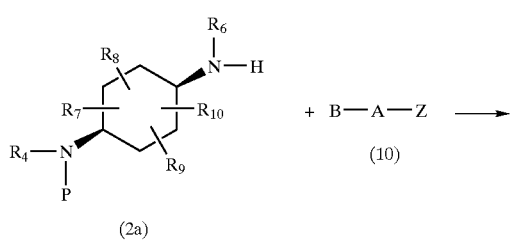

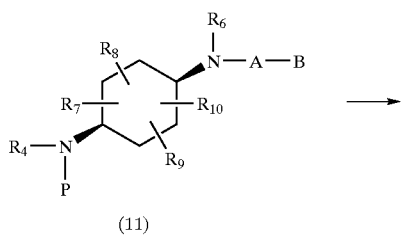

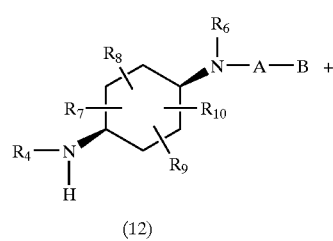

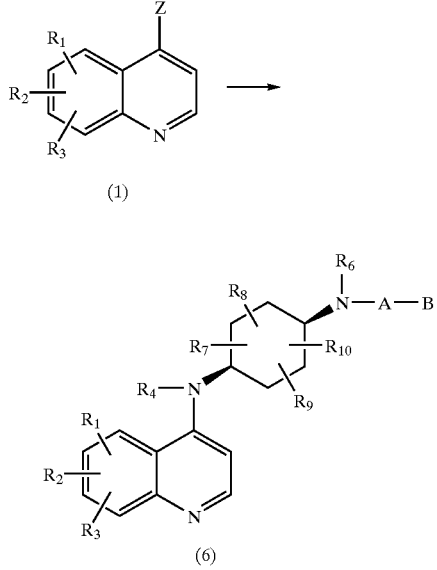

(1)

(6)

Alternatively, as shown in Scheme 4, the synthesis of a compound of formula (6) can be achieved in a reverse fashion using the same reaction conditions as mentioned in Schemes 1 and 2 by first reacting a compound of formula (2a) (P is an optionally incorporated nitrogen protecting group as described above) with a compound of formula (10) (wherein B is aryl, aryloxyalkyl, biarylalkyl, cycloalkyl or heterocycle; A is alkylene; Z is halide) to provide a compound of formula (11). Conditions required for removal of the amine protecting group (P) of a compound of formula (11) are commonly known by those skilled in the art to provide a compound of formula (12). A compound of formula (12) is reacted with a compound of formula (1) (Z is halogen) to provide the compound of formula (6) using conditions listed previously in Schemes 1 and 2.

Scheme 5

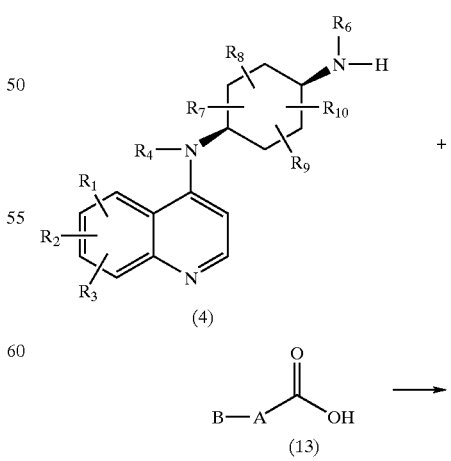

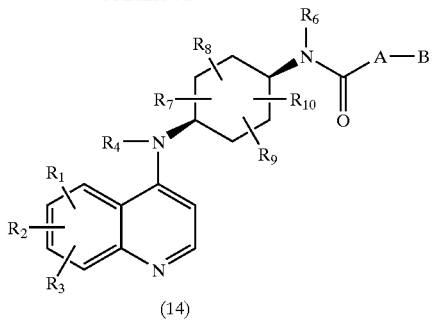

(14)

As shown in Scheme 5, compounds of formula (4) can be reacted with compounds of formula (13) (wherein B is aryl, arylalkenyl, aryloxyalkyl, biarylalkyl, cycloalkyl or heterocycle; A is absent or alkylene) in the presence of MP-dicyclohexylcarbodiimide, N-hydroxybenzotriazole and a base in a solvent to provide compounds of formula (14). Typical bases include but are not limited to di-isopropylethylamine or N-methylmorpholine. Examples of solvents used in these reactions include but are not limited to N,N-dimethylformamide and dichloromethane. These reactions are typically done at room temperature and reaction times are typically between 6 and 24 hours. Alternatively, in the reaction of Scheme 5, dicyclohexylcarbodiimide or 1-(3-dimethylaminopropyl)-3-ethylcarbodiimide hydrochloride can be substituted for MP-dicyclohexylcarbodiimide.

Scheme 6

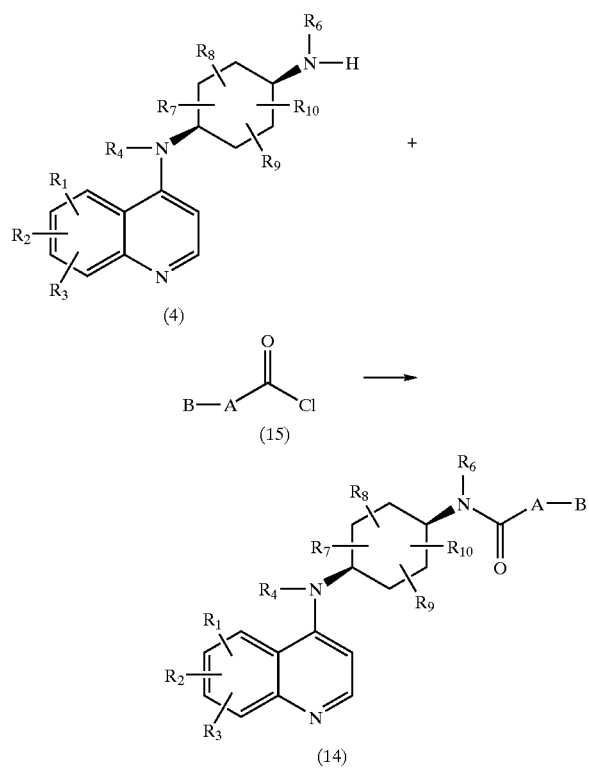

Alternatively, compounds of formula (14) can be made by reacting compounds of formula (4) with compounds of formula (15) (wherein B is aryl, arylalkenyl, aryloxyalkyl, biarylalkyl, cycloalkyl or heterocycle; A is absent or alkylene) in the presence of base in a solvent. Typical bases used in these reactions are the same as in Scheme (5). Typical solvents include but are not limited to tetrahydrofuran and N,N-dimethylformamide and reaction times are typically between 4 and 16 hours.

Alternatively, the synthesis of a compound of formula (14) can be achieved in a reverse fashion by reacting either compounds of formula (13) with compounds of formula (2a) (P is a nitrogen protecting group which is later removed prior to the next step) using the same reaction conditions as mentioned in Scheme 5 or by reacting compounds of formula (15) with compounds of formula (2a) using the same reaction conditions as mentioned in Scheme 6. The products would then be treated with compounds of formula (1) using conditions listed previously in Scheme 1 to provide a compounds of formula (14).

Scheme 7

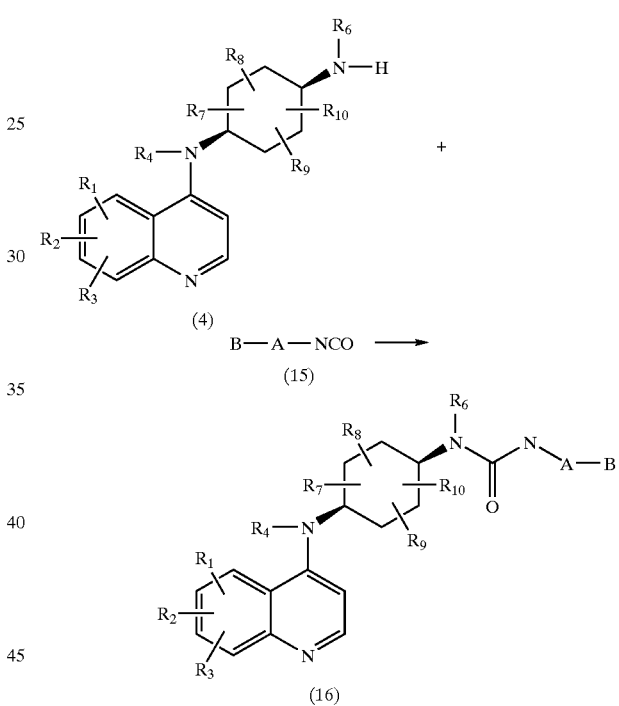

As shown in Scheme 7, compounds of formula (4) can be reacted with compounds of formula (15) (wherein B is aryl, arylalkenyl, aryloxyalkyl, biarylalkyl, cycloalkyl or heterocycle; A is absent or alkylene) in solvents such as but not limited to chloroform, dichloromethane and tetrahydrofuran, to provide compounds of formula (16). These reactions are done at room temperature and reaction times are typically between 6 and 24 hours.

Alternatively, the synthesis of a compound of formula (16) can be achieved in a reverse fashion by reacting compounds of formula (15) with compounds of formula (2a) (P is a nitrogen protecting group which is later removed prior to the second reaction in this sequence) using the same reaction conditions as mentioned in Scheme 7. The product would then be treated with compound of formula (1) to provide a compound of formula (16) using conditions listed previously in Scheme 1.

Scheme 8

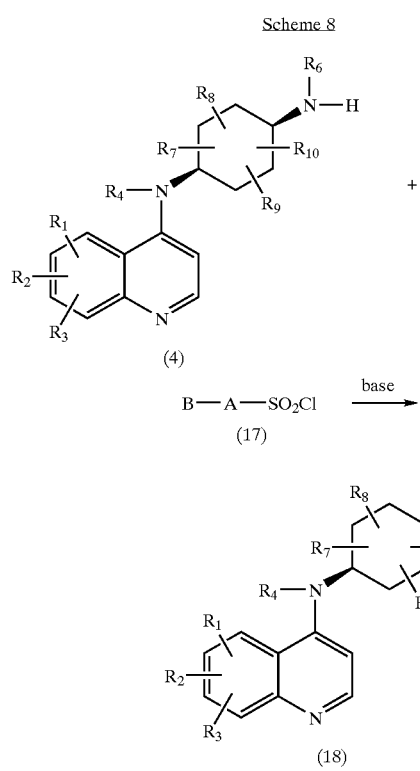

As shown in Scheme 8, compounds of formula (4) can be reacted with compounds of formula (17) (wherein B is aryl, arylalkenyl, aryloxyalkyl, biarylalkyl, cycloalkyl or heterocycle; A is absent or alkylene) in the presence of a base to provide compounds of formula (18). Typical bases include but are not limited to di-isopropylethylamine or N-methylmorpholine. Typical solvents include but are not limited to tetrahydrofuran and N,N-dimethylformamide and reaction times are between 4 and 16 hours.

Alternatively, the synthesis of a compound of formula (18) can be achieved in a reverse fashion by reacting compounds of formula (17) with compounds of formula (2a) (P is a nitrogen protecting group which is later removed prior to the next step) using the same reaction conditions as mentioned in Scheme 8. The product would then be treated with compound of formula (1) to provide a compound of formula (18) using conditions listed previously in Scheme 1.

The present invention will now be described in connection with certain preferred embodiments which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purposes of illustration of certain preferred embodiments and are presented to provide what is believed to be the most useful and readily understood description of its procedures and conceptual aspects.

Compounds of the invention were named by ACD/ChemSketch version 5.01 (developed by Advanced Chemistry Development, Inc., Toronto, ON, Canada) or were given names which appeared to be consistent with ACD nomenclature.

EXAMPLE 1 cis-N,N'-bis(7-chloroquinolin-4-yl)cyclohexane-1,4-diamine

A solution of 4,7-dichloroquinoline (5.4 g, 28.1 mmol), 1,4-diaminocyclohexane(1.4 g, 12.3 mmol, 2:1 cis:trans), and triethylamine(3.6 g, 36.9 mmol) in 1-methyl-2-pyrrolidinone (7 ml) was heated to 150° C. for 15 hours, cooled to room temperature, diluted with diethyl ether and water, and filtered. The residue was flash chromatographed through silica gel column with dichloromethane, methanol and triethylamine (8:1:1 ratio by vol) to provide the desired compound as white solid. MS (ESI(+)Q1MS m/z 437 (M+H)$^+$; $^1$H NMR (300 MHz, DMSO) δ ppm 8.43 (d, 2 H), 8.41 (s, 2 H), 7.79 (d, 2 H), 7.46 (dd, 2 H), 6.92 (d, 2 H), 6.59 (d, 2 H), 3.77 (br.s, 2 H), 1.99 (m, 4 H), 1.83 (m, 4 H).

EXAMPLE 2 cis-N-(4-chlorophenyl)-N'-{4-((7-chloroquinolin-4-yl)amino)cyclohexyl}urea

A solution of N-(7-chloroquinolin-4-yl)-cyclohexane-1,4-diamine (20 mg, 0.07 mmol) in chloroform (0.5 mL) at 20° C. was treated with 4-chlorophenyl isocyanate (11 mg,0.07 mmol). The mixture was shaken at room temperature for 18 hours then concentrated under reduced pressure. The compound was purified by reverse phase HPLC to provide the desired compound. MS (ESI (+)) m/e 429 (M+H)$^+$; $^1$H NMR (500 MHz, DMSO) δ ppm 8.55 (s, 1 H), 8.52 (d, 1 H), 8.45 (d, 1 H), 7.83 (s, 1 H), 7.57 (d, 1 H), 7.41 (d, 2 H), 7.26 (d, 2 H), 6.70 (s, 1 H), 6.31 (d, 1 H), 3.78 (s, 1 H), 3.71 (s, 1 H), 1.63–1.93 (m, 8 H).

EXAMPLE 3 cis-N-(2,8-bis(trifluoromethyl)quinolin-4-yl)-N'-(7-chloroquinolin-4-yl)cyclohexane-1,4-diamine A solution of N-(7-chloroquinolin-4-yl)-cyclohexane-1,4-diamine (20 mg, 0.07 mmol) in N-methylpyrrolidine (0.5 mL) at 150° C. was treated with 4-chloro-2,8-bis(trifluoromethyl)quinoline (21 mg, 0.07 mmol), and triethylamine (10 μl, 0.07 mmol). The mixture was stirred at 150° C. for 18 hours then concentrated under reduced pressure. The compound was purified by reverse phase HPLC to provide the desired compound.

MS (ESI(+)Q1MS m/z 539 (M+H)$^+$; $^1$H NMR (300 MHz, DMSO) δ ppm 8.82 (d, 1 H), 8.81 (d, 1 H), 8.73 (d, 1 H), 8.20 (d, 1 H), 7.93 (d, 1 H), 7.83 (dd, 1 H), 7.71 (t, 1 H), 7.51 (d, 1 H), 7.05 (d. 1 H), 6.98 (s, 1 H), 4.12–4.02 (m, 2 H), 2.10–2.02 (m, 4 H), 1.93–1.86 (m, 4 H).

EXAMPLE 4 cis-N-(7-chloroquinolin-4-yl)-N'-(8-(trifluoromethyl)quinolin-4-yl)cyclohexane-1,4-diamine The titled compound was prepared according to the method described in Example 3 by substituting 4-chloro-8-trifluoromethylquinoline for 4-chloro-2,8-bis(trifluoromethyl)-quinoline. MS (ESI(+)Q1MS m/z 471 (M+H)$^+$; $^1$H NMR (300 MHz, DMSO) δ ppm 13.83–13.76 (br s, 1 H), 8.82 (d, 2 H), 8.75 (d, 1 H), 8.59 (d, 1 H), 8.50 (d, 1 H), 8.20 (br s, 1 H), 7.95 (d, 1 H), 7.81 (dd, 1 H), 7.70 (br s, 1 H), 7.03 (d. 1 H), 6.87 (br s, 1 H), 4.15–4.07 (m, 1 H), 4.06–3.98 (m, 1 H), 2.15–2.02 (m, 4 H), 1.95–1.84 (m, 4 H).

EXAMPLE 5 cis-N-(7-chloroquinolin-4-yl)-N'-(7-(trifluoromethyl)quinolin-4-yl)cyclohexane-4-diamine The titled compound was prepared according to the method described in Example 3 by substituting 4-chloro-7- trifluoromethylquinoline for 4-chloro-2,8-bis (trifluoromethyl)-quinoline. MS (ESI(+)Q1MS m/z 471 (M+H)$^+$; $^1$H NMR (300 MHz, DMSO) δ ppm 8.95 (d, 1 H), 8.90 (br s, 1 H), 8.80 (d, 1 H), 8.77 (d, 1 H), 8.73 (d, 1 H), 8.60 (d, 1 H), 8.26 (s, 1 H), 8.06 (d, 1 H), 7.97 (d, 1 H), 7.82 (dd, 1 H), 7.14 (d, 1 H), 7.04 (d, 1 H), 6.87 (br s, 1 H), 4.20–4.10 (m, 2 H), 2.15–2.03 (m, 4 H), 1.95–1.85 (m, 4 H).

EXAMPLE 6 cis-N-(7-chloroquinolin-4-yl)-N'-(2-(trifluoromethyl) quinolin-4-yl)cyclohexane-1,4-diamine The titled compound was prepared according to the method described in Example 3 by substituting 4-chloro-2-trifluoromethylquinoline for 4-chloro-2,8-bis (trifluoromethyl)-quinoline. MS (ESI(+)Q1MS m/z 471 (M+H)$^+$; $^1$H NMR (300 MHz, DMSO) δ ppm 8.83 (d, 1 H), 8.75 (d, 1 H), 8.59 (d, 1 H), 8.50 (d, 1 H), 7.95 (d, 1 H), 7.92 (d, 1 H), 7.80 (dd, 1 H), 7.77(ddd, 1 H), 7.60 (ddd, 1 H), 7.21 (d, 1 H), 7.03 (d. 1 H), 6.82 (s, 1 H), 4.14–4.05 (m, 1 H), 4.02–3.95(m, 1 H); 2.13–2.00 (m, 4 H), 1.93–1.82 (m, 4 H).

EXAMPLE 7 cis-N-(7-chloroquinolin-4-yl)-N'-(2-methylquinolin-4-yl)cyclohexane-1,4-diamine The titled compound was prepared according to the method described in Example 3 by substituting 4-chloro-2-methylquinoline for 4-chloro-2,8-bis(trifluoromethyl)-quinoline.

MS (ESI(+)Q1MS m/z 417 (M+H)$^+$; $^1$H NMR (300 MHz, DMSO) δ ppm 8.72 (d, 1 H), 8.62 (d, 1 H), 8.59 (d, 1 H), 8.45 (d, 1 H), 7.95 (d, 1 H), 7.92 (ddd, 1 H), 7.84 (d, 1 H), 7.82–7.78 (m, 1 H), 7.70(s, 1 H), 7.68 (ddd, 1 H), 6.98 (d. 1 H), 6.92 (s, 1 H), 4.15–4.05 (m, 2 H), 2.65 (s, 3 H), 2.13–2.00 (m, 4 H), 1.93–1.82 (m, 4 H).

EXAMPLE 8 cis-N-(7-chloroquinolin-4-yl)-N'-(quinolin-3-ylmethyl)cyclohexane-1,4-diamine A solution of N-(7-chloroquinolin-4-yl)-cyclohexane-1,4-diamine (40 mg, 0.14 mmol) and 3-quinolinecarboxaldehyde (22 mg, 0.14 mmol) in dichloroethane (0.5 mL) and methanol (0.5 mL) was treated acetic acid (0.018 mg, 0.28 mmol) and MP-cyanoborohydride (100 mg, 0.436 mmol, Argonaut Technologies). The mixture was stirred at 60° C. for 18 hours, filtered, and purified by reverse phase HPLC to provide the desired compound.

MS(ESI) m/e 417 (M+H)$^+$; $^1$H NMR (500 MHz, DMSO-D6) δ ppm 9.17 (br.s, 1 H), 9.04 (d, 1 H), 8.78 (d, 1 H), 8.70 (d, 1 H), 8.61 (d, 1 H), 8.56 (d, 1 H), 8.10 (d, 1 H), 8.03 (dd, 1 H), 8.00 (d, 1 H), 7.85 (ddd, 1 H), 7.80 (dd, 1 H), 7.70 (ddd, 1 H), 6.98 (d, 1 H), 4.48 (br.s, 2 H), 4.12 (br.s, 1 H), 3.40 (br s, 1 H), 2.08–1.80 (m, 8 H).

EXAMPLE 9 cis-N-(7-chloroquinolin-4-yl)-N'-(quinolin-4-ylmethyl)cyclohexane-1,4-diamine The titled compound was prepared according to the method described in Example 8 by substituting 4-quinolinecarboxaldehyde for 3-quinolinecarboxaldehyde. MS(ESI) m/e 417 (M+H)$^+$; $^1$H NMR (500 MHz, DMSO-D6) δ ppm 9.22 (br.s, 1 H), 9.02 (d, 1 H), 8.78 (d, 1 H), 8.68 (d, 1 H), 8.61 (d, 1 H), 8.26 (d, 1 H), 8.15 (d, 1 H), 7.99 (d, 1 H), 7.88 (ddd, 1 H), 7.80 (dd, 1 H), 7.77 (ddd, 1 H), 7.76 (d, 1 H), 6.98 (d, 1 H), 4.80 (br.s, 2 H), 4.18 (br.s, 1 H), 3.51 (br s, 1 H), 2.20–1.80 (m, 8 H).

EXAMPLE 10 cis-N-(4-bromobenzyl)-N'-(7-chloroquinolin-4-yl) cyclohexane-1,4-diamine

The titled compound was prepared according to the method described in Example 8 by substituting 4-bromobenzaldehyde for 3-quinolinecarboxaldehyde. MS(ESI) m/e 446 (M+H)$^+$; $^1$H NMR (500 MHz, DMSO-D6) δ ppm 8.98 (br.s, 1 H), 8.77 (d, 1 H), 8.60 (d, 1 H), 8.59 (d, 1 H), 7.98 (d, 1 H), 7.78 (dd, 1 H), 7.67(d, 2 H), 7.50 (d, 2 H), 6.95 (d, 1 H), 4.21 (br.s, 2 H), 4.08 (m, 1 H), 3.23 (m, 1 H), 2.12–1.77 (m, 8 H).

EXAMPLE 11 cis-N-(7-chloroquinolin-4-yl)-N'-(3,4-difluorobenzyl)cyclohexane-1,4-diamine The titled compound was prepared according to the method described in Example 8 by substituting 3,4-difluorobenzaldehyde for 3-quinolinecarboxaldehyde. MS(ESI) m/e 402 (M+H)$^+$; $^1$H NMR (500 MHz, DMSO-D6) δ ppm 9.05 (br.s, 1 H), 8.77 (d, 1 H), 8.65 (d, 1 H), 8.60 (d, 1 H), 7.99 (d, 1 H), 7.78 (dd, 1 H), 7.65 (ddd, 1 H), 7.55 (dd, 1 H), 7.40 (dd, 1 H), 6.95 (d, 1 H), 4.23 (br.s, 2 H), 4.09 (m, 1 H), 3.25 (m, 1 H), 2.12–1.77 (m, 8 H).

EXAMPLE 12 cis-N-(3-bromobenzyl)-N'-(7-chloroquinolin-4-yl) cyclohexane-1,4-diamine

The titled compound was prepared according to the method described in Example 8 by substituting 3-bromobenzaldehyde for 3-quinolinecarboxaldehyde. MS(ESI) m/e 446 (M+H)$^+$; $^1$H NMR (500 MHz, DMSO-D6) δ ppm 9.01 (br.s, 1 H), 8.78 (d, 1 H), 8.65 (d, 1 H), 8.60 (d, 1 H), 8.00 (d, 1 H), 7.80 (s, 1 H), 7.77 (dd, 1 H), 7.65 (d, 1 H), 7.55 (d, 1 H), 7.42 (dd, 1 H), 6.95 (d, 1 H), 4.22 (br.s, 2 H), 4.10 (m, 1 H), 3.25 (m, 1 H), 2.12–1.77 (m, 8 H).

EXAMPLE 13 cis-N-(7-chloroquinolin-4-yl)-N'-{(4-(dimethylamino)-1-naphthyl)methyl}cyclohexane-1,4-diamine The titled compound was prepared according to the method described in Example 8 by substituting 4-dimethylamino-1-naphthaldehyde for 3-quinolinecarboxaldehyde. MS(ESI) m/e 459 (M+H)$^+$; $^1$H NMR (500 MHz, DMSO-D6) δ ppm 8.82 (br.s, 1 H), 8.78 (d, 1 H), 8.62 (d, 1 H), 8.61 (d, 1 H), 8.26 (dd, 1 H), 8.15 (dd, 1 H), 7.99 (d, 1 H), 7.80 (dd, 1 H), 7.67–7.58 (m, 3 H), 7.18 (d, 1 H), 6.95 (d, 1 H), 4.62 (m, 2 H), 4.15 (m, 1 H), 3.50 (m, 1 H), 2.18–1.80(m, 8 H).

EXAMPLE 14 cis-N-(7-chloroquinolin-4-yl)-N'-(4-pyridin-2-ylbenzyl)cyclohexane-1,4-diamine The titled compound was prepared according to the method described in Example 8 by substituting 4-(2- pyridine)-benzaldehyde for 3-quinolinecarboxaldehyde. MS(ESI) m/e 443 (M+H)$^+$; $^1$H NMR (500 MHz, DMSO-D6) δ ppm 9.01 (br.s, 1 H), 8.78 (d, 1 H), 8.70 (m, 1 H), 8.67 (d, 1 H), 8.60 (d, 1 H), 8.19 (d, 2 H), 8.05 (d, 1 H), 8.00 (d, 1 H), 7.95 (ddd, 1 H), 7.80 (dd, 1 H), 7.65 (d, 2 H), 7.40 (m, 1 H), 6.98 (d, 1 H), 4.35 (m, 2 H), 4.12 (m, 1 H), 3.30 (m, 1 H), 2.14–1.78 (m, 8 H).

EXAMPLE 15 cis-4-chloro-N-{4-((7-chloroquinolin-4-yl)amino) cyclohexyl}benzenesulfonamide

A solution of N-(7-chloroquinolin-4-yl)-cyclohexane-1,4-diamine (20 mg, 0.07 mmol) in pyridine (1.0 mL) at 20 C was treated with 4-chlorobenzenesulfonyl chloride (15 mg, 0.07 mmol). The reaction was shaken at room temperature for 18 hours then concentrated. The crude compound was purified by reverse phase HPLC to provide the desired compound. MS (ESI (+)) m/e 450 (M+H)$^+$; $^1$H NMR (500 MHz, DMSO) δ ppm 8.88 (d, 1 H), 8.71 (d, 1 H), 8.53 (d, 1 H), 7.93 (d, 1 H), 7.87 (d, 2 H), 7.81 (dd, 1 H), 7.70 (d, 3 H), 6.95 (d, 1 H), 3.86 (br.s, 1 H), 3.14 (m, 1 H), 1.89 (m, 2 H), 1.74 (m, 4 H), 1.58 (m, 2 H).

EXAMPLE 16 cis-N-(7-chloroquinolin-4-yl)-N'-(2-phenylquinolin-4-yl)cyclohexane-4-diamine

The titled compound was prepared according to the method described in Example 3 by substituting 4-chloro-2-phenylquinoline for 4-chloro-2,8-bis(trifluoromethyl)-quinoline.

MS (ESI(+)Q1MS m/z 479 (M+H)$^+$.

EXAMPLE 17 cis-N-(7-chloroquinolin-4-yl)-N'-(6-(trifluoromethyl) quinolin-4-yl)cyclohexane-1,4-diamine The titled compound was prepared according to the method described in Example 3 by substituting 4-chloro-6-trifluoromethylquinoline for 4-chloro-2,8-bis(trifluoromethyl)-quinoline. MS (ESI(+)Q1MS m/z 471 (M+H)$^+$; $^1$H NMR (300 MHz, DMSO) δ ppm 9.20 (br s, 1 H), 9.06 (d, 1 H), 8.80 (d, 1 H), 8.76 (d, 1 H), 8.67 (d, 1 H), 8.60 (d, 1 H), 8.25 (dd, 1 H), 8.10 (d, 1 H), 7.96 (d, 1 H), 7.82 (dd, 1 H), 7.13 (d, 1 H), 7.03 (d. 1 H), 4.20–4.10 (m, 2 H), 2.15–2.04 (m, 4 H), 1.99–1.88 (m, 4 H).

EXAMPLE 18 cis-N-(7-chloroquinolin-4-yl)-N'-(6-methyl-2-(trifluoromethyl)quinolin-4-yl)cyclohexane-1,4-diamine The titled compound was prepared according to the method described in Example 3 by substituting 4-chloro-6-methyl-2-trifluoromethylquinoline for 4-chloro-2,8-bis(trifluoromethyl)-quinoline. MS (ESI(+)Q1MS m/z 485 (M+H)$^+$; $^1$H NMR (300 MHz, DMSO) δ ppm 8.88 (d, 1 H), 8.75 (d, 1 H), 8.59 (d, 1 H), 8.30 (s, 1 H), 7.94 (s, 1 H), 7.84–7.78 (m, 2 H), 7.61 (dd, 1 H), 7.10 (d, 1 H), 7.05 (d. 1 H), 6.79 (s, 1 H), 4.13–4.05 (m, 1 H), 4.00–3.93 (m, 1 H), 2.55 (s, 3 H), 2.17–2.00 (m, 4 H), 1.93–1.80 (m, 4 H).

EXAMPLE 19 cis-N-(7-chloroquinolin-4-yl)-N'-(6-fluoro-2-(trifluoromethyl)quinolin-4-yl)cyclohexane-1,4-diamine The titled compound was prepared according to the method described in Example 3 by substituting 4-chloro-6-fluoro-2-trifluoromethylquinoline for 4-chloro-2,8-bis(trifluoromethyl)-quinoline. MS (ESI(+)Q1MS m/z 489 (M+H)$^+$; $^1$H NMR (300 MHz, DMSO) δ ppm 8.85 (d, 1 H), 8.72 (d, 1 H), 8.58 (d, 1 H), 8.40 (dd, 1 H), 8.00 (dd, 1 H), 7.94 (d, 1 H), 7.81 (dd, 1 H), 7.69 (ddd, 1 H), 7.17 (d, 1 H), 7.04 (d. 1 H), 6.85 (s, 1 H), 4.15–4.04 (m, 1 H), 4.02–3.95 (m, 1 H), 2.12–2.00 (m, 4 H), 1.94–1.83 (m, 4 H).

EXAMPLE 20 cis-N-(7-chloroquinolin-4-yl)-N'-(8-chloro-2-(trifluoromethyl)quinolin-4-yl)cyclohexane-1,4-diamine The titled compound was prepared according to the method described in Example 3 by substituting 4-chloro-6-fluoro-2-trifluoromethylquinoline for 4-chloro-2,8-bis(trifluoromethyl)-quinoline. MS (ESI(+)Q1MS m/z 505 (M+H)$^+$; $^1$H NMR (300 MHz, DMSO) δ ppm 8.85 (d, 1 H), 8.74 (d, 1 H), 8.58 (d, 1 H), 8.50 (dd, 1 H), 7.97 (dd, 1 H), 7.95 (d, 1 H), 7.81 (dd, 1 H), 7.57 (dd, 1 H), 7.39 (d, 1 H), 7.04 (d. 1 H), 6.93 (s, 1 H), 4.12–4.05 (m, 1 H), 4.04–3.98 (m, 1 H), 2.12–2.00 (m, 4 H), 1.94–1.83 (m, 4 H).

EXAMPLE 21 cis-N-(7-chloroquinolin-4-yl)-N'-quinolin-4-ylcyclohexane-1,4-diamine

The titled compound was prepared according to the method described in Example 3 by substituting 4-chloroquinoline for 4-chloro-2,8-bis(trifluoromethyl)-quinoline. MS (ESI(+)Q1MS m/z 403 (M+H)$^+$; $^1$H NMR (300 MHz, DMSO) δ ppm 8.83 (d, 1 H), 8.78 (d, 1 H), 8.72 (d, 1 H), 8.68 (d, 1 H), 8.60 (d, 1 H), 8.59 (d, 1 H), 7.98 (dd, 1 H), 7.98 (d, 1 H), 7.95 (m, 1 H), 7.81 (dd, 1 H), 7.75 (ddd, 1 H), 7.03 (d. 1 H), 7.01 (d, 1 H), 4.18–4.10 (m, 2 H), 2.15–2.03 (m, 4 H), 1.96–1.86 (m, 4 H).

EXAMPLE 22 cis-N-(7-chloroquinolin-4-yl)-N'-(5,7-dichloro-2-(trifluoromethyl)quinolin-4-yl)cyclohexane-1,4-diamine The titled compound was prepared according to the method described in Example 3 by substituting 4,5,7-tichloro-2-trifluoromethylquinoline for 4-chloro-2,8-bis(trifluoromethyl)-quinoline. MS (ESI(+)Q1MS m/z 540 (M+H)$^+$; $^1$H NMR (300 MHz, DMSO) δ ppm 8.76 (d, 1 H), 8.55 (d, 1 H), 8.00 (d, 1 H), 7.97 (d, 1 H), 7.82 (d, 1 H), 7.78–7.71 (m, 3 H), 7.00 (d. 1 H), 6.95 (s, 1 H), 4.18–4.10 (m, 1 H), 4.05–3.98 (m, 1 H), 2.10–2.01 (m, 4 H), 1.96–1.86 (m, 4 H).

EXAMPLE 23 cis-N-{4-((7-chloroquinolin-4-yl)amino) cyclohexyl}-1 H-indole-6-carboxamide

EXAMPLE 23A cis-N-(7-chloroquinolin-4-yl)cyclohexane-1,4-diamine

A mixture of 4,7-dichloroquinoline(2 g, 10.2 mmol) and 1,4-cyclohexanediamine (2.5 g, 21.9 mmol) was heated at 250° C. for 15 hours, cooled to room temperature, diluted with ethanol, and filtered. The residue was extracted with chloroform from 50%NaOH solution. The extract was dried with Na$_2$SO$_4$ and MgSO$_4$, filtered and concentrated to give the desired compound. MS (ESI(+)Q1MS m/z 276 (M+H)$^+$.

EXAMPLE 23B cis-N-{4-((7-chloroquinolin-4-yl)amino)cyclohexyl}-1 H-indole-6-carboxamide A mixture Example 23A (50 mg, 0.18 mmol), indole-6-carboxylic acid (30 mg, 0.18 mmol), solid supported dicyclohexanecarbodiimide (0.36 mmol), 1-hydroxy-7-azabenzotriazole (5 mg, 0.036 mmol) and diisopropylethylamine (46 mg, 0.36 mmol) in 1 ml N,N-dimethylformamide was shaken for 15 hours, filtered. The filtrate was the concentrated and the residue was purified by HPLC to provide the desired compound as its trifluoroacetic acid salt. MS (ESI(+)Q1MS m/z 419 (M+H)$^+$; $^1$H NMR (300 MHz, DMSO) δ ppm 13.71 (s, 1 H), 11.32 (s, 1 H), 8.83 (d, 1 H), 8.72 (d, 1 H), 8.57 (d, 1 H), 7.97 (d, 1 H), 7.95 (s, 1 H), 7.93 (d, 1 H), 7.81 (dd, 1 H), 7.58 (s, 2 H), 7.50 (t, 2 H), 7.00 (d, 2 H), 6.49 (m, 1 H), 4.02 (s, 1 H), 1.90–2.15 (m, 3 H), 1.68–1.90 (m, 3 H).

EXAMPLE 24 cis-N-{4-((7-chloroquinolin-4-yl)amino)cyclohexyl}-1-(3,4-dichlorophenyl)methanesulfonamide The titled compound was prepared according to the method described in Example 15 by substituting (3,4-dichlorophenyl)methanesulfonyl chloride for 4-chlorobenzene sulfonyl chloride. MS (ESI (+)) m/e 499 (M+H)$^+$; $^1$H NMR (500 MHz, DMSO) δ ppm 8.84 (d, 1 H), 8.70 (d, 1 H), 8.54 (d, 1 H), 7.94 (d, 1 H), 7.79 (dd, 1 H), 7.67 (m, 2 H), 7.40 (dd, 1 H), 7.12 (d, 1 H), 6.96 (d, 1 H), 4.45 (s, 2 H), 3.90 (br.s, 1 H), 3.50 (m, 1 H), 1.87 (m, 4 H), 1.70 (m, 4 H).

EXAMPLE 25 cis-N-(7-chloroquinolin-4-yl)-N'-(1 H-indol-6-ylmethyl)cyclohexane-1,4-diamine

A mixture of example 23A (30 mg, 0.11 mmol), 6-formylindole (19.2 mg, 0.132 mmol) and solid supported cyanoborohydride (0.22 mmol) was shaken in 1:1 mixture tetrahydrofuran and acetic acid for 15 hours, filtered and concentrated. The residue was purified with a high throughput HPLC system to provide the desired compound as its bis TRIFLUOROACETIC ACID salt. MS (ESI(+)Q1MS m/z 405 (M+H)$^+$; $^1$H NMR (300 MHz, DMSO-D6) δ ppm 11.31 (s, 1 H), 8.74 (d, 1 H), 8.49–8.79 (m, 2 H), 7.96 (d, 1 H), 7.85 (dd, 1 H), 7.62 (d, 1 H), 7.56 (s, 1 H), 7.45 (t, 1 H), 7.13 (d, 1 H), 6.94 (d, 1 H), 6.47 (t, 1 H), 4.28 (br.s, 1 H), 4.08 (br.s, 1 H), 2.27 (s, 2 H), 1.73–2.13 (m, 9 H).

EXAMPLE 26 cis-N-{4-((7-chloroquinolin-4-yl)amino)cyclohexyl}-1-(3,5-dichlorophenyl)methanesulfonamide The titled compound was prepared according to the method described in Example 15 by substituting (3,5-dichlorophenyl)methanesulfonyl chloride for 4-chlorobenzene sulfonyl chloride. MS (ESI (+)) m/e 500 (M+H)$^+$; $^1$H NMR (500 MHz, DMSO) δ ppm 8.82 (d, 1 H), 8.70 (d, 1 H), 8.53 (d, 1 H), 7.92 (d, 1 H), 7.79 (dd, 1 H), 7.63 (t, 1 H), 7.46 (d, 2 H), 7.17 (d, 1 H), 6.95 (d, 1 H), 4.47 (s, 2 H), 3.89 (br.s, 1 H), 3.49 (br.s, 1 H), 1.62–1.93 (m, 8 H).

EXAMPLE 27 cis-N-{4-((7-chloroquinolin-4-yl)amino)cyclohexyl}-N'-(3-(methylthio)phenyl)urea The titled compound was prepared according to the method described in Example 2 by substituting 3-(methylthio)phenyl isocyanate for 4-chlorophenyl isocyanate. MS (ESI (+)) m/e 441 (M+H)$^+$; $^1$H NMR (500 MHz, DMSO) δ ppm 8.77 (d, 1 H), 8.70 (d, 1 H), 8.55 (d, 1 H), 8.50 (s, 1 H), 7.93 (d, 1 H), 7.78 (dd, 1 H), 7.44 (t, 1 H), 7.16 (t, 1 H), 7.05 (m, 1 H), 6.97 (d, 1 H), 6.79 (m, 1 H), 6.36 (d, 1 H), 3.91 (br.s, 1 H), 3.80 (br.s, 1 H), 2.43 (s, 3 H), 1.79 (m, 8 H).

EXAMPLE 28 cis-N-(2-chlorophenyl)-N'-{4-((7-chloroquinolin-4-yl)amino)cyclohexyl}urea

The titled compound was prepared according to the method described in Example 2 by substituting 2-chlorophenyl isocyanate for 4-chlorophenyl isocyanate. MS (ESI (+)) m/e 429 (M+H)$^+$; $^1$H NMR (500 MHz, DMSO) δ ppm 8.89 (d, 1 H), 8.72 (d, 1 H), 8.55 (d, 1 H), 8.21 (dd, 1 H), 8.09 (s, 1 H), 7.94 (d, 1 H), 7.79 (dd, 1 H), 7.40 (dd, 1 H), 7.22 (m, 2 H), 7.00 (d, 1 H), 6.94 (td, 1 H), 3.93 (br.s, 1 H), 3.82 (m, 1 H), 1.67–1.96 (m, 8 H).

EXAMPLE 29 cis-N-{4-((7-chloroquinolin-4-yl)amino)cyclohexyl}-N'-(2-(trifluoromethyl)phenyl)urea The titled compound was prepared according to the method described in Example 2 by substituting 2-(trifluoromethyl)phenyl isocyanate for 4-chlorophenyl isocyanate. MS (ESI (+)) m/e 463 (M+H)$^+$; $^1$H NMR (500 MHz, DMSO) δ ppm 8.88 (d, 1 H), 8.72 (d, 1 H), 8.55 (d, 1 H), 8.03 (d, 1 H), 7.94 (d, 1 H), 7.83 (s, 1 H), 7.79 (dd, 1 H), 7.61 (d, 1 H), 7.57 (m, 1 H), 7.18 (m, 2 H), 7.00 (d, 1 H), 3.93 (br.s, 1 H), 3.81 (br.s, 1 H), 1.70–1.94 (m, 8 H).

EXAMPLE 30 cis-N-{4-((7-chloroquinolin-4-yl)amino)cyclohexyl}-N'-(3-(trifluoromethyl)phenyl)urea The titled compound was prepared according to the method described in Example 2 by substituting 3-(trifluoromethyl)phenyl isocyanate for 4-chlorophenyl isocyanate. MS (ESI (+)) m/e 463 (M+H)$^+$; $^1$H NMR (500 MHz, DMSO) δ ppm 8.89 (s, 1 H), 8.78 (d, 1 H), 8.71 (d, 1 H), 8.55 (d, 1 H), 8.01 (s, 1 H), 7.93 (d, 1 H), 7.79 (dd, 1 H), 7.46 (d, 2 H), 7.23 (m, 1 H), 6.98 (d, 1 H), 6.52 (d, 1 H), 3.92 (br.s, 1 H), 3.82 (br.s, 1 H), 1.69–1.93 (m, 8 H).

EXAMPLE 31 cis-N-{4-((7-chloroquinolin-4-yl)amino)cyclohexyl}-N'-(4-(trifluoromethyl)phenyl)urea The titled compound was prepared according to the method described in Example 2 by substituting 4-(trifluoromethyl)phenyl isocyanate for 4-chlorophenyl isocyanate. MS (ESI (+)) m/e 463 (M+H)$^+$; $^1$H NMR (500 MHz, DMSO) δ ppm 8.94 (s, 1 H), 8.82 (d, 1 H), 8.71 (d, 1 H), 8.55 (d, 1 H), 7.94 (d, 1 H), 7.79 (dd, 1 H), 7.58 (dd, 4 H), 6.99 (d, 1 H), 6.55 (d, 1 H), 3.94 (br.s, 1 H), 3.83 (br.s, 1 H), 1.68–1.91 (m, 8 H).

EXAMPLE 32 cis-N-{4-((7-chloroquinolin-4-yl)amino)
cyclohexyl}-N'-(4-(trifluoromethoxy)phenyl)urea The titled compound was prepared according to the method described in Example 2 by substituting 4-trifluoromethoxyphenyl isocyanate for 4-chlorophenyl isocyanate. MS (ESI (+)) m/e 479 (M+H)$^+$; $^1$H NMR (500 MHz, DMSO) δ ppm 8.86 (d, 1 H), 8.71 (s, 2 H), 8.55 (d, 1 H), 7.94 (d, 1 H), 7.80 (dd, 1 H), 7.49 (d, 2 H), 7.22 (d, 2 H), 7.00 (d, 1 H), 6.44 (d, 1 H), 3.94 (br.s, 1 H), 3.81 (br.s, 1 H), 1.68–1.93 (m, 8 H).

EXAMPLE 33 cis-N-1,3-benzodioxol-5-yl-N'-{4-((7-chloroquinolin-4-yl)amino)cyclohexyl}urea

The titled compound was prepared according to the method described in Example 2 by substituting 3,4-(Methylenedioxy)phenyl isocyanate for 4-chlorophenyl isocyanate. MS (ESI (+)) m/e 439 (M+H)$^+$; $^1$H NMR (500 MHz, DMSO) δ ppm 8.79 (d, 1 H), 8.70 (d, 1 H), 8.55 (d, 1 H), 8.30 (s, 1 H), 7.92 (d, 1 H), 7.79 (dd, 1 H), 7.18 (d, 1 H), 6.98 (d, 1 H), 6.77 (d, 1 H), 6.66 (dd, 1 H), 6.22 (d, 1 H), 5.93 (s, 2 H), 3.91 (br.s, 1 H), 3.78 (br.s, 1 H), 1.67–1.89 (m, 8 H).

EXAMPLE 34 cis-N-{4-((7-chloroquinolin-4-yl)amino)
cyclohexyl}-N'-3-((trifluoromethyl)thio)phenyl}urea The titled compound was prepared according to the method described in Example 2 by substituting 3-trifluoromethylthiophenyl isocyanate for 4-chlorophenyl isocyanate. MS (ESI (+)) m/e 496 (M+H)$^+$; $^1$H NMR (500 MHz, DMSO) δ ppm 8.81 (m, 2 H), 8.71 (d, 1 H), 8.55 (d, 1 H), 7.96 (m, 1 H), 7.93 (d, 1 H), 7.79 (dd, 1 H), 7.46 (m, 1 H), 7.39 (t, 1 H), 7.23 (d, 1 H), 6.99 (d, 1 H), 6.48 (d, 1 H), 3.93 (br.s, 1 H), 3.81 (br.s, 1 H), 1.65–1.92 (m, 8 H).

EXAMPLE 35 cis-N-(3-bromophenyl)-N'-{4-((7-chloroquinolin-4-yl)amino)cyclohexyl}urea

The titled compound was prepared according to the method described in Example 2 by substituting 3-bromophenyl isocyanate for 4-chlorophenyl isocyanate. MS (ESI (+)) m/e 474 (M+H)$^+$; $^1$H NMR (500 MHz, DMSO) δ ppm 8.84 (d, 1 H), 8.71 (m, 2 H), 8.55 (d, 1 H), 7.94 (d, 1 H), 7.84 (m, 1 H), 7.79 (dd, 1 H), 7.19 (m, 2 H), 7.07 (m, 1 H), 6.99 (d, 1 H), 6.48 (d, 1 H), 3.93 (br.s, 1 H), 3.78 (br.s, 1 H), 1.64–1.92 (m, 8 H).

EXAMPLE 36 cis-N-(4-bromophenyl)-N'-{4-((7-chloroquinolin-4-yl)amino)cyclohexyl}urea

The titled compound was prepared according to the method described in Example 2 by substituting 4-bromophenyl isocyanate for 4-chlorophenyl isocyanate. MS (ESI (+)) m/e 474 (M+H)$^+$; $^1$H NMR (500 MHz, DMSO) δ ppm 8.82 (d, 1 H), 8.71 (d, 1 H), 8.63 (s, 1 H), 8.55 (d, 1 H), 7.93 (d, 1 H), 7.79 (dd, 1 H), 7.38 (d, 1 H), 7.38 (d, 4 H), 6.41 (d, 1 H), 3.92 (br.s, 1 H), 3.81 (br.s, 1 H), 1.70–1.91 (m, 8 H).

EXAMPLE 37 cis-N-{4-((7-chloroquinolin-4-yl)amino)
cyclohexyl}-N'-(3,4-dichlorophenyl)urea

The titled compound was prepared according to the method described in Example 2 by substituting 3,4-dichlorophenyl isocyanate for 4-chlorophenyl isocyanate. MS (ESI (+)) m/e 464 (M+H)$^+$; $^1$H NMR (500 MHz, DMSO) δ ppm 8.87 (s, 1 H), 8.76 (d, 1 H), 8.70 (d, 1 H), 8.55 (d, 1 H), 7.93 (d, 1 H), 7.87 (d, 1 H), 7.78 (dd, 1 H), 7.45 (d, 1 H), 7.23 (dd, 1 H), 6.97 (d, 1 H), 6.54 (d, 1 H), 3.92 (br.s, 1 H), 3.80 (br.s, 1 H), 1.68–1.92 (m, 8 H).

EXAMPLE 38 cis-N,N'-bis((4E)-7-chloro-1-methylquinolin-4(1H)-ylidene)cyclohexane-1,4-diamine A mixture of example 1 (200 mg, 0.46 mmol), and sodium hydride (10 mg, 4.6 mmol) in THF at 0° C. was treated with methyl iodide (261 mg, 1.8 mmol), warmed up to room temperature, stirred for 15 hours, cooled down to 0° C., treated with water, treated with methanol, and filtered to provide the titled compound. MS (ESI(+)Q1MS m/z 465 (M+H)$^+$; $^1$H NMR (300 MHz, DMSO-D6) δ ppm 8.32 (d, 2 H), 7.32 (s, 2 H), 7.11–7.28 (m, 4 H), 5.92 (d, 2 H), 3.49 (s, 6 H), 1.47–1.93 (m, 10 H).

EXAMPLE 39 cis-N-{4-((7-chloroquinolin-4-yl)amino)
cyclohexyl}-N'-(2,4-dichlorophenyl)urea

The titled compound was prepared according to the method described in Example 2 by substituting 2,4-dichlorophenyl isocyanate for 4-chlorophenyl isocyanate. MS (ESI (+)) m/e 465 (M+H)$^+$; $^1$H NMR (500 MHz, DMSO) δ ppm 8.77 (d, 1 H), 8.70 (d, 1 H), 8.55 (s, 1 H), 8.25 (d, 1 H), 8.18 (s, 1 H), 7.93 (d, 1 H), 7.77 (dd, 1 H), 7.55 (d, 1 H), 7.32 (dd, 1 H), 7.24 (d, 1 H), 6.97 (d, 1 H), 3.91 (br.s, 1 H), 3.81 (br.s, 1 H), 1.66–1.95 (m, 8 H).

EXAMPLE 40 cis-N-{4-((7-chloroquinolin-4-yl)amino)
cyclohexyl}-N'-(3,5-dichlorophenyl)urea

The titled compound was prepared according to the method described in Example 2 by substituting 3,5-dichlorophenyl isocyanate for 4-chlorophenyl isocyanate. MS (ESI (+)) m/e 464 (M+H)$^+$; $^1$H NMR (500 MHz, DMSO) δ ppm 8.92 (s, 1 H), 8.74 (d, 1 H), 8.70 (d, 1 H), 8.54 (d, 1 H), 7.92 (d, 1 H), 7.78 (dd, Hz, 1 H), 7.47 (d2 H), 7.07 (t, 1 H), 6.97 (d, 1 H), 6.58 (d, 1 H), 3.92 (br.s, 1 H), 3.80 (br.s, 1 H), 1.65–1.91 (m, 8 H).

EXAMPLE 41 cis-N-{4-((7-chloroquinolin-4-yl)amino)
cyclohexyl}-N'-1-naphthylurea

The titled compound was prepared according to the method described in Example 2 by substituting 1-naphthyl isocyanate for 4-chlorophenyl isocyanate. MS (ESI (+)) m/e 445 (M+H)$^+$; $^1$H NMR (500 MHz, DMSO) δ ppm 8.91 (d, 1 H), 8.74 (d, 1 H), 8.57 (m, 2 H), 8.12 (d, 1 H), 8.08 (dd, 1 H), 7.95 (d, 1 H), 7.90 (d, 1 H), 7.80 (dd, 1 H), 7.54 (m, 3 H), 7.42 (t, 1 H), 7.02 (d, 1 H), 6.86 (d, 1 H), 3.97 (br.s, 1 H), 3.88 (br.s, 1 H), 1.72–1.97 (m, 8 H).

EXAMPLE 42 cis-N-{4-((7-chloroquinolin-4-yl)amino)cyclohexyl}-N'-2-naphthylurea

The titled compound was prepared according to the method described in Example 2 by substituting 2-naphthyl isocyanate for 4-chlorophenyl isocyanate. MS (ESI (+)) m/e 445 (M+H)$^+$; $^1$H NMR (500 MHz, DMSO) δ ppm 8.80 (m, 1 H), 8.71 (d, 1 H), 8.66 (s, 1 H), 8.55 (d, 1 H), 8.03 (d, 1 H), 7.93 (d, 1 H), 7.80 (m, 3 H), 7.73 (d, 1 H), 7.43 (m (m, 1 H), 6.99 (d, 1 H), 6.42 (d, 1 H), 3.92 (br.s, 1 H), 3.92 (br.s, 1 H), 1.72–1.94

EXAMPLE 43 cis-N-benzyl-N'-{4-((7-chloroquinolin-4-yl)amino)cyclohexyl}urea

The titled compound was prepared according to the method described in Example 2 by substituting benzyl isocyanate for 4-chlorophenyl isocyanate. MS (ESI (+)) m/e 409 (M+H)$^+$; $^1$H NMR (500 MHz, DMSO) δ ppm 8.75 (m, 1 H), 8.69 (d, 1 H), 8.53 (d, 1 H 7.92 (d, 1 H), 7.77 (dd, 1 H), 7.28 (m, 5 H), 6.95 (d, 1 H), 6.28 (t, 1 H), 6.03 ( 2 H), 3.86 (br.s, 1 H), 3.71 (br.s, 1 H), 1.60–1.86 (m, 8 H).

EXAMPLE 44 cis-N-(3-chlorophenyl)-N'-{4-((7-chloroquinolin-4-yl)amino)cyclohexyl}urea

The titled compound was prepared according to the method described in Example 2 by substituting 3-chlorophenyl isocyanate for 4-chlorophenyl isocyanate. MS (ESI (+)) m/e 429 (M+H)$^+$; $^1$H NMR (500 MHz, DMSO) δ ppm 8.71 (m, 2 H), 8.64 (s, 1 H), 8.54 (d, 1 H), 7.92 (d, 1 H), 7.78 (dd, 1 H), 7.69 (t, 1 H), 7.24 (t, 1 H), 7.15 (d, 1 H), 6.96 (m, 2 H), 6.39 (d, 1 H), 3.91 (br.s, 1 H), 3.80 (br.s, 1 H), 1.67–1.91 (m, 8 H).

EXAMPLE 45 cis-N-{4-((7-chloroquinolin-4-yl)amino)cyclohexyl}-3-methylbenzamide

The titled compound was prepared according to the methods described in Example 23, substituting m-toluic acid for indole-6-carboxylic acid. MS (ESI(+)Q1MS m/z 394 (M+H)$^+$; $^1$H NMR (500 MHz, DMSO-D6) δ ppm 8.69 (d, 2 H), 8.55 (d, 1 H), 8.03 (d, 1 H), 7.92 (d, 1 H), 7.79 (d, 1 H), 7.69 (s, 1 H), 7.66 (m, 1 H), 7.35 (m, 2 H), 6.97 (d, 1 H), 3.98 (m, 2 H), 2.37 (s, 3 H), 1.99 (m, 4 H), 1.77 (m, 4 H).

EXAMPLE 46 cis-N-{4-((7-chloroquinolin-4-yl)amino)cyclohexyl}-4-methylbenzamide

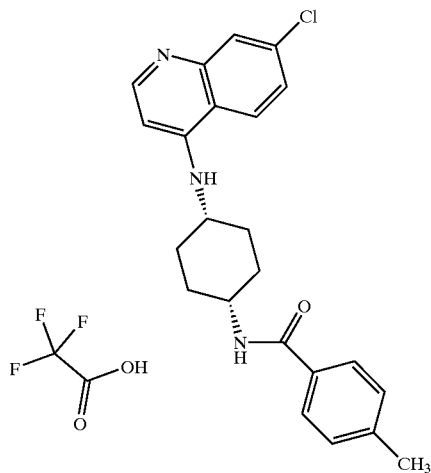

The titled compound was prepared according to the methods described in Example 23, substituting p-toluic acid for indole-6-carboxylic acid. MS (ESI(+)Q1MS m/z 394 (M+H)$^+$); $^1$H NMR (500 MHz, DMSO-D6) δ ppm 8.80 (d, 1 H), 8.71 (d, 1 H), 8.56 (d, 1 H), 7.98 (d, 1 H), 7.93 (d, 1 H), 7.81 (d, 1 H), 7.79 (d, 2 H), 7.27 (d, 2 H), 6.99 (d, 1 H), 3.99 (m, 2 H), 2.36 (s, 3 H), 1.90–2.06 (m, 4 H), 1.65–1.86 (m, 4 H).

EXAMPLE 47 cis-2-amino-N-{4-((7-chloroquinolin-4-yl)amino)cyclohexyl}benzamide

The titled compound was prepared according to the methods described in Example 23, substituting N-Boc-2-aminobenzoic acid for indole-6-carboxylic acid. MS (ESI(+)Q1MS m/z 395 (M+H)$^+$); $^1$H NMR (500 MHz, DMSO-D6) δ ppm 8.82 (d, 1 H), 8.71 (d, 1 H), 8.55 (d, 1 H), 7.94 (s, 1 H), 7.86 (d, 1 H), 7.80 (dd, 1 H), 7.56 (d, 1 H), 7.17 (t, 1 H), 6.99 (d, 1 H), 6.73 (d, 1 H), 6.57 (t, 1 H), 4.88 (t, 1 H), 4.05 (t, 1 H), 3.99 (br.s, 2 H), 1.91–2.06 (m, 4 H), 1.66–1.85 (m, 4 H).

EXAMPLE 48 cis-N-{4-((7-chloroquinolin-4-yl)amino)cyclohexyl}-2-hydroxybenzamide

The titled compound was prepared according to the methods described in Example 23, substituting salicylic acid for indole-6-carboxylic acid. MS (ESI(+)Q1MS m/z 396 (M+H)$^+$); $^1$H NMR (500 MHz, DMSO-D6) δ ppm 8.83 (d, 1 H), 8.63 (d, 1 H), 7.78 (dd, 2 H), 7.73 (d, 1 H), 7.59 (dd, 2 H), 7.48 (t, 1 H), 7.42 (m, 1 H), 6.85–6.94 (m, 2 H), 6.82 (d, 1 H), 4.88 (t, 1 H), 4.05 (t, 1 H), 2.02–2.10 (m, 4 H), 1.85–1.93 (m, 4 H).

EXAMPLE 49 cis-N-{4-((7-chloroquinolin-4-yl)amino)cyclohexyl}-3-hydroxybenzamide

The titled compound was prepared according to the methods described in Example 23, substituting 3-Hydoxybenzoic acid for indole-6-carboxylic acid. MS (ESI(+)Q1MS m/Z 396 (M+H)+); ¹H NMR (500 MHz, DMSO-D6) δ ppm 8.83 (d, 1 H), 8.80 (d, 1 H), 8.71 (d, 1 H), 8.62 (d, 1 H), 8.56 (d, 1 H), 7.97 (d, 1 H), 7.93 (d, 1 H), 7.80 (dd, 1 H), 7.59 (dd, 1 H), 7.22–7.32 (m, 3 H), 6.99 (d, 1 H), 6.92 (m, 1 H), 4.88 (t, 1 H), 4.05 (t, 1 H), 1.91–2.04 (m, 3H), 1.68–1.84 (m, 3 H).

EXAMPLE 50 cis-N-{4-((7-chloroquinolin-4-yl)amino)cyclohexyl}-3-methoxybenzamide

The titled compound was prepared according to the methods described in Example 23, substituting m-anisic acid for indole-6-carboxylic acid. MS (ESI(+)Q1MS m/z 410 (M+H)+); ¹H NMR (500 MHz, DMSO-D6) δ ppm 8.78 (d, 1 H), 8.71 (d, 1 H), 8.56 (d, 1 H), 8.06 (d, 1 H), 7.93 (d, 1 H), 7.80 (dd, 1 H), 7.46 (d, 1 H), 7.33–7.43 (m, 2 H), 7.11 (ddd, 1 H), 6.99 (d, 1 H), 3.98 (br.s, 2 H), 3.81 (s, 3 H), 1.89–2.12 (m, 4 H), 1.65–1.88 (m, 4 H).

EXAMPLE 51 cis-N-{4-((7-chloroquinolin-4-yl)amino)cyclohexyl}-4-methoxybenzamide

The titled compound was prepared according to the methods described in Example 23, substituting p-anisic acid for indole-6-carboxylic acid. MS (ESI(+)Q1MS m/z 410 (M+H)+); ¹H NMR (500 MHz, DMSO-D6) δ ppm 8.68 (d, 1 H), 8.54 (d, 1 H), 7.91 (d, 2 H), 7.87 (d, 2 H), 7.77 (d, 1 H), 6.99 (d, 2 H), 6.95 (d, 1 H), 3.96 (m, 2 H), 3.81 (s, 3 H), 1.91–2.04 (m, 5 H), 1.76 (m, 4 H).

EXAMPLE 52 cis-N-{4-((7-chloroquinolin-4-yl)amino)cyclohexyl}-3-fluorobenzamide

The titled compound was prepared according to the methods described in Example 23, substituting 3-fluorobenzoic acid for indole-6-carboxylic acid. MS (ESI(+)Q1MS m/z 398 (M+H)+; ¹H NMR (500 MHz, DMSO-D6) δ ppm 8.69 (d, 2 H), 8.55 (d, 1 H), 8.20 (d, 1 H), 7.92 (d, 1 H), 7.79 (dd, 1 H), 7.73 (d, 1 H), 7.69 (ddd, 1 H), 7.53 (td, 1 H), 7.39 (m, 1 H), 6.98 (d, 1 H), 3.98 (m, 2 H), 1.91–2.11 (m, 4 H), 1.66–1.86 (m, 4 H).

EXAMPLE 53 cis-N-{4-((7-chloroquinolin-4-yl)amino)cyclohexyl}-4-fluorobenzamide

The titled compound was prepared according to the methods described in Example 23, substituting 4-fluorobenzoic acid for indole-6-carboxylic acid. MS (ESI(+)Q1MS m/z 398 (M+H)+; ¹H NMR (500 MHz, DMSO-D6) δ ppm 8.74 (d, 1 H), 8.70 (d, 1 H), 8.55 (d, 1 H), 8.12 (d, 1 H), 7.90–7.99 (m, 3 H), 7.79 (dd, 1 H), 7.30 (t, 2 H), 6.98 (d, 1 H), 3.98 (m, 2 H), 1.89–2.11 (m, 4 H), 1.68–1.87 (m, 4 H).

EXAMPLE 54 cis-4-chloro-N-{4-((7-chloroquinolin-4-yl)amino)cyclohexyl}benzamide

The titled compound was prepared according to the methods described in Example 23, substituting 4-chlorobenzoic acid for indole-0.6-carboxylic acid. MS (ESI(+)Q1MS m/z 414 (M+H)+; ¹H NMR (500 MHz, DMSO-D6) δ ppm 8.69 (d, 1 H), 8.65 (br.s, 1 H), 8.55 (d, 1 H), 8.19 (d, 1 H), 7.92 (m, 3 H), 7.78 (dd, 1 H), 7.56 (t, 2 H), 6.96 (d, 1 H), 3.98 (m, 2 H), 1.90–2.07 (m, 4 H), 1.68–1.84 (m, 4 H).

EXAMPLE 55 cis-2-bromo-N-{4-((7-chloroquinolin-4-yl)amino)cyclohexyl}benzamide

The titled compound was prepared according to the methods described in Example 23, substituting 2-bromobenzoic acid for indole-6-carboxylic acid. MS (ESI(+)Q1MS m/z 458 and 460 (M+H)+); ¹H NMR (500 MHz, DMSO-D6) δ ppm 8.73 (br.s, 1 H), 8.71 (d, 1 H), 8.34 (d, 1 H), 7.91 (d, 1 H), 7.77 (d, 1 H), 7.65 (d, 1 H), 7.30–7.50 (m, 3 H), 6.96 (d, 1 H), 4.00 (m, 1 H), 3.90 (m, 1 H), 1.87–2.12 (m, 4 H), 1.58–1.89 (m, 5 H).

EXAMPLE 56 cis-3-bromo-N-{4-((7-chloroquinolin-4-yl)amino)cyclohexyl}benzamide

The titled compound was prepared according to the methods described in Example 23, substituting 3-bromobenzoic acid for indole-6-carboxylic acid. MS (ESI(+)Q1MS m/z 458 and 460 (M+H)+); ¹H NMR (500 MHz, DMSO-D6) δ ppm 8.70 (d, 1 H), 8.55 (d, 1 H), 8.25 (d, 1 H), 8.08 (t, 1 H), 7.92 (d, 1 H), 7.87 (d, 1 H), 7.79 (dd, 1 H), 7.74 (m, 1 H), 7.46 (m, 1 H), 6.97 (d, 1 H), 6.49 (s, 1 H), 3.98 (m, 2 H), 1.90–2.07 (m, 4 H), 1.69–1.87 (m, 4 H).

EXAMPLE 57 cis-4-bromo-N-{4-((7-chloroquinolin-4-yl)amino)cyclohexyl}benzamide

The titled compound was prepared according to the methods described in Example 23, substituting 4-bromobenzoic acid for indole-6-carboxylic acid. MS (ESI(+)Q1MS m/z 458 and 460 (M+H)+); ¹H NMR (500 MHz, DMSO-D6) δ ppm 8.70 (d, 1 H), 8.55 (d, 1 H), 8.19 (d, 1 H), 7.81–7.88 (m, 3 H), 7.79 (dd, 1 H), 7.67–7.73 (m, 3 H), 6.97 (d, 1 H), 3.99 (br.s, 2 H), 1.88–2.06 (m, 4 H), 1.66–1.86 (m, 4 H).

EXAMPLE 58 cis-N-{4-((7-chloroquinolin-4-yl)amino)cyclohexyl}-4-cyanobenzamide

The titled compound was prepared according to the methods described in Example 23, substituting 4-cyanobenzoic acid for indole-6-carboxylic acid. MS (ESI(+)Q1MS m/z 405 (M+H)+); ¹H NMR (500 MHz, DMSO-D6) δ ppm 8.68 (d, 1 H), 8.38 (d, 1 H), 8.02 (d, 2 H), 7.98 (d, 2 H), 7.91 (d, 1 H), 7.78 (dd, 1 H), 6.96 (d, 1 H), 6.48 (s, 1 H), 3.96 (m, 2 H), 1.90–2.08 (m, 4 H), 1.69–1.86 (m, 4 H).

EXAMPLE 59 cis-N-{4-((7-chloroquinolin-4-yl)amino)cyclohexyl}-3-(dimethylamino)benzamide

The titled compound was prepared according to the methods described in Example 23, substituting 3-dimethylaminobenzoic acid for indole-6-carboxylic acid. MS (ESI(+)Q1MS m/z 423 (M+H)+); ¹H NMR (500 MHz, DMSO-D6) δ ppm 8.80 (d, 1 H), 8.71 (d, 1 H), 8.56 (d, 1 H), 7.91–7.96 (m, 2 H), 7.80 (dd, 1 H), 7.26 (t, 1 H), 7.17 (d, 1 H), 6.99 (d, 1 H), 6.88 (dd, 1 H), 4.88 (t, 1 H), 4.05 (t, 1 H), 3.94–4.08 (m, 2 H), 2.54 (s, 6 H), 1.88–2.09 (m, 4 H), 1.54–1.89 (m, 4 H).

EXAMPLE 60 cis-N-{4-((7-chloroquinolin-4-yl)amino)cyclohexyl}-3-cyanobenzamide

The titled compound was prepared according to the methods described in Example 23, substituting 3-cyanobenzoic acid for indole-6-carboxylic acid. MS (ESI(+)Q1MS m/z 405 (M+H)+); ¹H NMR (500 MHz, DMSO-D6) δ ppm 8.72 (br.s, 1 H), 8.69 (d, 1 H), 8.55 (d, 1 H), 8.33 (d, 1 H), 8.17 (d, 1 H), 8.02 (d, 1 H), 7.92 (d, 1 H), 7.79 (dd, 1 H), 7.71 (t, 1 H), 6.98 (d, 1 H), 6.48 (s, 1 H), 3.99 (m, 2 H), 1.91–2.12 (m, 4 H), 1.78 (m, 4 H).

EXAMPLE 61 cis-N-{4-((7-chloroquinolin-4-yl)amino)cyclohexyl}-4-(dimethylamino)benzamide

The titled compound was prepared according to the methods described in Example 23, substituting 4-dimethylaminobenzoic acid for indole-6-carboxylic acid. MS (ESI(+)Q1MS m/z 423 (M+H)+); ¹H NMR (500 MHz, DMSO-D6) δ ppm 8.81 (d, 1 H), 8.71 (d, 1 H), 8.63 (d, 1 H), 8.55 (d, 1 H), 7.93 (d, 1 H), 7.80 (dd, 1 H), 7.77 (d, 2 H), 7.66 (d, 1 H), 7.59 (dd, 1 H), 6.99 (d, 2 H), 4.88 (t, 1 H), 4.05 (t, 1 H), 2.99 (s, 6 H), 1.88–1.97 (m, 4H), 1.65–1.86 (m, 4 H).

EXAMPLE 62 cis-N-{4-((7-chloroquinolin-4-yl)amino)cyclohexyl}-3-(trifluoromethyl)benzamide

The titled compound was prepared according to the methods described in Example 23, substituting 3-(trifluoromethyl)benzoic acid for indole-6-carboxylic acid. MS (ESI(+)Q1MS m/z 448 (M+H)+); ¹H NMR (500 MHz, DMSO-D6) δ ppm 8.83 (d, 1 H), 8.72 (d, 1 H), 8.56 (d, 1 H), 8.40 (d, 1 H), 8.22 (s, 1 H), 8.19 (d, 1 H), 7.93 (d, 1 H), 7.91 (s, 1 H), 7.81 (dd, 1 H), 7.73 (t, 1 H), 7.00 (d, 1 H), 3.94–4.08 (m, 2 H), 1.92–2.07 (m, 4 H), 1.70–1.88 (m, 4 H).

EXAMPLE 63 cis-N-{4-((7-chloroquinolin-4-yl)amino)cyclohexyl}-4-(trifluoromethyl)benzamide

The titled compound was prepared according to the methods described in Example 23, substituting 4-(trifluoromethyl)benzoic acid for indole-6-carboxylic acid. MS (ESI(+)Q1MS m/z 448 (M+H)+); ¹H NMR (500 MHz, DMSO-D6) δ ppm 8.81 (d, 1 H), 8.71 (d, 1 H), 8.56 (d, 1 H), 8.36 (d, 1 H), 8.06 (d, 2 H), 7.93 (d, 1 H), 7.86 (d, 2 H), 7.81 (dd, 1 H), 7.00 (d, 1 H), 3.90–4.08 (m, 2 H), 1.88–2.12 (m, 4 H), 1.63–1.87 (m, 4 H).

EXAMPLE 64 cis-N-{4-((7-chloroquinolin-4-yl)amino)cyclohexyl}-2,3-dimethylbenzamide

The titled compound was prepared according to the methods described in Example 23, substituting 2,3-dimethylbenzoic acid for indole-6-carboxylic acid. MS (ESI(+)Q1MS m/z 408 (M+H)+); ¹H NMR (500 MHz, DMSO-D6) δ ppm 8.71 (d, 1 H), 8.56 (d, 1 H), 8.12 (d, 1 H), 7.91 (s, 1 H), 7.80 (d, 1 H), 7.22 (t, 1 H), 7.13 (d, 1 H), 7.12 (s, 1 H), 6.99 (d, 1 H), 3.97 (br.s, 2 H), 2.26 (s, 3 H), 2.22 (s, 3 H), 1.94 (m, 5 H), 1.78 (m, 4 H).

EXAMPLE 65 cis-N-{4-((7-chloroquinolin-4-yl)amino)cyclohexyl}-2,4-dimethylbenzamide

The titled compound was prepared according to the methods described in Example 23, substituting 2,4-dimethylbenzoic acid for indole-6-carboxylic acid. MS (ESI(+)Q1MS m/z 408 (M+H)+); ¹H NMR (500 MHz, DMSO-D6) δ ppm 8.78 (s, 1 H), 8.70 (d, 1 H), 8.55 (d, 1 H), 8.03 (d, 1 H), 7.92 (s, 1 H), 7.25 (d, 1 H), 7.06 (s, 1 H), 7.04 (d, 1 H), 6.98 (d, 1 H), 6.52 (s, 1 H), 3.96 (m, 2 H), 2.33 (s, 3 H), 2.30 (s, 3 H), 1.76 (m, 4 H), 1.67–1.85 (m, 4 H).

EXAMPLE 66 cis-N-{4-((7-chloroquinolin-4-yl)amino)cyclohexyl}-3-(trifluoromethoxy)benzamide The titled compound was prepared according to the methods described in Example 23, substituting 3-(trifluoromethoxy)benzoic acid for indole-6-carboxylic acid. MS (ESI(+)Q1MS m/z 464 (M+H)+); ¹H NMR (500 MHz, DMSO-D6) δ ppm 8.70 (d, 1 H), 8.56 (d, 1 H), 8.32 (d, 1 H), 7.97 (dd, 1 H), 7.92 (d, 1 H), 7.82 (d, 1 H), 7.66 (t, 1 H), 7.63 (d, 1 H), 7.56 (d, 1 H), 6.98 (d, 1 H), 6.53 (s, 1 H), 4.00 (m, 2 H), 1.88–2.14 (m, 4 H), 1.66–1.88 (m, 4 H).

EXAMPLE 67 cis-N-{4-((7-chloroquinolin-4-yl)amino)cyclohexyl}-2,5-dimethylbenzamide

The titled compound was prepared according to the methods described in Example 23, substituting 25-dimethylbenzoic acid for indole-6-carboxylic acid. MS (ESI(+)Q1MS m/z 408 (M+H)+); ¹H NMR (500 MHz, DMSO-D6) δ ppm 8.82 (d, 1 H), 8.72 (d, 1 H), 8.56 (d, 1 H), 8.11 (d, 1 H), 7.92 (d, 1 H), 7.80 (dd, 1 H), 7.13 (br,s, 3 H), 6.99 (d, 1 H), 2.64 (m, 2 H), 2.30 (s, 3 H), 2.29 (s, 3 H), 1.96 (m, 4 H), 1.77 (m, 4 H).

EXAMPLE 68 cis-N-{4-((7-chloroquinolin-4-yl)amino)cyclohexyl}-3,4-dimethylbenzamide

The titled compound was prepared according to the methods described in Example 23, substituting 3,4-dimethylbenzoic acid for indole-6-carboxylic acid. MS (ESI(+)Q1MS m/z 408 (M+H)+); ¹H NMR (500 MHz, DMSO-D6) δ ppm 8.72 (d, 1 H), 8.57 (d, 1 H), 7.96 (d, 1 H), 7.93 (d, 1 H), 7.81 (d, 1 H), 7.70 (d, 1 H), 7.66 (d, 1 H), 7.62 (d, 1 H), 7.24 (dd, 1 H), 7.00 (d, 1 H), 3.98 (m, 2 H), 2.28 (s, 3 H), 2.27 (s, 3 H), 1.64–2.10 (m, 8 H).

EXAMPLE 69 cis-N-{4-((7-chloroquinolin-4-yl)amino)cyclohexyl}-2,4-dimethoxybenzamide

The titled compound was prepared according to the methods described in Example 23, substituting 2,4- dimethoxybenzoic acid for indole-6-carboxylic acid. MS (ESI(+)Q1MS m/z 440 (M+H)+); $^1$H NMR (500 MHz, DMSO-D6) δ ppm 8.88 (d, 1 H), 8.71 (d, 1 H), 8.56 (d, 1 H), 8.06 (d, 1 H), 7.96 (d, 1 H), 7.87 (d, J=1 H), 7.80 (dd, 1 H), 7.02 (d, 1 H), 6.71 (d, 1 H), 6.66 (dd, 1 H), 4.13 (br.s, 1 H), 4.01 (s, 3 H), 3.98 (br.s, 1 H), 3.84 (s, 3 H), 1.68–2.01 (m, 8 H).

EXAMPLE 70 cis-N-{4-((7-chloroquinolin-4-yl)amino) cyclohexyl}-3,4-dimethoxybenzamide

The titled compound was prepared according to the methods described in Example 23, substituting 3,4-dimethoxybenzoic acid for indole-6-carboxylic acid. MS (ESI(+)Q1MS m/z 440 (M+H)+); $^1$H NMR (500 MHz, DMSO-D6) δ ppm 8.84 (d, 1 H), 8.81 (d, 1 H), 8.72 (d, 1 H), 8.64 (d, 1 H), 8.57 (d, 1 H), 7.93 (d, 1 H), 7.81 (dd, 1 H), 7.54 (dd, 1 H), 7.45 (d, 1 H), 7.00 (t, 1 H), 3.99 (br.s, 2 H), 3.82 (br,s, 6 H), 1.67–2.07 (m, 8 H).

EXAMPLE 71 cis-N-{4-((7-chloroquinolin-4-yl)amino) cyclohexyl}-3,5-dimethoxybenzamide

The titled compound was prepared according to the methods described in Example 23, substituting 3,5-dimethoxybenzoic acid for indole-6-carboxylic acid. MS (ESI(+)Q1MS m/z 440 (M+H)+; $^1$H NMR (500 MHz, DMSO-D6) δ ppm 8.69 (d, 1 H), 8.56 (d, 1 H), 8.06 (d, 1 H), 7.92 (s, 2 H), 7.79 (dd, 1 H), 7.02 (s, 2 H), 6.97 (d, 1 H), 6.67 (s, 1 H), 3.98 (br.s, 2 H), 3.80 (s, 6 H), 1.87–2.10 (m, 5 H), 1.66–1.88 (m, 4 H).

EXAMPLE 72 cis-N-{4-((7-chloroquinolin-4-yl)amino) cyclohexyl}-1,3-benzodioxole-5-carboxamide The titled compound was prepared according to the methods described in Example 23, substituting piperonylic acid for indole-6-carboxylic acid. MS (ESI(+)Q1MS m/z 424 (M+H)+); $^1$H NMR (500 MHz, DMSO-D6) δ ppm 8.79 (d, 1 H), 8.71 (d, 1 H), 8.64 (dd, 1 H), 7.93 (d, 1 H), 7.81 (dd, 1 H), 7.60 (dd, 1 H), 7.49 (dd, 1 H), 7.44 (d, 1 H), 7.00 (d, 1 H), 6.99 (d, 1 H), 6.10 (s, 2 H), 3.97 (br.s, 2 H), 1.64–2.08 (m, 8 H).

EXAMPLE 73 cis-N-{4-((7-chloroquinolin-4-yl)amino) cyclohexyl}-3,4,5-trimethoxybenzamide

The titled compound was prepared according to the methods described in Example 23, substituting 3,4,5-trimethoxybenzoic acid for indole-6-carboxylic acid. MS (ESI(+)Q1MS m/z 470 (M+H)+; $^1$H NMR (500 MHz, DMSO-D6) δ ppm 8.72 (d, 1 H), 8.64 (d, 1 H), 8.57 (d, 1 H), 8.03 (d, 1 H), 7.93 (d, 1 H), 7.81 (d, 1 H), 7.60 (dd, 1 H), 7.20 (s, 2 H), 6.98 (d, 6 H), 6.98 (d, 1 H), 3.98 (br.s, 1 H), 3.71 (s, 3 H), 1.67–2.06 (m, 8 H).

EXAMPLE 74 cis-2,4-dichloro-N-{4-((7-chloroquinolin-4-yl) amino)cyclohexyl}benzamide

The titled compound was prepared according to the methods described in Example 23, substituting 2,4-dichlorobenzoic acid for indole-6-carboxylic acid. MS (ESI(+)Q1MS m/z 448 (M+H)+; $^1$H NMR (500 MHz, DMSO-D6) δ ppm 8.88 (d, 1 H), 8.74 (d, 1 H), 8.55 (d, 1 H), 8.44 (d, 1 H), 7.98 (d, 1 H), 7.77 (dd, 1 H), 7.67 (d, 1 H), 7.49 (d, 1 H), 7.47 (s, 1 H), 6.98 (d, 1 H), 4.03 (br.s, 1 H), 3.93 (br.s, 1 H), 1.69–2.01 (m, 8 H).

EXAMPLE 75 cis-3,4-dichloro-N-{4-((7-chloroquinolin-4-yl) amino)cyclohexyl}benzamide

The titled compound was prepared according to the methods described in Example 23, substituting 3,4-dichlorobenzoic acid for indole-6-carboxylic acid. MS (ESI (+)Q1MS m/z 450 (M+H)+); $^1$H NMR (500 MHz, DMSO-D6) δ ppm 8.66 (d, 1 H), 8.54 (d, 1 H), 8.34 (d, 1 H), 8.15 (d, 1 H), 8.07 (s, 1 H), 8.07 (s, 1 H), 7.84–7.91 (m, 2 H), 7.73–7.80 (m, 2 H), 3.87–4.07 (br.s, 2 H), 1.66–2.09 (m, 8 H).

EXAMPLE 76 cis-N-{4-((7-chloroquinolin-4-yl)amino) cyclohexyl}-2-furamide

The titled compound was prepared according to the methods described in Example 23, substituting furane-2-carboxylic acid for indole-6-carboxylic acid. MS (ESI(+) Q1MS m/z 370 (M+H)+); $^1$H NMR (500 MHz, DMSO-D6) δ ppm 8.68 (d, 1 H), 8.63 (dd, 1 H), 8.55 (d, 1 H), 7.92 (s, 2 H), 7.92 (d, 1 H), 7.83 (s, 1 H), 7.80 (dd, 1 H), 7.15 (dd, 1 H), 6.98 (d, 1 H), 6.63 (dd, 1 H), 4.88 (t, 1 H), 4.05 (t, 1 H), 1.66–2.04 (m, 8 H).

EXAMPLE 77 cis-N-{4-((7-chloroquinolin-4-yl)amino) cyclohexyl}-3-furamide

The titled compound was prepared according to the methods described in Example 23, substituting furane-3-carboxylic acid for indole-6-carboxylic acid. MS (ESI(+) Q1MS m/z 370 (M+H)+); $^1$H NMR (500 MHz, DMSO-D6) δ ppm 8.83 (dd, 1 H), 8.72 (d, 1 H), 8.56 (d, 1 H), 8.25 (d, 1 H), 7.93 (d, 1 H), 7.80 (dd, 1 H), 7.77 (d, 1 H), 7.72 (t, 1 H), 6.99 (d, 1 H), 6.92 (dd, 1 H), 4.88 (t, 1 H), 4.05 (t, 1 H), 1.67–2.03 (m, 8 H).

EXAMPLE 78 cis-N-{4-((7-chloroquinolin-4-yl)amino) cyclohexyl}-2,5-dimethyl-3-furamide

The titled compound was prepared according to the methods described in Example 23, substituting 2,5-dimethyl-3-furoic acid for indole-6-carboxylic acid. MS (ESI(+)Q1MS m/z 398 (M+H)+); $^1$H NMR (500 MHz, DMSO-D6) δ ppm 8.79 (d, 1 H), 8.71 (d, 1 H), 8.55 (d, 1 H), 7.93 (d, 1 H), 7.80 (dd, 1 H), 7.42 (d, 1 H), 6.98 (d, 1 H), 6.55 (s, 1 H), 3.84–4.03 (m, 2 H), 2.46 (s, 3 H), 2.22 (s, 3 H), 1.63–2.01 (m, 8 H).

EXAMPLE 79 cis-N-{4-((7-chloroquinolin-4-yl)amino) cyclohexyl}thiophene-2-carboxamide

The titled compound was prepared according to the methods described in Example 23, substituting thiophene- 2-carboxylic acid for indole-6-carboxylic acid. MS (ESI(+) Q1MS m/z 386 (M+H)+); $^1$H NMR (500 MHz, DMSO-D6) δ ppm 8.78 (d, 1 H), 8.71 (d, 1 H), 8.56 (d, 1 H), 8.09 (d, 1 H), 7.93 (d, 1 H), 7.89 (dd, 1 H), 7.80 (dd, 1 H), 7.15 (dd, 1 H), 6.98 (d, 1 H), 4.88 (t, 1 H), 4.05 (t, 1 H), 3.93–4.02 (m, 1 H), 1.68–2.08 (m, 8 H).

EXAMPLE 80 cis-N-{4-((7-chloroquinolin-4-yl)amino) cyclohexyl}thiophene-3-carboxamide

The titled compound was prepared according to the methods described in Example 23, substituting thiophene-3-carboxylic acid for indole-6-carboxylic acid. MS (ESI(+) Q1MS m/z 386 (M+H)+); $^1$H NMR (500 MHz, DMSO-D6) δ ppm 8.78 (d, 1 H), 8.71 (d, 1 H), 8.21 (d, 1 H), 7.93 (d, 1 H), 7.88 (d, 1 H), 7.79 (dd, 1 H), 7.54–7.62 (m, 2 H), 6.98 (d, 1 H), 4.88 (t, 1 H), 4.05 (t, 1 H), 3.94–4.02 (m, 1 H), 1.67–2.05 (m, 8 H).

EXAMPLE 81 cis-N-{4-((7-chloroquinolin-4-yl)amino) cyclohexyl}-3-methylthiophene-2-carboxamide The titled compound was prepared according to the methods described in Example 23, substituting 3-methylthiophene-2-carboxylic acid for indole-6-carboxylic acid. MS (ESI(+)Q1MS m/z 400 (M+H)+); $^1$H NMR (500 MHz, DMSO-D6) δ ppm 8.81 (d, 1 H), 8.73 (d, 1 H), 8.55 (d, 1 H), 7.93 (d, 1 H), 7.80 (dd, 1 H), 7.64 (d, 1 H), 7.57 (d, 1 H), 6.97–7.00 (m, 2 H), 3.90–4.04 (m, 2 H), 2.45 (s, 3 H), 1.68–2.03 (m, 8 H).

EXAMPLE 82 cis-N-{4-((7-chloroquinolin-4-yl)amino) cyclohexyl}-1 H-pyrrole-2-carboxamide

The titled compound was prepared according to the methods described in Example 23, substituting pyrolle-2-carboxylic acid for indole-6-carboxylic acid. MS (ESI(+) Q1MS m/z 369 (M+H)+); $^1$H NMR (500 MHz, DMSO-D6) δ ppm 8.80 (d, 1 H), 8.71 (d, 1 H), 8.55 (d, 1 H), 7.93 (d, 1 H), 7.79 (dd, 1 H), 7.54 (d, 1 H), 6.98 (d, 1 H), 6.84–6.89 (m, 2 H), 6.09 (dd, 1 H), 4.88 (t, 1 H), 4.88 (t, 1 H), 3.93–4.01 (m, 1 H), 1.62–2.05 (m, 8 H).

EXAMPLE 83 cis-N-{4-((7-chloroquinolin-4-yl)amino) cyclohexyl}-3,5-dimethylbenzamide

The titled compound was prepared according to the methods described in Example 23, substituting 3,5-dimethylbenzoic acid for indole-6-carboxylic acid. MS (ESI (+)Q1MS m/z 408 (M+H)+); $^1$H NMR (500 MHz, DMSO-D6) δ ppm 8.69 (d, 1 H), 8.55 (d, 1 H), 8.00 (d, 1 H), 7.92 (s, 1 H), 7.79 (d, 1 H), 7.49 (s, 2 H), 7.16 (s, 1 H), 6.97 (d, 1 H), 3.88–4.02 (m, 1 H), 2.32 (s, 6 H), 1.66–2.05 (m, 10H).

EXAMPLE 84 cis-N-{4-((7-chloroquinolin-4-yl)amino)cyclohexyl-5-methylthiophene-2-carboxamide The titled compound was prepared according to the methods described in Example 23, substituting 5-methylthiophene-2-carboxylic acid for indole-6-carboxylic acid. MS (ESI(+)Q1MS m/z 400 (M+H)+); $^1$H NMR (500 MHz, DMSO-D6) δ ppm 8.77 (d, 1 H), 8.71 (d, 1 H), 8.55 (d, 1 H), 7.94 (d, 1 H), 7.93 (d, 1 H), 7.80 (dd, 1 H), 7.69 (d, 1 H), 6.98 (d, 1 H), 6.84 (d, 1 H), 3.83–4.06 (m, 2 H), 2.46 (s, 3 H), 1.64–2.08 (m, 8 H).

EXAMPLE 85 cis-N-{4-((7-chloroquinolin-4-yl)amino) cyclohexyl}-2,5-dimethyl-1 H-pyrrole-3-carboxamide The titled compound was prepared according to the methods described in Example 23, substituting 2,5-dimethyltpyrrole-3-carboxylic acid for indole-6-carboxylic acid. MS (ESI(+)Q1MS m/z 397 (M+H)+); $^1$H NMR (500 MHz, DMSO-D6) δ ppm 8.83 (dd, 1 H), 8.78 (d, 1 H), 8.69 (d, 1 H), 8.63 (dd, 1 H), 8.55 (d, 1 H), 7.93 (d, 1 H), 7.59 (dd, 1 H), 6.98 (d, 1 H), 6.83 (d, 1 H), 4.88 (t, 1 H), 4.05 (t, 1 H), 2.11 (s, 3 H), 2.08 (s, 3 H), 1.61–1.99 (m, 8 H).

EXAMPLE 86 cis-N-{4-((7-chloroquinolin-4-yl)amino) cyclohexyl}-1,2,5-trimethyl-1 H-pyrrole-3-carboxamide The titled compound was prepared according to the methods described in Example 23, substituting 1,2,5-trimethyltpyrrole-3-carboxylic acid for indole-6-carboxylic acid. MS (ESI(+)Q1MS m/z 411 (M+H)+); $^1$H NMR (500 MHz, DMSO-D6) δ ppm 8.83 (dd, 1 H), 8.69 (d, 1 H), 8.55 (d, 1 H), 8.55 (d, 1 H), 7.80 (dd, 1 H), 6.98 (d, 1 H), 4.88 (t, 1 H), 4.05 (t, 1 H), 3.89–4.01 (m, 2 H), 3.35 (s, 3 H), 2.43 (s, 3 H), 2.15 (s, 3 H), 1.60–1.99 (m, 8 H).

EXAMPLE 87 cis-N-{4-((7-chloroquinolin-4-yl)amino) cyclohexyl}-1,3-thiazole-2-carboxamide

The titled compound was prepared according to the methods described in Example 23, substituting 1,3-thiazole carboxylic acid for indole-6-carboxylic acid. MS (ESI(+) Q1MS m/z 386 (M+H)+); $^1$H NMR (500 MHz, DMSO-D6) δ ppm 8.76 (d, 1 H), 8.65 (d, 1 H), 8.56 (d, 1 H), 8.21 (d, 1 H), 8.07 (d, 1 H), 8.03 (d, 1 H), 7.95 (d, 1 H), 7.79 (dd, 1 H), 7.00 (d, 1 H), 3.94–4.16 (m, 2 H), 1.70–2.07 (m, 8 H).

EXAMPLE 88 cis-N-{4-((7-chloroquinolin-4-yl)amino) cyclohexyl}}-1-methyl-1 H-pyrrole-2-carboxamide The titled compound was prepared according to the methods described in Example 23, substituting 1-methyltpyrrole-2-carboxylic acid for indole-6-carboxylic acid. MS (ESI(+)Q1MS m/z 383 (M+H)+); $^1$H NMR (500 MHz, DMSO-D6) δ ppm 8.76 (d, 1 H), 8.70 (d, 1 H), 8.55 (d, 1 H), 7.92 (d, 1 H), 7.80 (dd, 1 H), 6.98 (d, 1 H), 6.88 (d, 1 H), 6.01 (dd, 1 H), 4.88 (t, 1 H), 4.05 (t, 1 H), 3.88–4.02 (m, 2 H), 3.83 (s, 3 H), 1.62–2.03 (m, 8 H).

EXAMPLE 89 cis-N-{4-((7-chloroquinolin-4-yl)amino) cyclohexyl}-1,3-thiazole-4-carboxamide

The titled compound was prepared according to the methods described in Example 23, substituting 1,3-thiazole- 4-carboxylic acid for indole-6-carboxylic acid. MS (ESI(+) Q1MS m/z 387 (M+H)$^+$; $^1$H NMR (500 MHz, DMSO-D6) δ ppm 9.21 (d, 1 H), 8.83 (dd, 1 H), 8.77 (d, 1 H), 8.56 (d 1 H), 8.36 (d, 1 H), 7.93 (s, 1 H), 7.79 (dd, 1 H), 7.59 (dd, 1 H), 7.01 (d, 1 H), 4.54 (t, 1 H), 3.95 (t, 1 H), 1.69–2.04 (m, 8 H).

EXAMPLE 90 cis-N-{4-((7-chloroquinolin-4-yl)amino) cyclohexyl}-1,3-thiazole-5-carboxamide

The titled compound was prepared according to the methods described in Example 23, substituting 1,3-thiazole-5-carboxylic acid for indole-6-carboxylic acid. MS (ESI(+) Q1MS m/z 387 (M+H)$^+$; $^1$H NMR (500 MHz, DMSO-D6) δ ppm 8.83 (dd, 1 H), 8.72 (d, 1 H), 8.59 (d, 1 H), 8.56 (d, 1 H), 8.35 (d, 1 H), 7.93 (d, 1 H), 7.81 (dd, 1 H), 6.99 (d, 1 H), 4.88 (t, 1 H), 4.05 (t, 1 H), 3.91–4.03 (m, 1 H), 1.67–2.07 (m, 8 H).

EXAMPLE 91 cis-N-{4-((7-chloroquinolin-4-yl)amino) cyclohexyl}isoxazole-5-carboxamide

The titled compound was prepared according to the methods described in Example 23, substituting isoxazole-5-carboxylic acid for indole-6-carboxylic acid. MS (ESI(+) Q1MS m/z 371 (M+H)$^+$; $^1$H NMR (500 MHz, DMSO-D6) δ ppm 8.83 (dd, 1 H), 8.63 (dd, 1 H), 8.54 (d, 1 H), 7.91 (s, 1 H), 7.77 (d, 1 H), 7.59 (dd, 1 H), 4.88 (t, 1 H), 4.05 (t, 1 H), 3.96 (m, 2 H), 1.65–2.19 (m, 9 H).

EXAMPLE 92 cis-N-{4-((7-chloroquinolin-4-yl)amino) cyclohexyl}-5-methyl-3-phenylisoxazole-4-carboxamide The titled compound was prepared according to the methods described in Example 23, substituting 5-methyl-3-phenylisoxazole-4-carboxylic acid for indole-6-carboxylic acid. MS (ESI(+)Q1MS m/z 461 (M+H)$^+$; $^1$H NMR (500 MHz, DMSO-D6) δ ppm 8.79 (d, 1 H), 8.72 (d, 1 H), 8.55 (d, 1 H), 8.38 (d, 1 H), 7.93 (d, 1 H), 7.80 (dd, 1 H), 7.67–7.73 (m, 2 H), 7.47–7.52 (s, 3 H), 6.97 (d, 1 H), 3.84–4.08 (m, 2 H), 2.55 (s, 3 H), 1.67–1.95 (m, 8 H).

EXAMPLE 93 cis-N-{4-((7-chloroquinolin-4-yl)amino) cyclohexyl}pyridine-2-carboxamide

The titled compound was prepared according to the methods described in Example 23, substituting pyridine-2-carboxylic acid for indole-6-carboxylic acid. MS (ESI(+) Q1MS m/z 381 (M+H)$^+$; $^1$H NMR (500 MHz, DMSO-D6) δ ppm 8.83 (d, 1 H), 8.68 (d, 1 H), 8.64 (t, 1 H), 8.56 (d, 1 H), 8.40 (d, 1 H), 8.09 (d, 1 H), 8.04 (td, 1 H), 7.92 (d, 1 H), 7.79 (dd, 1 H), 7.59 (dd, 1 H), 7.01 (d, 1 H), 4.88 (t, 1 H), 4.05 (t, 1 H), 1.58–2.07 (m, 8 H).

EXAMPLE 94 cis-N-{4-((7-chloroquinolin-4-yl)amino) cyclohexyl}-3-hydroxypyridine-2-carboxamide.

The titled compound was prepared according to the methods described in Example 23, substituting 3-hydroxy picolinic acid for indole-6-carboxylic acid. MS (ESI(+) Q1MS m/z 397 (M+H)$^+$; $^1$H NMR (500 MHz, DMSO-D6) δ ppm 8.80 (d, 1 H), 8.66 (d, 1 H), 8.62 (d, 1 H), 8.57 (d, 1 H), 8.19 (dd, 1 H), 7.95 (d, 1 H), 7.81 (dd, 1 H), 7.57 (dd, 1 H), 7.46 (dd, 1 H), 7.02 (d, 1 H), 3.64–4.35 (m, 3 H), 1.71–2.13 (m, 8 H).

EXAMPLE 96 cis-N-{4-((7-chloroquinolin-4-yl)amino) cyclohexyl}-5-methylpyrazine-2-carboxamide The titled compound was prepared according to the methods described in Example 23, substituting 5-methylpyrazine-2-carboxylic acid for indole-6-carboxylic acid. MS (ESI(+)Q1MS m/z 396 (M+H)$^+$; $^1$H NMR (500 MHz, DMSO-D6) δ ppm 9.09 (dd, 1 H), 8.83 (dd, 1 H), 8.56 (d, 1 H), 8.29 (d, 1 H), 7.92 (d, 1 H), 7.80 (d, 1 H), 7.59 (dd, 1 H), 7.01 (d, 1 H), 7.01 (d, 3 H), 4.60 (t, 1 H), 4.15 (m, 1 H), 3.98 (t, 1 H), 1.72–2.11 (m, 8 H).

EXAMPLE 97 cis-N-{4-((7-chloroquinolin-4-yl)amino) cyclohexyl}-1 H-indole-3-carboxamide

The titled compound was prepared according to the methods described in Example 23, substituting indole-3-carboxylic acid for indole-6-carboxylic acid. MS (ESI(+) Q1MS m/z 419 (M+H)$^+$; $^1$H NMR (500 MHz, DMSO-D6) δ ppm 8.84 (d, 1 H), 8.72 (d, 1 H), 8.56 (d, 1 H), 8.15 (d, 1 H), 8.13 (d, 1 H), 7.94 (d, 1 H), 7.80 (dd, 1 H), 7.47 (d, 1 H), 7.43 (d, 1 H), 7.15 (td, 1 H), 7.10 (td, 1 H), 7.00 (d, 1 H), 4.88 (t, 1 H), 4.04 (d, 1 H), 4.00 (s, 1 H), 1.69–2.08 (m, 8 H).

EXAMPLE 98 cis-N-{4-((7-chloroquinolin-4-yl)amino) cyclohexyl}-8-methyl-4-oxo-4 H-pyrido(1,2-a) pyrimidine-3-carboxamide The titled compound was prepared according to the methods described in Example 23, substituting 8-methyl-4-oxo-4 H-pyrido(1,2-a)pyrimidine-3-carboxylic acid for indole-6-carboxylic acid. MS (ESI(+)Q1MS m/z 462 (M+H)$^+$; $^1$H NMR (300 MHz, DMSO-D6) δ ppm 9.35 (d, 1 H), 9.10 (d, 1 H), 9.04 (s, 1 H), 9.01 (d, 1 H), 8.72 (d, 1 H), 8.57 (d, 1 H), 7.93 (d, 1 H), 7.75–7.80 (m, 2 H), 7.50 (dd, 1 H), 7.05 (d, 1 H), 3.50–4.28 (m, 2 H), 2.57 (s, 3H), 1.68–2.00 (m, 8 H).

EXAMPLE 99 cis-N-{4-((7-chloroquinolin-4-yl)amino) cyclohexyl}-5-methyl-1-phenyl-1 H-pyrazole-4-carboxamide The titled compound was prepared according to the methods described in Example 23, substituting 5-methyl-1-phenyl-1 H-pyrazole-4-carboxylic acid for indole-6-carboxylic acid. MS (ESI(+)Q1MS m/z 460 (M+H)$^+$; $^1$H NMR (500 MHz, DMSO-D6) δ ppm 8.80 (d, 1 H), 8.72 (d, 1 H), 8.56 (d, 1 H), 8.22 (s, 1 H), 7.93 (d, 1 H), 7.81 (dd, 1 H), 7.70 (d, 1 H), 7.46–7.62 (m, 5 H), 6.99 (d, 1 H), 4.88 (t, 1 H), 4.05 (t, 1 H), 2.52 (s, 3 H), 1.68–2.05 (m, 8 H).

EXAMPLE 100 cis-N-{4-((7-chloroquinolin-4-yl)amino) cyclohexyl}-4-oxo-4,5,6,7-tetrahydro-1-benzofuran-3-carboxamide The titled compound was prepared according to the methods described in Example 23, substituting 4-oxo-4,5, 6,7-tetrahydro-1-benzofuran-3-carboxylic acid for indole-6-carboxylic acid. MS (ESI(+)Q1MS m/z 460 (M+H)+); $^1$H NMR (500 MHz, DMSO-D6) δ ppm 9.93 (d, 1 H), 8.88 (s, 1 H), 8.74 (d, 1 H), 8.54 (d, 1 H), 8.26 (s, 1 H), 7.91 (s, 1 H), 7.78 (dd, 1 H), 7.00 (d, 1 H), 4.08 (br,s, 1 H), 3.92 (br,s, 1 H), 2.98 (t, 2 H), 2.62 (t, 2 H), 2.14 (t, 2 H), 1.73–2.00 (m, 8 H).

EXAMPLE 101 cis-6-chloro-N-{4-((7-chloroquinolin-4-yl)amino)cyclohexyl}-2 H-chromene-3-carboxamide The titled compound was prepared according to the methods described in Example 23, substituting 2 H-chromene-3-carboxylic acid for indole-6-carboxylic acid. MS (ESI(+)Q1MS m/z 468 (M+H)+); $^1$H NMR (500 MHz, DMSO-D6) δ ppm 8.73 (s, 1 H), 8.71 (d, 1 H), 8.55 (d, 1 H), 7.93 (d, 1 H), 7.80 (dd, 1 H), 7.25–7.30 (m, 3 H), 6.96 (d, 1 H), 6.89 (d, 1 H), 4.95 (s, 2 H), 4.93 (s, 1 H), 3.94 (m, 2 H), 1.66–2.02 (m, 8 H).

EXAMPLE 102 cis-N-{4-((7-chloroquinolin-4-yl)amino)cyclohexyl}-4-ethylbenzamide

The titled compound was prepared according to the methods described in Example 23, substituting 4-ethylbenzoic acid for indole-6-carboxylic acid. MS (ESI(+)Q1MS m/z 408 (M+H)+); $^1$H NMR (500 MHz, DMSO-D6) δ ppm 8.82 (d, 1 H), 8.71 (d, 1 H), 8.56 (d, 1 H), 8.02 (d, 1 H), 7.93 (d, 1 H), 7.81 (dd, 1 H), 7.80 (d, 2 H), 7.80 (d, 2 H), 7.00 (d, 1 H), 3.94–4.04 (br,s, 2 H), 2.66 (q, 2 H), 1.66–2.06 (m, 8 H), 1.20 (t, 3 H).

EXAMPLE 103 cis-N-{4-((7-chloroquinolin-4-yl)amino)cyclohexyl}-2-hydroxy-4-methylbenzamide

The titled compound was prepared according to the methods described in Example 23, substituting 2-hydrozy-4-methylbenzoic acid for indole-6-carboxylic acid. MS (ESI(+)Q1MS m/z 410 (M+H)+); $^1$H NMR (500 MHz, DMSO-D6) δ ppm 8.79 (d, 1 H), 8.70 (d, 1 H), 8.57 (d, 1 H), 8.42 (d, 1 H), 7.93 (d, 1 H), 7.86 (d, 1 H), 7.80 (dd, 1 H), 7.66 (d, 1 H), 7.00 (d, 1 H), 6.76 (d, 1 H), 6.73 (s, 1 H), 3.97–4.09 (m, 2 H), 2.30 (s, 3 H), 1.72–2.03 (m, 8 H).

EXAMPLE 104 cis-N-{4-((7-chloroquinolin-4-yl)amino)cyclohexyl}-3-hydroxy-4-methylbenzamide

The titled compound was prepared according to the methods described in Example 23, substituting 3-hydrozy-4-methylbenzoic acid for indole-6-carboxylic acid. MS (ESI(+)Q1MS m/z 410 (M+H)+); $^1$H NMR (500 MHz, DMSO-D6) δ ppm 8.84 (d, 1 H), 8.72 (br,s, 1 H), 8.70 (d, 1 H), 8.63 (d, 1 H), 8.56 (d, 1 H), 7.92 (d, 1 H), 7.90 (d, 1 H), 7.80 (dd, 1 H), 7.26 (d, 1 H), 6.97 (d, 1 H), 4.88 (t, 1 H), 4.05 (t, 1 H), 3.91–4.01 (br.s, 1 H), 2.16 (s, 3 H), 1.62–2.05 (m, 8 H).

EXAMPLE 105 cis-N-{4-((7-chloroquinolin-4-yl)amino)cyclohexyl}-5-fluoro-2-methylbenzamide

The titled compound was prepared according to the methods described in Example 23, substituting 5-fluoro-2-methylbenzoic acid for indole-6-carboxylic acid. MS (ESI(+)Q1MS m/z 412 (M+H)+); $^1$H NMR (500 MHz, DMSO-D6) δ ppm 8.82 (d, 1 H), 8.70 (d, 1 H), 8.56 (d, 1 H), 8.25 (d, 1 H), 7.92 (d, 1 H), 7.80 (dd, 1 H), 7.29 (dd, 1 H), 7.19 (dd, 1 H), 7.15 (d, 1 H), 6.99 (d, 1 H), 3.88–4.04 (m, 2 H), 2.32 (s, 3 H), 1.68–2.04 (m, 8 H).

EXAMPLE 106 cis-N-{4-((7-chloroquinolin-4-yl)amino)cyclohexyl}-3-fluoro-4-methylbenzamide

The titled compound was prepared according to the methods described in Example 23, substituting 3-fluoro-4-methylbenzoic acid for indole-6-carboxylic acid. MS (ESI(+)Q1MS m/z 412 (M+H)+); $^1$H NMR (500 MHz, DMSO-D6) δ ppm 8.78 (d, 1 H), 8.70 (d, 1 H), 8.56 (d, 1 H), 8.13 (d, 1 H), 7.92 (s, 1 H), 7.81 (dd, 1 H), 7.66 (d, 1 H), 7.65 (s, 1 H), 7.40 (d, 1 H), 6.99 (d, 1 H), 3.88–4.02 (br.s, 2 H), 2.29 (s, 3 H), 1.65–2.06 (m, 8 H).

EXAMPLE 107 cis-N-{4-((7-chloroquinolin-4-yl)amino)cyclohexyl}-2,3-difluorobenzamide

The titled compound was prepared according to the methods described in Example 23, substituting 2,3-difluorobenzoic acid for indole-6-carboxylic acid. MS (ESI(+)Q1MS m/z 416 (M+H)+); $^1$H NMR (500 MHz, DMSO-D6) δ ppm 8.84 (d, 1 H), 8.72 (d, 1 H), 8.56 (d, 1 H), 8.17 (d, 1 H), 7.92 (d, 1 H), 7.80 (dd, 1 H), 7.67 (d, 1 H), 7.37 (d, 1 H), 7.18 (t, 1 H), 6.99 (d, 1 H), 4.02 (br,s, 1 H), 3.94 (br,s, 1 H), 1.70–2.02 (m, 8 H).

EXAMPLE 108 cis-N-{4-((7-chloroquinolin-4-yl)amino)cyclohexyl}-2,4-difluorobenzamide

The titled compound was prepared according to the methods described in Example 23, substituting 2,4-difluorobenzoic acid for indole-6-carboxylic acid. MS (ESI(+)Q1MS m/z 416 (M+H)+); $^1$H NMR (500 MHz, DMSO-D6) δ ppm 8.86 (d, 1 H), 8.72 (d, 1 H), 8.56 (d, 1 H), 8.18 (d, 1 H), 7.93 (s, 1 H), 7.80 (d, 1 H), 7.67 (dd, 1 H), 7.36 (t, 1 H), 7.18 (t, 1 H), 6.99 (d, 1 H), 4.02 (br,s, 1 H), 3.94 (br,s, 1 H), 1.68–2.02 (m, 8 H).

EXAMPLE 109 cis-N-{4-((7-chloroquinolin-4-yl)amino)cyclohexyl}-2,5-difluorobenzamide

The titled compound was prepared according to the methods described in Example 23, substituting 2,5-difluorobenzoic acid for indole-6-carboxylic acid. MS (ESI(+)Q1MS m/z 416 (M+H)+); $^1$H NMR (500 MHz, DMSO-D6) δ ppm 8.82 (br,s, 1 H), 8.72 (d, 1 H), 8.56 (d, 1 H), 8.29 (d, 1 H), 7.92 (s, 1 H), 7.80 (dd, 1 H), 7.32–7.43 (m, 3 H), 6.99 (d, 1 H), 3.85–4.09 (m, 2 H), 1.69–2.04 (m, 8 H).

EXAMPLE 110 cis-N-{4-((7-chloroquinolin-4-yl)amino)cyclohexyl}-3,5-difluorobenzamide

The titled compound was prepared according to the methods described in Example 23, substituting 3,5-difluorobenzoic acid for indole-6-carboxylic acid. MS (ESI (+)Q1MS m/z 416 (M+H)+); 1H NMR (500 MHz, DMSO-D6) δ ppm 8.81 (d, 1 H), 8.70 (d, 1 H), 8.57 (d, 1 H), 8.30 (d, 1 H), 7.93 (d, 1 H), 7.82 (dd, 1 H), 7.60 (d, 1 H), 7.56 (d, 1 H), 7.48 (t, 1 H), 7.00 (d, 1 H), 3.98 (br,s, 2 H), 1.68–2.07 (m, 8 H).

EXAMPLE 111 cis-2-N-{4-((7-chloroquinolin-4-yl)amino)cyclohexyl}glycyl)benzaldehyde

The titled compound was prepared according to the methods described in Example 23, substituting 2-acetylbenzoic acid for indole-6-carboxylic acid. 1H NMR (500 MHz, DMSO-D6) δ ppm 8.90 (d, 1 H), 8.84 (d, 1 H), 8.64 (d, 1 H), 8.61 (t, 1 H), 8.56 (d, 1 H), 8.01 (dd, 1 H), 7.95 (d, 1 H), 7.71 (d, 1 H), 7.68 (t, 1 H), 7.60 (s, 1 H), 7.57 (d, 1 H), 4.11–4.32 (m, 2 H), 1.74–2.29 (m, 8 H), 1.63 (s, 3 H).

EXAMPLE 112 cis-4-acetyl-N-{4-((7-chloroquinolin-4-yl)amino)cyclohexyl}benzamide

The titled compound was prepared according to the methods described in Example 23, substituting 4-acetylbenzoic acid for indole-6-carboxylic acid. MS (ESI (+)Q1MS m/z 422 (M+H)+); 1H NMR (500 MHz, DMSO-D6) δ ppm 8.79 (d, 1 H), 8.71 (d, 1 H), 8.57 (d, 1 H), 8.32 (d, 2 H), 7.93 (d, 1 H), 7.81 (dd, 1 H), 6.99 (d, 1 H), 4.88 (t, 1 H), 4.05 (t, 1 H), 4.00 (br,s, 2 H), 2.63 (s, 3 H), 1.68–2.08 (m, 8 H).

EXAMPLE 113 cis-N-{4-((7-chloroquinolin-4-yl)amino)cyclohexyl}-3-methoxy-4-methylbenzamide The titled compound was prepared according to the methods described in Example 23, substituting 3-methoxy-4-methylbenzoic acid for indole-6-carboxylic acid. MS (ESI (+)Q1MS m/z 424 (M+H)+); 1H NMR (500 MHz, DMSO-D6) δ ppm 8.82 (d, 1 H), 8.72 (d, 1 H), 8.57 (d, 1 H), 8.02 (d, 1 H), 7.94 (d, 1 H), 7.81 (dd, 1 H), 7.41 (br.d, 2 H), 7.22 (d, 1 H), 7.00 (d, 1 H), 3.94–4.05 (br.s, 2 H), 3.85 (s, 3 H), 2.19 (s, 3 H), 1.69–2.06 (m, 8 H).

EXAMPLE 114 cis-N-{4-((7-chloroquinolin-4-yl)amino)cyclohexyl}-2-ethoxybenzamide

The titled compound was prepared according to the methods described in Example 23, substituting 2-ethoxybenzoic acid for indole-6-carboxylic acid. MS (ESI (+)Q1MS m/z 424 (M+H)+); 1H NMR (500 MHz, DMSO-D6) δ ppm 8.83 (d, 1 H), 8.66 (d, 1 H), 8.57 (d, 1 H), 8.24 (d, 1 H), 7.92 (s, 1 H), 7.89 (d, 1 H), 7.81 (dd, 1 H), 7.50 (t, 1 H), 7.18 (d, 1 H), 7.07 (t, 1 H), 7.03 (d, 1 H), 4.23 (dd, 2 H), 4.06–1.16 (br.s, 1 H), 3.92–4.02 (br.s, 1 H), 1.71–2.05 (m, 8 H), 1.47(t, 3 H).

EXAMPLE 115 cis-N-{4-((7-chloroquinolin-4-yl)amino)cyclohexyl}-4-(methylthio)benzamide

The titled compound was prepared according to the methods described in Example 23, substituting 4-methylthiobenzoic acid for indole-6-carboxylic acid. MS (ESI(+)Q1MS m/z 426 (M+H)+); 1H NMR (500 MHz, DMSO-D6) δ ppm 8.79 (d, 1 H), 8.71 (d, 1 H), 8.56 (d, 1 H), 8.06 (d, 1 H), 7.93 (d, 1 H), 7.77–7.87 (m, 3 H), 7.30–7.36 (m, 3 H), 6.99 (d, 1 H), 3.90–4.00 (br,s, 1 H), 2.52 (s, 3 H), 1.68–2.06 (m, 8 H).

EXAMPLE 116 cis-N-{4-((7-chloroquinolin-4-yl)amino)cyclohexyl}-3-fluoro-4-methoxybenzamide The titled compound was prepared according to the methods described in Example 23, substituting 3-fluoro-4-methoxybenzoic acid for indole-6-carboxylic acid. MS (ESI (+)Q1MS m/z 428 (M+H)+); 1H NMR (500 MHz, DMSO-D6) δ ppm 8.72–8.78 (br,s, 1 H), 8.70 (d, 1 H), 8.56 (d, 1 H), 8.04 (d, 1 H), 7.92 (s, 1 H), 7.72–7.83 (m, 3 H), 7.25 (t, 1 H), 6.98 (d, 1 H), 3.93–4.02 (br.s, 2 H), 3.90 (s, 3 H), 1.68–2.06 (m, 8 H).

EXAMPLE 117 cis-N-{4-((7-chloroquinolin-4-yl)amino)cyclohexyl}-2-naphthamide

The titled compound was prepared according to the methods described in Example 23, substituting 2-naphtoic acid for indole-6-carboxylic acid. MS (ESI(+)Q1MS m/z 430 (M+H)+); 1H NMR (500 MHz, DMSO-D6) δ ppm 8.80–8.85 (s, 1 H), 8.72 (d, 1 H), 8.61 (s, 1 H), 8.57 (d, 1 H), 8.49 (s, 1 H), 8.29 (d, 1 H), 8.12 (d, 1 H), 8.01 (m, 2 H), 7.93 (d, 1 H), 7.81 (dd, 1 H), 7.63 (m, 2 H), 7.01 (d, 1 H), 4.03 (m, 2 H), 1.67–2.16 (m, 8 H).

EXAMPLE 118 cis-N-{4-((7-chloroquinolin-4-yl)amino)cyclohexyl}-1-naphthamide

The titled compound was prepared according to the methods described in Example 23, substituting 1-naphtoic acid for indole-6-carboxylic acid. MS (ESI(+)Q1MS m/z 430 (M+H)+); 1H NMR (500 MHz, DMSO-D6) δ ppm 8.73–8.79 (br,s, 1 H), 8.68 (d, 1 H), 8.56 (d, 1 H), 8.42 (d, 1 H), 8.16 (d, 1 H), 8.02 (d, 1 H), 7.99 (d, 1 H), 7.91 (d, 1 H), 7.77 (dd, 1 H), 7.52–7.66 (m, 4 H), 6.99 (d, 1 H), 4.14 (br.s, 1 H), 3.97 (br.s, 1 H), 3.97 (m, 8 H).

EXAMPLE 119 cis-5-chloro-N-{4-((7-chloroquinolin-4-yl)amino)cyclohexyl}-2-hydroxybenzamide The titled compound was prepared according to the methods described in Example 23, substituting 5-chloro-2-hydroxybenzoic acid for indole-6-carboxylic acid. MS (ESI (+)Q1MS m/z 430 (M+H)+); 1H NMR (500 MHz, DMSO-D6) δ ppm 12.40 (s, 1 H), 8.68 (m, 2 H), 8.56 (d, 1 H), 8.03 (d, 1 H), 7.91 (d, 1 H), 7.79 (d, 1 H), 7.45 (d, 1 H), 6.98 (m, 2 H), 3.90–4.14 (m, 2 H), 1.66–2.07 (m, 8 H).

EXAMPLE 121 cis-4-(acetylamino)-N-{4-((7-chloroquinolin-4-yl)amino)cyclohexyl}benzamide

The titled compound was prepared according to the methods described in Example 23, substituting 4-acetylaminobenzoic acid for indole-6-carboxylic acid. MS (ESI(+)Q1MS m/z 437 (M+H)+); 1H NMR (500 MHz, DMSO-D6) δ ppm 10.15 (s, 1 H), 8.81 (d, 1 H), 8.71 (d, 1 H), 8.56 (d, 1 H), 7.96 (d, 1 H), 7.93 (d, 1 H), 7.77–7.82 (m, 3 H), 7.64–7.66 (m, 2 H), 7.00 (d, 1 H), 4.88 (t, 1 H), 4.05 (t, 1 H), 2.07 (s, 3 H), 1.64–2.07 (m, 8 H).

EXAMPLE 122 cis-N-{4-((7-chloroquinolin-4-yl)amino) cyclohexyl}-4-isopropoxybenzamide

The titled compound was prepared according to the methods described in Example 23, substituting 4-isopropoxybenzoic acid for indole-6-carboxylic acid. MS (ESI(+)Q1MS m/z 438 (M+H)$^+$); $^1$H NMR (500 MHz, DMSO-D6) δ ppm 8.80 (d, 1 H), 8.71 (d, 1 H), 8.56 (d, 1 H), 7.92–7.94 (m, 2 H), 7.80–7.89 (m, 3 H), 6.93–7.02 (m, 4 H), 4.69 (m, 1 H), 3.99 (br.s, 1 H), 1.64–2.06 (m, 8 H), 1.28 (d, 6 H).

EXAMPLE 123 cis-5-chloro-N-{4-((7-chloroquinolin-4-yl)amino) cyclohexyl}-2-methoxybenzamide

The titled compound was prepared according to the methods described in Example 23, substituting 5-chloro-2-methoxybenzoic acid for indole-6-carboxylic acid. MS (ESI (+)Q1MS m/z 444 (M+H)$^+$); $^1$H NMR (500 MHz, DMSO-D6) δ ppm 8.87 (d, 1 H), 8.72 (d, 1 H), 8.56 (d, 1 H), 8.19 (d, 1 H), 7.95 (d, 1 H), 7.80 (dd, 1 H), 7.70 (d, 1 H), 7.54 (dd, 1 H), 7.23 (d, 1 H), 7.01 (d, 1 H), 4.09 (br.s, 1 H), 3.96 (s, 3 H), 3.96 (br.s, 1 H), 1.73–2.02 (m, 8 H).

EXAMPLE 124 cis-N-{4-((7-chloroquinolin-4-yl)amino) cyclohexyl}-4-fluoro-1-naphthamide

The titled compound was prepared according to the methods described in Example 23, substituting 4-fluoro-1-naphtoic acid for indole-6-carboxylic acid. MS (ESI(+) Q1MS m/z 448 (M+H)$^+$); $^1$H NMR (500 MHz, DMSO-D6) δ ppm 8.71 (br,s, 1 H), 8.67 (d, 1 H), 8.55 (d, 1 H), 8.44 (d, 1 H), 8.25 (m, 1 H), 8.13 (m, 1 H), 7.91 (d, 1 H), 7.77 (dd, 1 H), 7.70 (m, 2 H), 7.64 (dd, 1 H), 7.41 (t, 1 H), 6.98 (d, 1 H), 4.13 (br.s, 1 H), 3.96 (br.s, 1 H), 1.75–2.12 (m, 8 H).

EXAMPLE 125 cis-N-{4-((7-chloroquinolin-4-yl)amino) cyclohexyl}-3,4-diethoxybenzamide

The titled compound was prepared according to the methods described in Example 23, substituting 3,4-diethoxybenzoic acid for indole-6-carboxylic acid. MS (ESI (+)Q1MS m/z 468 (M+H)$^+$); $^1$H NMR (500 MHz, DMSO-D6) δ ppm 8.81 (d, 1 H), 8.72 (d, 1 H), 8.56 (d, 1 H), 7.93 (s, 1 H), 7.91 (s, 1 H), 7.81 (dd, 1 H), 7.48–7.55 (m, 2 H), 7.40–7.46 (m, 2 H), 6.96–7.05 (m, 2 H), 4.02–4.12 (m, 4 H), 1.64–2.06 (m, 8 H), 1.28–1.39 (m, 6 H).

EXAMPLE 126 cis-2-benzyl-N-{4-((7-chloroquinolin-4-yl)amino) cyclohexyl}benzamide

The titled compound was prepared according to the methods described in Example 23, substituting 2-benzylbenzoic acid for indole-6-carboxylic acid. MS (ESI (+)Q1MS m/z 470 (M+H)$^+$); $^1$H NMR (500 MHz, DMSO-D6) δ ppm 8.80 (d, 1 H), 8.70 (d, 1 H), 8.55 (d, 1 H), 8.19 (d, 1 H), 7.92 (s, 1 H), 7.80 (d, 1 H), 7.37 (m, 3 H), 7.24 (m, 6 H), 6.98 (d, 1 H), 4.12 (s, 2 H), 3.97 (m, 2 H), 1.65–1.96 (m, 8 H).

EXAMPLE 127 cis-N-{4-((7-chloroquinolin-4-yl)amino) cyclohexyl}-2-(2-phenylethyl)benzamide

The titled compound was prepared according to the methods described in Example 23, substituting 2-bibenzylcarboxylic acid for indole-6-carboxylic acid. MS (ESI(+)Q1MS m/z 484 (M+H)$^+$); $^1$H NMR (500 MHz, DMSO-D6) δ ppm 8.81 (d, 1 H), 8.70 (d, 1 H), 8.55 (d, 1 H), 8.22 (d, 1 H), 7.97 (d, 1 H), 7.77 (dd, 1 H), 7.33–7.40 (m, 2 H), 7.24–7.30 (m, 4 H), 7.20–7.23 (m, 2 H), 7.16 (t, 1 H), 6.98 (d, 1 H), 4.06 (br.s, 1 H), 3.94 (br.s, 1 H), 2.99 (m, 2 H), 2.84 (m, 2 H), 1.72–2.05 (m, 8 H).

EXAMPLE 128 cis-2-bromo-N-{4-((7-chloroquinolin-4-yl)amino) cyclohexyl}-5-methoxybenzamide

The titled compound was prepared according to the methods described in Example 23, substituting 2-bromo-5-methoxybenzoic acid for indole-6-carboxylic acid. MS (ESI (+)Q1MS m/z 490 (M+H)$^+$); $^1$H NMR (500 MHz, DMSO-D6) δ ppm 8.70 (d, 1 H), 8.54 (d, 1 H), 8.33 (d, 1 H), 7.91 (d, 1 H), 7.77 (dd, 1 H), 7.59 (d, 1 H), 7.53 (d, 1 H), 7.26 (d, 1 H), 7.03 (dd, 1 H), 6.96 (d, 1 H), 3.85–4.05 (m, 2 H), 3.79 (s, 3 H), 1.70–2.03 (m, 8 H).

EXAMPLE 129 cis-N-{4-((7-chloroquinolin-4-yl)amino) cyclohexyl}-2-(4-methylbenzoyl)benzamide The titled compound was prepared according to the methods described in Example 23, substituting 2-(4-methylbenzoyl)benzoic acid for indole-6-carboxylic acid. $^1$H NMR (500 MHz, DMSO-D6) δ ppm 8.81 (d, 1 H), 8.78 (d, 1 H), 8.73 (d, 1 H), 8.55 (dd, 2 H), 8.49 (d, 1 H), 8.31 (d, 1 H), 7.95 (d, 1 H), 7.92 (dd, 1 H), 7.68–7.75 (m, 4 H), 7.38 (d, 1 H), 6.85 (d, 1 H), 3.20–3.56 (br.s, 2 H), 2.36 (s, 3 H), 1.40–2.14 (m, 8 H).

EXAMPLE 130 cis-N-{4-((7-chloroquinolin-4-yl)amino) cyclohexyl}-2-iodobenzamide

The titled compound was prepared according to the methods described in Example 23, substituting 2-iodobenzoic acid for indole-6-carboxylic acid. MS (ESI (+)Q1MS m/z 506 (M+H)$^+$); $^1$H NMR (500 MHz, DMSO-D6) δ ppm 8.70 (d, 1 H), 8.54 (d, 1 H), 8.32 (d, 1 H), 7.91 (d, 1 H), 7.88 (d, 1 H), 7.77 (dd, 1 H), 7.39–7.52 (m, 2 H), 7.33 (dd, 1 H), 7.17 (td, 1 H), 6.95 (d, 1 H), 4.00 (br.s, 1 H), 3.91 (br.s, 1 H), 1.68–2.03 (m, 8 H).

EXAMPLE 131 cis-N-{4-((7-chloroquinolin-4-yl)amino) cyclohexyl}-3-iodobenzamide

The titled compound was prepared according to the methods described in Example 23, substituting 3-iodobenzoic acid for indole-6-carboxylic acid. MS (ESI (+)Q1MS m/z 506 (M+H)⁺; ¹H NMR (500 MHz, DMSO-D6) δ ppm 8.81 (d, 1 H), 8.71 (d, 1 H), 8.56 (d, 1 H), 8.21–8.27 (m, 2 H), 7.99 (d, 1 H), 7.89 (t, 1 H), 7.81 (dd, 1 H), 7.24–7.36 (m, 2 H), 6.99 (d, 1 H), 3.93–4.03 (br.s, 2 H), 1.67–2.07 (m, 8 H).

EXAMPLE 132 cis-N-{4-((7-chloroquinolin-4-yl)amino)cyclohexyl}-4-iodobenzamide

The titled compound was prepared according to the methods described in Example 23, substituting 4-iodobenzoic acid for indole-6-carboxylic acid. MS (ESI (+)Q1MS m/z 506 (M+H)⁺); ¹H NMR (500 MHz, DMSO-D6) δ ppm 8.83 (d, 1 H), 8.71 (d, 1 H), 8.56 (d, 1 H), 8.20 (d, 1 H), 7.93 (d, 1 H), 7.86 (d, 2 H), 7.81 (dd, 1 H), 7.67 (d, 2 H), 7.00 (d, 1 H), 3.89–4.04 (br.s, 2 H), 1.68–2.05 (m, 8 H).

EXAMPLE 133 cis-N-{4-((7-chloroquinolin-4-yl)amino)cyclohexyl}-2-(4-fluorophenyl)acetamide

A solution of N-(7-chloroquinolin-4-yl)-cyclohexane-1,4-diamine (20 mg, 0.07 mmol) in dichloromethane (1.0 mL) and triethylamine (0.01 mL) at 20° C. was treated with (4-fluoro-phenyl)-acetyl chloride (12 mg, 0.07 mmol). The reaction was shaken at room temperature for 18 hours then concentrated. The crude compound was purified by reverse phase HPLC to provide the desired compound. MS (ESI (+)) m/e 412 (M+H)⁺; ¹H NMR (500 MHz, DMSO) δ ppm 8.87 (d, 1 H), 8.74 (d, 1 H), 8.54 (d, 1 H), 8.01 (d, 1 H), 7.95 (m, 1 H), 7.80 (dd, 1 H), 7.31 (m, 2 H), 7.12 (m, 2 H), 6.97 (d, 1 H), 3.91 (br.s, 1 H), 3.80 (br.s, 1 H), 3.47 (s, 2 H), 1.57–1.98 (m, 8 H).

EXAMPLE 134 cis-bis-3-({4-((7-chloroquinolin-4-yl)amino)cyclohexyl}amino)-1-(4-fluorophenyl)propan-1-one 3-Chloro-4-fluoropropiophenone (13 mg, 0.07 mmol) was treated with a solution of sodium iodide (0.07 mmol) in acetonitrile (0.5 mL). A solution of N-(7-chloroquinolin-4-yl)-cyclohexane-1,4-diamine (20 mg, 0.07 mmol) in acetonitrile (0.5 mL) was added followed by potassium carbonate (20 mg, 0.14 mmol). The reaction was heated to 75 C for 18 hours then filtered and concentrated. The crude compound was purified by reverse phase HPLC to provide the desired compound. MS (ESI (+)) m/e 576 (M+H)⁺; ¹H NMR (500 MHz, DMSO) δ ppm 9.96 (br.s, 1 H), 8.78 (d, 1 H), 8.62 (d, 1 H), 8.54 (m, 1 H), 7.97 (d, 1 H), 7.79 (dd, 1 H), 7.49 (m, 2 H), 7.34 (m, 2 H), 7.07 (t, 2 H), 6.94 (m, 3 H), 5.66 (br.s, 1 H), 4.54 (m, 1 H), 4.19 (br.s, 1 H), 3.47–3.72 (m, 5 H), 1.79–2.23 (m, 10H).

EXAMPLE 135 cis-5-({4-((7-chloroquinolin-4-yl)amino)cyclohexyl}amino)-1-(4-fluorophenyl)pentan-1-one The titled compound was prepared according to the method described in Example 134 by substituting 4-(fluorophenyl)-5-chloro-1-oxopentane for 3-Chloro-4-fluoropropiophenone. MS (ESI (+)) m/e 454 (M+H)⁺; ¹H NMR (500 MHz, DMSO) δ ppm 8.74 (d, 1 H), 8.58 (m, 2 H), 8.45 (br.s, 2 H), 8.07 (m, 2 H), 7.97 (d, 1 H), 7.79 (dd, 1 H), 7.36 (t, 2 H), 6.94 (m, 1 H), 4.07 (br.s, 1 H), 3.23 (m, 2 H), 3.10 (m, 2 H), 2.99 (br.s, 2 H), 2.03 (m, 2 H), 1.74–1.96 (m, 5H), 1.69 (m, 4 H).

EXAMPLE 136 cis-N-(4,4-bis(4-fluorophenyl)butyl)-N'-(7-chloroquinolin-4-yl)cyclohexane-1,4-diamine The titled compound was prepared according to the method described in Example 134 by substituting 1,1'-(4-chlorobutylidene) bis(4-fluorobenzene) for 3-Chloro-4-fluoropropiophenone. MS (ESI (+)) m/e 520 (M+H)⁺; ¹H NMR (500 MHz, DMSO) δ ppm 8.72 (d, 1 H), 8.59 (d, 1 H), 8.51 (br.s, 1 H), 8.37 (br.s, 2 H), 7.96 (d, 1 H), 7.77 (dd, 1 H), 7.35 (m, 4 H), 7.14 (m, 4 H), 6.92 (d, 1 H), 4.04 (m, 2 H), 3.17 (br.s, 1 H), 2.97 (m, 2 H), 2.05 (m, 4 H), 1.71–1.92 (m, 5 H), 1.50 (m, 2 H).

EXAMPLE 137 cis-N-(7-chloroquinolin-4-yl)-N'-(4-phenylbutyl)cyclohexane-1,4-diamine

The titled compound was prepared according to the method described in Example 134 by substituting 1-chloro-4-phenyl butane for 3-Chloro-4-fluoropropiophenone. MS (ESI (+)) m/e 408 (M+H)⁺; ¹H NMR (500 MHz, DMSO) δ ppm 8.74 (d, 1 H), 8.59 (d, 1 H), 8.56 (m, 1 H), 8.44 (br.s, 2 H), 7.97 (d, 1 H), 7.78 (dd, 1 H), 7.30 (m, 2 H), 7.20 (m, 3 H), 6.93 (d, 1 H), 4.06 (m, 1 H), 3.20 (br.s, 1 H), 2.98 (br.s, 2 H), 2.62 (t, 2 H), 2.04 (m, 2 H), 1.73–1.94 (m, 6 H), 1.62 (m, 4 H).

EXAMPLE 138 cis-N-(7-chloroquinolin-4-yl)-N'-(5-phenylpentyl)cyclohexane-1,4-diamine

The titled compound was prepared according to the method described in Example 134 by substituting 1-chloro-5-phenyl pentane for 3-Chloro-4-fluoropropiophenone. MS (ESI (+)) m/e 422 (M+H)⁺; ¹H NMR (500 MHz, DMSO) δ ppm 8.74 (d, 1 H), 8.60 (d, 2 H), 8.46 (br.s, 2 H), 7.97 (d, 1 H), 7.78 (dd, 1 H), 7.28 (m, 2 H), 7.19 (m, 3 H), 6.94 (d, 1 H), 4.08 (m, 1 H), 3.23 (br.s, 1 H), 2.95 (br.s, 1 H), 2.59 (t, 2 H), 2.04 (m, 2 H), 1.72–1.95 (m, 6 H), 1.63 (m, 4 H), 1.36 (m, 2 H).

EXAMPLE 139 cis-N-(7-chloroquinolin-4-yl)-N'-(3,5-difluorobenzyl)cyclohexane-1,4-diamine

The titled compound was prepared according to the methods described in Example 23, substituting 3,5-difluorobanzaldehyde for 6-formylindole. MS (ESI(+) Q1MS m/z 402 (M+H)⁺); ¹H NMR (300 MHz, DMSO-D6) δ ppm 8.75 (d, 1 H), 8.67 (d, 1 H), 8.61 (d, 1 H), 7.98 (d, 1 H), 7.80 (dd, 1 H), 7.24–7.42 (m, 4 H), 6.96 (d, 1 H), 4.26 (br.s, 1 H), 4.08 (br.s, 1 H), 2.07 (s, 2 H), 1.73–2.16 (m, 8 H).

EXAMPLE 140 cis-N-(7-chloroquinolin-4-yl)-N'-(3,5-difluorophenyl)cyclohexane-1,4-diamine

A mixture of example 23A (30 mg, 0.11 mmol), 1-bromo-3,5-difluorobenzene (25 mg, 0.132 mmol), Pd₂(dba)₃ (1 mg, 0.001 mmol), 2,2'-bis(diphenylphosphino)-1,1'-binaphtyl (1.6 mg, 002 mmol) and sodium-tert-btoxide (14 mg, 0.132 mmol) was heated for 15 hours in ethyleneglycoldimethylether, concentrated and the residue was purified with high throughput HPLC system to provide the desired compound as its bis trifluoroacetic acid salt. MS (ESI(+)Q1MS m/z 388 (M+H)$^+$); $^1$H NMR (300 MHz, DMSO-D6) δ ppm 8.91 (d, 1 H), 8.71 (d, 1 H), 8.55 (d, 1 H), 7.92 (d, 1 H), 7.80 (dd, 1 H), 7.01 (d, 1 H), 6.25 (m, 4 H), 3.86–4.10 (br.s, 1 H), 3.54 (br.s, 1 H), 3.54 (m, 8 H).

EXAMPLE 141 cis-N-(7-chloroquinolin-4-yl)-N'-(3-fluorobenzyl) cyclohexane-1,4-diamine

To 4-fluorobenzyl alcohol (9.2 mg, 0.073 mmol) was added Dess-Martin periodinane (31.0 mg, 0.073 mmol) in dichloromethane (2 mL). The mixture was stirred at room temperature for 0.5 hour and was added to a mixture of N-(7-chloroquinolin-4-yl)-cyclohexane-1,4-diamine (20 mg, 0.073 mmol), acetic acid (0.008 mg, 0.13 mmol) and MP-cyanoborohydride (51 mg, 0.219 mmol, Argonaut Technologies) in dichloromethane (5 mL). The mixture was stirred at room temperature for 18 hours, filtered and concentrated under reduced pressure to provide the τιτλεδ compound. MS(ESI) m/e 384 (M+H)$^+$; $^1$H NMR (500 MHz, DMSO-D6) δ ppm 8.91 (br.s, 2 H), 8.75 (d, 1 H), 8.61 (d, 1 H), 7.97 (d, 1 H), 7.81 (dd, 1 H), 7.52 (dd, 1 H), 7.42 (d, 1 H), 7.37 (d, 1 H), 7.29 (td, 1 H), 4.25 (br.s, 2 H), 4.09 (br.s, 2 H), 1.76–2.13 (m, 8 H).

EXAMPLE 142 cis-N-(3-chlorobenzyl)-N'-(7-chloroquinolin-4-yl) cyclohexane-1,4-diamine

The titled compound was prepared according to method described in Example 141, substituting 3-chlorobenzyl alcohol for 4-fluorobenzyl alcohol. MS(ESI) m/c 394 (M+H)$^+$; $^1$H NMR (500 MHz, DMSO-D6) δ ppm 8.85 (br.s, 2 H), 8.73 (d, 1 H), 8.60 (d, 1 H), 7.96 (d, 1 H), 7.82 (dd, 1 H), 7.65 (s, 1 H), 7.51 (m, 3 H), 6.93 (d, 1 H), 4.24 (s, 2 H), 4.07 (s, 2 H), 1.71–2.15 (m, 8 H).

EXAMPLE 143 cis-N-(4-chlorobenzyl)-N'-(7-chloroquinolin-4-yl) cyclohexane-1,4-diamine

The titled compound was prepared according to method described in Example 141, substituting 4-chlorobenzyl alcohol for 4-fluorobenzyl alcohol. MS(ESI) m/e 399 (M+H)$^+$; $^1$H NMR (500 MHz, DMSO-D6) δ ppm 8.86 (br. s, 2 H), 8.73 (d, 1 H), 8.60 (d, 1 H), 7.96 (d, 1 H), 7.80 (d, 1 H), 7.42–7.67 (m, 4 H), 6.93 (d, 1 H), 4.22 (s, 2 H), 4.07 (s, 2 H), 1.71–2.15 (m, 8 H).

EXAMPLE 144 cis-N-(7-chloroquinolin-4-yl)-N'-(3-(trifluoromethyl) benzyl)cyclohexane-1,4-diamine The titled compound was prepared according to method described in Example 141, substituting 3-(trifluoromethyl) benzyl alcohol for 4-fluorobenzyl alcohol. MS(ESI) m/e 434 (M+H)$^+$; $^1$H NMR (500 MHz, DMSO-D6) δ ppm 8.81–9.05 (br.s, 2 H), 8.75 (d, 1 H), 8.61 (d, 1 H), 7.96 (d, 1 H), 7.82 (m, 4 H), 7.71 (d, 1 H), 6.95 (d, 1 H), 4.20–4.44 (br.s, 2 H), 4.09 (br.s, 2 H), 1.71–2.33 (m, 8 H).

EXAMPLE 145 cis-N-(7-chloroquinolin-4-yl)-N'-(4-(trifluoromethyl) benzyl)cyclohexane-1,4-diamine The titled compound was prepared according to method described in Example 141, substituting 4-(trifluoromethyl) benzyl alcohol for 4-fluorobenzyl alcohol. MS(ESI) m/e 434 (M+H)$^+$; $^1$H NMR (500 MHz, DMSO-D6) δ ppm 8.84–9.06 (br.s, 2 H), 8.73 (d, 1 H), 8.60 (d, 1 H), 7.96 (d, 1 H), 7.87 (m, 2 H), 7.73 (m, 3 H), 6.93 (d, 1 H), 4.32 (d, 2 H), 4.07 (s, 2 H), 1.60–2.18 (m, 8 H).

EXAMPLE 146 cis-N-(7-chloroquinolin-4-yl)-N'-(4-phenoxybenzyl) cyclohexane-1,4-diamine

The titled compound was prepared according to method described in Example 141, substituting 4-phenoxybenzyl alcohol for 4-fluorobenzyl alcohol. MS(ESI) m/e 458 (M+H)$^+$; $^1$H NMR (500 MHz, DMSO-D6) δ ppm 8.89 (br.s, 2 H), 8.73 (d, 1 H), 8.60 (d, 1 H), 8.54 (br.s, 1 H), 7.96 (d, 1 H), 7.81 (dd, 1 H), 7.48 (t, 1 H), 7.42 (t, 2 H), 7.29 (d, 1 H), 7.24 (s, 1 H), 7.18 (t, 1 H), 7.06 (m, 3 H), 6.93 (d, 1 H), 4.21 (br.s, 2 H), 4.07 (s, 2 H), 1.73–2.14 (m, 8 H).

EXAMPLE 147 cis-N-(4-(benzyloxy)benzyl)-N'-(7-chloroquinolin-4-yl)cyclohexane-1,4-diamine

The titled compound was prepared according to method described in Example 141, substituting 4-benzyloxybenzyl alcohol for 4-fluorobenzyl alcohol. MS(ESI) m/e 472 (M+H)$^+$; $^1$H NMR (500 MHz, DMSO-D6) δ ppm 8.72 (m, 2 H), 8.60 (d, 1 H), 7.96 (d, 1 H), 7.80 (dd, 1 H), 7.39 (m, 6 H), 7.09 (d, 2 H), 6.91 (d, 1 H), 5.15 (s, 2 H), 3.97–4.25 (m, 2 H), 3.08–3.43 (m, 3 H), 1.70–2.16 (m, 8 H).

EXAMPLE 148 cis-N-(7-chloroquinolin-4-yl)-N'-(2,4-dimethylbenzyl)cyclohexane-1,4-diamine

The titled compound was prepared according to method described in Example 141, substituting 2,4-dimethylbenzyl alcohol for 4-fluorobenzyl alcohol. MS(ESI) m/e 394 (M+H)$^+$; $^1$H NMR (500 MHz, DMSO-D6) δ ppm 8.74 (d, 1 H), 8.61 (d, 1 H), 7.96 (d, 1 H), 7.82 (dd, 1 H), 7.33 (br.s, 2 H), 7.33 (m, 1 H), 7.08 (m, 2 H), 6.94 (d, 1 H), 3.92–4.34 (m, 4H), 2.35 (s, 3 H), 2.29 (s, 3 H), 1.72–2.18 (m, 8 H).

EXAMPLE 149 cis-N-(7-chloroquinolin-4-yl)-N'-(2,5-dimethylbenzyl)cyclohexane-1,4-diamine

The titled compound was prepared according to method described in Example 141, substituting 2,5-dimethylbenzyl alcohol for 4-fluorobenzyl alcohol. MS(ESI) m/e 394 (M+H)$^+$; $^1$H NMR (500 MHz, DMSO-D6) δ ppm 8.74 (d, 1 H), 8.74 (br.s, 2 H), 8.61 (d, 1 H), 8.53 (br.s, 1 H), 7.97 (d, 1 H), 7.80 (dd, 1 H), 7.28 (m, 1 H), 7.18 (m, 2 H), 6.93 (d, 1 H), 4.03–4.27 (m, 2 H), 2.33 (s, 3 H), 2.30 (s, 3 H), 1.73–2.22 (m, 8 H).

EXAMPLE 150 cis-N-(7-chloroquinolin-4-yl)-N'-(3,4-dimethylbenzyl)cyclohexane-1,4-diamine

The titled compound was prepared according to method described in Example 141, substituting 3,4-dimethylbenzyl alcohol for 4-fluorobenzyl alcohol. MS(ESI) m/e 394 (M+H)$^+$; $^1$H NMR (500 MHz, DMSO-D6) δ ppm 8.79 (br.s, 2 H), 8.74 (d, 1 H), 8.60 (d, 1 H), 8.58 (br.s, 1 H), 8.58 (m, 10H), 7.97 (s, 1 H), 7.80 (d, 1 H), 7.25 (m, 3 H), 6.93 (d, 1 H), 3.98–4.24 (m, 4 H), 2.24 (s, 3 H), 2.24 (s, 3 H), 1.73–2.22 (m, 8 H).

EXAMPLE 151 cis-N-(7-chloroquinolin-4-yl)-N'-(3,5-dimethylbenzyl)cyclohexane-1,4-diamine

The titled compound was prepared according to method described in Example 141, substituting 3,5-dimethylbenzyl alcohol for 4-fluorobenzyl alcohol. MS(ESI) m/c 394 (M+H)$^+$; $^1$H NMR (500 MHz, DMSO-D6) δ ppm 8.74 (br.s, 2 H), 8.73 (d, 1 H), 8.60 (d, 1 H), 8.55 (br.s, 1 H), 7.96 (d, 1 H), 7.81 (dd, 1 H), 7.12 (s, 1 H), 7.08 (d, 2 H), 6.93 (d, 1 H), 3.98–4.19 (m, 4 H), 2.49 (s, 3 H), 2.30 (s, 3 H), 1.69–2.16 (m, 8 H).

EXAMPLE 152 cis-N-(7-chloroquinolin-4-yl)-N'-(3,5-dimethoxybenzyl)cyclohexane-1,4-diamine

The titled compound was prepared according to method described in Example 141, substituting 3,5-dimethoxybenzyl alcohol for 4-fluorobenzyl alcohol. MS(ESI) m/e 426 (M+H)$^+$; $^1$H NMR (500 MHz, DMSO-D6) δ ppm 8.85 (br.s, 2 H), 8.73 (d, 1 H), 8.60 (d, 1 H), 8.51 (br.s, 1 H), 7.96 (s, 1 H), 7.80 (dd, 1 H), 6.92 (d, 1 H), 6.72 (d, 2 H), 6.57 (m, 1 H), 4.01–4.29 (m, 2 H), 3.77 (s, 6 H), 1.70–2.15 (m, 8 H).

EXAMPLE 153 cis-N-(1,3-benzodioxol-5-ylmethyl)-N'-(7-chloroquinolin-4-yl)cyclohexane-1,4-diamine The titled compound was prepared according to method described in Example 141, substituting 3,4-methylenedioxybenzyl alcohol for 4-fluorobenzyl alcohol. MS(ESI) m/e 410 (M+H)$^+$; $^1$H NMR (500 MHz, DMSO-D6) δ ppm 8.73 (d, 1 H), 8.73 (br.s, 2 H), 8.60 (d, 1 H), 8.51 (br.s, 1 H), 7.96 (d, 1 H), 7.81 (d, 1 H), 7.10 (s, 1 H), 7.00 (s, 2 H), 6.92 (d, 1 H), 6.06 (s, 2 H), 3.96–4.24 (m, 4 H), 1.72–2.14 (m, 8 H).

EXAMPLE 154 cis-N-(7-chloroquinolin-4-yl)-N'-(3,4,5-trimethoxybenzyl)cyclohexane-1,4-diamine The titledd compound was prepared according to method described in Example 141, substituting 3,4,5-trimethoxybenzyl alcohol for 4-fluorobenzyl alcohol. MS(ESI) m/e 456 (M+H)$^+$; $^1$H NMR (500 MHz, DMSO-D6) δ ppm 8.87 (br.s, 2 H), 8.75 (d, 1 H), 8.61 (d, 1 H), 8.60 (br.s, 1 H), 7.97 (d, 1 H), 7.81 (dd, 1 H), 6.95 (d, 1 H), 6.87 (m, 2 H), 3.99–4.26 (m, 2 H), 3.80 (s, 6 H), 3.67 (s, 3 H), 1.70–2.15 (m, 8 H).

EXAMPLE 155 cis-N-(7-chloroquinolin-4-yl)-N'-(2,3-dichlorobenzyl)cyclohexane-1,4-diamine

The titled compound was prepared according to method described in Example 141, substituting 2,3-dichlorobenzyl alcohol for 4-fluorobenzyl alcohol. MS(ESI) m/e 436 (M+H)$^+$; $^1$H NMR (500 MHz, DMSO-D6) δ ppm 8.84–9.08 (br.s, 2 H), 8.75 (d, 1 H), 8.61 (d, 1 H), 8.60 (br.s, 1 H), 7.97 (d, 1 H), 7.81 (d, 1 H), 7.76 (d, 1 H), 7.63 (m, 1 H), 7.50 (m, 1 H), 6.95 (d, 1 H), 4.37 (s, 2 H), 1.72–2.22 (m, 8 H).

EXAMPLE 156 cis-N-(7-chloroquinolin-4-yl)-N'-(2,4-dichlorobenzyl)cyclohexane-1,4-diamine

The titled compound was prepared according to method described in Example 141, substituting 2,4-dichlorobenzyl alcohol for 4-fluorobenzyl alcohol. MS(ESI) m/e 436 (M+H)$^+$; $^1$H NMR (500 MHz, DMSO-D6) δ ppm 8.73 (d, 1 H), 8.60 (d, 1 H), 8.56 (br.s, 1 H), 7.95 (s, 1 H), 7.80 (m, 1 H), 7.68 (m, 2 H), 7.59 (m, 1 H), 6.93 (d, 1 H), 4.03–4.50 (br.s, 2 H), 4.03–4.50 (m, 2 H), 1.70–2.32 (m, 8 H).

EXAMPLE 157 cis-N-(7-chloroquinolin-4-yl)-N'-(2,5-dichlorobenzyl)cyclohexane-1,4-diamine

The titled compound was prepared according to method described in Example 141, substituting 2,5-dichlorobenzyl alcohol for 4-fluorobenzyl alcohol. MS(ESI) m/e 434 (M+H)$^+$; $^1$H NMR (500 MHz, DMSO-D6) δ ppm 8.78–9.11 (br.s, 2 H), 8.74 (d, 1 H), 8.60 (d, 1 H), 8.59 (br.s, 1 H), 7.96 (d, 1 H), 7.80 (m, 2 H), 7.60 (m, 2 H), 6.94 (d, 1 H), 3.99–4.47 (m, 2 H), 1.73–2.31 (m, 8 H).

EXAMPLE 158 cis-N-(7-chloroquinolin-4-yl)-N'-(3,4-dichlorobenzyl)cyclohexane-1,4-diamine

The titled compound was prepared according to method described in Example 141, substituting 3,4-dichlorobenzyl alcohol for 4-fluorobenzyl alcohol. MS(ESI) m/e 434 (M+H)$^+$; $^1$H NMR (500 MHz, DMSO-D6) δ ppm 8.81 (br.s, 2 H), 8.69 (br.s, 1 H), 8.58 (d, 1 H), 7.98 (d, 1 H), 7.94 (s, 1 H), 7.68–7.88 (m, 3 H), 7.49 (m, 2 H), 3.86–4.41 (m, 2 H), 1.62–2.24 (m, 8 H).

EXAMPLE 159 cis-N-(7-chloroquinolin-4-yl)-N'-(3,5-dichlorobenzyl)cyclohexane-1,4-diamine

The titled compound was prepared according to method described in Example 141, substituting 3,5-dichlorobenzyl alcohol for 4-fluorobenzyl alcohol. MS(ESI) m/e 434 (M+H)$^+$; $^1$H NMR (500 MHz, DMSO-D6) δ ppm 8.85 (br.s, 2 H), 8.73 (d, 1 H), 8.61 (d, 1 H), 8.60 (br.s, 1 H), 7.96 (d, 1 H), 7.82 (dd, 1 H), 7.72 (s, 1 H), 7.62 (d, 2 H), 6.94 (d, 1 H), 4.01–4.41 (m, 2 H), 1.73–2.28 (m, 8 H).

EXAMPLE 160 cis-N-(7-chloroquinolin-4-yl)-N'-phenylcyclohexane-1,4-diamine

The titled compound was prepared according to the methods described in Example 140, substituting bromobenzene for 1-bromo-3,5-difluorobenzene. MS (ESI(+)Q1MS m/z 352 (M+H)$^+$); $^1$H NMR (300 MHz, DMSO-D6) δ ppm 8.90 (d, 1 H), 8.71 (d, 1 H), 8.55 (d, 1 H), 7.91 (s, 1 H), 7.80 (dd, 1 H), 7.08 (t, 2 H), 7.00 (d, 1 H), 6.63 (d, 1 H), 6.52 (t, 1 H), 3.87–4.08 (br.s, 2 H), 1.66–2.16 (m, 8 H).

EXAMPLE 161 cis-N-{4-((7-chloroquinolin-4-yl)amino)cyclohexyl}propane-1-sulfonamide

The titled compound was prepared according to the method described in Example 15 by substituting 1-propanesulfonyl chloride for 4-chlorobenzene sulfonyl chloride. MS (ESI (+)) m/e 382 (M+H)+; 1H NMR (500 MHz, DMSO) δ ppm 8.73 (m, 2 H), 8.52 (d, 1 H), 7.91 (d, 1 H), 7.78 (dd, 1 H), 6.93 (m, 2 H), 3.89 (br.s, 1 H), 3.49 (m, 1 H), 3.02 (m, 2 H), 1.89 (m, 4 H), 1.71 (m, 6 H), 1.00 (t, 3 H).

EXAMPLE 162 cis-N-{4-((7-chloroquinolin-4-yl)amino)cyclohexyl}butane-1-sulfonamide

The titled compound was prepared according to the method described in Example 15 by substituting 1-butanesulfonyl chloride for 4-chlorobenzene sulfonyl chloride. MS (ESI (+)) m/e 396 (M+H)+; 1H NMR (500 MHz, DMSO) δ ppm 8.79 (m, 1 H), 8.70 (d, 1 H), 8.53 (d, 1 H), 7.91 (d, 1 H), 7.79 (dd, 1 H), 6.95 (d, 1 H), 6.91 (d, 1 H), 3.90 (m, 1 H), 3.49 (m, 1 H), 3.04 (m, 2 H), 1.89 (m, 4 H), 1.59–1.80 (m, 6 H), 1.42 (m, 2 H), 0.90 (t, 3 H).

EXAMPLE 163 cis-N-{4-((7-chloroquinolin-4-yl)amino)cyclohexyl}benzenesulfonamide

The titled compound was prepared according to the method described in Example 15 by substituting benzenesulfonyl chloride for 4-chlorobenzene sulfonyl chloride. MS (ESI (+)) m/e 416 (M+H)+; 1H NMR (500 MHz, DMSO) δ ppm 8.83 (m, 1 H), 8.70 (d, 1 H), 8.51 (d, 1 H), 7.91 (d, 1 H), 7.87 (m, 2 H), 7.79 (dd, 1 H), 7.64 (m, 3 H), 7.56 (d, 1 H), 6.93 (d, 1 H), 3.86 (m, 1 H), 3.12 (m, 1 H), 1.89 (m, 2 H), 1.74 (m, 4 H), 1.57 (m, 2 H).

EXAMPLE 164 cis-2-chloro-N-{4-((7-chloroquinolin-4-yl)amino)cyclohexyl}-4-fluorobenzenesulfonamide The titled compound was prepared according to the method described in Example 15 by substituting 2-chloro-4-fluorbenzenesulfonyl chloride for 4-chlorobenzene sulfonyl chloride. MS (ESI (+)) m/e 468 (M+H)+; 1H NMR (500 MHz, DMSO) δ ppm 8.76 (m, 1 H), 8.72 (d, 1 H), 8.52 (d, 1 H), 8.07 (m, 1 H), 7.92 (d, 1 H), 7.87 (d, 1 H), 7.80 (dd, 1 H), 7.72 (dd, 1 H), 7.44 (td, 1 H), 6.91 (d, 1 H), 3.85 (m, 1 H), 1.90 (m, 2 H), 1.75 (m, 4 H), 1.58 (m, 2 H).

EXAMPLE 165 cis-N-{4-((7-chloroquinolin-4-yl)amino)cyclohexyl}thiophene-2-sulfonamide

The titled compound was prepared according to the method described in Example 15 by substituting 2-thiophenesulfonyl chloride for 4-chlorobenzene sulfonyl chloride. MS (ESI (+)) m/e 422 (M+H)+; 1H NMR (500 MHz, DMSO) δ ppm 8.82 (m, 1 H), 8.70 (d, 1 H), 8.51 (d, 1 H), 7.94 (dd, 1 H), 7.91 (d, 1 H), 7.78 (m, 2 H), 7.63 (dd, 1 H), 7.21 (m, 1 H), 6.93 (d, 1 H), 3.87 (m, 1 H), 1.87 (m, 4 H), 1.73 (m, 2 H), 1.62 (m, 2 H).

EXAMPLE 166 cis-N-{4-((7-chloroquinolin-4-yl)amino)cyclohexyl}-2-(trifluoromethoxy)benzenesulfonamide The titled compound was prepared according to the method described in Example 15 by substituting 3-(trifluoromethoxy)benzenesulfonyl chloride for 4-chlorobenzene sulfonyl chloride. MS (ESI (+)) m/e 500 (M+H)+; 1H NMR (500 MHz, DMSO) δ ppm 8.78 (d, 1 H), 8.71 (d, 1 H), 8.52 (d, 1 H), 7.97 (dd, 1 H), 7.92 (d, 1 H), 7.79 (m, 3 H), 7.59 (t, 2 H), 6.92 (d, 1 H), 3.87 (m, 1 H), 1.87 (m, 4 H), 1.73 (m, 2 H), 1.62 (m, 2 H).

EXAMPLE 167 cis-N-{4-((7-chloroquinolin-4-yl)amino)cyclohexyl}-3-methylbenzenesulfonamide

The titled compound was prepared according to the method described in Example 15 by substituting m-tolylsulfonyl chloride for 4-chlorobenzene sulfonyl chloride. MS (ESI (+)) m/e 430 (M+H)+; 1H NMR (500 MHz, DMSO) δ ppm 8.86 (d, 1 H), 8.71 (d, 1 H), 8.51 (d, 1 H), 7.92 (d, 1 H), 7.80 (dd, 1 H), 7.68 (m, 2 H), 7.47 (m, 3 H), 6.94 (d, 1 H), 3.86 (m, 1 H), 3.13 (m, 1 H), 2.41 (s, 3 H), 1.90 (m, 2 H), 1.75 (m, 4 H), 1.57 (m, 2 H).

EXAMPLE 168 cis-N-{4-((7-chloroquinolin-4-yl)amino)cyclohexyl}-4-methylbenzenesulfonamide

The titled compound was prepared according to the method described in Example 15 by substituting p-tolylsulfonyl chloride for 4-chlorobenzene sulfonyl chloride. MS (ESI (+)) m/e 430 (M+H)+; 1H NMR (500 MHz, DMSO) δ ppm 8.85 (d, 1 H), 8.71 (d, 1 H), 8.51 (d, 1 H), 7.92 (d, 1 H), 7.79 (dd, 1 H), 7.74 (d, 2 H), 7.46 (d, 1 H), 7.41 (d, 2 H), 6.93 (d, 1 H), 3.85 (m, 1 H), 3.10 (m, 1 H), 2.39 (s, 3 H), 1.89 (m, 2 H), 1.75 (m, 4 H), 1.56 (m, 2 H).

EXAMPLE 169 cis-N-{4-((7-chloroquinolin-4-yl)amino)cyclohexyl}-2-fluorobenzenesulfonamide

The titled compound was prepared according to the method described in Example 15 by substituting 2-fluorobenzene sulfonyl chloride for 4-chlorobenzene sulfonyl chloride. MS (ESI (+)) m/e 434 (M+H)+; 1H NMR (500 MHz, DMSO) δ ppm 8.79 (m, 1 H), 8.71 (d, 1 H), 8.51 (d, 1 H), 7.92 (d, 1 H), 7.87 (m, 2 H), 7.79 (dd, 1 H), 7.72 (m, 1 H), 7.44 (m, 2 H), 6.92 (d, 1 H), 3.85 (m, 1 H), 1.91 (m, 2 H), 1.76 (m, 4 H), 1.60 (m, 2 H).

EXAMPLE 170 cis-N-{4-((7-chloroquinolin-4-yl)amino)cyclohexyl}-3-fluorobenzenesulfonamide

The titled compound was prepared according to the method described in Example 15 by substituting 3-fluorobenzene sulfonyl chloride for 4-chlorobenzene sulfonyl chloride. MS (ESI (+)) m/e 434 (M+H)+; 1H NMR (500 MHz, DMSO) δ ppm 8.83 (d, 1 H), 8.70 (d, 1 H), 8.51 (d, 1 H), 7.92 (d, 1 H), 7.80 (dd, 1 H), 7.68 (m, 4 H), 7.54 (m, 1 H), 6.94 (d, 1 H), 3.86 (m, 1 H), 3.19 (m, 1 H), 1.88 (m, 2 H), 1.75 (m, 4 H), 1.58 (m, 2 H).

EXAMPLE 171 cis-N-{4-((7-chloroquinolin-4-yl)amino)cyclohexyl}-4-fluorobenzenesulfonamide

The titled compound was prepared according to the method described in Example 15 by substituting 4-fluorobenzene sulfonyl chloride for 4-chlorobenzene sulfonyl chloride. MS (ESI (+)) m/e 434 (M+H)+; $^1$H NMR (500 MHz, DMSO) δ ppm 8.83 (d, 1 H), 8.70 (d, 1 H), 8.51 (d, 1 H), 7.93 (m, 3 H), 7.79 (dd, 1 H), 7.60 (d, 1 H), 7.46 (t, 2 H), 6.93 (d, 1 H), 3.86 (m, 1 H), 3.14 (m, 1 H), 1.88 (m, 2 H), 1.75 (m, 4 H), 1.58 (m, 2 H).

EXAMPLE 172 cis-N-{4-((7-chloroquinolin-4-yl)amino) cyclohexyl}-2-cyanobenzenesulfonamide

The titled compound was prepared according to the method described in Example 15 by substituting 2-cyanobenzene sulfonyl chloride for 4-chlorobenzene sulfonyl chloride. MS (ESI (+)) m/e 441 (M+H)+; $^1$H NMR (500 MHz, DMSO) δ ppm 8.79 (d, 1 H), 8.71 (d, 1 H), 8.52 (d, 1 H), 8.09 (m, 3 H), 7.94 (m, 2 H), 7.84 (td, 1 H), 7.80 (dd, 1 H), 6.93 (d, 1 H), 3.88 (m, 1 H), 3.41 (m, 1 H), 1.87 (m, 4 H), 1.73 (m, 2 H), 1.65 (m, 2 H).

EXAMPLE 173 cis-N-{4-((7-chloroquinolin-4-yl)amino) cyclohexyl}-3-cyanobenzenesulfonamide

The titled compound was prepared according to the method described in Example 15 by substituting 3-cyanobenzene sulfonyl chloride for 4-chlorobenzene sulfonyl chloride. MS (ESI (+)) m/e 441 (M+H)+; $^1$H NMR (500 MHz, DMSO) δ ppm 8.83 (d, 1 H), 8.70 (d, 1 H), 8.52 (d, 1 H), 8.27 (t, 1 H), 7.92 (d, 1 H), 7.82 (m, 3 H), 6.94 (d, 1 H), 3.88 (m, 1 H), 3.21 (m, 1 H), 1.88 (m, 2 H), 1.75 (m, 4 H), 1.65 (m, 2 H), 1.59 (m, 2 H).

EXAMPLE 174 cis-N-{4-((7-chloroquinolin-4-yl)amino) cyclohexyl}-4-cyanobenzenesulfonamide

The titled compound was prepared according to the method described in Example 15 by substituting 4-cyanobenzene sulfonyl chloride for 4-chlorobenzene sulfonyl chloride. MS (ESI (+)) m/e 441 (M+H)+; $^1$H NMR (500 MHz, DMSO) δ ppm 8.78 (d, 1 H), 8.69 (d, 1 H), 8.51 (d, 1 H), 8.11 (d, 2 H), 8.03 (d, 2 H), 7.91 (d, 1 H), 7.88 (d, 1 H), 7.79 (dd, 1 H), 6.93 (d, 1 H), 3.87 (m, 1 H), 3.20 (m, 1 H), 1.87 (m, 2 H), 1.74 (m, 4 H), 1.59 (m, 2 H).

EXAMPLE 175 cis-N-{4-((7-chloroquinolin-4-yl)amino) cyclohexyl}-2,5-dimethylbenzenesulfonamide The titled compound was prepared according to the method described in Example 15 by substituting p-xylene-2-sulfonyl chloride for 4-chlorobenzene sulfonyl chloride. MS (ESI (+)) m/e 444 (M+H)+; $^1$H NMR (500 MHz, DMSO) δ ppm 8.76 (d, 1 H), 8.71 (d, 1 H), 8.51 (d, 1 H), 7.91 (d, 1 H), 7.79 (dd, 1 H), 7.68 (s, 1 H), 7.54 (d, 1 H), 7.31 (m, 2 H), 6.90 (d, 1 H), 3.83 (m, 1 H), 3.20 (m, 1 H), 2.57 (s, 3 H), 2.34 (s, 3 H), 1.88 (m, 2 H), 1.73 (m, 4 H), 1.54(m, 2 H).

EXAMPLE 176 cis-N-{4-((7-chloroquinolin-4-yl)amino) cyclohexyl}-3-methoxybenzenesulfonamide

The titled compound was prepared according to the method described in Example 15 by substituting 3-methoxybenzene sulfonyl chloride for 4-chlorobenzene sulfonyl chloride. MS (ESI (+)) m/e 446 (M+H)+; $^1$H NMR (500 MHz, DMSO) δ ppm 8.83 (d, 1 H), 8.70 (d, 1 H), 8.51 (d, 1 H), 7.92 (d, 1 H), 7.80 (dd, 1 H), 7.54 (m, 2 H), 7.44 (m, 1 H), 7.39 (m, 1 H), 7.22 (m, 1 H), 6.93 (d, 1 H), 3.86 (m, 4 H), 3.13 (m, 1 H), 1.90 (m, 2 H), 1.75 (m, 4 H), 1.57 (m, 2 H).

EXAMPLE 177 cis-N-{4-((7-chloroquinolin-4-yl)amino) cyclohexyl}-4-methoxybenzenesulfonamide

The titled compound was prepared according to the method described in Example 15 by substituting 4-methoxybenzene sulfonyl chloride for 4-chlorobenzene sulfonyl chloride. MS (ESI (+)) m/e 446 (M+H)+; $^1$H NMR (500 MHz, DMSO) δ ppm 8.84 (d, 1 H), 8.70 (d, 1 H), 8.51 (d, 1 H), 7.92 (d, 1 H), 7.79 (m, 3 H), 7.38 (d, 1 H), 7.13 (d, 2 H), 6.93 (d, 1 H), 3.86 (m, 4 H), 3.08 (m, 1 H), 1.89 (m, 2 H), 1.75 (m, 4 H), 1.56 (m, 2 H).

EXAMPLE 178 cis-2-chloro-N-{4-((7-chloroquinolin-4-yl)amino) cyclohexyl}benzenesulfonamide

The titled compound was prepared according to the method described in Example 15 by substituting 2-chlorobenzene sulfonyl chloride for 4-chlorobenzene sulfonyl chloride. MS (ESI (+)) m/e 451 (M+H)+; $^1$H NMR (500 MHz, DMSO) δ ppm 8.79 (d, 1 H), 8.72 (d, 1 H), 8.52 (d, 1 H), 8.01 (d, 1 H), 7.92 (d, 1 H), 7.80 (m, 2 H), 7.67 (m, 2 H), 7.57 (m, 1 H), 6.92 (d, 1 H), 3.85 (m, 1 H), 1.91 (m, 2 H), 1.75 (m, 4 H), 1.59 (m, 2 H).

EXAMPLE 179 cis-N-(7-chloroquinolin-4-yl)-N'-(3,5-dimethylphenyl)cyclohexane-1,4-diamine

The titled compound was prepared according to the methods described in Example 140, substituting 5-bromo-m-xylene for 1-bromo-3,5-difluorobenzene. MS (ESI(+) Q1MS m/z 380 (M+H)+); $^1$H NMR (500 MHz, DMSO-D6) δ ppm 8.87 (d, 1 H), 8.71 (d, 1 H), 8.54 (d, 1 H), 7.93 (d, 1 H), 7.79 (dd, 1 H), 6.99 (d, 1 H), 6.27 (s, 2 H), 6.20 (s, 1 H), 3.86–4.23 (m, 2 H), 2.15 (s, 6 H), 1.67–2.01 (m, 8 H).

EXAMPLE 180 cis-N-(7-chloroquinolin-4-yl)-N'-(2-fluorophenyl) cyclohexane-1,4-diamine

The titled compound was prepared according to the methods described in Example 140, substituting 1-bromo-2-fluorobenzene for 1-bromo-3,5-difluorobenzene. MS (ESI (+)Q1MS m/z 370 (M+H)+); $^1$H NMR (500 MHz, DMSO-D6) δ ppm 8.84 (d, 1 H), 8.67 (d, 1 H), 8.55 (d, 1 H), 7.93 (s, 1 H), 7.80 (dd, 1 H), 6.97–7.08 (m, 3 H), 6.81 (t, 1 H), 6.58 (dd, 1 H), 4.68–4.92 (br.s, 1 H), 4.01 (br.s, 1 H), 3.66 (s, 1 H), 1.68–2.02 (m, 8 H).

EXAMPLE 181 cis-N-(7-chloroquinolin-4-yl)-N'-(3-fluorophenyl) cyclohexane-1,4-diamine

The titled compound was prepared according to the methods described in Example 140, substituting 1-bromo- 3-fluorobenzene for 1-bromo-3,5-difluorobenzene. MS (ESI (+)Q1MS m/z 370 (M+H)⁺); ¹H NMR (500 MHz, DMSO-D6) δ ppm 8.91 (d, 1 H), 8.72 (d, 1 H), 8.54 (d, 1 H), 7.93 (d, 1 H), 7.79 (dd, 1 H), 6.97–7.07 (m, 3 H), 6.47 (d, 1 H), 6.40 (d, 1 H), 6.28 (t, 1 H), 3.96 (m, 2 H), 1.70–1.98 (m, 8 H).

EXAMPLE 182 cis-N-(7-chloroquinolin-4-yl)-N'-2-naphthylcyclohexane-1,4-diamine

The titled compound was prepared according to the methods described in Example 140, substituting 2-bromonaphtalene for 1-bromo-3,5-difluorobenzene. MS (ESI(+)Q1MS m/z 402 (M+H)⁺); ¹H NMR (500 MHz, DMSO-D6) δ ppm 8.93 (d, 1 H), 8.73 (d, 1 H), 8.55 (d, 1 H), 7.94 (d, 1 H), 7.79 (dd, 1 H), 7.54–7.65 (m, 3 H), 7.30 (t, 1 H), 7.06–7.13 (m, 2 H), 7.02 (d, 1 H), 6.77 (d, 1 H), 5.75–5.95 (br.s., 1 H), 4.01 (s, 1 H), 3.69 (s, 1 H), 1.72–2.12 (m, 8 H).

EXAMPLE 183 cis-N-(7-chloroquinolin-4-yl)-N'-(3-fluoro-4-methylphenyl)cyclohexane-1,4-diamine The titled compound was prepared according to the methods described in Example 140, substituting 4-bromo-2-fluorotoluene for 1-bromo-3,5-difluorobenzene. MS (ESI (+)Q1MS m/z 384 (M+H)⁺); ¹H NMR (500 MHz, DMSO-D6) δ ppm 8.89 (d, 1 H), 8.71 (d, 1 H), 8.54 (d, 1 H), 7.93 (d, 1 H), 7.79 (dd, 1 H), 7.00 (d, 1 H), 6.94 (t, 1 H), 6.35–6.41 (m, 2 H), 5.50–5.70 (br.s., 1 H), 3.96 (s, 1 H), 3.50 (s, 1 H), 2.06 (s, 3 H), 1.67–1.97 (m, 8 H).

EXAMPLE 184 cis-N-(7-chloroquinolin-4-yl)-N'-1-naphthylcyclohexane-1,4-diamine

The titled compound was prepared according to the methods described in Example 140, substituting 1-bromotoluene for 1-bromo-3,5-difluorobenzene. MS (ESI (+)Q1MS m/z 402 (M+H)⁺); ¹H NMR (500 MHz, DMSO-D6) δ ppm 8.90 (d, 1 H), 8.72 (d, 1 H), 8.56 (d, 1 H), 8.27 (d, 1 H), 7.94 (d, 1 H), 7.73–7.83 (m, 2 H), 7.44 (m, 1 H), 7.31 (t, 1 H), 7.14 (d, 1 H), 7.03 (d, 1 H), 6.62 (d, 1 H), 5.61 (s, 1 H), 5.41–5.76 (br.s., 1 H), 4.03 (s, 1 H), 3.80 (s, 1 H), 1.69–2.26 (m, 8 H).

EXAMPLE 185 cis-3-chloro-N-{4-((7-chloroquinolin-4-yl)amino)cyclohexyl}benzenesulfonamide

The titled compound was prepared according to the method described in Example 15 by substituting 3-chlorobenzene sulfonyl chloride for 4-chlorobenzene sulfonyl chloride. MS (ESI (+)) m/e 451 (M+H)⁺; ¹H NMR (500 MHz, DMSO) δ ppm 8.84 (d, 1 H), 8.70 (d, 1 H), 8.52 (d, 1 H), 7.92 (d, 1 H), 7.89 (t, 1 H), 7.75 (m, 1 H), 7.71 (d, 1 H), 7.66 (t, 1 H), 6.94 (d, 1 H), 3.85 (m, 1 H), 3.85 (m, 2 H), 3.17 (m, 1 H), 1.88 (m, 2 H), 1.75 (m, 4 H), 1.58 (m, 2 H).

EXAMPLE 186 cis-4-(2-chloro-6-nitrophenoxy)-N-{4-((7-chloroquinolin-4-yl)amino)cyclohexyl}benzenesulfonamide The titled compound was prepared according to the method described in Example 15 by substituting 2'-chloro-6'-nitro-4-phenoxybenzene sulfonyl chloride for 4-chlorobenzene sulfonyl chloride. MS (ESI (+)) m/e 589 (M+H)⁺; ¹H NMR (500 MHz, DMSO) δ ppm 8.83 (d, 1 H), 8.70 (d, 1 H), 8.51 (d, 1 H), 8.18 (dd, 1 H), 8.08 (dd, 1 H), 7.92 (d, 1 H), 7.85 (d, 2 H), 7.79 (dd, 1 H), 7.65 (t, 1 H), 7.55 (d, 1 H), 7.12 (d, 2 H), 6.94 (d, 1 H), 3.83 (m, 1 H), 3.15 (m, 1 H), 1.89(m, 2 H), 1.75 (m, 4 H), 1.56 (m, 2 H).

EXAMPLE 187 cis-N-{4-((7-chloroguinolin-4-yl)amino)cyclohexyl}-2,4-difluorobenzenesulfonamide The titled compound was prepared according to the method described in Example 15 by substituting 2,4-difluorobenzene sulfonyl chloride for 4-chlorobenzene sulfonyl chloride. MS (ESI (+)) m/e 452 (M+H)⁺; ¹H NMR (500 MHz, DMSO) δ ppm 8.79 (d, 1 H), 8.71 (d, 1 H), 8.52 (d, 1 H), 7.92 (m, 3 H), 7.79 (dd, 1 H), 7.55 (m, 1 H), 7.31 (m, 1 H), 6.92 (d, 1 H), 3.87 (m, 1 H), 1.90 (m, 2 H), 1.76 (m, 4 H), 1.61 (m, 2 H).

EXAMPLE 188 cis-N-{4-((7-chloroquinolin-4-yl)amino)cyclohexyl}-3,4-difluorobenzenesulfonamide The titled compound was prepared according to the method described in Example 15 by substituting 3,4-difluorobenzene sulfonyl chloride for 4-chlorobenzene sulfonyl chloride. MS (ESI (+)) m/e 452 (M+H)⁺; ¹H NMR (500 MHz, DMSO) δ ppm 8.81 (m, 1 H), 8.69 (d, 1 H), 8.52 (d, 1 H), 7.92 (m, 2 H), 7.79 (d, 1 H), 7.72 (m, 3 H), 6.94 (d, 1 H), 3.86 (m, 1 H), 3.18 (m, 1 H), 1.66–1.94 (m, 6 H), 1.57 (m, 2 H).

EXAMPLE 189 cis-N-{4-((7-chloroquinolin-4-yl)amino)cyclohexyl}-4-propylbenzenesulfonamide

The titled compound was prepared according to the method described in Example 15 by substituting 4-n-propylbenzene sulfonyl chloride for 4-chlorobenzene sulfonyl chloride. MS (ESI (+)) m/e 458 (M+H)⁺; ¹H NMR (500 MHz, DMSO) δ ppm 8.82 (d, 1 H), 8.70 (d, 1 H), 8.51 (d, 1 H), 7.91 (d, 1 H), 7.77 (m, 3 H), 7.47 (d, 1 H), 7.42 (d, 2 H), 6.92 (d, 1 H), 3.84 (m, 1 H), 3.12(m, H), 2.65 (m, 2 H), 1.89 (m, 2 H), 1.75 (m, 4 H), 1.58 (m, 4 H), 0.89 (t, 3 H).

EXAMPLE 190 cis-N-{4-((7-chloroquinolin-4-yl)amino)cyclohexyl}-4-isopropylbenzenesulfonamide The titled compound was prepared according to the method described in Example 15 by substituting 4-isopropylbenzene sulfonyl chloride for 4-chlorobenzene sulfonyl chloride. MS (ESI (+)) m/e 458 (M+H)⁺; ¹H NMR (500 MHz, DMSO) δ ppm 8.81 (d, 1 H), 8.70 (d, 1 H), 8.51 (d, 1 H), 7.91 (d, 1 H), 7.77 (m, 3 H), 7.48 (m, 3 H), 6.93 (d, 1 H), 3.85 (m, 1 H), 3.11 (m, 1 H), 3.00 (m, 1 H), 1.90 (m, 2 H), 1.64–1.84 (m, 4 H), 1.57 (m, 2 H), 1.23 (d, 6 H).

EXAMPLE 191 cis-4-chloro-N-({5-(({4-((7-chloroquinolin-4-yl)amino)cyclohexyl}amino)sulfonyl)thien-2-yl}methyl)benzamide The titled compound was prepared according to the method described in Example 15 by substituting 5-((4- chloro-benzoylamino)-methyl)-thiophene-2-sulfonyl chloride for 4-chlorobenzene sulfonyl chloride. MS (ESI (+)) m/e 591 (M+H)$^+$; $^1$H NMR (500 MHz, DMSO) δ ppm 9.34 (t, 1 H), 8.87 (d, 1 H), 8.70 (d, 1 H), 8.52 (d, 1 H), 7.90 (m, 3 H), 7.79 (dd, 1 H), 7.70 (d, 1 H), 7.56 (m, 2 H), 7.47 (d, 1 H), 7.09 (d, 1 H), 6.94 (d, 1 H), 4.65 (m, 2 H), 3.87 (m, 1 H), 3.25 (m, 1 H), 1.85 (m, 4 H), 1.72 (m, 2 H), 1.61 (m, 2 H).

EXAMPLE 192 cis-5-bromo-6-chloro-N-{4-((7-chloroquinolin-4-yl)amino)cyclohexyl}pyridine-3-sulfonamide The titled compound was prepared according to the method described in Example 15 by substituting 5-bromo-6-chloro-pyridine-3-sulfonyl chloride for 4-chlorobenzene sulfonyl chloride. MS (ESI (+)) m/e 531 (M+H)$^+$; $^1$H NMR (500 MHz, DMSO) δ ppm 8.86 (d, 1 H), 8.83 (d, 1 H), 8.70 (d, 1 H), 8.59 (d, 1 H), 8.53 (d, 1 H), 7.92 (m, 2 H), 7.81 (dd, 1 H), 6.97 (d, 1 H), 3.91 (m, 1 H), 1.71–1.93 (m, 6 H), 1.63 (m, 2 H).

EXAMPLE 193 cis-4-tert-butyl-N-{4-((7-chloroquinolin-4-yl)amino)cyclohexyl}benzenesulfonamide The titled compound was prepared according to the method described in Example 15 by substituting 4-t-butylphenyl sulfonyl chloride for 4-chlorobenzene sulfonyl chloride. MS (ESI (+)) m/e 474 (M+H)$^+$; $^1$H NMR (500 MHz, DMSO) δ ppm 8.78 (d, 1 H), 8.70 (d, 1 H), 8.50 (d, 1 H), 7.91 (d, 1 H), 7.79 (m, 3 H), 7.63 (d, 2 H), 7.48 (d, 1 H), 6.92 (d, 1 H), 3.73–3.93 (m, 1 H), 3.09 (m, 1 H), 1.84–2.05 (m, 2 H), 1.64–1.84 (m, 4 H), 1.55 (m, 2 H), 1.31 (s, 9 H).

EXAMPLE 194 cis-3-chloro-N-{4-((7-chloroquinolin-4-yl)amino)cyclohexyl}-4-fluorobenzenesulfonamide The titled compound was prepared according to the method described in Example 15 by substituting 3-chloro-4-fluorobenzenesulfonyl chloride for 4-chlorobenzene sulfonyl chloride. MS (ESI (+)) m/e 469 (M+H)$^+$; $^1$H NMR (500 MHz, DMSO) δ ppm 8.81 (d, 1 H), 8.69 (d, 1 H), 8.52 (d, 1 H), 8.05 (dd, 1 H), 7.92 (d, 1 H), 7.88 (m, 1 H), 7.79 (dd, 1 H), 7.68 (m, 2 H), 6.94 (d, 1 H), 3.86 (m, 1 H), 3.18 (m, 1 H), 1.67–1.94 (m, 6 H), 1.59 (m, 2 H).

EXAMPLE 195 cis-N-{4-(({4-((7-chloroquinolin-4-yl)amino)cyclohexyl}amino)sulfonyl)phenyl}acetamide The titled compound was prepared according to the method described in Example 15 by substituting N-acetylsulfanilyl chloride for 4-chlorobenzene sulfonyl chloride. MS (ESI (+)) m/e 473 (M+H)$^+$; $^1$H NMR (500 MHz, DMSO) δ ppm 10.30 (s, 1 H), 8.84 (d, 1 H), 8.70 (d, 1 H), 8.51 (d, 1 H), 7.91 (d, 1 H), 7.78 (m, 5 H), 7.42 (d, 1 H), 6.93 (d, 1 H), 3.84 (m, 1 H), 3.10 (m, 1 H), 2.09 (s, 3 H), 1.89 (m, 2 H), 1.73 (m, 4 H), 1.55 (m, 2 H).

EXAMPLE 196 cis-N-{4-((7-chloroquinolin-4-yl)amino)cyclohexyl}-2,5-dimethoxybenzenesulfonamide The titled compound was prepared according to the method described in Example 15 by substituting 2,5-dimethoxybenzene sulfonyl chloride for 4-chlorobenzene sulfonyl chloride. MS (ESI (+)) m/e 476 (M+H)$^+$; $^1$H NMR (500 MHz, DMSO) δ ppm 8.74 (d, J=6.6 Hz, 1 H), 8.69 (d, J=9.4 Hz, 1 H), 8.51 (d, J=7.2 Hz, 1 H), 7.91 (d, J=2.2 Hz, 1 H), 7.79 (dd, J=9.0, 1.9 Hz, 1 H), 7.29 (m, 1 H), 7.20 (m, 2 H), 7.02 (d, J=5.0 Hz, 1 H), 6.91 (d, J=7.2 Hz, 1 H), 3.86 (m, 4 H), 3.76 (s, 3 H), 3.19 (m, 1 H), 1.92 (m, 2 H), 1.74 (m, 4 H), 1.55 (m, 2 H).

EXAMPLE 197 cis-N-{4-((7-chloroquinolin-4-yl)amino)cyclohexyl}-3,4-dimethoxybenzenesulfonamide The titled compound was prepared according to the method described in Example 15 by substituting 3,4-dimethoxybenzene sulfonyl chloride for 4-chlorobenzene sulfonyl chloride. MS (ESI (+)) m/e 476 (M+H)$^+$; $^1$H NMR (500 MHz, DMSO) δ ppm 8.71 (d, 1 H), 8.51 (d, 1 H), 7.92 (d, 1 H), 7.80 (dd, 1 H), 7.42 (dd, 1 H), 7.39 (d, 1 H), 7.36 (d, 1 H), 7.20 (m, 1 H), 7.13 (d, 1 H), 6.94 (d, 1 H), 3.84 (m, 7 H), 3.06 (m, 1 H), 1.91 (m, 2 H), 1.76 (m, 4 H), 1.55 (m, 2 H).

EXAMPLE 198 cis-N-{4-((7-chloroquinolin-4-yl)amino)cyclohexyl}-3-(trifluoromethyl)benzenesulfonamide The titled compound was prepared according to the method described in Example 15 by substituting 3-trifluoromethylbenzene sulfonyl chloride for 4-chlorobenzene sulfonyl chloride. MS (ESI (+)) m/e 484 (M+H)$^+$; $^1$H NMR (500 MHz, DMSO) δ ppm 8.87 (d, 1 H), 8.70 (d, 1 H), 8.52 (d, 1 H), 8.18 (m, 2 H), 8.06 (d, 1 H), 7.90 (m, 2 H), 7.81 (m, 2 H), 6.95 (d, 1 H), 3.88 (m, 1 H), 3.18 (m, 1 H), 1.88 (m, 2 H), 1.76 (m, 4 H), 1.59 (m, 2 H).

EXAMPLE 199 cis-N-{4-((7-chloroquinolin-4-yl)amino)cyclohexyl}-4-(trifluoromethyl)benzenesulfonamide The titled compound was prepared according to the method described in Example 15 by substituting 4-trifluoromethylbenzene sulfonyl chloride for 4-chlorobenzene sulfonyl chloride. MS (ESI (+)) m/e 484 (M+H)$^+$; $^1$H NMR (500 MHz, DMSO) δ ppm 8.86 (d, 1 H), 8.71 (d, 1 H), 8.52 (d, 1 H), 8.08 (d, 2 H), 8.02 (d, 2 H), 7.92 (d, 1 H), 7.84 (d, 1 H), 7.80 (dd, 1 H), 6.95 (d, 1 H), 3.84 (m, 1 H), 3.16 (m, 1 H), 1.91 (m, 2 H), 1.75 (m, 4 H), 1.48–1.69 (m, 2 H).

EXAMPLE 200 cis-2,3-dichloro-N-{4-((7-chloroquinolin-4-yl)amino)cyclohexyl}benzenesulfonamide The titled compound was prepared according to the method described in Example 15 by substituting 2,3-dichlorobenzenesulfonyl chloride for 4-chlorobenzene sulfonyl chloride.

MS (ESI (+)) m/e 486 (M+H)$^+$; $^1$H NMR (500 MHz, DMSO) δ ppm 8.78 (d, 1 H), 8.72 (d, 1 H), 8.52 (d, 1 H), 8.02 (m, 2 H), 7.95 (dd, 1 H), 7.92 (d, 1 H), 7.81 (dd, 1 H), 7.59 (t, 1 H), 6.92 (d, 1 H), 3.84 (m, 1 H), 1.92 (m, 2 H), 1.76 (m, 4 H), 1.60 (m, 2 H).

EXAMPLE 201 cis-2,4-dichloro-N-{4-((7-chloroquinolin-4-yl)amino)cyclohexyl}benzenesulfonamide The titled compound was prepared according to the method described in Example 15 by substituting 2,4-dichlorobenzenesulfonyl chloride for 4-chlorobenzene sulfonyl chloride.

MS (ESI (+)) m/e 486 (M+H)$^+$; $^1$H NMR (500 MHz, DMSO) δ ppm 8.78 (d, 1 H), 8.72 (d, 1H), 8.52 (d, 1 H), 8.00 (d, 1 H), 7.94 (m, 2 H), 7.89 (d, 1 H), 7.80 (dd, 1 H), 7.66 (dd, 1 H), 6.92 (d, 1 H), 3.84 (m, 1 H), 1.91 (m, 2 H), 1.74 (m, 4 H), 1.59 (m, 2 H).

EXAMPLE 202 cis-2,5-dichloro-N-{4-((7-chloroquinolin-4-yl) amino)cyclohexyl}benzenesulfonamide The titled compound was prepared according to the method described in Example 15 by substituting 2,5-dichlorobenzenesulfonyl chloride for 4-chlorobenzene sulfonyl chloride.

MS (ESI (+)) m/e 486 (M+H)$^+$; $^1$H NMR (500 MHz, DMSO) δ ppm 8.78 (d, 1 H), 8.72 (d, 1 H), 8.52 (d, 1 H), 8.02 (d, 1 H), 7.97 (d, 1 H), 7.92 (d, 1 H), 7.80 (dd, 1 H), 7.74 (m, 2 H), 6.92 (d, 1 H), 3.86 (m, 1 H), 1.90 (m, 2 H), 1.76 (m, 4 H), 1.61 (m, 2 H).

EXAMPLE 203 cis-3,4-dichloro-N-{4-((7-chloroquinolin-4-yl) amino)cyclohexyl}benzenesulfonamide The titled compound was prepared according to the method described in Example 15 by substituting 3,4-dichlorobenzenesulfonyl chloride for 4-chlorobenzene sulfonyl chloride.

MS (ESI (+)) m/e 486 (M+H)$^+$; $^1$H NMR (500 MHz, DMSO) δ ppm 8.86 (d, 1 H), 8.70 (d, 1 H), 8.52 (d, 1 H), 8.06 (d, 1 H), 7.92 (m, 2 H), 7.80 (m, 3 H), 6.95 (d, 1 H), 3.88 (m, 1 H), 3.21 (m, 1 H), 1.68–1.93 (m, 6 H), 1.60 (m, 2 H).

EXAMPLE 204 cis-3,5-dichloro-N-{4-((7-chloroquinolin-4-yl) amino)cyclohexyl}benzenesulfonamide The titled compound was prepared according to the method described in Example 15 by substituting 3,5-dichlorobenzenesulfonyl chloride for 4-chlorobenzene sulfonyl chloride.

MS (ESI (+)) m/e 486 (M+H)$^+$; $^1$H NMR (500 MHz, DMSO) δ ppm 8.87 (d, 1 H), 8.70 (d, 1 H), 8.52 (d, 1 H), 7.92 (d, 1 H), 7.86 (d, 1 H), 7.86 (d, 2 H), 7.81 (m, 2 H), 6.96 (d, 1 H), 3.90 (m, 1 H), 3.23 (m, 1 H), 1.69–1.94 (m, 6 H), 1.61 (m, 2 H).

EXAMPLE 205 cis-N-{4-((7-chloroquinolin-4-yl)amino) cyclohexyl}-1,1'-biphenyl-4-sulfonamide

The titled compound was prepared according to the method described in Example 15 by substituting 4-biphenyl sulfonyl chloride for 4-chlorobenzene sulfonyl chloride. MS (ESI (+)) m/e 492 (M+H)$^+$; $^1$H NMR (500 MHz, DMSO) δ ppm 8.85 (d, 1 H), 8.71 (d, 1 H), 8.51 (d, 1 H), 7.93 (m, 5 H), 7.80 (dd, 1 H), 7.75 (m, 2 H), 7.61 (d, 1 H), 7.52 (m, 2 H), 7.45 (m, 1 H), 6.94 (d, 1 H), 3.87 (m, 1 H), 3.18 (m, 1 H), 1.68–1.96 (m, 6 H), 1.60 (m, 2 H).

EXAMPLE 206 cis-2-bromo-N-{4-((7-chloroquinolin-4-yl)amino) cyclohexyl}benzenesulfonamide

The titled compound was prepared according to the method described in Example 15 by substituting 2-bromobenzene sulfonyl chloride for 4-chlorobenzene sulfonyl chloride. MS (ESI (+)) m/e 496 (M+H)$^+$; $^1$H NMR (500 MHz, DMSO) δ ppm 8.73 (m, 2 H), 8.51 (d, 1 H), 8.04 (dd, 1 H), 7.92 (d, 1 H), 7.87 (dd, 1 H), 7.79 (dd, 1 H), 7.73 (d, 1 H), 7.58 (m, 2 H), 6.91 (d, 1 H), 3.83 (m, 1 H), 1.93 (m, 2 H), 1.75 (m, 4 H), 1.61 (m, 2 H).

EXAMPLE 207 cis-3-bromo-N-{4-((7-chloroquinolin-4-yl)amino) cyclohexyl}benzenesulfonamide

The titled compound was prepared according to the method described in Example 15 by substituting 3-bromobenzene sulfonyl chloride for 4-chlorobenzene sulfonyl chloride. MS (ESI (+)) m/e 496 (M+H)$^+$; $^1$H NMR (500 MHz, DMSO) δ ppm 8.86 (d, 1 H), 8.70 (d, 1 H), 8.52 (d, 1 H), 8.02 (t, 1 H), 7.92 (d, 1 H), 7.88 (m, 2 H), 7.80 (dd, 1 H), 7.70 (d, 1 H), 7.59 (t, 1 H), 6.95 (d, 1 H), 3.89 (m, 1 H), 3.18 (m, 1 H), 1.90 (m, 2 H), 1.76 (m, 4 H), 1.60 (m, 2 H).

EXAMPLE 208 cis-4-bromo-N-{4-((7-chloroquinolin-4-yl)amino) cyclohexyl}benzenesulfonamide

The titled compound was prepared according to the method described in Example 15 by substituting 4-bromobenzene sulfonyl chloride for 4-chlorobenzene sulfonyl chloride. MS (ESI (+)) m/e 496 (M+H)$^+$; $^1$H NMR (500 MHz, DMSO) δ ppm 8.86 (d, 1 H), 8.71 (d, 1 H), 8.52 (d, 1 H), 7.92 (d, 1 H), 7.85 (m, 2 H), 7.79 (m, 3 H), 7.67 (d, 1 H), 6.94 (d, 1 H), 3.86 (m, 1 H), 3.15 (m, 1 H), 1.89 (m, 2 H), 1.74 (m, 4 H), 1.58 (m, 2 H).

EXAMPLE 209 cis-N-{4-((7-chloroquinolin-4-yl)amino) cyclohexyl}-4-(trifluoromethoxy) benzenesulfonamide The titled compound was prepared according to the method described in Example 15 by substituting 4-trifluoromethoxyphenyl sulfonyl chloride for 4-chlorobenzene sulfonyl chloride. MS (ESI (+)) m/e 500 (M+H)$^+$; $^1$H NMR (500 MHz, DMSO) δ ppm 8.87 (d, 1 H), 8.71 (d, 1 H), 8.52 (d, 1 H), 8.00 (m, 2 H), 7.92 (d, 1 H), 7.80 (dd, 1 H), 7.71 (d, 1 H), 7.62 (d, 2 H), 6.95 (d, 1 H), 3.88 (m, 1 H), 3.18 (m, 1 H), 1.67–1.94 (m, 6 H), 1.59 (m, 2 H).

EXAMPLE 210 cis-N-{4-((7-chloroquinolin-4-yl)amino) cyclohexyl}-3,5-dimethylisoxazole-4-sulfonamide The titled compound was prepared according to the method described in Example 15 by substituting 3,5-dimethyl-isoxalzole-4-sulfonyl chloride sulfonyl chloride for 4-chlorobenzene sulfonyl chloride. MS (ESI (+)) m/e 435 (M+H)$^+$; $^1$H NMR (500 MHz, DMSO) δ ppm 8.71 (m, 2 H), 8.51 (d, 1 H), 7.90 (d, 1 H), 7.83 (d, 1 H), 7.77 (dd, 1 H), 6.91 (d, 1 H), 3.84 (m, 1 H), 2.60 (s, 3 H), 2.36 (s, 3 H), 1.69–1.92 (m, 6 H), 1.63 (m, 2 H).

EXAMPLE 211 cis-(E)—N-{4-((7-chloroquinolin-4-yl)amino) cyclohexyl}-2-phenylethylenesulfonamide The titled compound was prepared according to the method described in Example 15 by substituting trans-beta-styrenesulfonyl chloride for 4-chlorobenzene sulfonyl chloride.

MS (ESI (+)) m/e 442 (M+H)⁺; ¹H NMR (500 MHz, DMSO) δ ppm 8.81 (m, 1 H), 8.70 (d, 1 H), 8.52 (d, 1 H), 7.91 (d, 1 H), 7.78 (dd, 1 H), 7.71 (m, 2 H), 7.46 (m, 3 H), 7.38 (d, 1 H), 7.21 (d, 1 H), 7.18 (d, 1 H), 6.95 (d, 1 H), 3.89 (m, 1 H), 3.42 (m, 1 H), 1.91 (m, 4 H), 1.72 (m, 4 H).

EXAMPLE 212 cis-N-{4-((7-chloroquinolin-4-yl)amino)cyclohexyl}-4-vinylbenzenesulfonamide

The titled compound was prepared according to the method described in Example 15 by substituting p-styrenesulfonyl chloride for 4-chlorobenzene sulfonyl chloride. MS (ESI (+)) m/e 442 (M+H)⁺; ¹H NMR (500 MHz, DMSO) δ ppm 8.84 (d, 1 H), 8.70 (d, 1 H), 8.51 (d, 1 H), 7.91 (d, 1 H), 7.82 (m, 3 H), 7.70 (d, 2 H), 7.55 (d, 1 H), 6.93 (d, 1 H), 6.82 (m, 1 H), 6.01 (d, 1 H), 5.45 (d, 1 H), 3.86 (m, 1 H), 3.13 (m, 1 H), 1.89 (m, 2 H), 1.75 (m, 4 H), 1.57(m, 2 H).

EXAMPLE 213 cis-5-chloro-N-{4-((7-chloroquinolin-4-yl)amino)cyclohexyl}thiophene-2-sulfonamide The titled compound was prepared according to the method described in Example 15 by substituting 5-chlorothiophene-2-sulfonyl chloride for 4-chlorobenzene sulfonyl chloride.

MS (ESI (+)) m/e 458 (M+H)⁺; ¹H NMR (500 MHz, DMSO) δ ppm 8.78 (m, 1 H), 8.69 (d, 1 H), 8.52 (d, 1 H), 7.94 (d, 1 H), 7.91 (d, 1 H), 7.78 (dd, 1 H), 7.52 (d, 1 H), 7.27 (d, 1 H), 6.94 (d, 1 H), 3.89 (m, 1 H), 1.79–2.00 (m, 4 H), 1.74 (m, 2 H), 1.63 (m, 2 H).

EXAMPLE 214 cis-N-{4-((7-chloroquinolin-4-yl)amino)cyclohexyl}-2,1,3-benzoxadiazole-4-sulfonamide The titled compound was prepared according to the method described in Example 15 by substituting benzo(1,2,5)oxadiazole-4-sulfonyl chloride for 4-chlorobenzene sulfonyl chloride. MS (ESI (+)) m/e 458 (M+H)⁺; ¹H NMR (500 MHz, DMSO) δ ppm 8.69 (m, 2 H), 8.50 (d, 1 H), 8.37 (d, 1 H), 8.16 (d, 1 H), 8.12 (d, 1 H), 7.91 (d, 1 H), 7.79 (m, 2 H), 6.89 (d, 1 H), 3.84 (m, 1 H), 3.54 (m, 1 H), 1.88 (m, 2 H), 1.75 (m, 4 H), 1.59 (m, 2 H).

EXAMPLE 215 cis-N-{4-((7-chloroquinolin-4-yl)amino)cyclohexyl}-3-nitrobenzenesulfonamide

The titled compound was prepared according to the method described in Example 15 by substituting 3-nitrobenzenesulfonyl chloride for 4-chlorobenzene sulfonyl chloride. MS (ESI (+)) m/e 461 (M+H)⁺; ¹H NMR (500 MHz, DMSO) δ ppm 8.81 (m, 1 H), 8.69 (d, 1 H), 8.63 (t, 1 H), 8.51 (m, 2 H), 8.28 (d, 1 H), 7.93 (m, 3 H), 7.79 (dd, 1 H), 6.93 (d, 1 H), 3.88 (m, 1 H), 3.20 (m, 1 H), 1.67–1.93 (m, 6 H), 1.60 (m, 2 H).

EXAMPLE 216 cis-N-{4-((7-chloroquinolin-4-yl)amino)cyclohexyl}-4-nitrobenzenesulfonamide

The titled compound was prepared according to the method described in Example 15 by substituting 4-nitrobenzene sulfonyl chloride for 4-chlorobenzene sulfonyl chloride. MS (ESI (+)) m/e 461 (M+H)⁺; ¹H NMR (500 MHz, DMSO) δ ppm 8.79 (d, 1 H), 8.69 (d, 1 H), 8.51 (d, 1 H), 8.44 (d, 2 H), 8.12 (d, 2 H), 7.95 (d, 1 H), 7.92 (d, 1 H), 7.79 (dd, 1 H), 6.93 (d, 1 H), 3.86 (m, 1 H), 3.23 (m, 1 H), 1.67–1.93 (m, 6 H), 1.60 (m, 2 H).

EXAMPLE 217 cis-3-chloro-N-{4-((7-chloroquinolin-4-yl)amino)cyclohexyl}-4-methylbenzenesulfonamide The titled compound was prepared according to the method described in Example 15 by substituting 3-chloro-4-methyl-benzenesulfonyl chloride for 4-chlorobenzene sulfonyl chloride. MS (ESI (+)) m/e 465 (M+H)⁺; ¹H NMR (500 MHz, DMSO) δ ppm 8.81 (d, 1 H), 8.70 (d, 1 H), 8.51 (d, 1 H), 7.92 (d, 1 H), 7.86 (d, 1 H), 7.79 (dd, 1 H), 7.72 (dd, 1 H), 7.61 (m, 2 H), 6.93 (d, 1 H), 3.86 (m, 1 H), 3.14 (m, 1 H), 2.42 (s, 3 H), 1.64–1.94 (m, 6 H), 1.58 (m, 2 H).

EXAMPLE 218 cis-N-{4-((7-chloroquinolin-4-yl)amino)cyclohexyl}quinoline-8-sulfonamide

The titled compound was prepared according to the method described in Example 15 by substituting 8-quinolinesulfonyl chloride for 4-chlorobenzene sulfonyl chloride. MS (ESI (+)) m/e 467 (M+H)⁺; ¹H NMR (500 MHz, DMSO) δ ppm 9.12 (dd, 1 H), 8.80 (d, 1 H), 8.66 (d, 1 H), 8.60 (dd, 1 H), 8.50 (d, 1 H), 8.36 (m, 2 H), 7.91 (d, 1 H), 7.81 (m, 2 H), 7.75 (m, 1 H), 6.95 (d, 1 H), 6.91 (d, 1 H), 3.85 (m, 1 H), 1.91 (m, 2 H), 1.63 (m, 4 H), 1.49 (m, 2 H).

EXAMPLE 219 cis-5-chloro-N-{4-((7-chloroquinolin-4-yl)amino)cyclohexyl}-1,3-dimethyl-1H-pyrazole-4-sulfonamide The titled compound was prepared according to the method described in Example 15 by substituting 5-chloro-1,3-dimethyl-1H-pyrazole-4-sulfonyl chloride for 4-chlorobenzene sulfonyl chloride. MS (ESI (+)) m/e 469 (M+H)⁺; ¹H NMR (500 MHz, DMSO) δ ppm 8.77 (m, 1 H), 8.70 (d, 1 H), 8.52 (d, 1 H), 7.91 (d, 1 H), 7.79 (dd, 1 H), 7.57 (d, 1 H), 6.92 (d, 1 H), 3.85 (m, 1 H), 3.78 (s, 3 H), 3.22 (m, 1 H), 2.33 (s, 3 H), 1.89 (m, 4 H), 1.71 (m, 2 H), 1.58 (m, 2 H).

EXAMPLE 220 cis-N-{4-((7-chloroquinolin-4-yl)amino)cyclohexyl}-2,1,3-benzothiadiazole-4-sulfonamide The titled compound was prepared according to the method described in Example 15 by substituting benzo(1,2,5)thiadiazole-4-sulfonyl chloride for 4-chlorobenzene sulfonyl chloride. MS (ESI (+)) m/e 474 (M+H)⁺; ¹H NMR (500 MHz, DMSO) δ ppm 8.71 (m, 2 H), 8.50 (d, 1 H), 8.41 (d, 1 H), 8.25 (d, 1 H), 7.90 (m, 2 H), 7.79 (dd, 1 H), 7.73 (d, 1 H), 6.89 (d, 1 H), 3.82 (m, 1 H), 3.50 (m, 1 H), 1.89 (m, 2 H), 1.60–1.81 (m, 4 H), 1.55 (m, 2 H).

EXAMPLE 221 cis-N-{4-((7-chloroquinolin-4-yl)amino)cyclohexyl}-2-methyl-5-nitrobenzenesulfonamide The titled compound was prepared according to the method described in Example 15 by substituting 2-methyl- 5-nitrobenzenesulfonyl chloride for 4-chlorobenzene sulfonyl chloride. MS (ESI (+)) m/e 475 (M+H)+; 1H NMR (500 MHz, DMSO) δ ppm 8.74 (m, 2 H), 8.60 (d, 1 H), 8.51 (d, 1 H), 8.37 (dd, 1 H), 8.09 (d, 1 H), 7.92 (d, 1 H), 7.79 (dd, 1 H), 7.74 (d, 1 H), 6.91 (d, 1 H), 4.07 (m, 1 H), 3.84 (m, 1 H), 2.75 (s, 3 H), 1.66–1.95 (m, 6 H), 1.60 (m, 2 H).

EXAMPLE 222 cis-methyl 3-(({4-((7-chloroquinolin-4-yl)amino) cyclohexyl}amino)sulfonyl)thiophene-2-carboxylate The titled compound was prepared according to the method described in Example 15 by substituting 3-chlorosulfonyl-thiophene-2-carboxylic acid methyl ester for 4-chlorobenzene sulfonyl chloride. MS (ESI (+)) m/e 480 (M+H)+; 1H NMR (500 MHz, DMSO) δ ppm 8.77 (m, 1 H), 8.66 (d, 1 H), 8.52 (d, 1 H), 8.04 (d, 1 H), 7.91 (d, 1 H), 7.80 (dd, 1 H), 7.52 (d, 1 H), 7.01 (d, 1 H), 6.94 (d, 1 H), 3.90 (m, 4 H), 3.40 (m, 1 H), 1.69–1.92 (m, 6 H), 1.62 (m, 2 H).

EXAMPLE 223 cis-N-{4-((7-chloroquinolin-4-yl)amino) cyclohexyl}-4-(1,1-dimethylpropyl) benzenesulfonamide The titled compound was prepared according to the method described in Example 15 by substituting 4-n-amylbenzenesulfonyl chloride for 4-chlorobenzene sulfonyl chloride. MS (ESI(+)) m/e 486 (M+H)+; 1H NMR (500-MHz, DMSO) δ ppm 8.80 (m, 1 H), 8.50 (d, 1 H), 8.50 (d, 1 H), 7.91 (d, 1 H), 7.79 (m, 3 H), 7.56 (d, 2 H), 7.48 (d, 1 H), 6.92 (d, 1 H), 3.83 (m, 1 H), 3.11 (m, 1 H), 1.89 (m, 2 H), 1.49–1.83 (m, 8 H), 1.28 (s, 6 H), 0.61 (t, 3 H).

EXAMPLE 224 cis-4-butoxy-N-{4-((7-chloroquinolin-4-yl)amino) cyclohexyl}benzenesulfonamide

The titled compound was prepared according to the method described in Example 15 by substituting 4-butoxybenzenesulfonyl chloride for 4-chlorobenzene sulfonyl chloride. MS (ESI (+)) m/e 488 (M+H)+; 1H NMR (500 MHz, DMSO) δ ppm 8.82 (d, 1 H), 8.70 (d, 1 H), 8.51 (d, 1 H), 7.91 (d, 1 H), 7.77 (m, 3 H), 7.37 (d, 1 H), 7.11 (d, 2 H), 6.92 (d, 1 H), 4.06 (t, 2 H), 3.85 (m, 1 H), 3.08 (m, 1 H), 1.65–1.97 (m, 8 H), 1.55 (m, 2 H), 1.44 (m, 2 H), 0.94 (t, 3 H).

EXAMPLE 225 cis-N-{4-((7-chloroquinolin-4-yl)amino) cyclohexyl}-5-isoxazol-3-ylthiophene-2-sulfonamide The titled compound was prepared according to the method described in Example 15 by substituting 5-isoxazol-3-yl-thiophene-2-sulfonyl chloride for 4-chlorobenzene sulfonyl chloride. MS (ESI (+)) m/e 490 (M+H)+; 1H NMR (500 MHz, DMSO) δ ppm 8.81 (d, 1 H), 8.73 (d, 1 H), 8.69 (d, 1 H), 8.52 (d, 1 H), 8.04 (d, 1 H), 7.91 (d, 1 H), 7.78 (m, 2 H), 7.72 (d, 1 H), 7.10 (d, 1 H), 6.94 (d, 1 H), 3.88 (m, 1 H), 3.37 (m, 1 H), 1.89 (m, 4 H), 1.77 (m, 2 H), 1.65 (m, 2 H).

EXAMPLE 226 cis-N-{4-((7-chloroquinolin-4-yl)amino) cyclohexyl}-1-((1S,4R)-7,7-dimethyl-2-oxobicyclo (2.2.1)hept-1-yl)methanesulfonamide The titled compound was prepared according to the method described in Example 15 by substituting (+)-10-camphorsulfonyl chloride for 4-chlorobenzene sulfonyl chloride. MS (ESI (+)) m/e 491 (M+H)+; 1H NMR (500 MHz, DMSO) δ ppm 8.85 (d, 1 H), 8.70 (d, 1 H), 8.53 (d, 1 H), 7.92 (d, 1 H), 7.79 (dd, 1 H), 6.97 (m, 2 H), 3.92 (m, 1 H), 3.60 (m, 1 H), 3.39 (m, 1 H), 2.97 (d, 1 H), 2.38 (m, 2 H), 2.07 (m, 1 H), 1.91 (m, 6 H), 1.74 (m, 4 H), 1.54 (m, 1 H), 1.40 (m, 1 H), 1.05 (s, 3 H), 0.83 (s, 3 H).

EXAMPLE 227 cis-2,5-dichloro-N-{4-((7-chloroquinolin-4-yl) amino)cyclohexyl}thiophene-3-sulfonamide The titled compound was prepared according to the method described in Example 15 by substituting 2,5-dichlorothiophene-3-sulfonyl chloride for 4-chlorobenzene sulfonyl chloride. MS (ESI (+)) m/e 491 (M+H)+; 1H NMR (500 MHz, DMSO) δ ppm 8.77 (m, 1 H), 8.70 (d, 1 H), 8.52 (d, 1 H), 7.98 (d, 1 H), 7.91 (d, 1 H), 7.79 (dd, 1 H), 7.34 (s, 1 H), 6.94 (d, 1 H), 3.87 (m, 1 H), 3.40 (m, 1 H), 1.87 (m, 4 H), 1.76 (m, 2 H), 1.65 (m, 2 H).

EXAMPLE 228 cis-4,5-dichloro-N-{4-((7-chloroquinolin-4-yl) amino)cyclohexyl}thiophene-2-sulfonamide The titled compound was prepared according to the method described in Example 15 by substituting 2,3-dichlorothiophene-5-sulfonyl chloride for 4-chlorobenzene sulfonyl chloride. MS (ESI (+)) m/e 491 (M+H)+; 1H NMR (500 MHz, DMSO) δ ppm 8.77 (d, 1 H), 8.69 (d, 1 H), 8.52 (d, 1 H), 8.09 (d, 1 H), 7.91 (d, 1 H), 7.79 (dd, 1 H), 7.73 (s, 1 H), 6.95 (d, 1 H), 3.89 (m, 1 H), 3.40 (m, 1 H), 1.85 (m, 4 H), 1.77 (m, 2 H), 1.66 (m, 2 H).

EXAMPLE 229 cis-7-chloro-N-{4-((7-chloroquinolin-4-yl)amino) cyclohexyl}-2,1,3-benzoxadiazole-4-sulfonamide The titled compound was prepared according to the method described in Example 15 by substituting 7-chloro-benzo(1,2,5)oxadiazole-4-sulfonyl chloride for 4-chlorobenzene sulfonyl chloride. MS (ESI (+)) m/e 493 (M+H)+; 1H NMR (500 MHz, DMSO) δ ppm 8.71 (m, 2 H), 8.51 (d, 1 H), 8.22 (d, 1 H), 8.06 (d, 1 H), 7.93 (m, 2 H), 7.79 (dd, 1 H), 6.90 (d, 1 H), 3.85 (m, 1 H), 3.50 (m, 1 H), 1.65–1.97 (m, 6 H), 1.58 (m, 2 H).

EXAMPLE 230 cis-N-{4-((7-chloroquinolin-4-yl)amino) cyclohexyl}-4-(methylsulfonyl)benzenesulfonamide The titled compound was prepared according to the method described in Example 15 by substituting 4-methylsulfonylbenzenesulfonyl chloride for 4-chlorobenzene sulfonyl chloride. MS (ESI (+)) m/e 494 (M+H)+; 1H NMR (500 MHz, DMSO) δ ppm 8.77 (m, 1 H), 8.69 (d, 1 H), 8.51 (d, 1 H), 8.17 (d, 2 H), 8.11 (d, 2 H), 7.91 (d, 1 H), 7.87 (d, 1 H), 7.79 (dd, 1 H), 6.93 (d, 1 H), 3.86 (m, 1 H), 3.21 (m, 1 H), 1.68–1.95 (m, 6 H), 1.60 (m, 2 H).

EXAMPLE 231 cis-4-chloro-N-{4-((7-chloroquinolin-4-yl)amino) cyclohexyl}-3-nitrobenzenesulfonamide The titled compound was prepared according to the method described in Example 15 by substituting 4-chloro- 3-nitrobenzenesulfonyl chloride for 4-chlorobenzene sulfonyl chloride. MS (ESI (+)) m/e 495 (M+H)$^+$; $^1$H NMR (500 MHz, DMSO) δ ppm 8.81 (d, 1 H), 8.69 (d, 1 H), 8.52 (m, 2 H), 8.13 (dd, 1 H), 8.05 (d, 1 H), 7.92 (m, 2 H), 7.80 (dd, 1 H), 6.94 (d, 1 H), 3.89 (m, 1 H), 3.27 (m, 1 H), 1.69–1.95 (m, 6 H), 1.61 (m, 2 H).

EXAMPLE 232 cis-6-chloro-N-{4-((7-chloroquinolin-4-yl)amino)cyclohexyl}-3H-1lambda-4-imidazo(2,1-b)(1,3)thiazole-5-sulfonamide The titled compound was prepared according to the method described in Example 15 by substituting 6-chloro-3H-1λ$^4$-imidazo(2,1-b)thiazole-5-sulfonyl chloride for 4-chlorobenzene sulfonyl chloride. MS (ESI (+)) m/e 498 (M+H)$^+$; $^1$H NMR (500 MHz, DMSO) δ ppm 8.76 (m, 1 H), 8.69 (d, 1 H), 8.52 (d, 1 H), 8.23 (d, 1 H), 8.05 (d, 1 H), 7.91 (d, 1 H), 7.79 (dd, 1 H), 7.64 (d, 1 H), 6.92 (d, 1 H), 3.86 (m, 1 H), 2.54 (m, 1 H), 1.70–1.93 (m, 6 H), 1.64(m, 2 H).

EXAMPLE 233 cis-N-{4-((7-chloroquinolin-4-yl)amino)cyclohexyl}-2-(trifluoroacetyl)-1,2,3,4-tetrahydroisoguinoline-7-sulfonamide The titled compound was prepared according to the method described in Example 15 by substituting 2-(2,2,2-trifluoro-acetyl)-1,2,3,4-tetrahydro-isoquinoline-7-sulfonyl chloride for 4-chlorobenzene sulfonyl chloride. MS (ESI (+)) m/e 567 (M+H)$^+$; $^1$H NMR (500 MHz, DMSO) δ ppm 8.86 (d, 1 H), 8.70 (d, 1 H), 8.51 (d, 1 H), 7.92 (d, 1 H), 7.76 (m, 3 H), 7.51 (m, 1 H), 7.45 (m, 1 H), 6.94 (d, 1 H), 4.86 (d, 2 H), 3.85 (m, 3 H), 3.14 (m, 1 H), 2.98 (m, 2 H), 1.75–2.02 (m, 4 H), 1.70 (m, 2 H), 1.56 (m, 2 H).

EXAMPLE 234 cis-N-{4-((7-chloroquinolin-4-yl)amino)cyclohexyl}-5-fluoro-2-methylbenzenesulfonamide The titled compound was prepared according to the method described in Example 15 by substituting 5-fluoro-2-methylbenzenesulfonyl chloride for 4-chlorobenzene sulfonyl chloride. MS (ESI (+)) m/e 448 (M+H)$^+$; $^1$H NMR (500 MHz, DMSO) δ ppm 8.78 (d, 1 H), 8.71 (d, 1 H), 8.52 (d, 1 H), 7.92 (d, 1 H), 7.80 (m, 2 H), 7.62 (dd, 1 H), 7.44 (m, 2 H), 6.92 (d, 1 H), 3.85 (m, 1 H), 3.85 (m, 1 H), 2.59 (s, 3 H), 1.87 (m, 2 H), 1.73 (m, 4 H), 1.60 (m, 2 H).

EXAMPLE 235 cis-4-chloro-N-{4-((7-chloroquinolin-4-yl)amino)cyclohexyl}-3-(trifluoromethyl)benzenesulfonamide The titled compound was prepared according to the method described in Example 15 by substituting 4-chloro-3-(trifluoromethylbenzene)sulfonyl chloride for 4-chlorobenzene sulfonyl chloride. MS (ESI (+)) m/e 518 (M+H)$^+$; $^1$H NMR (500 MHz, DMSO) δ ppm 8.84 (d, 1 H), 8.69 (d, 1 H), 8.52 (d, 1 H), 8.25 (d, 1 H), 8.15 (dd, 1 H), 8.01 (d, 1 H), 7.91 (d, 1 H), 7.87 (d, 1 H), 7.80 (dd, 1 H), 6.95 (d, 1 H), 3.87 (m, 1 H), 3.21 (m, 1 H), 1.89 (m, 2 H), 1.75 (m, 4 H), 1.61 (m, 2 H).

EXAMPLE 236 cis-2,4,5-trichloro-N-{4-((7-chloroquinolin-4-yl)amino)cyclohexyl}benzenesulfonamide The titled compound was prepared according to the method described in Example 15 by substituting 2,4,5-trichlorobenzenesulfonyl chloride for 4-chlorobenzene sulfonyl chloride. MS (ESI (+)) m/e 520 (M+H)$^+$; $^1$H NMR (500 MHz, DMSO) δ ppm 8.70 (m, 2 H), 8.52 (d, 1 H), 8.11 (m, 3 H), 7.91 (d, 1 H), 7.79 (dd, 1 H), 6.91 (d, 1 H), 3.86 (m, 1 H), 3.38 (m, 1 H), 1.91 (m, 2 H), 1.76 (m, 4 H), 1.61 (m, 2 H).

EXAMPLE 237 cis-2,4,6-trichloro-N-{4-((7-chloroquinolin-4-yl)amino)cyclohexyl}benzenesulfonamide The titled compound was prepared according to the method described in Example 15 by substituting 2,4,6-trichlorobenzenesulfonyl chloride for 4-chlorobenzene sulfonyl chloride. MS (ESI (+)) m/e 520 (M+H)$^+$; $^1$H NMR (500 MHz, DMSO) δ ppm 8.68 (m, 2 H), 8.51 (d, 1 H), 8.12 (d, 1 H), 7.91 (d, 1 H), 7.89 (s, 1 H), 7.79 (dd, 1 H), 6.89 (d, 1 H), 3.84 (m, 1 H), 3.39 (m, 1 H), 1.88 (m, 2 H), 1.76 (m, 4 H), 1.62 (m, 2 H).

EXAMPLE 238 cis-2,3,4-trichloro-N-{4-((7-chloroquinolin-4-yl)amino)cyclohexyl}benzenesulfonamide The titled compound was prepared according to the method described in Example 15 by substituting 2,3,4-trichlorobenzenesulfonyl chloride for 4-chlorobenzene sulfonyl chloride. MS (ESI (+)) m/e 520 (M+H)$^+$; $^1$H NMR (500 MHz, DMSO) δ ppm 8.72 (m, 2 H), 8.52 (d, 1 H), 8.11 (d, 1 H), 7.99 (d, 1 H), 7.92 (d, 1 H), 7.89 (d, 1 H), 7.80 (dd, 1 H), 6.91 (d, 1 H), 3.85 (m, 1 H), 3.36 (m, 1 H), 1.90 (m, 2 H), 1.75 (m, 4 H), 1.61 (m, 2 H).

EXAMPLE 239 cis-5-chloro-N-{4-((7-chloroquinolin-4-yl)amino)cyclohexyl}-3-methyl-1-benzothiophene-2-sulfonamide The titled compound was prepared according to the method described in Example 15 by substituting 5-chloro-3-methyl-benzo(b)thiophene-2-sulfonyl chloride for 4-chlorobenzene sulfonyl chloride. MS (ESI (+)) m/e 521 (M+H)$^+$; $^1$H NMR (500 MHz, DMSO) δ ppm 8.82 (d, 1 H), 8.71 (d, 1 H), 8.51 (d, 1 H), 8.15 (d, 1 H), 8.10 (d, 1 H), 8.05 (d, 1 H), 7.92 (d, 1 H), 7.80 (dd, 1 H), 7.59 (dd, 1 H), 6.93 (d, 1 H), 3.85 (m, 1 H), 3.38 (m, 1 H), 2.66 (s, 3 H), 1.68–1.96 (m, 6 H), 1.62 (m, 2 H).

EXAMPLE 240 cis-5-bromo-N-{4-((7-chloroquinolin-4-yl)amino)cyclohexyl}-2-methoxybenzenesulfonamide The titled compound was prepared according to the method described in Example 15 by substituting 5-bromo-2-methoxybenzenesulfonyl chloride for 4-chlorobenzene sulfonyl chloride. MS (ESI (+)) m/e 525 (M+H)$^+$; $^1$H NMR (500 MHz, DMSO) δ ppm 8.73 (m, 2 H), 8.51 (d, 1 H), 7.92 (d, 1 H), 7.80 (m, 3 H), 7.30 (d, 1 H), 7.24 (d, 1 H), 6.92 (d, 1 H), 3.93 (s, 3 H), 3.83 (m, 1 H), 3.23 (m, 1 H), 1.90 (m, 2 H), 1.74 (m, 4 H), 1.58 (m, 2 H).

EXAMPLE 241 cis-N-{4-((7-chloroquinolin-4-yl)amino)cyclohexyl}-2-nitro-4-(trifluoromethyl)benzenesulfonamide The titled compound was prepared according to the method described in Example 15 by substituting 2-nitro-4-

(trifluoromethyl)benzenesulfonyl chloride for 4-chlorobenzene sulfonyl chloride. MS (ESI (+)) m/e 529 (M+H)+; 1H NMR (500 MHz, DMSO) δ ppm 8.79 (d, 1 H), 8.70 (d, 1 H), 8.57 (d, 1 H), 8.53 (d, 1 H), 8.32 (m, 3 H), 7.92 (d, 1 H), 7.81 (dd, 1 H), 6.95 (d, 1 H), 3.90 (m, 1 H), 3.39 (m, 1 H), 1.72–1.96 (m, 6 H), 1.66 (m, 2 H).

EXAMPLE 242 cis-N-({5-(({4-((7-chloroquinolin-4-yl)amino) cyclohexyl}amino)sulfonyl)thien-2-yl}methyl) benzamide The titled compound was prepared according to the method described in Example 15 by substituting 5-(benzoylamino-methyl)-thiophene-2-sulfonyl chloride for 4-chlorobenzene sulfonyl chloride. MS (ESI (+)) m/e 557 (M+H)+; 1H NMR (500 MHz, DMSO) δ ppm 9.26 (t, 1 H), 8.84 (d, 1 H), 8.69 (d, 1 H), 8.51 (d, 1 H), 7.91 (d, 1 H), 7.88 (m, 2 H), 7.79 (dd, 1 H), 7.69 (d, 1 H), 7.55 (m, 1 H), 7.47 (m, 3 H), 7.09 (d, 1 H), 6.93 (d, 1 H), 4.66 (d, 2 H), 3.86 (m, 1 H), 3.25 (m, 1 H), 1.85 (m, 4 H), 1.71 (m, 2 H), 1.61 (m, 2 H).

EXAMPLE 243 cis-N-{4-((7-chloroquinolin-4-yl)amino) cyclohexyl}-5-(2-(methylthio)pyrimidin-4-yl) thiophene-2-sulfonamide The titled compound was prepared according to the method described in Example 15 by substituting 5-(2-methylsulfanyl-pyrimidin-4-yl)-thiophene-2-sulfonyl chloride for 4-chlorobenzene sulfonyl chloride. MS (ESI (+)) m/e 546 (M+H)+; 1H NMR (500 MHz, DMSO) δ ppm 8.87 (d, 1 H), 8.71 (m, 2 H), 8.52 (d, 1 H), 8.11 (d, 1 H), 7.97 (d, 1 H), 7.92 (d, 1 H), 7.80 (m, 2 H), 7.72 (d, 1 H), 6.95 (d, 1 H), 3.88 (m, 1 H), 3.88 (m, 1 H), 2.57 (s, 3 H), 1.89 (m, 4 H), 1.76 (m, 2 H), 1.65 (m, 2 H).

EXAMPLE 244 cis-N-{4-((7-chloroquinolin-4-yl)amino) cyclohexyl}-3,5-bis(trifluoromethyl) benzenesulfonamide The titled compound was prepared according to the method described in Example 15 by substituting 3,5-bis (trifluoromethyl)benzenesulfonyl chloride for 4-chlorobenzene sulfonyl chloride. MS (ESI (+)) m/e 552 (M+H)+; 1H NMR (500 MHz, DMSO) δ ppm 8.81 (m, 1 H), 8.68 (d, 1 H), 8.52 (m, 2 H), 8.47 (s, 2 H), 7.98 (d, 1 H), 7.91 (d, 1 H), 7.80 (dd, 1 H), 6.94 (d, 1 H), 3.88 (m, 1 H), 1.87 (m, 2 H), 1.75 (m, 4 H), 1.60 (m, 2 H).

EXAMPLE 245 cis-2,6-dichloro-N-{4-((7-chloroquinolin-4-yl) amino)cyclohexyl}-4-(trifluoromethyl) benzenesulfonamide The titled compound was prepared according to the method described in Example 15 by substituting 2,6-dichloro-4-trifluoromethyl-phenyl-sulfonyl chloride for 4-chlorobenzene sulfonyl chloride. MS (ESI (+)) m/e 553 (M+H)+; 1H NMR (500 MHz, DMSO) δ ppm 8.73 (m, 2 H), 8.52 (d, 1 H), 8.31 (d, 1 H), 8.11 (s, 2 H), 7.92 (d, 1 H), 7.80 (dd, 1 H), 6.91 (d, 1 H), 3.86 (m, 1 H), 3.43 (m, 1 H), 1.90 (m, 2 H), 1.76 (m, 4 H), 1.62 (m, 2 H).

EXAMPLE 246 cis-2-butoxy-N-{4-((7-chloroquinolin-4-yl)amino) cyclohexyl}-5-(1,1-dimethylpropyl) benzenesulfonamide The titled compound was prepared according to the method described in Example 15 by substituting 2-butoxy-5-tert-pentylbenzenesulfonyl chloride for 4-chlorobenzene sulfonyl chloride. MS (ESI (+)) m/e 558 (M+H)+; 1H NMR (500 MHz, DMSO) δ ppm 8.67 (d, 2 H), 8.51 (d, 1 H), 7.90 (d, 1 H), 7.78 (dd, 1 H), 7.68 (d, 1 H), 7.54 (dd, 1 H), 7.17 (d, 1 H), 6.90 (d, 1 H), 6.66 (d, 1 H), 4.13 (t, 2 H), 3.84 (m, 1 H), 1.90 (m, 2 H), 1.75 (m, 6 H), 1.60 (m, 4 H), 1.48 (m, 2 H), 1.24 (s, 6 H), 0.94 (t, 3 H), 0.62 (t, 3 H).

EXAMPLE 247 cis-N-{4-((7-chloroquinolin-4-yl)amino) cyclohexyl}-5-(phenylsulfonyl)thiophene-2-sulfonamide The titled compound was prepared according to the method described in Example 15 by substituting 5-benzenesulfonyl-thiophene-2-sulfonyl chloride for 4-chlorobenzene sulfonyl chloride. MS (ESI (−)) m/e 560 (M−1); 1H NMR (500 MHz, DMSO) δ ppm 8.83 (d, 1 H), 8.69 (d, 1 H), 8.52 (d, 1 H), 8.18 (d, 1 H), 8.05 (m, 2 H), 7.91 (d, 2 H), 7.79 (m, 2 H), 7.67 (m, 3 H), 6.95 (d, 1 H), 3.88 (m, 1 H), 3.23 (m, 1 H), 1.55–1.91 (m, 8 H).

EXAMPLE 248 cis-4-(3-chloro-2-cyano-phenoxy)-N-{4-((7-chloroquinolin-4-yl)amino) cyclohexyl}benzenesulfonamide The titled compound was prepared according to the method described in Example 15 by substituting 4-(3-chloro-2-cyano-phenoxy)-benzenesulfonyl chloride for 4-chlorobenzene sulfonyl chloride. MS (ESI (+)) m/e 568 (M+H)+; 1H NMR (500 MHz, DMSO) δ ppm 8.77 (m, 1 H), 8.69 (d, 1 H), 8.51 (d, 1 H), 7.92 (m, 3 H), 7.77 (m, 2 H), 7.59 (m, 2 H), 7.39 (d, 2 H), 7.17 (d, 1 H), 6.92 (d, 1 H), 3.85 (m, 1 H), 3.17 (m, 1 H), 1.68–1.95 (m, 6 H), 1.59 (m, 2 H).

EXAMPLE 249 cis-N-{4-((7-chloroquinolin-4-yl)amino) cyclohexyl}-4-ethylbenzenesulfonamide

The titled compound was prepared according to the method described in Example 15 by substituting 4-ethylbenzenesulfonyl chloride for 4-chlorobenzene sulfonyl chloride. MS (ESI (+)) m/e 444 (M+H)+; 1H NMR (500 MHz, DMSO) δ ppm 8.87 (d, 1 H), 8.71 (d, 1 H), 8.51 (d, 1 H), 7.92 (d, 1 H), 7.78 (m, 3 H), 7.45 (m, 3 H), 6.94 (d, 1 H), 3.86 (m, 1 H), 3.10 (m, 1 H), 2.70 (q, 2 H), 1.90 (m, 2 H), 1.76 (m, 4 H), 1.57 (m, 2 H), 1.21 (t, 3 H).

EXAMPLE 250 cis-4-bromo-2,5-dichloro-N-{4-((7-chloroquinolin-4-yl)amino)cyclohexyl}thiophene-3-sulfonamide The titled compound was prepared according to the method described in Example 15 by substituting 4-bromo-2,5-dichlorothiophene-3-sulfonyl chloride for 4-chlorobenzene sulfonyl chloride. 1H NMR (500 MHz, DMSO) δ ppm 8.73 (m, 2 H), 8.53 (d, 1 H), 8.17 (d, 1 H), 7.92 (d, 1 H), 7.80 (dd, 1 H), 6.92 (d, 1 H), 3.87 (m, 1 H), 3.42 (m, 1 H), 1.56–2.04 (m, 8 H).

EXAMPLE 251 cis-N-{4-((7-chloroquinolin-4-yl)amino) cyclohexyl}-2-methoxy-5-methylbenzenesulfonamide The titled compound was prepared according to the method described in Example 15 by substituting 6-methoxy-m-tonuenesulfonyl chloride for 4-chlorobenzene sulfonyl chloride.

MS (ESI (+)) m/e 460 (M+H)+; $^1$H NMR (500 MHz, DMSO) δ ppm 8.82 (d, 1 H), 8.70 (d, 1 H), 8.51 (d, 1 H), 7.92 (d, 1 H), 7.81 (dd, 1 H), 7.57 (d, 1 H), 7.42 (dd, 1 H), 7.14 (d, 1 H), 6.92 (m, 2 H), 3.87 (m, 4 H), 3.15 (m, 1 H), 2.30 (s, 3 H), 1.92 (m, 2 H), 1.73 (m, 4 H), 1.42–1.66 (m, 2 H).

EXAMPLE 252 cis-N-{4-((7-chloroquinolin-4-yl)amino)cyclohexyl}-2-nitrobenzenesulfonamide

The titled compound was prepared according to the method described in Example 15 by substituting 2-nitrobenzenesulfonyl chloride for 4-chlorobenzene sulfonyl chloride. MS (ESI (+)) m/e 461 (M+H)+; $^1$H NMR (500 MHz, DMSO) δ ppm 8.76 (d, 1 H), 8.70 (d, 1 H), 8.52 (d, 1 H), 8.07 (m, 1 H), 8.02 (d, 1 H), 7.96 (m, 1 H), 7.92 (d, 1 H), 7.88 (m, 2 H), 7.80 (dd, 1 H), 6.93 (d, 1 H), 3.87 (m, 1 H), 1.67–2.00 (m, 6 H), 1.63 (m, 2 H).

EXAMPLE 253 cis-2-chloro-N-{4-((7-chloroquinolin-4-yl)amino)cyclohexyl}isonicotinamide

The titled compound was prepared according to the methods described in Example 23, substituting 2-chloro isonicotinic acid for indole-6-carboxylic acid. MS (ESI(+) Q1MS m/z 415 (M+H)+; $^1$H NMR (300 MHz, DMSO-D6) δ ppm 8.56 (d, 2 H), 8.41 (s, 1 H), 8.39 (d, 1 H), 7.90 (s, 1 H), 7.78 (m, 2 H), 7.45 (dd, 1 H), 6.82 (d, 1 H), 6.54 (d, 1 H), 3.98 (br.s, 1 H), 3.67 (br.s, 1 H), 1.61–2.04 (m, 8 H).

EXAMPLE 254 cis-2-chloro-N-{4-((7-chloroquinolin-4-yl)amino)cyclohexyl}-6-methylisonicotinamide The titled compound was prepared according to the methods described in Example 23, substituting 2-chloro-6-methylisonicotinic acid for indole-6-carboxylic acid. MS (ESI(+)Q1MS m/z 429 (M+H)+; $^1$H NMR (300 MHz, DMSO-D6) δ ppm 8.62 (d, 1 H), 8.42 (s, 1 H), 8.39 (d, 1 H), 7.92 (s, 2 H), 7.79 (d, 1 H), 7.46 (dd, 1 H), 6.84 (d, 1 H), 6.55 (d, 1 H), 3.96 (br.s, 1 H), 3.69 (br.s, 1 H), 2.51 (s, 3 H), 1.62–1.99 (m, 8 H).

EXAMPLE 255 cis-2,6-dichloro-N-{4-((7-chloroquinolin-4-yl)amino)cyclohexyl}isonicotinamide

The titled compound was prepared according to the methods described in Example 23, substituting 2,6-dichloroisonicotinic acid for indole-6-carboxylic acid. MS (ESI(+)Q1MS m/z 449 (M+H)+; $^1$H NMR (300 MHz, DMSO-D6) δ ppm 8.48 (d, 1 H), 8.40 (s, 1 H), 8.38 (d, 1 H), 7.78 (d, 1 H), 7.68 (s, 1 H), 7.65 (s, 1 H), 7.44 (dd, 1 H), 6.81 (d, 1 H), 6.53 (d, 1 H), 3.96 (br.s, 1 H), 3.68 (m, 1 H), 1.62–2.02 (m, 8 H).

EXAMPLE 256 cis-N-{4-((7-chloroquinolin-4-yl)amino)cyclohexyl}-5-phenylpentanamide 31 mg (0.16 mmol) of 5-phenylvaleric acid, 112 mg (0.22 mmol) of PS-carbodiimide and 28 mg (0.18 mmol) HOBT in DMF (1 mL) were mixed for 15 min. 30 mg (0.11 mmol) of N-(7-chloroquinolin-4-yl)-cyclohexane-1,4-diamine was added and the reaction was allowed to proceed overnight. 116 mg (0.54 mmol) of PS-trisamine was added and the reaction mixture was filtered after two hours. The solvent was evaporated and the product was purified by reverse phase HPLC to provide the titled compound. MS (ESI(+)) m/e 436 (M+H)+; $^1$H NMR (500 MHz, DMSO) δ ppm 13.86 (brs, 1 H), 8.82 (d, 1 H), 8.72 (d, 1 H), 8.54 (d, 1 H), 7.94 (d, 1 H), 7.78 (dd, 1 H), 7.69 (d, 1 H), 7.21 (m, 5 H), 6.96 (d, 1 H), 3.89 (m, 1 H), 3.80 (m, 1 H), 2.58 (m, 2 H), 2.50 (m, 2 H), 2.16 (m, 2 H), 1.82 (m, 6 H), 1.47–1.70 (m, 6 H).

EXAMPLE 257 cis-($N^1$-{4-((7-chloroquinolin-4-yl)amino)cyclohexyl}glycinamide)benzamide

The titled compound was prepared according to the methods described in Example 256, substituting hippuric acid for 5-phenylvaleric acid. MS (ESI(+)) m/e 437 (M+H)+; $^1$H NMR (500 MHz, DMSO) δ ppm 13.74–14.03 (br.s, 1 H), 8.88 (d, 1 H), 8.74 (d, 1 H), 8.65 (t, 1 H), 8.55 (d, 1 H), 7.95 (d, 1 H), 7.87 (m, 3 H), 7.79 (dd, 1 H), 7.55 (m, 1 H), 7.48 (m, 2 H), 6.98 (d, 1 H), 3.94 (d, 2 H), 3.91 (m, 1 H), 3.85 (m, 1 H), 1.63–1.93 (m, 8 H).

EXAMPLE 258 cis-N-{4-((7-chloroquinolin-4-yl)amino)cyclohexyl}-4-phenoxybutanamide

The titled compound was prepared according to the methods described in Example 256, substituting 4-phenoxybutyric acid for 5-phenylvaleric acid. MS (ESI (+)) m/e 438 (M+H)+; $^1$H NMR (500 MHz, DMSO) δ ppm 13.73–13.96 (br.s, 1 H), 8.86 (d, 1 H), 8.72 (d, 1 H), 8.54 (d, 1 H), 7.94 (d, 1 H), 7.78 (m, 2 H), 7.27 (dd, 2 H), 6.97 (d, 1 H), 6.91 (m, 3 H), 3.97 (t, 2 H), 3.90 (m, 1 H), 3.82 (m, 1 H), 2.31 (m, 2 H), 1.95 (m, 2 H), 1.81 (m, 6 H), 1.66 (m, 2 H).

EXAMPLE 259 cis-N-{4-((7-chloroquinolin-4-yl)amino)cyclohexyl}-3-(3-methyl-1H-indol-1-yl)propanamide The titled compound was prepared according to the methods described in Example 256, substituting 3-(3-methylindol-1-yl)propionic acid for 5-phenylvaleric acid. MS (ESI(+)) m/e 461 (M+H)+; $^1$H NMR (500 MHz, DMSO) δ ppm 13.52–14.11 (br.s, 1 H), 8.82 (d, 1 H), 8.69 (d, 1 H), 8.53 (d, 1 H), 7.93 (d, 1 H), 7.80 (d, 1 H), 7.77 (dd, 1 H), 7.45 (d, 1 H), 7.42 (d, 1 H), 7.11 (m, 1 H), 7.06 (m, 1 H), 6.99 (m, 1 H), 6.94 (d, 1 H), 4.35 (t, 2 H), 3.87 (m, 1 H), 3.80 (m, 1 H), 2.60 (t, 2 H), 2.21 (s, 3 H), 1.57–1.81 (m, 8 H).

EXAMPLE 260 cis-N-{4-((7-chloroquinolin-4-yl)amino)cyclohexyl}-3-(1-methyl-1H-benzimidazol-2-yl)propanamide The titled compound was prepared according to the methods described in Example 256, substituting 3-(1-methyl-1H-benzo(D)imidazol-2-yl)propanoic acid for 5-phenylvaleric acid. MS (ESI(+)) m/e 462 (M+H)+; $^1$H NMR (500 MHz, DMSO) δ ppm 13.56–14.31 (br.s, 1 H), 8.87 (d, 1 H), 8.73 (d, 1 H), 8.54 (d, 1 H), 8.05 (d, 1 H), 7.96 (d, 1 H), 7.85 (d, 1 H), 7.79 (dd, 1 H), 7.75 (d, 1 H), 7.49

(m, 2 H), 6.95 (d, 1 H), 3.96 (s, 3 H), 3.90 (m, 1 H), 3.81 (m, 1 H), 3.32 (t, 2 H), 2.83 (t, 2 H), 1.57–1.94 (m, 8 H).

EXAMPLE 261 cis-N-{4-((7-chloroquinolin-4-yl)amino)cyclohexyl}-2-(6-methoxy-3-oxo-2,3-dihydro-1H-inden-1-yl)acetamide The titled compound was prepared according to the methods described in Example 256, substituting 5-methoxy-1-indanone-3-acetic acid for 5-phenylvaleric acid. MS (ESI (+)) m/e 478 (M+H)$^+$; $^1$H NMR (500 MHz, DMSO) δ ppm 13.60–13.80 (br.s, 1 H), 8.76 (br.s, 1 H), 8.69 (d, 1 H), 8.54 (d, 1 H), 7.91 (d, 1 H), 7.84 (d, 1 H), 7.78 (dd, 1 H), 7.56 (d, 1 H), 7.15 (d, 1 H), 6.98 (dd, 1 H), 6.95 (d, 1 H), 3.87 (m, 2 H), 3.85 (s, 3 H), 3.71 (m, 1 H), 2.80 (dd, 1 H), 2.72 (dd, 1 H), 2.36 (m, 2 H), 1.61–1.90 (m, 8 H).

EXAMPLE 262 cis-1-benzoyl-N-{4-((7-chloroquinolin-4-yl)amino)cyclohexyl}piperidine-4-carboxamide The titled compound was prepared according to the methods described in Example 256, substituting 1-benzoylpiperidine-4-carboxylic acid for 5-phenylvaleric acid. MS (ESI(+)) m/e 491 (M+H)$^+$; $^1$H NMR (500 MHz, DMSO) δ ppm 13.87 (br.s, 1 H), 8.86 (d, 1 H), 8.72 (d, 1 H), 8.54 (d, 1 H), 7.95 (d, 1 H), 7.79 (dd, 1 H), 7.72 (d, 1 H), 7.45 (m, 3 H), 7.37 (m, 2 H), 6.97 (d, 1 H), 4.37–4.62 (br.s, 1 H), 3.91 (m, 1 H), 3.80 (m, 1 H), 2.72–3.12 (m, 2 H), 2.54 (m, 2 H), 1.41–1.96 (m, 12 H).

EXAMPLE 263 cis-(N$^1$-{4-((7-chloroquinolin-4-yl)amino)cyclohexyl}β-alaninamide) 4-nitrobenzamide The titled compound was prepared according to the methods described in Example 256, substituting N-(4-nitrobenzoyl)-beta-alanine for 5-phenylvaleric acid. MS (ESI(+)) m/e 496 (M+H)$^+$; $^1$H NMR (500 MHz, DMSO) δ ppm 13.66–14.02 (br.s, 1 H), 8.86 (t, 1 H), 8.83 (d, 1 H), 8.70 (d, 1 H), 8.54 (d, 1 H), 8.28 (d, 2 H), 8.05 (d, 2 H), 7.94 (d, 1 H), 7.83 (d, 1 H), 7.78 (dd, 1 H), 6.95 (d, 1 H), 3.88 (m, 2 H), 3.52 (m, 2 H), 2.47 (t, 2 H), 1.59–1.91 (m, 8 H).

EXAMPLE 264 cis-(N$^1$-{4-((7-chloroquinolin-4-yl)amino)cyclohexyl}-β-alaninamide)benzamide.

The titled compound was prepared according to the methods described in Example 256, substituting N-benzoyl-beta-alanine for 5-phenylvaleric acid. MS (ESI(+)) m/e 451 (M+H)$^+$; $^1$H NMR (500 MHz, DMSO) δ ppm 8.83 (d, 1 H), 8.71 (d, 1 H), 8.54 (d, 1 H), 8.49 (m, 1 H), 8.49 (br.s, 1 H), 7.93 (d, 1 H), 7.83 (m, 2 H), 7.79 (dd, 1 H), 7.46 (m, 4 H), 6.96 (d, 1 H), 3.90 (m, 1 H), 3.82 (m, 1 H), 3.49 (m, 2 H), 2.45 (t, 2 H), 1.58–1.92 (m, 8 H).

EXAMPLE 265 cis-N-{4-((7-chloroquinolin-4-yl)amino)cyclohexyl}-N'-(4-propoxyphenyl)urea

The titled compound was prepared according to the method described in Example 2 by substituting 4-propoxyphenyl isocyanate for 4-chlorophenyl isocyanate. MS (ESI (−)) m/e 451 (M−1); $^1$H NMR (500 MHz, DMSO) δ ppm 8.77 (br.s, 1 H), 8.70 (d, 1 H), 8.54 (d, 1 H), 8.19 (s, 1 H), 7.92 (d, 1 H), 7.79 (dd, 1 H), 7.26 (d, 2 H), 6.97 (d, 1 H), 6.81 (d, 2 H), 6.17 (d, 1 H), 3.91 (m, 1 H), 3.85 (t, 2 H), 3.78 (m, 1 H), 1.62–1.89 (m, 10 H), 0.96 (t, 3 H).

EXAMPLE 266 cis-N-(5-tert-butyl-2-methoxyphenyl)-N'-{4-((7-chloroquinolin-4-yl)amino)cyclohexyl}urea The titled compound was prepared according to the method described in Example 2 by substituting 4-propoxyphenyl isocyanate for 4-chlorophenyl isocyanate. MS (ESI(+)) m/e 481 (M+H)$^+$; $^1$H NMR (500 MHz, DMSO) δ ppm 8.86 (m, 1 H), 8.72 (d, 1 H), 8.55 (d, 1 H), 8.26 (s, 1 H), 7.93 (m, 2 H), 7.80 (m, 1 H), 6.99 (d, 2 H), 6.86 (s, 2 H), 3.90 (m, 1 H), 3.82 (s, 3 H), 3.79 (m, 1 H), 1.67–1.92 (m, 8 H), 1.23 (s, 9 H).

EXAMPLE 268 cis-N-{4-((7-chloroquinolin-4-yl)amino)cyclohexyl}-N'-(2-furylmethyl)urea

The titled compound was prepared according to the method described in Example 2 by substituting 2-furan isocyanate for 4-chlorophenyl isocyanate. MS (ESI (+)) m/e 399 (M+H)$^+$; $^1$H NMR (500 MHz, DMSO) δ ppm 8.84 (d, 1 H), 8.71 (d, 1 H), 8.54 (d, 1 H), 7.92 (s, 1 H), 7.79 (dd, 1 H), 7.56 (s, 1 H), 6.97 (d, 1 H), 6.39 (m, 1 H), 6.20 (m, 2 H), 6.02 (d, 1 H), 4.21 (d, 2 H), 3.89 (m, 1 H), 3.70 (m, 1 H), 1.56–1.93 (m, 8 H).

EXAMPLE 269 cis-N-{4-((7-chloroquinolin-4-yl)amino)cyclohexyl}-N'-(3-furylmethyl)urea

The titled compound was prepared according to the method described in Example 2 by substituting 2-furan isocyanate for 4-chlorophenyl isocyanate. MS (ESI (+)) m/e 399 (M+H)$^+$; $^1$H NMR (500 MHz, DMSO) δ ppm 8.84 (d, 1 H), 8.70 (d, 1 H), 8.54 (d, 1 H), 7.92 (d, 1 H), 7.79 (dd, 1 H), 7.58 (m, 1 H), 7.51 (m, 1 H), 6.97 (d, 1 H), 6.41 (m, 1 H), 6.01 (m, 1 H), 4.04 (d, 2 H), 3.88 (m, 1 H), 3.73 (m, 1 H), 1.57–1.88 (m, 8 H).

EXAMPLE 271 cis-N-{4-((7-chloroquinolin-4-yl)amino)cyclohexyl}-2-cyclohexylacetamide

The titled compound was prepared according to the method described in Example 23 by substituting cyclohexylacetic acid for indole-6-carboxylic acid. MS (ESI(+)Q1MS m/z 400 (M+H)$^+$; $^1$H NMR (300 MHz, DMSO) δ ppm 8.82 (d, 1 H), 8.74 (d, 1 H), 8.55 (d, 1 H), 7.93 (d, 1 H), 7.80 (dd, 1 H), 7.65 (d, 1 H), 6.96 (d, 1 H), 3.92–3.78 (m, 2 H), 2.0 (d, 2 H), 1.88–1.75 (m, 6 H), 1.70–1.58 (m, 7 H), 1.25–1.08 (m, 4 H), 0.98–0.88 (m, 2 H).

EXAMPLE 272 cis-N-{4-((7-chloroquinolin-4-yl)amino)cyclohexyl}-2-cycloheptylacetamide

The titled compound was prepared according to the method described in Example 23 by substituting cycloheptylacetic acid for indole-6-carboxylic acid. MS (ESI(+)

Q1MS m/z 414 (M+H)+; 1H NMR (300 MHz, DMSO) δ ppm 8.82 (d, 1 H), 8.74 (d, 1 H), 8.55 (d, 1 H), 7.95 (d, 1 H), 7.80 (dd, 1 H), 7.52 (d, 1 H), 6.97 (d, 1 H), 3.95–3.85 (m, 1 H), 3.78–3.71 (m, 1 H), 2.40–2.34 (m, 2 H), 1.87–1.36 (m, 21 H).

EXAMPLE 273 cis-2-((1R,4S)-bicyclo(2.2.1)hept-2-yl)-N-{4-((7-chloroquinolin-4-yl)amino)cyclohexyl}acetamide The titled compound was prepared according to the method described in Example 23 by substituting 2-norbornaneacetic acid for indole-6-carboxylic acid. MS (ESI(+)Q1MS m/z 412 (M+H)+; 1H NMR (300 MHz, DMSO) δ ppm 8.82 (d, 1 H), 8.74 (d, 1 H), 8.55 (d, 1 H), 7.95 (d, 1 H), 7.80 (dd, 1 H), 7.63 (m, 1 H), 6.97 (d, 1 H), 3.92–3.83 (m, 1 H), 3.82–3.76 (m, 1 H), 2.20–2.15 (m, 2 H), 2.10–1.03 (m, 19 H).

EXAMPLE 274 cis-2-(1-adamantyl)-N-{4-((7-chloroquinolin-4-yl)amino)cyclohexyl}acetamide

The titled compound was prepared according to the method described in Example 23 by substituting 1-adamantylacetic acid for indole-6-carboxylic acid. MS (ESI(+)Q1MS m/z 452 (M+H)+; 1H NMR (300 MHz, DMSO) δ ppm 8.81 (d, 1 H), 8.74 (d, 1 H), 8.55 (d, 1 H), 7.93 (d, 1 H), 7.79 (dd, 1 H), 7.58 (d, 1 H), 6.96 (d, 1 H), 3.91–3.83 (m, 1 H), 3.82–3.78 (m, 1 H), 1.92 (s, 2 H), 1.90–1.55 (m, 24 H).

EXAMPLE 275 cis-N-{4-((7-chloroquinolin-4-yl)amino)cyclohexyl}-2-(3-fluorophenyl)acetamide

The titled compound was prepared according to the method described in Example 23 by substituting 3-fluorophenylacetic acid for indole-6-carboxylic acid. MS-(ESI(+)Q1MS m/z 412 (M+H)+; 1H NMR (300 MHz, DMSO) δ ppm 8.63 (d, 1 H), 8.50 (d, 1 H), 8.28 (br s, 1 H), 8.02 (d, 1 H), 7.89 (d, 1 H), 7.70 (d, 1 H), 7.38–7.30 (m, 1 H), 7.10–7.03 (m, 3 H), 6.83 (d, 1 H), 3.85–3.78 (m, 2 H), 3.50 (s, 2 H), 1.86–1.62 (m, 8 H).

EXAMPLE 276 cis-N-{4-((7-chloroquinolin-4-yl)amino)cyclohexyl}-2-(3-(trifluoromethyl)phenyl)acetamide The titled compound was prepared according to the method described in Example 23 by substituting 3-(trifluormethyl)phenylacetic acid for indole-6-carboxylic acid. MS (ESI(+)Q1MS m/z 462 (M+H)+; 1H NMR (300 MHz, DMSO) δ ppm 8.82 (d, 1 H), 8.74 (d, 1 H), 8.55 (d, 1 H), 8.10 (d, 1 H), 7.93 (d, 1 H), 7.80 (dd, 1 H), 7.62 (s, 1 H), 7.60–7.53 (m, 3 H), 6.98 (d, 1 H), 3.95–3.86 (m, 1 H), 3.83–3.79 (m, 1 H), 3.60 (s, 2 H), 1.90–1.63 (m, 8 H).

EXAMPLE 277 cis-N-{4-((7-chloroquinolin-4-yl)amino)cyclohexyl}-2-(4-(trifluoromethyl)phenyl)acetamide The titled compound was prepared according to the method described in Example 23 by substituting 4-(trifluormethyl)phenylacetic acid for indole-6-carboxylic acid. MS (ESI(+)Q1MS m/z 462 (M+H)+; 1H NMR (300 MHz, DMSO) δ ppm 8.82 (d, 1 H), 8.74 (d, 1 H), 8.55 (d, 1 H), 8.10 (d, 1 H), 7.93 (d, 1 H), 7.80 (dd, 1 H), 7.66 (d, 2 H), 7.50 (d, 2 H), 6.98 (d, 1 H), 3.95–3.86 (m, 1 H), 3.83–3.79 (m, 1 H), 3.60 (s, 2 H), 1.90–1.63 (m, 8 H).

EXAMPLE 278 cis-3,5-difluoro-N-(4-{(6-fluoro-2-(trifluoromethyl)quinolin-4-yl)amino}cyclohexyl)benzamide A solution of N-(4-Amino-cyclohexyl)-3,5-difluorobenzamide (30 mg, 0.12 mmol) in NMP (1.0 mL) was treated with 4-chloro-6-fluoro-2-trifluoromethyl-quinoline (1 eq) and 3 eq (0.045 mL) TEA. The reaction was heated to 220 C in the microwave for 15 minutes. The crude compound was purified by reverse phase HPLC to provide the desired compound. MS (ESI (+)) m/e 468 (M+H)+; 1H NMR (500 MHz, DMSO) δ ppm 8.32 (m, 2 H), 7.98 (m, 1 H), 7.67 (m, 1 H), 7.58 (m, 2 H), 7.44 (m, 1 H), 7.15 (d, 1 H), 6.82 (s, 1 H), 1.95 (m, 4 H), 1.65–1.88 (m, 4 H).

EXAMPLE 279 cis-3,5-difluoro-N-(4-{(8-(trifluoromethoxy)-2-(trifluoromethyl)quinolin-4-yl)amino}cyclohexyl)benzamide The titled compound was prepared according to the method described in Example 278 by substituting 4-chloro-8-trifluoromethoxy-2-trifluoromethyl quinoline for 4-chloro-6-fluoro-2-trifluoromethyl-quinoline. MS (ESI (+)) m/e 534 (M+H)+; 1H NMR (500 MHz, DMSO) δ ppm 8.51 (d, 1 H), 8.30 (d, 1 H), 7.80 (d, 1 H), 7.61 (m, 3 H), 7.43 (m, 2 H), 6.91 (s, 1 H), 1.94 (m, 4 H), 1.75 (m, 4 H).

EXAMPLE 280 cis-N-(4-{(5,7-dichloro-2-(trifluoromethyl)quinolin-4-yl)amino}cyclohexyl)-3,5-difluorobenzamide The titled compound was prepared according to the method described in Example 278 by substituting 4,5,7-trichloro-2-trifluoromethyl quinoline for 4-chloro-6-fluoro-2-trifluoromethyl-quinoline. MS (ESI (+)) m/e 520 (M+H)+; 1H NMR (500 MHz, DMSO) δ ppm 8.41 (d, 1 H), 7.96 (m, 1 H), 7.81 (m, 1 H), 7.69 (d, 1 H), 7.55 (d, 2 H), 7.44 (t, 1 H), 6.91 (s, 1 H), 4.04 (m, 1 H), 3.93 (m, 1 H), 1.96 (m, 2 H), 1.80 (m, 4 H), 1.68 (m, 2 H).

EXAMPLE 281 cis-3,5-difluoro-N-(4-{(6-methyl-2-(trifluoromethyl)quinolin-4-yl)amino}cyclohexyl)benzamide The titled compound was prepared according to the method described in Example 278 by substituting 4-chloro-6-methyl-2-trifluoromethyl quinoline for 4-chloro-6-fluoro-2-trifluoromethyl-quinoline. MS (ESI (+)) m/e 464 (M+H)+; 1H NMR (500 MHz, DMSO) δ ppm 8.31 (d, 1 H), 8.25 (s, 1 H), 7.80 (d, 1 H), 7.59 (m, 3 H), 7.43 (m, 1 H), 7.08 (m, 1 H), 6.76 (s, 1 H), 3.99 (m, 1 H), 3.83 (m, 1 H), 2.53 (s, 3 H), 1.86–2.13 (m, 3 H), 1.51–1.87 (m, 5 H).

EXAMPLE 282 cis-N-(7-chloroquinolin-4-yl)-N'-(3,5-dichlorophenyl)cyclohexane-1,4-diamine

The titled compound was prepared according to the methods described in Example 140, substituting 1-bromo- 3,5-dichlorobenzene for 1-bromo-3,5-difluorbenzene. MS (ESI(+)Q1MS m/z 420 (M+H)$^+$); $^1$H NMR (300 MHz, DMSO-D6) δ ppm 8.84 (d, 1 H), 8.71 (d, 1 H), 8.55 (d, 1 H), 7.91 (d, 1 H), 7.80 (dd, 2.0 Hz, 1 H), 7.00 (d, 1 H), 6.63 (d, 2 H), 6.60 (t, 1 H), 6.25 (d, 1 H), 3.95 (br.s, 1 H), 3.57 (br.s, 1 H), 1.68–1.95 (m, 8 H).

EXAMPLE 283 cis-N-(7-chloroquinolin-4-yl)-N'-(3-methylphenyl) cyclohexane-1,4-diamine

The titled compound was prepared according to the methods described in Example 140, substituting 3-bromotoluene for 1-bromo-3,5-difluorbenzene. MS (ESI(+)Q1MS m/z 366 (M+H)$^+$); $^1$H NMR (300 MHz, DMSO-D6) δ ppm 8.89 (d, 1 H), 8.71 (d, 1 H), 8.54 (d, 1 H), 8.25 (d, 1 H), 8.19 (d, 1 H), 7.91 (d, 1 H), 7.80 (dd, 1 H), 6.89–7.07 (m, 3 H), 6.38 (d, 1 H), 3.24–3.58 (m, 2 H), 2.19 (s, 3 H), 1.61–2.03 (m, 8 H).

EXAMPLE 284 cis-N-(3,5-bis(trifluoromethyl)phenyl)-N'-(7-chloroquinolin-4-yl)cyclohexane-1,4-diamine The titled compound was prepared according to the methods described in Example 140, substituting 3,5-di(triflurormethyl)benzoic acid for 1-bromo-3,5-difluorbenzene. MS (ESI(+)Q1MS m/z 516 (M+H)$^+$); $^1$H NMR (300 MHz, DMSO-D6) δ ppm 8.84 (d, 1 H), 8.72 (d, 1 H), 8.67 (d, 1 H), 8.51–8.61 (m, 3 H), 8.33 (s, 1 H), 7.92 (d, 1 H), 7.81 (dd, 1 H), 7.00 (d, 1 H), 4.03 (m, 2 H), 1.70–2.16 (m, 8 H).

EXAMPLE 285 cis-N-1,1'-biphenyl-3-yl-N'-(7-chloroquinolin-4-yl) cyclohexane-1,4-diamine

The titled compound was prepared according to the methods described in Example 140, substituting 3-bromobiphenyl for 1-bromo-3,5-difluorbenzene. MS (ESI(+)Q1MS m/z 428 (M+H)$^+$); $^1$H NMR (300 MHz, DMSO-D6) δ ppm 8.93 (d, 1 H), 8.72 (d, 1 H), 8.55 (d, 1 H), 7.91 (d, 1 H), 7.80 (dd, 1 H), 7.58 (d, 2 H), 7.44 (t, 2 H), 7.34 (t, 1 H), 7.18 (t, 1 H), 7.02 (d, 1 H), 6.89 (s, 1 H), 6.81 (d, 1 H), 6.66 (dd, 1 H), 5.50–5.81 (br.s., 1 H), 3.99 (br.s, 1 H), 3.65 (br.s, 1 H), 1.70–2.02 (m, 8 H).

EXAMPLE 286 cis-N-(7-chloroquinolin-4-yl)-N'-(3-(trifluoromethyl) phenyl)cyclohexane-1,4-diamine The titled compound was prepared according to the methods described in Example 140, substituting 3-trifluoromethylbromobenzene for 1-bromo-3,5-difluorbenzene. MS (ESI(+)Q1MS m/z 420 (M+H)$^+$); $^1$H NMR (300 MHz, DMSO-D6) δ ppm 8.90 (d, 1 H), 8.71 (d, 1 H), 8.55 (d, 1 H), 7.91 (d, 1 H), 7.80 (dd, 1 H), 7.29 (t, 1 H), 7.01 (d, 1 H), 6.92 (s, 1 H), 6.88 (d, 1 H), 6.80 (d, 1 H), 6.09 (d, 1 H), 3.97 (br.s, 1 H), 3.62 (br.s, 1 H), 1.72–2.00 (m, 8 H).

EXAMPLE 287 cis-4-({4-((7-chloroquinolin-4-yl)amino) cyclohexyl}amino)-2H-chromen-2-one

The titled compound was prepared according to the method described in Example 3 by substituting 4-chlorocoumarin for 4-chloro-2,8-bis(trifluoromethyl)-quinoline. MS (ESI(+)Q1MS m/z 420 (M+H)$^+$; $^1$H NMR (300 MHz, DMSO) δ ppm 8.80 (d, 1 H), 8.72 (d, 1 H), 8.58 (d, 1 H), 8.22 (d, 1 H), 7.95 (d, 1 H), 7.82 (dd, 1 H), 7.62 (ddd, 1 H), 7.33–7.29 (m, 2 H), 7.14 (d, 1 H), 7.03 (d, 1 H), 5.30 (s, 1 H), 4.10–4.00 (m, 1 H), 3.85–3.75 (m, 1 H), 2.08–1.75 (m, 8 H).

EXAMPLE 289 cis-N,N'-bis(7-chloro-4-aminoquinolin-4-yl) cyclohexane-1,4-diamine

EXAMPLE 289A 4,7-dichloroquinoline 1-oxide

A mixture of 4,7-dichloroquinoline (9.9 g, 50 mmol) and methyltrioxorhenium (80 mg, 0.32 mmol) was stirred in the mixture of hydrogenperoxide (40%, 20 mL) and dichloromethane at room temperature for 24 hours. Pale yellow solid was collected by filtration and dried under vacuum. MS (ESI(+)Q1MS m/z 215 (M+H)$^+$.

EXAMPLE 289B

N-(4,7-dichloroquinolin-2-yl)benzamide

A mixture of example 289A (10.0 g, 46.7 mmol) and benzoyl chloride (23.5 g, 168 mmol) and benzamide (5.9 g, 49.1 mmol) was heated at 180° C. for 6 hours, cooled to room temperature, filtered. Yellow solid as washed with large quantity of water and ethyl acetate (20 mL) and dried under vacuum. MS (ESI(+)Q1MS m/z 318 (M+H)$^+$.

EXAMPLE 289C 4,7-dichloroquinolin-2-amine

A mixture of example 289B (5.0 g, 15.8 mmol) and hydrochloric acid (22%, 150 mL) was heated to reflux for 24 hours, cooled to room temperature, filtered. Filtrate was basified with 50% sodium hydroxide. Pale green solid was collected by filtration, washed with large quantity of water and dried under vacuum. MS (ESI(+)Q1MS m/z 291 (M+H)$^+$.

EXAMPLE 289D cis-N,N'-bis(7-chloro-4-aminoquinolin-4-yl) cyclohexane-1,4-diamine A mixture of example 289C (500 mg, 2.35 mmol), 1,4-cyclohexanediamine (133 mg, 1.17 mmol), sodium t-butoxide (275 mg, 2.86 mmol), tris(dibenzylideneacetone)-dipalladium(0) (55 mg, 0.06 mmol) and (R)-(+)-2,2'-bis(diphenylphosphinol)-1,1'-binaphthyl was heated at 90° C. in 1,2-dimethoxyethane (5 mL) for 6 hours, cooled to room temperature, filtered. The 1,2-dimethoxyethane was removed via vacuum and the residue was purified by high throughput HPLC to provide the desired compound as its TRIFLUOROACETIC ACID salt. MS (ESI(+)Q1MS m/z 467 (M+H)$^+$. $^1$H NMR (300 MHz, DMSO) δ ppm 13.05 (s, 1 H), 9.66 (s, 1 H), 8.89(s, 1 H), 8.57 (d, 1 H), 8.37 (d, 1 H), 7.93 (d, 1 H), 7.85 (s, 2 H), 7.70 (d, 1 H), 7.65 (dd, 1 H), 7.44 (dd, 1 H), 6.81 (s, 1 H), 6.71 (s, 1 H), 3.69 (s, 2 H), 2.06 (m, 2 H), 1.80 (m, 6 H).

EXAMPLE 291

4-{4-[(7-chloroquinolin-4-yl)amino] cyclohexyl}amino)-2H-chromen-2-one

To a conical microwave vessel (7.5 mL) equipped with a septum cap and a magnetic stirring bar was added a solution of a trifluoro-methanesulfonic acid 6-chloro-2-oxo-2H-chromen-4-yl ester (0.014 g; 0.043 mmol)) in dry acetonitrile (1 mL) containing Et₃N (0.025 mL). Then, a solution of 4-amino-chromen-2-one (0.0178 g; 1.5 eq.) in 1:1:1 mixture of acetonitrile/dichloromethane/DMF (1 mL) was added to the vessel and the resulting suspension was irradiated in Personal Chemistry Smith Synthesizer (150° C. for 180 s; 300 W). The resulting solution was evaporated to dryness. The residue was dissolved in 1.5 mL of a 1:1 mixture of DMSO/MeOH and purified by preparative reverse-phase HPLC. MS (DCI/NH₃) m/z 419 [M+H]⁺.

EXAMPLE 292 cis-N-{4-((2-amino-7-chloroquinolin-4-yl)amino) cyclohexyl}-3,5-difluorobenzamide

EXAMPLE 292A cis-N-⁴-(4-aminocyclohexyl)-7-chloroquinoline-2,4-diamine

A mixture of 289C (500 mg, 2.35 mmol), 1,4-cyclohexanediamine (540 mg, 4.70 mmol), sodium t-butoxide(275 mg, 2.86 mmol), tris(dibenzylideneacetone)-dipalladium(0) (55 mg, 0.06 mmol) and (R)-(+)-2,2'-bis(diphenylphosphinol)-1,1'-binaphthyl was heated at 90° C. in 1,2-dimethoxyethane (5 mL) for 6 hours, cooled to room temperature, filtered. The 1,2-dimethoxyethane was removed via vacuum and the residue was purified by high throughput HPLC to provide the desired compound as its trifluoroacetic acid salt. MS (ESI(+)Q1MS m/z 291 (M+H)⁺.

EXAMPLE 292B cis-N-{4-((2-amino-7-chloroquinolin-4-yl)amino) cyclohexyl}-3,5-difluorobenzamide A mixture of example 292A (40 mg, 0.14 mmol), 3,5-difluorobenzoic acid (26 mg, 0.16 mmol), 1-hydroxybenzotriazole (25 mg, 0.16 mmol), 1-(3-dimethylaminopropyl)-3-ethylcarbodiimide(31 mg, 0.16 mmol) and N-methyl-morpholine (36 μL, 0.33 mmol) in 2 mL N,N-dimethylformamide was shaken for 18 hours. N,N-Dimethylformamide was removed via vacuum and the residue was purified by high throughput HPLC to provide the desired compound. MS (ESI(+)Q1MS m/z 431 (M+H)⁺; ¹H NMR (300 MHz, DMSO) δ ppm 12.39 (s, 1 H), 8.40 (d, 1 H), 8.32 (d, 1 H), 7.73 (s, 2H), 7.50–7.60 (m, 3H), 7.48 (dd, 1 H), 7.45 (dd, 1H), 5.91 (s, 1 H), 3.99 (s, 1 H), 3.60 (s, 1 H), 1.93–2.15 (m, 4 H), 1.48–1.85 (m, 4 H).

EXAMPLE 293 cis-N-{4-((2-amino-7-chloroquinolin-4-yl)amino) cyclohexyl}-3,5-dichlorobenzamide The titled compound was prepared according to the methods described in example 292, substituting 3,5-difluorobenzoic acid for 3,5-dichlorobenzoic acid. (ESI(+) Q1MS m/z 463 (M+H)⁺; ¹H NMR (300 MHz, DMSO) δ ppm 13.60 (s, 1 H), 8.41 (d, 1 H), 8.39 (d, 1 H), 7.87–7.91 (m, 4H), 7.67 (m, 2H),7.58 (dd, 1 H), 7.50 (dd, 1 H), 5.91 (s, 1 H), 3.98 (s, 1 H), 3.60 (s, 1 H), 1.90–2.00 (m, 4 H), 1.64–1.85 (m, 4 H).

EXAMPLE 294 cis-N-{4-((2-amino-7-chloroquinolin-4-yl)amino) cyclohexyl}-4-phenoxybutanamide

The titled compound was prepared according to the methods described in example 292, substituting 3,5-difluorolbenzoic acid for 4-phenoxybutanoic acid. (ESI(+) Q1MS m/z 453 (M+H)⁺; ¹H NMR (300 MHz, DMSO) δ ppm 12.31 (s, 1 H), 8.40 (d, 1 H), 7.76 (d, 1 H), 7.67 (s, 2H), 7.65 (d, 1H), 7.57 (d, 1H), 7.48 (dd, 1H), 7.27 (m, 2H), 6.92 (m, 3H), 5.88 (s, 1 H), 3.97 (t, 2H), 3.81 (s, 1 H), 3.50 (s, 1H), 2.29 (t, 2H), 1.90–2.00 (m, 4 H), 1.60–1.85 (m, 6 H).

EXAMPLE 295 cis-7-chloro-N-4-(4-{(3-(trifluoromethyl)benzyl) amino}cyclohexyl)quinoline-2,4-diamine A solution of example 292A (40 mg, 0.14 mmol), 3-trifluoromethylbenzaldehye (36 mg, 0.21 mmol), sodium cynoborohydride (1M THF solution, 0.41 mL, 0.41 mmol) in 2 mL tetrahydrofuran (THF) was shaken for 18 hours. THF was removed via vacuum and the residue was purified by high throughput HPLC to provide the desired compound as its trifluoroacetic acid salt. MS (ESI(+)Q1MS m/z 449 (M+H)⁺; ¹H NMR (300 MHz, DMSO) δ ppm 12.68 (s, 1 H), 8.95 (s, 2H), 8.42 (d, 1 H), 7.95 (d, 1 H), 7.87 (s, 1H), 7.82 (m, 1H), 7.70 (m, 1H), 7.59 (d, 1 H), 7.49 (dd, 1H), 5.90 (s, 1 H), 4.33 (s, 2H), 3.75 (s, 1 H), 2.05–2.15 (m, 2H), 1.92–2.01 (m, 2H), 1.82–1.92 (m, 2H), 1.71–1.85 (m, 2H).

EXAMPLE 296 cis-7-chloro-N-4-(4-{(3-(trifluoromethoxyl)benzyl) amino}cyclohexyl)quinoline-2,4-diamine The titled compound was prepared according to the methods described in example 295, substituting 3,5-difluorolbenzaldehyde for 3-trifluoromethoxybenzaldehyde. MS (ESI(+)Q1MS m/z 465 (M+H)⁺; ¹H NMR (300 MHz, DMSO) δ ppm 12.78 (s, 1 H), 9.01 (s, 2 H), 8.43 (d, 1 H), 7.91 (s, 1 H), 7.55–7.65 (m, 3 H), 7.40–7.52 (m, 2 H), 5.91 (s, 1 H), 4.29 (s, 2 H), 3.75 (s, 1 H), 2.05–2.15 (m, 2 H), 1.92–2.01 (m, 2 H), 1.82–1.92 (m, 2 H), 171–1.85 (m, 2 H).

EXAMPLE 297 cis-7-chloro-N-4-(4-{(3,5-dimethylbenzyl) amino}cyclohexyl)quinoline-2,4-diamine The titled compound was prepared according to the methods described in example 295, substituting 3,5-difluorolbenzaldehyde for 3,5-dimethylbenzaldehyde. MS (ESI(+)Q1MS m/z 409 (M+H)⁺; ¹H NMR (300 MHz, DMSO) δ ppm 12.80 (s, 1 H), 8.88 (s, 1 H), 8.82 (s, 1 H), 8.42 (d, 1 H), 7.92 (s, 1 H), 7.58 (d, 1 H), 7.46 (dd, 1 H), 7.45 (d, 1 H), 7.15 (s, 1 H), 7.13(s, 1 H), 7.06(s, 1 H), 5.90 (s, 1 H), 4.11 (s, 2 H), 3.75 (s, 1 H), 2.29 (s, 6 H), 1.62–2.12 (m, 8 H).

EXAMPLE 298 cis-7-chloro-N-4-(4-{(3,5-dichlorobenzyl) amino}cyclohexyl)quinoline-2,4-diamine The titled compound was prepared according to the methods described in example 295, substituting 3,5-difluorolbenzaldehyde for 3,5-dichlorobenzaldehyde. MS (ESI(+)Q1MS m/z 409 (M+H)⁺; ¹H NMR (300 MHz, DMSO) δ ppm 12.73 (s, 1 H), 8.94 (s, 2H), 8.42 (d, 1 H), 7.89 (s, 1H), 7.62–7.67 (m, 3H), 7.59 (d, 1 H), 7.45–7.50 (m, 2H), 5.91 (s, 1 H), 4.24 (s, 2H), 3.75 (s, 1 H), 1.62–2.12 (m, 8H).

EXAMPLE 299 cis-N-(7-chloroquinolin-4-yl)-N'-pyridin-2-ylcyclohexane-1,4-diamine

The titled compound was prepared according to the methods described in Example 140, substituting 2-bromopyridine for 1-bromo-3,5-difluorobenzene. MS (ESI(+)Q1MS m/z 353 (M+H)$^+$); $^1$H NMR (300 MHz, DMSO-D6) δ ppm 8.94 (d, 1 H), 8.77 (d, 1 H), 8.59 (d, 1 H), 7.99 (d, 1 H), 7.93 (m, 3 H), 7.82 (dd, 1 H), 7.20 (d, 1 H), 7.00 (d, 1 H), 6.87 (m, 1 H), 3.89–4.11 (br.s, 2 H), 1.69–2.23 (br.s, 8 H).

EXAMPLE 300 cis-N-(7-chloroquinolin-4-yl)-N'-isoguinolin-4-ylcyclohexane-1,4-diamine

The titled compound was prepared according to the methods described in Example 140, substituting 4-bromoisoquinoline for 1-bromo-3,5-difluorobenzene. MS (ESI(+)Q1MS m/z 403 (M+H)$^+$); $^1$H NMR (300 MHz, DMSO-D6) δ ppm 9.00 (s, 1 H), 8.94 (d, 1 H), 8.78 (d, 1 H), 8.72 (d, 1 H), 8.58 (d, 1 H), 8.37 (d, 1 H), 8.09 (t, 1 H), 8.01 (d, 1 H), 7.96 (t, 1 H), 7.83 (s, 1 H), 7.80 (dd, 1 H), 7.03 (d, 1 H), 6.98 (br.s, 1 H), 3.99–4.20 (br.s, 1 H), 3.88 (br.s, 1 H), 1.96–2.18 (m, 4 H), 1.73–1.96 (m, 4 H).

EXAMPLE 301 cis-N-(7-chloroquinolin-4-yl)-N'-quinolin-3-ylcyclohexane-1,4-diamine

The titled compound was prepared according to the methods described in Example 140, substituting 3-bromoquinoline for 1-bromo-3,5-difluorobenzene. MS (ESI(+)Q1MS m/z 403 (M+H)$^+$); $^1$H NMR (300 MHz, DMSO-D6) δ ppm 8.95 (d, 1 H), 8.73 (d, 1 H), 8.61 (d, 1 H), 8.57 (d, 1 H), 7.92 (d, 1 H), 7.81 (m, 2 H), 7.71 (d, 1 H), 7.41 (m, 2 H), 7.19 (s, 1 H), 7.04 (d, 1 H), 6.35 (br.s, 1 H), 3.89–4.15 (br.s, 2 H), 3.89–4.15 (m, 8 H).

EXAMPLE 302 cis-N-(7-chloroquinolin-4-yl)-N'-{(5-(4-nitrophenyl)-2-furyl)methyl}cyclohexane-1,4-diamine The title compound was prepared according to method described in Example 141, substituting 5-(4-Nitrophenyl) furfuryl alcohol for 4-fluorobenzyl alcohol. MS(ESI) m/e 477 (M+H)$^+$; $^1$H NMR (500 MHz, DMSO-D6) δ ppm 8.75 (dd, 1 H), 8.60 (dd, 1 H), 8.33 (d, 2H), 8.01 (d, 2 H), 7.97 (d, 1 H), 7.96 (d, 1 H), 7.82 (dt, 1 H), 7.71 (dd, 1 H), 7.36 (d, 1 H), 6.95 (d, 1 H), 6.86 (d, 1 H), 4.11 (m, 2 H), 1.72–2.15 (m, 10 H).

EXAMPLE 304 cis-N-(7-chloroquinolin-4-yl)-N'-{((2R)-1-(4-nitrophenyl)pyrrolidin-2-yl)methyl}cyclohexane-1,4-diamine The title compound was prepared according to method described in Example 141, substituting (S)-(−)-1-(4-Nitrophenyl)-2-pyrrolidinemethanol for 4-fluorobenzyl alcohol. MS(ESI) m/e 480 (M+H)$^+$; $^1$H NMR (500 MHz, DMSO-D6) δ ppm 8.74 (d, 1 H), 8.48 (d, 1 H), 8.24 (d, 1 H), 8.10 (m, 2 H), 7.82 (d, 2 H), 6.81 (d, 2 H), 4.11–4.42 (m, 2 H), 3.87–4.12 (m, 2 H), 3.55–3.84 (m, 2 H), 3.51 (m, 1 H), 3.13–3.44 (m, 3 H), 2.98 (m, 1 H), 1.54–2.28 (m, 10 H).

EXAMPLE 305 cis-3,5-difluoro-N-(4-(quinolin-4-ylamino) cyclohexyl)benzamide

The titled compound was prepared according to the method described in Example 278 by substituting 4-chloroquinoline for 4-chloro-6-fluoro-2-trifluoromethyl-quinoline. MS (ESI(+)Q1MS m/z 382 (M+H)$^+$; $^1$H NMR (300 MHz, DMSO) δ ppm 8.71–8.63 (m, 2 H), 8.59–8.53 (m, 1 H), 8.30 (d, 1 H), 8.00–7.87 (m, 3 H), 7.78–7.70 (ddd, 1 H), 7.63–7.55 (m, 2 H), 7.50–7.42 (m, 1 H), 6.98 (d, 1 H), 4.05–3.95 (m, 2 H), 2.05–1.63 (m, 8 H).

EXAMPLE 306 cis-tert-butyl (2R)-2-(({4-((7-chloroquinolin-4-yl) amino)cyclohexyl}amino)methyl)pyrrolidine-1-carboxylate The title compound was prepared according to method described in Example 141, substituting Boc-Prolinol for 4-fluorobenzyl alcohol. MS(ESI) m/e 459 (M+H)$^+$; $^1$H NMR (500 MHz, DMSO-D6) δ ppm 8.74 (d, 1 H), 8.61 (d, 1 H), 7.97 (d, 1 H), 7.78 (dd, 1 H), 6.95 (d, 1 H), 3.95–4.21 (m, 2 H), 3.78 (m, 2 H), 2.95–3.64 (m, 6 H), 1.99–2.25 (m, 4 H), 1.75–1.99 (m, 10 H), 1.56 (m, 1 H), 1.24–1.50 (m, 5 H).

EXAMPLE 307 cis-N-(7-chloroquinolin-4-yl)-N'-1,4-dithiaspiro(4.5) dec-8-ylcyclohexane-1,4-diamine The titled compound was prepared according to method described in Example 141, substituting 1,4-Dithiaspiro(4.5) decan-8-ol for 4-fluorobenzyl alcohol. MS(ESI) m/e 448 (M+H)$^+$; $^1$H NMR (500 MHz, DMSO-D6) δ ppm 8.73 (d, 1 H), 8.60 (d, 1 H), 7.96 (d, 1 H), 7.79 (dd, 1 H), 6.93 (d, 1 H), 1.96–2.18 (m, 14 H), 1.84 (m, 8 H), 1.59 (m, 3 H).

EXAMPLE 308 cis-N-(7-chloroquinolin-4-yl)-N'-((6-methylpyridin-2-yl)methyl)cyclohexane-1,4-diamine The titled compound was prepared according to method described in Example 141, substituting 6-Methyl-2-pyridinemethanol for 4-fluorobenzyl alcohol. MS(ESI) m/e 381 (M+H)$^+$; $^1$H NMR (500 MHz, DMSO-D6) δ ppm 8.74 (d, 1 H), 8.61 (d, 1 H), 7.97 (d, 1 H), 7.68–7.88 (m, 3 H), 7.29 (dt, 1 H), 6.95 (d, 1 H), 4.56 (m, 2 H), 4.33 (m, 2 H), 2.50 (s, 3 H), 1.66–2.22 (m, 10 H).

EXAMPLE 309 cis-N-(7-chloroquinolin-4-yl)-N'-(2-thien-3-ylethyl) cyclohexane-1,4-diamine

The titled compound was prepared according to method described in Example 141, substituting 2-(3-Thienyl)ethanol for 4-fluorobenzyl. MS(ESI) m/e 386 (M+H)$^+$; $^1$H NMR (500 MHz, DMSO-D6) δ ppm 8.75 (d, 1 H), 8.61 (d, 1 H), 7.97 (d, 1 H), 7.81 (dd, 1 H), 7.54 (m, 1 H), 7.35 (d, 1 H), 7.09 (dd, 1 H), 6.95 (d, 1 H), 4.09 (s, 1 H), 3.62 (m, 1 H), 2.96 (m, 2 H), 2.73 (m, 2 H), 1.69–2.19 (m, 10 H).

EXAMPLE 310 cis-N-(7-chloroquinolin-4-yl)-N'-{((2S)-1-(2-methoxybenzoyl)pyrrolidin-2-yl) methyl}cyclohexane-1,4-diamine The titled compound was prepared according to method described in Example 141, substituting (R)-(+)-1-(2-Methoxybenzoyl)-2-pyrrolidinemethanol for 4-fluorobenzyl alcohol. MS(ESI) m/e 493 (M+H)$^+$; $^1$H NMR (500 MHz, DMSO-D6) δ ppm 8.70 (d, 1 H), 8.46 (d, 1 H), 8.22 (d, 1 H), 7.78 (dd, 1 H), 7.43 (m, 1 H), 7.27 (dd, 1 H), 7.11 (d, 1 H), 7.01 (m, 1 H), 6.81 (d, 1 H), 4.21–4.42 (m, 2 H), 3.79 (m, 3 H), 3.79 (s, 3 H), 3.08–3.47 (m, 6 H), 1.51–2.23 (m, 10 H).

EXAMPLE 311 cis-N-(7-chloroquinolin-4-yl)-N'-(thien-3-ylmethyl)cyclohexane-1,4-diamine

The titled compound was prepared according to method described in Example 141, substituting 3-Thiophenemethanol for 4-fluorobenzylalcohol. MS(ESI) m/e 372 (M+H)$^+$; $^1$H NMR (500 MHz, DMSO-D6) δ ppm 8.75 (d, 1 H), 8.61 (d, 1 H), 7.97 (d, 1 H), 7.83 (m, 1 H), 7.73 (m, 1 H), 7.65 (m, 1 H), 7.26 (dd, 1 H), 6.94 (d, 1 H), 3.21 (m, 2 H), 2.07 (m, 2 H), 1.70–2.12 (m, 10 H).

EXAMPLE 312 cis-N-(7-chloroquinolin-4-yl)-N'-(2-thien-2-ylethyl)cyclohexane-1,4-diamine

The titled compound was prepared according to method described in Example 141, substituting 2-(2-Thienyl)ethanol for 4-fluorobenzylalcohol. MS(ESI) m/e 386 (M+H)$^+$; $^1$H NMR (500 MHz, DMSO-D6) δ ppm 8.75 (d, 1 H), 8.60 (d, 1 H), 7.97 (d, 1 H), 7.81 (dd, 1 H), 7.43 (m, 1 H), 7.29 (dd, 1 H), 7.01 (m, 1 H), 6.94 (m, 1 H), 4.08 (s, 1 H), 3.61 (t, 2 H), 3.19 (m, 1 H), 2.92 (t, 2 H), 1.69–2.16 (m, 10 H).

EXAMPLE 313 cis-N-(7-chloroquinolin-4-yl)-N'-(thien-2-ylmethyl)cyclohexane-1,4-diamine

The titled compound was prepared according to method described in Example 141, substituting Thiophene-2-methanol for 4-fluorobenzylalcohol. MS(ESI) m/e 372 (M+H)$^+$; $^1$H NMR (500 MHz, DMSO-D6) δ ppm 8.75 (d, 1 H), 8.61 (d, 1 H), 7.98 (d, 1 H), 7.82 (m, 1 H), 7.66 (m, 1 H), 7.32 (d, 1 H), 7.13 (m, 1 H), 6.94 (d, 1 H), 4.47 (s, 1 H), 3.27 (s, 1 H), 2.53 (m, 2 H), 1.70–2.14 (m, 10 H).

EXAMPLE 314 cis-6-{4-((7-chloroquinolin-4-yl)amino)cyclohexyl}amino)-1,3-dimethylpyrimidine-2,4(1H,3H)-dione The titled compound was prepared according to the method described in Example 3 by substituting 6-chloro-1,3-dimethyluracil for 4-chloro-2,8-bis(trifluoromethyl)-quinoline. MS (ESI(+)Q1MS m/z 414 (M+H)$^+$; $^1$H NMR (300 MHz, DMSO) δ ppm 8.80–8.75 (m, 1 H), 8.70 (d, 1 H), 8.57(dd, 1 H), 7.95 (d, 1 H), 7.80 (dd, 1 H), 7.00 (d, 1 H), 6.02–5.95 (m, 1 H), 4.81 (s, 1 H), 4.06–3.97 (m, 1 H), 3.61–3.51 (m, 1 H), 3.40 (s, 3 H), 3.10 (s, 3 H), 2.02–1.70 (m, 8 H).

EXAMPLE 315 cis-6-({4-((7-chloroquinolin-4-yl)amino)cyclohexyl}amino)pyrimidine-2,4(1H,3H)-dione The titled compound was prepared according to the method described in Example 3 by substituting 4-chlorouracil for 4-chloro-2,8-bis(trifluoromethyl)-quinoline. MS (ESI(+)Q1MS m/z 386(M+H)$^+$; $^1$H NMR (300 MHz, DMSO) δ ppm 10.22 (s, 1 H), 9.75 (s, 1 H), 8.90–8.84 (m, 1 H), 8.71 (d, 1 H), 8.60–8.55 (m, 1 H), 7.94 (d, 1 H), 7.82 (dd, 1 H), 7.00 (d, 1 H), 6.17 (d, 1 H), 4.48 (s, 1 H), 4.00–3.92 (m, 1 H), 3.61–3.51 (m, 1 H), 2.02–1.70 (m, 8 H).

EXAMPLE 316 cis-N-(7-chloroquinolin-4-yl)-N'-(3-(6-methylpyridin-2-yl)propyl)cyclohexane-1,4-diamine The titled compound was prepared according to method described in Example 141, substituting 6-Methyl-2-pyridinepropanol for 4-fluorobenzylalcohol. MS(ESI) m/e 409 (M+H)$^+$; $^1$H NMR (500 MHz, DMSO-D6) δ ppm 8.75 (d, 1 H), 8.63 (d, 1 H), 8.61 (d, 1 H), 8.53 (m, 1 H), 7.97 (d, 1 H), 7.82 (dd, 1 H), 7.25 (m, 1 H), 6.95 (d, 1 H), 4.08 (s, 1 H), 3.03 (s, 1 H), 2.87 (m, 2 H), 2.54 (s, 3 H), 2.35–2.60 (m, 4 H), 1.64–2.21 (m, 10 H).

EXAMPLE 317 cis-N-(7-chloroquinolin-4-yl)-N'-(3-furylmethyl)cyclohexane-1,4-diamine

The titled compound was prepared according to method described in Example 141, substituting 3-Furanmethanol for 4-fluorobenzylalcohol. MS(ESI) m/e 356 (M+H)$^+$; $^1$H NMR (500 MHz, DMSO-D6) δ ppm 8.75 (d, 1 H), 8.60 (d, 1 H), 7.97 (m, 1 H), 7.82 (m, 2 H), 7.76 (m, 1 H), 6.95 (d, 1 H), 6.66 (s, 1 H), 4.10 (s, 1 H), 3.22 (s, 1 H), 2.52 (m, 2 H), 1.70–2.15 (m, 10 H).

EXAMPLE 318 cis-N-(7-chloroquinolin-4-yl)-N'-(3-pyridin-2-ylpropyl)cyclohexane-1,4-diamine

The titled compound was prepared according to method described in Example 141, substituting 2-Pyridinepropanol for 4-fluorobenzylalcohol. MS(ESI) m/e 395 (M+H)$^+$; $^1$H NMR (500 MHz, DMSO-D6) δ ppm 8.75 (d, 1 H), 8.64 (d, 1 H), 8.61 (d, 1 H), 8.56 (d, 1 H), 7.97 (d, 1 H), 7.84 (m, 1 H), 7.36 (m, 2 H), 6.95 (d, 1 H), 3.25 (m, 2 H), 3.03 (m, 2 H), 2.89 (m, 2 H), 2.51 (m, 2 H), 1.68–2.21 (m, 10 H).

EXAMPLE 319 cis-N-(7-chloroquinolin-4-yl)-N'-(2-(2-methyl-5-nitro-1H-imidazol-1-yl)ethyl)cyclohexane-1,4-diamine The titled compound was prepared according to method described in Example 141, substituting Metronidazole for 4-fluorobenzylalcohol. MS(ESI) m/e 429 (M+H)$^+$; $^1$H NMR (500 MHz, DMSO-D6) δ ppm 8.77 (d, 1 H), 8.61 (d, 1 H), 8.08 (s, 1 H), 7.98 (d, 1 H), 7.80 (dd, 1 H), 6.96 (d, 1 H), 4.59 (m, 2 H), 4.09 (s, 1 H), 3.68 (s, 1 H), 3.37 (m, 2 H), 2.54 (s, 3 H), 1.72–2.16 (m, 10 H).

EXAMPLE 320 cis-N-(7-chloroquinolin-4-yl)-N'-(3-pyridin-3-ylpropyl)cyclohexane-1,4-diamine

The titled compound was prepared according to method described in Example 141, substituting 3-Pyridinepropanol for 4-fluorobenzylalcohol. MS(ESI) m/e 395 (M+H)$^+$; $^1$H NMR (500 MHz, DMSO-D6) δ ppm 8.75 (d, 1 H), 8.61 (d, 1 H), 8.57 (m, 5 H), 7.97 (d, 1 H), 7.80 (dd, 1 H), 6.95 (d, 1 H), 3.25 (m, 1 H), 2.86–3.08 (m, 2 H), 2.72 (m, 2 H), 2.51 (m, 2 H), 1.68–2.21 (m, 10 H).

EXAMPLE 321 cis-N-(7-chloroquinolin-4-yl)-N'-{((4R,5S)-2-methyl-5-phenyl-4,5-dihydro-1,3-oxazol-4-yl)methyl}cyclohexane-1,4-diamine The titled compound was prepared according to method described in Example 141, substituting (4S,5S)-(−)-2-Methyl-5-phenyl-2-oxazoline-4-methanol for 4-fluorobenzylalcohol. MS(ESI) m/e 349 (M+H)$^+$; $^1$H NMR (500 MHz, DMSO-D6) δ ppm 8.76 (d, 1 H), 8.59 (d, 1 H), 8.36 (d, 1 H), 7.81 (dd, 1 H), 7.81 (m, 1 H), 7.40 (m, 2 H), 7.33 (m, 2 H), 6.93 (d, 1 H), 2.24 (s, 3 H), 2.01 (m, 2 H), 1.70–1.91 (m, 10 H), 1.63 (m, 2 H), 1.47 (m, 2 H).

EXAMPLE 322 cis-N-(7-chloroquinolin-4-yl)-N'-(2-(4-methyl-1,3-thiazol-5-yl)ethyl)cyclohexane-1,4-diamine The titled compound was prepared according to method described in Example 141, substituting 4-Methyl-5-thiazoleethanol for 4-fluorobenzylalcohol. MS(ESI) m/e 401 (M+H)$^+$; $^1$H NMR (500 MHz, DMSO-D6) δ ppm 8.91 (s, 1 H), 8.75 (d, 1 H), 8.61 (d, 1 H), 7.97 (d, 1 H), 7.82 (dd, 1 H), 6.96 (d, 1 H), 4.08 (s, 1 H), 3.33 (s, 1 H), 2.52 (m, 2 H), 2.38 (s, 3 H), 2.37 (m, 2 H), 1.72–2.19 (m, 10 H).

EXAMPLE 323 cis-N-(7-chloroquinolin-4-yl)-N'-(tetrahydrofuran-2-ylmethyl)cyclohexane-1,4-diamine The titled compound was prepared according to method described in Example 141, substituting Tetrahydrofurfuryl alcohol for 4-fluorobenzylalcohol. MS(ESI) m/e 360 (M+H)$^+$; $^1$H NMR (500 MHz, DMSO-D6) δ ppm 8.72 (d, 1 H), 8.60 (d, 1 H), 7.97 (d, 1 H), 7.81 (dd, 1 H), 6.92 (d, 1 H), 4.09 (m, 2 H), 3.82 (m, 2 H), 3.73 (m, 2 H), 3.11 (m, 2 H), 2.96 (m, 1 H), 1.65–2.15 (m, 10 H), 1.57 (m, 2 H).

EXAMPLE 324 cis-N-(7-chloroquinolin-4-yl)-N'-(pyridin-3-ylmethyl)cyclohexane-1,4-diamine

The titled compound was prepared according to method described in Example 141, substituting Pyridine-3-methanol for 4-fluorobenzylalcohol. MS(ESI) m/e 367 (M+H)$^+$; $^1$H NMR (500 MHz, DMSO-D6) δ ppm 8.75 (d, 1 H), 8.61 (d, 1 H), 8.54 (m, 4 H), 7.97 (d, 1 H), 7.80 (dd, 1 H), 6.95 (d, 1 H), 4.08 (s, 1 H), 3.59 (s, 1 H), 2.98 (m, 2 H), 2.74 (m, 2 H), 2.50 (m, 2 H), 1.69–2.22 (m, 10 H).

EXAMPLE 325 cis-N-(7-chloroquinolin-4-yl)-N'-{2-(3-(6-methylpyridin-2-yl)propoxy)ethyl}cyclohexane-1,4-diamine The titled compound was prepared according to method described in Example 141, substituting 2-(3-(6-Methyl-2-pyridyl)propoxy)ethanol for 4-fluorobenzylalcohol. MS(ESI) m/e 453 (M+H)$^+$; $^1$H NMR (500 MHz, DMSO-D6) δ ppm 8.74 (d, 1 H), 8.61 (d, 1 H), 7.97 (m, 1 H), 7.84 (m, 1 H), 7.71 (m, 1 H), 7.48 (td, 1 H), 7.24 (td, 1 H), 6.94 (d, 1 H), 2.74–3.00 (m, 4 H), 2.54 (s, 3 H), 2.44–2.68 (m, 6 H), 2.09 (m, 2 H), 1.67–2.01 (m, 10 H).

EXAMPLE 326 cis-N-(7-chloroquinolin-4-yl)-N'-{((2R)-1-(2-methoxybenzoyl)pyrrolidin-2-yl)methyl}cyclohexane-1,4-diamine The title compound was prepared according to method described in Example 141, substituting (S)-(−)-1-(2-methoxybenzoyl)-2-pyrrolidinemethanol for 4-fluorobenzyl alcohol. $^1$H NMR (500 MHz, DMSO-D6) δ ppm 8.73 (d, 1 H), 8.60 (d, 1 H), 7.96 (d, 1 H), 7.80 (dd, 1 H), 7.27 (m, 1 H), 6.99 (m, 5 H), 4.31 (m, 2 H), 4.08 (m, 2 H), 3.78 (s, 3 H), 2.90–3.30 (m, 6 H), 1.56–2.04 (m, 10 H); MS(ESI) m/e 493 (M+H)$^+$.

EXAMPLE 327 cis-N-(7-chloroquinolin-4-yl)-N'-(tetrahydrofuran-3-ylmethyl)cyclohexane-1,4-diamine The title compound was prepared according to method described in Example 141, substituting tetrahydro-3-furanmethanol for 4-fluorobenzyl alcohol. $^1$H NMR (500 MHz, DMSO-D6) δ ppm 8.76 (d, 1 H), 8.61 (d, 1 H), 7.98 (d, 1 H), 7.80 (dd, 1 H), 6.95 (d, 1 H), 4.10 (s, 1 H), 3.76 (m, 2 H), 3.66 (m, 2 H), 3.00 (m, 2 H), 2.52 (m, 2 H), 1.69–2.23 (m, 10 H), 1.63 (m, 2 H); MS(ESI) m/e 360 (M+H)$^+$.

EXAMPLE 328 cis-N-(7-chloroquinolin-4-yl)-N'-(2-furylmethyl)cyclohexane-1,4-diamine

The title compound was prepared according to method described in Example 141, substituting furfuryl alcohol 0 for 4-fluorobenzyl alcohol. $^1$H NMR (500 MHz, DMSO-D6) δ ppm 8.74 (d, J=9.1 Hz, 1 H), 8.60 (d, J=7.2 Hz, 1 H), 7.97 (d, J=2.2 Hz, 1 H), 7.82 (d, 1 H), 7.81 (m, 1 H), 6.94 (d, 1 H), 6.66 (m, 1 H), 6.56 (m, 1 H), 4.31 (s, 1 H), 3.22 (s, 1 H), 2.50 (m, 2 H), 1.68–2.11 (m, 10 H); MS(ESI) m/e 356 (M+H)$^+$.

EXAMPLE 329 cis-N-(7-chloroquinolin-4-yl)-N'-((3-methyloxetan-3-yl)methyl)cyclohexane-1,4-diamine The title compound was prepared according to method described in Example 141, substituting 3-Methyl-3-oxetanemethanol for 4-fluorobenzyl alcohol. $^1$H NMR (500 MHz, DMSO-D6) δ ppm 8.72 (d, 1 H), 8.59 (d, 1 H), 7.96 (d, 1 H), 7.71 (d, 1 H), 6.91 (d, 1 H), 5.11 (s, 1 H), 4.39 (m, 2 H), 3.91–4.17 (m, 4 H), 2.99 (s, 1 H), 1.70–2.22 (m, 10 H), 0.91 (s, 3 H); MS(ESI) m/e 360 (M+H)$^+$.

EXAMPLE 330 cis-N-(7-chloroquinolin-4-yl)-N'-(3-pyridin-4-ylpropyl)cyclohexane-1,4-diamine

The title compound was prepared according to method described in Example 141, substituting 4-Pyridinepropanol for 4-fluorobenzyl alcohol. $^1$H NMR (500 MHz, DMSO-D6) δ ppm 8.79 (d, 1 H), 8.74 (d, 1 H), 7.98 (d, 1 H), 7.82 (d, 2 H), 7.76 (d, 1 H), 7.71 (d, 2 H), 6.95 (d, 1 H), 4.16 (s, 1 H), 3.12 (m, 1 H), 2.67–2.91 (m, 6 H), 1.71–2.16 (m, 10 H); MS(ESI) m/e 395 (M+H)$^+$.

EXAMPLE 331 cis-N-(7-chloroquinolin-4-yl)-N'-((3-ethyloxetan-3-yl)methyl)cyclohexane-1,4-diamine The title compound was prepared according to method described in Example 141, substituting 3-ethyl-3-oxetanemethanol for 4-fluorobenzyl alcohol. $^1$H NMR (500 MHz, DMSO-D6) δ ppm 8.76 (d, 1 H), 8.61 (d, 1 H), 7.97 (d, 1 H), 7.79 (dd, 1 H), 6.92 (d, 1 H), 3.42 (s, 1 H), 3.01 (m, 1 H), 2.13 (m, 2 H), 2.00 (m, 2 H), 1.59–2.05 (m, 10 H), 0.89 (s, 3 H), 0.85–1.06 (m, 4 H); MS(ESI) m/e 374 (M+H)$^+$.

EXAMPLE 332 cis-N-(7-chloroquinolin-4-yl)-N'-(pyridin-2-ylmethyl)cyclohexane-1,4-diamine

The title compound was prepared according to method described in Example 141, substituting pyridine-2-methanol for 4-fluorobenzyl alcohol. MS(ESI) m/e 367 (M+H)$^+$.

EXAMPLE 333 cis-N-(7-chloroquinolin-4-yl)-N'-(1H-imidazol-4-ylmethyl)cyclohexane-1,4-diamine The title compound was prepared according to method described in Example 141, substituting 4-(hydroxymethyl) imidazole hydrochloride for 4-fluorobenzyl alcohol. $^1$H NMR (500 MHz, DMSO-D6) δ ppm 8.75 (d, 1 H), 8.69 (d, 1 H), 8.60 (d, 1 H), 8.59 (d, 1 H), 7.97 (d, 1 H), 7.81 (d, 1 H), 6.96 (d, 1 H), 4.03 (s, 1 H), 4.03 (m, 1 H), 3.29 (m, 1 H), 2.49 (m, 2 H), 1.69–2.18 (m, 10 H); MS(ESI) m/e 356 (M+H)$^+$.

EXAMPLE 334 cis-N-(7-chloroquinolin-4-yl)-N'-{((4S)-2,2-dimethyl-1,3-dioxolan-4-yl)methyl}cyclohexane-1,4-diamine The title compound was prepared according to method described in Example 141, substituting (S)-(+)-2,2-Dimethyl-1,3-dioxolane-4-methanol for 4-fluorobenzyl alcohol. $^1$H NMR (500 MHz, DMSO-D6) δ ppm 8.73 (d, 1 H), 8.61 (d, 1 H), 7.98 (d, 1 H), 7.82 (dd, 1 H), 6.94 (d, 1 H), 3.81 (s, 1 H), 3.26 (s, 1 H), 2.98–3.19 (m, 2 H), 2.76–2.98 (m, 2 H), 2.51 (m, 1 H), 2.50 (s, 6 H), 1.63–2.15 (m, 10 H); MS(ESI) m/e 390 (M+H)$^+$.

EXAMPLE 335 cis-N-1,3-benzothiazol-2-yl-N'-(7-chloroquinolin-4-yl)cyclohexane-1,4-diamine

The titled compound was prepared according to the method described in Example 3 by substituting 2-chlorobenzothiazole for 4-chloro-2,8-bis (trifluoromethyl)-quinoline. MS (ESI(+)Q1MS m/z 409 (M+H)$^+$; $^1$H NMR (300 MHz, DMSO) δ ppm 8.94–8.89 (m, 1 H), 8.72 (d, 1 H), 8.59–8.54 (m, 1 H), 8.15–8.05 (m, 1 H), 7.91 (d, 1 H), 7.81 (dd, 1 H), 7.71 (d, 1 H), 7.40 (d, 1 H), 7.23 (ddd, 1 H), 7.06–6.98 (m, 2 H), 4.04–3.94 (m, 2 H), 2.17–1.77 (m, 8 H).

EXAMPLE 336 cis-6-({4-((7-chloroquinolin-4-yl)amino) cyclohexyl}amino)-3-methylpyrimidine-2,4(1H,3H)-dione The titled compound was prepared according to the method described in Example 3 by substituting 6-chloro-3-methyluracil for 4-chloro-2,8-bis(trifluoromethyl)-quinoline. MS (ESI(+)Q1MS m/z 400(M+H)$^+$; $^1$H NMR (300 MHz, DMSO) δ ppm 10.03 (br s, 1 H), 8.87 (d, 1 H), 8.72 (d, 1 H), 8.58 (d, 1 H), 7.95 (d, 1 H), 7.82 (dd, 1 H), 7.01 (d, 1 H), 6.15 (d, 1 H), 4.67 (d, 1 H), 4.00–3.57 (m, 2 H), 3.03 (s, 3 H), 1.90–1.70 (m, 8 H).

EXAMPLE 337

(1S,2R,4S,5R)-N,N'-bis(7-chloroquinolin-4-yl)-2,5-dimethylcyclohexane-1,4-diamine

Example 337 A (1S,2R,4S,5R)-2,5-dimethylcyclohexane-1,4-diamine

A solution of 1,3-dimethylphenylene-2,4-diamine (5 g, 36.7 mmol), 5% Ru on Al$_2$O$_3$ in ethanol (100 ml) was shaken under 950 psi hydrogen pressure at 100° C. for 72 hours, filtered and concentrated under reduced pressure to provide the titled compound. MS(Cl(+)Q1MS m/z 143 (M+H)$^+$).

EXAMPLE 337 B (1S,2R,4S,5R)-N,N'-bis(7-chloroquinolin-4-yl)-2,5-dimethylcyclohexane-1,4-diamine The titled compound was prepared according to the methods described in Example 140, substituting 4-bromo-7-chloroquinoline for 1-bromo-3,5-difluorobenzene and (1S,2R,4S,5R)-2,5-dimethylcyclohexane-1,4-diamine for Example 23A. MS(ESI(+)Q1MS m/z 465 (M+H)$^+$); $^1$H NMR (300 MHz, DMSO) δ ppm 8.87 (d, 2 H), 8.60 (d, 2 H), 8.32 (br.s, 2 H), 7.95 (d, 2 H), 7.85 (dd, 2 H), 7.05 (d, 2 H), 4.03–4.37 (br.s, 2 H), 2.27 (m, 4 H), 1.90 (m, 2 H), 1.02 (d, 6 H).

EXAMPLE 338

(1S,2R,4S,5R)-N-(7-chloroquinolin-4-yl)-N'-(3,5-dimethylphenyl)-2,5-dimethylcyclohexane-1,4-diamine

Example 338 A (1S,2R,4S,5R)-N-(7-chloroquinolin-4-yl)-2,5-dimethylcyclohexane-1,4-diamine A mixture of 4,7-dichloroquinoline (500 mg, 2.5 mmol) and (1S,2R,4S,5R)-2,5-dimethylcyclohexane-1,4-diamine (750 mg, 5.2 mmol) was heated at 150° C. for 5 hours, cooled to room temperature, and flash chromatographed through silica gel column with dichloromethane and methanol (3:1 ratio by vol) to provide the titled compound. MS(ESI(+)Q1MS m/z 304 (M+H)$^+$).

EXAMPLE 338 B (1S,2R,4S,5R)-N-(7-chloroquinolin-4-yl)-N'-(3,5-dimethylphenyl)-2,5-dimethylcyclohexane-1,4-diamine The titled compound was prepared according to the methods described in Example 140, substituting 5-bromo-m-xylene for 1-bromo-3,5-difluorobenzene and (1S,2R,4S,5R)-N-(7-chloroquinolin-4-yl)-2,5-dimethylcyclohexane-1,4-diamine for N-(7-chloroquinolin-4-yl)cyclohexane-1,4-diamine. $^1$H NMR (300 MHz, DMSO) δ ppm 8.89 (d, 1 H), 8.56 (m, 2 H), 7.92 (d, 1 H), 7.82 (dd, 1 H), 6.99 (d, 1 H), 6.31 (s, 2 H), 6.17 (s, 1 H), 4.10 (br.s, 2 H), 2.14 (s, 6 H), 2.03–2.33 (m, 4 H), 1.69 (m, 2 H), 0.97 (br.d, 6 H). MS(ESI(+)Q1MS m/z 408 (M+H)$^+$).

EXAMPLE 339

N-((1S,2R,4S,5R)-4-((7-chloroquinolin-4-yl)amino)-2,5-dimethylcyclohexyl)-3,5-difluorobenzamide The titled compound was prepared according to the method described in Example 23 substituting (1S,2R,4S, 5R)-N-(7-chloroquinolin-4-yl)-2,5-dimethylcyclohexane-1, 4-diamine for N-(7-chloroquinolin-4-yl)cyclohexane-1,4-diamine and 3,5-difluorobenzoic acid for indole-6-carboxylic acid. $^1$H NMR (300 MHz, DMSO) δ ppm 8.87 (d, 1 H), 8.55 (t, 1 H), 8.07 (d, 1 H), 7.93 (d, 1 H), 7.83 (dd, 1 H), 7.42–7.64 (m, 4 H), 7.00 (d, 1 H), 4.00–4.20 (m, 2 H), 1.63–2.34 (m, 6 H), 1.03 (d, 3 H), 1.00 (d, 3 H). MS(ESI (+)Q1MS m/z 444 (M+H)$^+$).

EXAMPLE 340

5-bromo-N-{4-((7-chloroquinolin-4-yl)amino) cyclohexyl}-2-hydroxybenzamide

The titled compound was prepared according to the methods described in Example 23, substituting 5-bromosalicylic acid for indole-6-carboxylic acid. MS (ESI (+)Q1MS m/z 474 and 476 (M+H)$^+$); $^1$H NMR (500 MHz, DMSO-D6) δ ppm 1.76–1.90 (m, 5 H) 1.97–2.05 (m, 2 H) 2.07 (s, 1 H) 4.00 (m, 1 H) 4.08 (m, 1 H) 6.93 (d, J=8.73 Hz, 1 H) 7.01 (d, J=7.18 Hz, 1 H) 7.56 (dd, J=8.74, 2.50 Hz, 1 H) 7.80 (dd, J=9.20, 2.03 Hz, 1 H) 7.94 (d, J=2.18 Hz, 1 H) 8.15 (d, J=2.50 Hz, 1 H) 8.56 (d, J=7.17 Hz, 1 H) 8.60 (d, J=5.93 Hz, 1 H) 8.71 (d, J=9.36 Hz, 1 H) 8.83 (d, J=7.17 Hz, 1 H).

EXAMPLE 341

3-bromo-N-{4-((7-chloroquinolin-4-yl)amino) cyclohexyl}-5-fluorobenzamide

A mixture of 23A cis-N,N'-bis(7-chloroquinolin-4-yl) cyclohexane-1,4-diamine (500 mg, 3.6 mmol), 3-bromo-5-fluorobenzoic acid (600 mg, 5.4 mmol), 1-hydroxybenzotriazole (245 mg, 3.6 mmol), 1-(3-dimethylaminopropyl)-3-ethylcarbodiimide(348 mg, 3.6 mmol) in 30 mL dichloromethane was stirred for 3 hours. The reaction was incomplete. 3-bromo-5-fluorobenzoic acid (160 mg, 0.9 mmol), 1-hydroxybenzotriazole (61 mg, 0.9 mmol), 1-(3-dimethylaminopropyl)-3-ethylcarbodiimide (87 mg, 0.9 mmol) was added and the solution was allowed to stir overnight. The solution was then washed with 1N NaOH, dried (Na$_2$SO$_4$), and concentrated. The residue was purified by flash chromatography (10% methanol in dichloromethane) to provide 700 mg of pure compound, an 81% yield. MS (ESI(+)Q1MS m/z 477 (M+2 H)$^+$; $^1$H NMR (300 MHz, MeOH) δ ppm 8.36–8.42 (m, 3 H), 7.95 (t, 1 H), 7.69–7.79 (m, 3 H), 7.45 (dd, 1 H), 6.83 (d, 1 H), 6.54 (d, 1 H), 3.95 (m, 1 H), 3.68 (m, 1 H), 1.66–1.98 (m, 8 H).

EXAMPLE 342

(1S,2R,4S,5R)—N,N'-bis(7-chloroquinolin-4-yl)-2, 5-dimethylcyclohexane-1,4-diamine The titled compound was prepared according to the methods described in Example 1, substituting 1,4-diamino-2,5-dimethylcyclohexane for 1,4-diaminocyclohexane. MS (ESI(+)Q1MS m/z 465 (M+H)$^+$); $^1$H NMR (300 MHz, DMSO-D6) δ ppm 1.02 (d, J=6.44 Hz, 6H) 1.86–1.94 (m, 2H) 2.22–2.37 (m, 4H) 4.17–4.25 (br.s, 2H) 7.05 (d, J=7.46 Hz, 2 H) 7.85 (dd, J=9.15, 2.03 Hz, 2H) 7.96 (d, J=2.37 Hz, 2H) 8.38 (d, J=7.12 Hz, 2H) 8.60 (d, J=7.12 Hz, 2H) 8.89 (d, J=9.15 Hz, 2H).

EXAMPLE 343

4-({4-((7-chloroquinolin-4-yl)amino) cyclohexyl}amino)-6-methyl-2H-chromen-2-one To a conical microwave vessel (7.5 mL) equipped with a septum cap and a magnetic stirring bar was added a solution of a trifluoro-methanesulfonic acid 6-chloro-2-oxo-2H-chromen-4-yl ester (0.014 g; 0.043 mmol)) in dry acetonitrile (1 mL) containing Et$_3$N (0.025 mL). Then, a solution of N-(7-chloro-quinolin-4-yl)-cyclohexane-1,4-diamine (0.0178 g; 1.5 eq.) in 1:1:1 mixture of acetonitrile/dichloromethane/DMF (1 mL) was added to the vessel and the resulting suspension was irradiated in Personal Chemistry Smith Synthesizer (150° C. for 180 s; 300 W). The resulting solution was evaporated to dryness. The residue was dissolved in 1.5 mL of a 1:1 mixture of DMSO/MeOH and purified by preparative reverse-phase HPLC. MS (DCI/NH$_3$) m/z 433 [M+H]$^+$.

EXAMPLE 344

N-{4-((7-chloroquinolin-4-yl)amino)cyclohexyl}-3-methyl-2-phenylpentanamide

General procedure: Syntheses were performed using a PE Biosystems (Applied Biosystems) Solaris 530 organic synthesizer. Each of the 48 round bottom flasks was charged with 3 equivalents of PS-dicyclohexane carbodiimide resin (PS-DCC) supplied by Argonaut Technologies. The reaction block was then assembled and placed on the Solaris 530. The acid monomers (0.6 mmol) were each dissolved N,N-dimethylacetamide (DMA) (3 mL). The amine core was dissolved in N,N-dimethylacetamide. Solutions of N-hydroxybenzotriazole in N,N-dimethylacetamide and diisopropylethylamine (DIEA) in DMA were placed on the instrument. The Solaris was primed with DMA then into each of the 48 vials containing PS-DCC resin was added 1.25 equivalents of each monomer solution, HOBt solution (0.75 mL, 1 eq), core solution (0.75 mL, 1 eq) and DIEA solution (0.75 mL, 3 eq). The reactions were heated to 55 C overnight, checked by LC/MS, and transferred with methanol to 20 mL vials containing 3 eq MP-Carbonate resin supplied by Argonaut Technologies. The MP-Carbonate resin was filtered and the reactions were concentrated to dryness under reduced pressure. The residues were dissolved in 1:1 dimethylsulfoxide/methanol and purified by reverse phase HPLC.

The titled compound was prepared using the procedure described above using N-(7-chloro-quinolin-4-yl)-cyclohexane-1,4-diamine and 3-methyl-2-phenyl-pentanoic acid. MS (CI(+)) m/e 450 (M)$^+$. $^1$H NMR (500 MHz, DMSO) δ ppm 8.86 (t, J=8.0 Hz, 1H), 8.75 (d, J=9.0 Hz, 1 H), 8.54 (d, J=7.2 Hz, 1 H), 7.93 (m, 2 H), 7.80 (dd, J=9.0, 1.9 Hz, 1 H), 7.37 (m, 2 H), 7.28 (t, J=7.5 Hz, 2 H), 7.20 (t, J=7.3 Hz, 1 H), 6.95 (dd, J=7.2, 3.7 Hz, 1 H), 3.27 (dd, J=19.2, 10.8 Hz, 1H), 2.07 (m, 1H), 1.74 (m, 8H), 1.14 (m, 1H), 0.94 (d, J=6.6 Hz, 1H), 0.90 (t, J=7.3 Hz, 2H), 0.84 (m, 1H), 0.73 (t, J=7.3 Hz, 1H), 0.58 (d, J=6.6 Hz, 2H).

EXAMPLE 345

N-{4-((7-chloroquinolin-4-yl)amino)cyclohexyl}-2-hydroxy-5-methylbenzamide

The titled compound was prepared according to the methods described in Example 23, substituting 5-methylsalicylic acid for indole-6-carboxylic acid. MS (ESI(+)Q1MS m/z 410 (M+H)$^+$); $^1$H NMR (500 MHz, DMSO-D6) δ ppm 1.75–2.02 (m, 8H) 2.27 (s, 3 4.02 (m, 1H) 4.02–4.10 (m, 1H) 6.83 (d, J=8.11 Hz, 1H) 6.99 (d, J=7.18 Hz, 1 H) 7.21 (dd, J=8.42, 1.87 Hz, 1H) 7.79 (m, 2H) 7.92 (d, J=2.18 Hz, 1H) 8.45 (d, J=6.24 Hz, 1H) 8.56 (d, J=7.18 Hz, 1H) 8.69 (d, J=9.05 Hz, 1H) 8.74 (br.s, 1H).

EXAMPLE 346

N-{4-((7-chloroquinolin-4-yl)amino)cyclohexyl}-2, 2-diphenylacetamide

The titled compound was prepared according to the procedure described in Example 344 by substituting diphenylacetic acid for 3-methyl-2-phenyl-pentanoic acid. MS (CI(+)) m/e 470 (M)+. ¹H NMR (500 MHz, DMSO) δ ppm 8.87 (d, J=6.9 Hz, 1H), 8.71 (d, J=9.4 Hz, 1H), 8.54 (d, J=7.2 Hz, 1H), 8.25 (d, J=5.9 Hz, 1H), 7.93 (d, J=2.2 Hz, 1H), 7.78 (dd, J=9.0, 2.2 Hz, 1H), 7.31 (m, 9H), 7.23 (m, 2H), 6.97 (d, J=7.2 Hz, 1H), 5.10 (s, 1H), 1.83 (m, 6H), 1.69 (m, 2H).

EXAMPLE 347

N-{4-((7-chloroquinolin-4-yl)amino)cyclohexyl}-5-fluoro-2-hydroxybenzamide

The titled compound was prepared according to the methods described in Example 23, substituting 5-fluorosalicylic acid for indole-6-carboxylic acid. MS (ESI (+)Q1MS m/z 414 (M+H)+); ¹H NMR (500 MHz, DMSO-D6) δ ppm 1.75–2.02 (m, 8H) 3.95–4.03 (m, 1 H) 4.05–4.10 (m, 1H) 6.94–7.00 (m, 2H) 7.24–7.30 (m, 1H) 7.78 (d, J=2.18 Hz, J=2.50 Hz, 1H) 7.92 (d, J=1.87 Hz, 1H) 8.55 (m, 2H) 8.68 (d, J=9.05 Hz, 1H) 8.71–8.74 (br.s, 1H).

EXAMPLE 348

N-{(1S,2R,4S,5R)-4-((7-chloroquinolin-4-yl) amino)-2,5-dimethylcyclohexyl}-3,5-difluorobenzamide

Example 348 A

N-(7-chloroquinolin-4-yl)-2,5-dimethyl-cyclohexane-1,4-diamine

The titled compound was prepared according to the methods described in Example 23A, substituting 2,5-Dimethyl-cyclohexane-1,4-cis-diamine for 1,4-cyclohexanediamine. MS (ESI(+)Q1MS m/z 304 (M+H)+.

EXAMPLE 348 B

N-{(1S,2R,4S,5R)-4-((7-chloroquinolin-4-yl) amino)-2,5-dimethylcyclohexyl}-3,5-difluorobenzamide The titled compound was prepared according to the methods described in Example 112, substituting Example 348A for example 23A. MS (ESI(+)Q1MS m/z 444 (M+H)+; ¹H NMR (300 MHz, DMSO-D6) δ ppm 0.93–1.04 (m, 6H) 1.66–2.30 (m, 6H) 4.03–4.17 (m, H) 7.00 (d, J=7.46 Hz, 1H) 7.45–7.61 (m, 2H) 7.83 (dd, J=9.16, 2.03 Hz, 1H) 7.93 (m, 1 H) 8.07 (d, J=6.78 Hz, 1H) 8.55 (t, J=7.29 Hz, 2H) 8.87 (d, J=9.16 Hz, 1H).

EXAMPLE 349

N-(7-chloroquinolin-4-yl)-N'-(2',5-dimethyl-1,1'-biphenyl-3-yl)cyclohexane-1,4-diamine The titled compound was prepared according to the method described in Example 418 by substituting 2-methylboronic acid for phenylboronic acid. MS (ESI(+) Q1MS m/z 456 (M+H)+; ¹H NMR (300 MHz, DMSO) δ ppm 8.92 (m, 1H), 8.69 (d, 1H), 8.54 (m, 1H), 7.94 (m, 1H), 7.80 (dd, 1H), 7.71–7.83 (m, 3H), 7.21–7.26 (m, 1H), 6.93–7.01 (m, 1H), 6.62 (dd, 1H), 6.48 (s, 1H), 6.40 (s, 1H), 6.32 (s, 1H), 3.7 (m, 1H), 3.54 (d, 1H), 2.29 (s, 3H), 2.25(s, 3H), 1.66–1.99 (m, 8H).

EXAMPLE 350

3-(5-acetylthien-2-yl)-N-{4-((7-chloroquinolin-4-yl) amino)cyclohexyl}-5-fluorobenzamide To a solution of 5-acetyl-2-thiophene boronic acid (7.14 mg, 0.042 mmol), Pd(PPh₃)₂Cl₂ (~1 mol %), and cesium carbonate (16.4 mg, 0.05 mmol) in dimethoxyethane/water/ethanol (7/3/2) was added 3-bromo-N-{4-((7-chloroquinolin-4-yl)amino)cyclohexyl}-5-fluorobenzamide (20 mg, 0.042 mmol). The solution was heated in the microwave at 160° C. for 5 minutes, concentrated, and purified by high throughput HPLC to provide the desired compound as its trifluoroacetic acid salt. MS (ESI(+)Q1MS m/z 522 (M+H)+; ¹H NMR (300 MHz, DMSO) δ ppm 8.84 (d, 1H), 8.73 (d, 1H), 8.57 (d, 1H), 8.39 (s, 1H), 8.05 (s, 1H), 8.01 (d, 1H), 7.95 (d, 1H), 7.87 (dt, 1H), 7.82 (d, 1H), 7.80 (d, 1H), 7.74 (d, 1H), 4.03 (m, 2H), 2.57 (s, 3H), 1.96–2.06 (m, 4H), 1.75–1.85 (m, 4H).

EXAMPLE 351

(2R)-N-{4-((7-chloroquinolin-4-yl)amino) cyclohexyl}-2-methoxy-2-phenylacetamide The titled compound was prepared according to the procedure described in Example 344 by substituting (R)-(–)-alpha-methoxyphenylacetic acid for 3-methyl-2-phenyl-pentanoic acid. MS (CI(+)) m/e 424 (M+H)+. ¹H NMR (500 MHz, DMSO) δ ppm 8.79 (d, J=7.2 Hz, 1H), 8.70 (d, J=9.4 Hz, 1H), 8.55 (d, J=7.2 Hz, 1H), 7.94 (d, J=2.2 Hz, 1H), 7.82 (dd, J=9.2, 2.0 Hz, 1H), 7.70 (d, J=6.9 Hz, 1H), 7.37 (m, 5H), 6.98 (d, J=7.2 Hz, 1H), 4.72 (s, 1H), 3.96 (m, 1H), 3.87 (m, 1H), 3.30 (s, 3H), 1.82 (m, 6H), 1.68 (m, 2H).

EXAMPLE 352

N-{4-((7-chloroquinolin-4-yl)amino)cyclohexyl}-2-hydroxy-5-methoxybenzamide

The titled compound was prepared according to the methods described in Example 23, substituting 5-methoxysalicylic acid for indole-6-carboxylic acid. MS (ESI(+)Q1MS m/z 426 (M+H)+); ¹H NMR (500 MHz, DMSO-D6) δ ppm 1.75–2.01 (m, 8H) 3.74 (s, 3 H) 3.94–3.97 (m, 1H) 4.05–4.13 (m, 1H) 6.88 (d, J=9.05 Hz, 1H) 6.94 (d, J=7.49 Hz, 1 H) 7.03 (dd, J=8.89, 2.96 Hz, 1H) 7.49 (d, J=3.12 Hz, 1H) 7.76 (d, J=8.73 Hz, 1H) 7.90 (d, J=1.87 Hz, 1H) 8.55 (m, 2H) 8.66 (d, J=9.05 Hz, 1H) 11.60 (s, 1H).

EXAMPLE 353

(2S)-N-{4-((7-chloroquinolin-4-yl)amino) cyclohexyl}-2-methoxy-2-phenylacetamide The titled compound was prepared according to the procedure described in Example 344 by substituting (S)-(+)-alpha-methoxyphenylacetic acid for 3-methyl-2-phenyl-pentanoic acid. MS (CI(+)) m/e 424 (M+H)+. ¹H NMR (500 MHz, DMSO) δ ppm 8.79 (d, J=7.2 Hz, 1H), 8.70 (d, J=9.4 Hz, 1H), 8.55 (d, J=7.2 Hz, 1H), 7.94 (d, J=2.2 Hz, 1H), 7.82 (dd, J=9.2, 2.0 Hz, 1H), 7.70 (d, J=6.9 Hz, 1H), 7.37 (m, 5H), 6.98 (d, J=7.2 Hz, 1H), 4.72 (s, 1H), 3.96 (m, 1H), 3.87 (m, 1H), 3.30 (s, 3H), 1.82 (m, 6 H), 1.68 (m, 2H).

EXAMPLE 354

4-chloro-N-{4-((7-chloroquinolin-4-yl)amino) cyclohexyl}-2-hydroxybenzamide

The titled compound was prepared according to the methods described in Example 23, substituting 4-chlorosalicylic acid for indole-6-carboxylic acid. MS (ESI (+)Q1MS m/z 430 (M+H)+); ¹H NMR (500 MHz, DMSO-D6) δ ppm 1.75–2.00 (m, 8H) 3.98–4.01 (m, 1 H) 4.07 (m, 1H) 6.97–7.01 (m, 3H) 7.78 (dd, J=9.20, 2.03 Hz, 1H) 7.93

(d, J=1.87 Hz, 1 H) 7.98 (d, J=8.42 Hz, 1H) 8.52 (d, J=6.24 Hz, 1H) 8.55 (d, J=7.18 Hz, 1H) 8.69 (d, J=9.05 Hz, 1H) 8.79 (d, J=6.86 Hz, 1H).

EXAMPLE 355

N-{4-((7-chloroquinolin-4-yl)amino)cyclohexyl}quinoline-3-carboxamide

The titled compound was prepared according to the methods described in Example 23, substituting quinoline-3-carboxylic acid for indole-6-carboxylic acid. MS (ESI(+) Q1MS m/z m/z 431 (M+H)$^+$); $^1$H NMR (500 MHz, DMSO-D6) δ ppm 1.78–2.08 (m, 8H) 4.01–4.11 (m, 2H) 7.02 (d, J=7.18 Hz, 1H) 7.71 (t, J=8.11 Hz, 1H) 7.82 (dd, J=9.05, 2.18 Hz, 1H) 7.88 (m, 1H) 7.93 (d, J=2.18 Hz, 1H) 8.10 (d, J=9.36 Hz, 2H) 8.54 (dd, J=31.35, 6.40 Hz, 2H) 8.73 (d, J=9.05 Hz, 1H) 8.86 (m, 2H) 9.31 (d, J=2.18 Hz, 1H).

EXAMPLE 356

N-{4-((7-chloroquinolin-4-yl)amino)cyclohexyl}-2-hydroxy-3-methylbenzamide

The titled compound was prepared according to the methods described in Example 23, substituting 3-methylsalicylic acid for indole-6-carboxylic acid. MS (ESI(+)Q1MS m/z 410 (M+H)$^+$); $^1$H NMR (500 MHz, DMSO-D6) δ ppm 1.73–2.06 (m, 8H) 2.15 (s, 3 H) 3.95–4.11 (m, 2H) 6.79 (t, J=7.64 Hz, 1H) 6.98 (d, J=7.49 Hz, 1H) 7.30 (d, J=7.49 Hz, 1H) 7.80 (m, 2H) 7.92 (d, J=1.87 Hz, 1H) 8.41 (d, J=5.93 Hz, 1H) 8.55 (d, J=7.18 Hz, 1 H) 8.70 (d, J=9.05 Hz, 1 H) 8.75 (d, J=6.24 Hz, 1 H).

EXAMPLE 357

N-{4-((7-chloroquinolin-4-yl)amino)cyclohexyl}-2,6-dimethoxynicotinamide

The titled compound was prepared according to the methods described in Example 23, substituting 2,6-dimethoxynicotinic acid for indole-6-carboxylic acid. MS (ESI(+)Q1MS m/z 441 (M+H)$^+$); $^1$H NMR (500 MHz, DMSO-D6) δ ppm 1.74–2.01(s, 8H) 3.94 (s, 3 H) 3.94 (m, 2 H) 4.10 (s, 3 H) 6.54 (d, J=8.11 Hz, 1 H) 7.02 (d, J=7.49 Hz, 1 H) 7.82 (dd, J=9.05, 2.18 Hz, 1H) 7.93 (d, J=1.87 Hz, 1 H) 7.97 (d, J=6.55 Hz, 1 H) 8.20 (d, J=8.11 Hz, 1 H) 8.56 (d, J=7.18 Hz, 1 H) 8.71 (d, J=9.05 Hz, 1 H) 8.84 (d, J=6.86 Hz, 1 H) 13.71 (s, 1 H).

EXAMPLE 358

N-{4-((7-chloroquinolin-4-yl)amino)cyclohexyl}-4-methylpentanamide

The titled compound was prepared according to the procedure described in Example 344 by substituting 4-methylpentanoic acid for 3-methyl-2-phenyl-pentanoic acid. MS (CI(+)) m/e 374 (M+H)$^+$. $^1$H NMR (500 MHz, DMSO) δ ppm 8.89 (d, J=6.9 Hz, 1 H), 8.73 (d, J=9.4 Hz, 1 H), 8.54 (d, J=7.2 Hz, 1 H), 7.95 (d, J=1.9 Hz, 1 H), 7.79 (dd, J=9.2, 2.0 Hz, 1 H), 7.69 (d, J=6.2 Hz, 1 H), 6.97 (d, J=7.2 Hz, 1 H), 3.91 (m, 1 H), 3.80 (m, 1 H), 2.13 (t, J=7.8 Hz, 2 H), 1.84 (m, 6 H), 1.65 (m, 2 H), 1.51 (m, 1 H), 1.42 (m, 2 H), 0.87 (d, J=6.6 Hz, 6 H).

EXAMPLE 359

N-(2-({4-((7-chloroquinolin-4-yl)amino)cyclohexyl}amino)-2-oxo-1-ethyl)-2-hydroxybenzamide The titled compound was prepared according to the procedure described in Example 344 by substituting o-hydroxyhippuric acid for 3-methyl-2-phenyl-pentanoic acid. MS (CI (+)) m/e 453 (M+H)$^+$. $^1$H NMR (500 MHz, DMSO) δ ppm 12.15 (s, 1 H), 9.00 (t, J=5.6 Hz, 1 H), 8.87 (d, J=7.2 Hz, 1 H), 8.73 (d, J=9.0 Hz, 1 H), 8.55 (d, J=6.9 Hz, 1 H), 7.95 (d, J=5.6 Hz, 1 H), 7.93 (d, J=1.9 Hz, 1 H), 7.88 (dd, J=7.8, 1.6 Hz, 1 H), 7.81 (dd, J=9.2, 2.0 Hz, 1 H), 7.40 (m, 1 H), 6.98 (d, J=7.5 Hz, 1 H), 6.91 (m, 2 H), 3.98 (d, J=5.3 Hz, 2 H), 3.92 (m, 1 H), 3.84 (m, 1 H), 1.85 (m, 6 H), 1.70 (m, 2 H).

EXAMPLE 360

3-chloro-N-{4-((7-chloroquinolin-4-yl)amino)cyclohexyl}-5-fluorobenzamide

A mixture of Example 23A (15 mg, 0.055 mmol), 3-chloro-5-fluorobenzoic acid (14 mg, 0.083 mmol), solid supported dicyclohexanecarbodiimide(0.110 mmol), 1-hydroxy-7-azabenzotriazole (11.3 mg, 0.094 mmol) 2.5 ml dimethylacetamide/dichloromethane (2/3) was shaken for 2 hours, and filtered. The filtrate was the concentrated and the residue was purified by HPLC to provide the desired compound as its trifluoroacetic acid salt. MS (ESI(+)Q1MS m/z 432 (M+H)$^+$; $^1$H NMR (300 MHz, DMSO) δ ppm 8.84 (d, 1H), 8.71 (d, 1 H), 8.56 (d, 1H), 8.35 (d, 1H), 7.95 (d, 1H), 7.83 (m, 1 H), 7.81 (dd, 1H), 7.69 (m, 1H), 7.65 (dt, 1H), 7.00 (d, 1H), 3.99 (m, 2H), 1.98–2.03 (m, 4H), 1.73–1.83 (m, 4H).

EXAMPLE 361

N-{4-((7-chloroquinolin-4-yl)amino)cyclohexyl}pentanamide

The titled compound was prepared according to the procedure described in Example 344 by substituting valeric acid for 3-methyl-2-phenyl-pentanoic acid. MS (CI(+)) m/e 360 (M+H)$^+$. $^1$H NMR (500 MHz, DMSO) δ ppm 8.88 (d, J=7.2 Hz, 1 H), 8.73 (d, J=9.0 Hz, 1 H), 8.54 (d, J=7.2 Hz, 1 H), 7.95 (d, J=1.9 Hz, 1 H), 7.79 (dd, J=9.0, 2.2 Hz, 1 H), 7.67 (d, J=5.9 Hz, 1 H), 6.97 (d, J=7.5 Hz, 1 H), 3.91 (m, 1 H), 3.81 (m, 1 H), 2.13 (t, J=7.3 Hz, 2H), 1.82 (m, 6 H), 1.65 (m, 2 H), 1.50 (m, 2 H), 1.29 (m, 2 H), 0.88 (t, J=7.3 Hz, 3 H).

EXAMPLE 362

3'-amino-N-{4-((7-chloroquinolin-4-yl)amino)cyclohexyl}-5-fluoro-1,1'-biphenyl-3-carboxamide The titled compound was prepared according to the method described in Example 350 by substituting 3-aminobenzeneboronic acid for 5-acetyl-2-thiophene boronic acid. MS ESI(+)Q1MS m/z 522 (M+H)$^+$; $^1$H NMR (300 MHz, DMSO) δ ppm 8.85 (d, 1 H), 8.73 (d, 1 H), 8.57 (d, 1 H), 8.34 (s, 1H), 7.97 (d, 1H), 7.95 (m, 1 H), 7.80 (dd, 1H), 7.70 (d, 1 H), 7.59 (d, 1H), 7.31 (t, 1H), 7.20 (m, 2H), 7.00 (d, 1H), 6.91 (d, 1H), 4.03 (m, 2H), 3.97 (s, 1H), 3.17 (s, 1H), 1.97–2.05 (m, 4H), 1.75–1.84 (m, 4H).

EXAMPLE 363

N-2-acetyl-N-1-{4-((7-chloroquinolin-4-yl)amino)cyclohexyl}-L-leucinamide

The titled compound was prepared according to the procedure described in Example 344 by substituting N-acetyl-1-leucine for 3-methyl-2-phenyl-pentanoic acid. MS (CI(+)) m/e 431 (M+H)$^+$. $^1$H NMR (500 MHz, DMSO) δ ppm 8.87 (d, J=6.9 Hz, 1 H), 8.75 (d, J=9.0 Hz, 1 H), 8.55

(d, J=7.2 Hz, 1 H), 7.93 (m, 2 H), 7.86 (d, J=6.2 Hz, 1 H), 7.80 (dd, J=9.2, 2.0 Hz, 1 H), 6.96 (d, J=7.5 Hz, 1 H), 4.39 (m, 1 H), 3.89 (m, 1 H), 3.79 (m, 1 H), 1.84 (m, 9 H), 1.63 (m, 3 H), 1.43 (m, 2 H), 0.88 (dd, J=18.1, 6.6 Hz, 6 H).

EXAMPLE 364

N-{4-((7-chloroquinolin-4-yl)amino)cyclohexyl}-2-(3,5-difluorophenyl)acetamide

The titled compound was prepared according to the procedure described in Example 344 by substituting 3,5-difluorophenylacetic acid for 3-methyl-2-phenyl-pentanoic acid. MS (CI(+)) m/e 430 (M+H)+. $^1$H NMR (500 MHz, DMSO) δ ppm 8.87 (d, J=6.9 Hz, 1 H), 8.73 (d, J=9.0 Hz, 1 H), 8.55 (d, J=7.2 Hz, 1 H), 8.07 (d, J=5.9 Hz, 1 H), 7.93 (d, J=1.9 Hz, 1 H), 7.81 (dd, J=9.2, 2.0 Hz, 1 H), 7.09 (t, J=2.3 Hz, 1 H), 6.98 (m, 3 H), 3.91 (m, 1 H), 3.81 (m, 1 H), 3.53 (s, 2 H), 1.82 (m, 6 H), 1.69 (m, 2 H).

EXAMPLE 365

N-{4-((7-chloroquinolin-4-yl)amino)cyclohexyl}-2-((4-methylpyrimidin-2-yl)thio)acetamide The titled compound was prepared according to the procedure described in Example 344 by substituting 2-(carboxymethylthio)-4-pyrimidine for 3-methyl-2-phenyl-pentanoic acid. MS (CI(+)) m/e 442 (M+H)+. $^1$H NMR (500 MHz, DMSO) δ ppm 8.87 (d, J=6.9 Hz, 1 H), 8.72 (d, J=9.0 Hz, 1 H), 8.54 (d, J=7.2 Hz, 1 H), 8.47 (d, J=5.0 Hz, 1 H), 8.05 (d, J=6.2 Hz, 1 H), 7.94 (d, J=2.2 Hz, 1 H), 7.80 (dd, J=9.0, 2.2 Hz, 1 H), 7.10 (d, J=5.3 Hz, 1 H), 6.98 (d, J=7.5 Hz, 1 H), 3.91 (m, 3 H), 3.84 (m, 1 H), 2.40 (s, 3 H), 1.83 (m, 6 H), 1.68 (m, 2H).

EXAMPLE 366

N-{4-((7-chloroquinolin-4-yl)amino)cyclohexyl}-5-fluoro-3'-hydroxy-1,1'-biphenyl-3-carboxamide The titled compound was prepared according to the method described in Example 350 by substituting 3-(4,4,5,5-Tetramethyl-1,3,2-dioxaborolan-2-yl)phenol for 5-acetyl-2-thiophene boronic acid. MS ESI(+)Q1MS m/z 490 (M+H)+; $^1$H NMR (300 MHz, DMSO)δ ppm 9.80 (s, 1H), 8.85 (d, 1 H), 8.72 (d, 1 H), 8.56 (d, 1 H), 8.27 (d, 1H), 7.98 (d, 1H), 7.89 (m, 1 H), 7.78 (dd, 1H), 7.63 (d, 1 H), 7.55 (d, 1H), 7.38 (dd, 1H), 7.23 (t, 1H), 6.69–7.01 (m, 2H), 6.92 (t, 1H), 3.99–4.04 (m, 2H), 1.96–2.05 (m, 4H), 1.74–1.83 (m, 4H).

EXAMPLE 367

N-{4-((7-chloroquinolin-4-yl)amino)cyclohexyl}-5-fluoro-3'-(hydroxymethyl)-1,1'-biphenyl-3-carboxamide The titled compound was prepared according to the method described in Example 350 by substituting 3-hydroxymethylbenzeneboronic acid for 5-acetyl-2-thiophene boronic acid. MS ESI(+)Q1MS m/z 504 (M+H)+; $^1$H NMR (300 MHz, DMSO) δ ppm 8.86 (d, 1 H), 8.73 (d, 1 H), 8.57 (d, 1 H), 8.37 (d, 1H), 8.01 (s, 1H), 7.98 (d, 1 H), 7.79 (dd, 1H), 7.60–7.74 (m, 4 H), 7.47 (t, 1H), 7.40 (d, 1H), 7.00(d, 1H), 4.60 (s, 2H), 4.97–4.05 (m, 3H), 1.98–2.07 (m, 4H), 1.75–1.84 (m, 4H).

EXAMPLE 368

3-(2-chlorophenyl)-N-{4-((7-chloroquinolin-4-yl)amino)cyclohexyl}propanamide

The titled compound was prepared according to the procedure described in Example 344 by substituting 3-(2-chlorophenyl)propionic acid for 3-methyl-2-phenyl-pentanoic acid. MS (CI(+)) m/e 442 (M)+. $^1$H NMR (500 MHz, DMSO) δ ppm 8.85 (d, J=6.9 Hz, 1 H), 8.72 (d, J=9.0 Hz, 1 H), 8.54 (d, J=7.2 Hz, 1 H), 7.93 (d, J=2.2 Hz, 1 H), 7.78 (m, 2 H), 7.41 (dd, J=7.6, 1.4 Hz, 1 H), 7.33 (dd, J=7.5, 1.9 Hz, 1 H), 7.25 (m, 2 H), 6.96 (d, J=7.2 Hz, 1 H), 3.89 (m, 1 H), 3.81 (m, 1 H), 2.94 (m, 2 H), 2.46 (t, J=7.6 Hz, 2 H), 1.80 (m, 6 H), 1.65 (m, 2 H).

EXAMPLE 369

N-{4-((7-chloroquinolin-4-yl)amino)cyclohexyl}-5-fluoro-4'-hydroxy-1,1'-biphenyl-3-carboxamide The titled compound was prepared according to the method described in Example 350 by substituting 4-(4,4,5,5-Tetramethyl-1,3,2-dioxaborolan-2-yl)phenol for 5-acetyl-2-thiophene boronic acid. MS ESI(+)Q1MS m/z 490 (M+H)+; $^1$H NMR (300 MHz, DMSO) δ ppm 9.72 (s, 1H), 8.84 (d, 1 H), 8.73 (d, 1 H), 8.57 (d, 1 H), 8.31 (d, 1H), 7.96 (d, 1H), 7.93 (m, 1 H), 7.80 (dd, 1H), 7.57–7.62 (m, 4 H), 7.00 (d, 1H), 6.89 (d, 2H), (m, 2H), 1.96–2.06 (m, 4H), 1.74–1.84 (m, 4H).

EXAMPLE 370

N-(5-bromopyridin-3-yl)-N'-(7-chloroquinolin-4-yl)cyclohexane-1,4-diamine

The titled compound was prepared according to the methods described in Example 140, substituting 3,5-dibromopyridine for 1-bromo-3,5-difluorobenzene. MS (ESI(+)Q1MS m/z 431 and 433 (M+H)+); $^1$H NMR (500 MHz, DMSO-D6) δ ppm 1.64–1.93 (m, 8 H) 3.60 (m, 1 H) 3.98 (m, 1 H) 7.01 (d, J=7.49 Hz, 1 H) 7.19 (t, J=2.34 Hz, 1 H) 7.81 (m, 2 H) 7.92 (d, J=2.18 Hz, 1 H) 8.03 (d, J=2.50 Hz, 1 H) 8.55 (d, J=7.18 Hz, 1 H) 8.71 (d, J=9.36 Hz, 1 H) 8.89 (d, J=7.49 Hz, 1H).

EXAMPLE 371

N-{4-((7-chloroquinolin-4-yl)amino)cyclohexyl}-1H-indole-4-carboxamide

The titled compound was prepared according to the methods described in Example 23, substituting indole-4-carboxylic acid for indole-6-carboxylic acid. MS (ESI(+) Q1MS m/z 419 (M+H)+); $^1$H NMR (500 MHz, DMSO-D6) δ ppm 1.92 (m, 8 H) 4.00 (m, 1 H) 4.11 (m, 1 H) 6.82 (d, J=2.18 Hz, 1 H) 7.01 (d, J=7.49 Hz, 1 H) 7.15 (m, 1 H) 7.45 (m, 2 H) 7.55 (d, J=8.11 Hz, 1 H) 7.80 (m, 2 H) 7.94 (d, J=2.18 Hz, 1 H) 8.56 (d, J=7.17 Hz, 1 H) 8.71 (d, J=9.05 Hz, 1 H) 8.84 (d, J=7.17 Hz, 1 H).

EXAMPLE 372

N-{4-((7-chloroquinolin-4-yl)amino)cyclohexyl}hexanamide

The titled compound was prepared according to the procedure described in Example 344 by substituting hexanoic acid for 3-methyl-2-phenyl-pentanoic acid. MS (CI (+)) m/e 374 (M+H)+. $^1$H NMR (500 MHz, DMSO) δ ppm 8.88 (d, J=6.9 Hz, 1 H), 8.73 (d, J=9.4 Hz, 1 H), 8.54 (d, J=7.2 Hz, 1 H), 7.95 (d, J=2.2 Hz, 1 H), 7.79 (dd, J=9.0, 2.2 Hz, 1 H), 7.66 (d, J=6.2 Hz, 1 H), 6.97 (d, J=7.2 Hz, 1 H), 3.91 (m, 1 H), 3.80 (m, 1 H), 2.12 (t, J=7.3 Hz, 2 H), 1.81 (m, 6 H), 1.65 (m, 2 H), 1.51 (m, 2 H), 1.27 (m, 4 H), 0.86 (t, J=7.0 Hz, 3H).

EXAMPLE 373

N-{4-((7-chloroquinolin-4-yl)amino)cyclohexyl}cyclopentanecarboxamide

The titled compound was prepared according to the procedure described in Example 344 by substituting cyclopentanecarboxylic acid for 3-methyl-2-phenyl-pentanoic acid. MS (CI(+)) m/e 372 (M+H)+. ¹H NMR (500 MHz, DMSO) δ ppm 8.85 (d, J=7.2 Hz, 1 H), 8.72 (d, J=9.0 Hz, 1 H), 8.54 (d, J=7.2 Hz, 1 H), 7.93 (d, J=1.9 Hz, 1 H), 7.80 (dd, J=9.0, 2.2 Hz, 1 H), 7.60 (d, J=5.9 Hz, 1 H), 6.97 (d, J=7.5 Hz, 1 H), 3.91 (m, 1 H), 3.77 (m, 1H), 2.66 (m, 1 H), 1.84 (m, 3 H), 1.76 (m, 3 H), 1.64 (m, 4 H), 1.50 (m, 1H).

EXAMPLE 374

N-{4-((7-chloroquinolin-4-yl)amino)cyclohexyl}-2-(3-methoxyphenoxy)acetamide

The titled compound was prepared according to the procedure described in Example 344 by substituting 3-methoxyphenoxyacetic acid for 3-methyl-2-phenyl-pentanoic acid. MS (CI(+)) m/e 440 (M+H)+. ¹H NMR (500 MHz, DMSO) δ ppm 8.82 (d, J=7.2 Hz, 1 H), 8.71 (d, J=9.0 Hz, 1 H), 8.56 (d, J=6.9 Hz, 1 H), 7.94 (d, J=2.2 Hz, 1 H), 7.80 (m, 2 H), 7.19 (m, 1 H), 6.98 (d, J=7.2 Hz, 1 H), 6.56 (m, 1 H), 6.54 (m, 2 H), 4.51 (s, 2 H), 3.96 (m, 1 H), 3.91 (m, 1 H), 3.73 (s, 3 H), 1.83 (m, 6 H), 1.70 (m, 2 H).

EXAMPLE 375

N-1-{4-((7-chloroquinolin-4-yl)amino)cyclohexyl}-N-2-((4-methylphenyl)sulfonyl)glycinamide The titled compound was prepared according to the procedure described in Example 344 by substituting N-p-tosylglycine for 3-methyl-2-phenyl-pentanoic acid. MS (CI(+)) m/e 487 (M)+. ¹H NMR (500 MHz, DMSO) δ ppm 8.85 (d, J=6.9 Hz, 1 H), 8.72 (d, J=9.0 Hz, 1 H), 8.54 (d, J=7.2 Hz, 1 H), 7.93 (d, J=1.9 Hz, 1 H), 7.80 (m, 2 H), 7.68 (m, 3 H), 7.38 (d, J=7.8 Hz, 2 H), 6.96 (d, J=7.5 Hz, 1 H), 3.88 (m, 1 H), 3.73 (m, 1 H), 2.37 (s, 3 H), 1.76 (m, 6 H), 1.63 (m, 2 H).

EXAMPLE 376

N-{4-((7-chloroquinolin-4-yl)amino)cyclohexyl}quinoxaline-2-carboxamide

The titled compound was prepared according to the methods described in Example 23, substituting quinaxoline-2-carboxylic acid for indole-6-carboxylic acid. MS (ESI(+) Q1MS m/z 432 (M+H)+); ¹H NMR (500 MHz, DMSO-D6) δ ppm 1.82–2.13 (m, 8 H) 4.07 (m, 1 H) 4.19 (m, 1 H) 7.03 (d, J=7.49 Hz, 1 H) 7.81 (dd, J=9.05, 2.18 Hz, 1 H) 7.96 (d, J=2.18 Hz, 1 H) 8.01 (m, 2 H) 8.23 (m, 2 H) 8.55 (d, J=6.86 Hz, 1 H) 8.58 (d, J=7.18 Hz, 1 H) 8.71 (d, J=9.05 Hz, 1 H) 8.85 (d, J=7.17 Hz, 1 H).

EXAMPLE 377

N-{4-((7-chloroquinolin-4-yl)amino)cyclohexyl}-2-(3-methylphenoxy)acetamide

The titled compound was prepared according to the procedure described in Example 344 by substituting 3-methylphenoxyacetic acid for 3-methyl-2-phenyl-pentanoic acid. MS (CI(+)) m/e 424 (M+H)+. ¹H NMR (500 MHz, DMSO) δ ppm 8.81 (d, J=6.9 Hz, 1 H), 8.71 (d, J=9.4 Hz, 1 H), 8.55 (d, J=7.2 Hz, 1 H), 7.93 (d, J=2.2 Hz, 1 H), 7.81 (dd, J=9.0, 2.2 Hz, 1 H), 7.77 (d, J=6.2 Hz, 1 H), 7.18 (t, J=7.8 Hz, 1 H), 6.98 (d, J=7.2 Hz, 1 H), 6.78 (m, 3 H), 4.50 (s, 2 H), 3.93 (m, 2 H), 2.27 (s, 3 H), 1.84 (m, 6 H), 1.70 (m, 2 H).

EXAMPLE 378

N-{4-((7-chloroquinolin-4-yl)amino)cyclohexyl}-2-cyclopentylacetamide

The titled compound was prepared according to the procedure described in Example 344 by substituting cyclopentylacetic acid for 3-methyl-2-phenyl-pentanoic acid. MS (CI(+)) m/e 386 (M+H)+. ¹H NMR (500 MHz, DMSO) δ ppm 8.88 (d, J=7.2 Hz, 1 H), 8.74 (d, J=9.0 Hz, 1 H), 8.54 (d, J=7.2 Hz, 1 H), 7.95 (d, J=1.9 Hz, 1 H), 7.79 (dd, J=9.0, 2.2 Hz, 1 H), 7.66 (d, J=6.2 Hz, 1 H), 6.97 (d, J=7.2 Hz, 1 H), 3.89 (m, 1 H), 3.81 (m, 1 H), 2.13 (m, 3 H), 1.68 (m, 14 H), 1.15 (m, 2 H).

EXAMPLE 379

(2S)—N-{4-((7-chloroquinolin-4-yl)amino)cyclohexyl}-2-phenylbutanamide

The titled compound was prepared according to the procedure described in Example 344 by substituting (S)-(+)-2-phenylbutyric acid for 3-methyl-2-phenyl-pentanoic acid. MS (CI(+)) m/e 422 (M+H)+. ¹H NMR (500 MHz, DMSO) δ ppm 8.86 (d, J=6.9 Hz, 1 H), 8.73 (d, J=9.4 Hz, 1 H), 8.54 (d, J=7.2 Hz, 1 H), 7.93 (d, J=2.2 Hz, 2 H), 7.79 (dd, J=9.0, 2.2 Hz, 1 H), 7.35 (d, J=7.2 Hz, 2 H), 7.29 (t, J=7.6 Hz, 2 H), 7.20 (t, J=7.3 Hz, 1 H), 6.96 (d, J=7.5 Hz, 1 H), 3.88 (m, 1 H), 3.79 (m, 1 H), 3.48 (dd, J=9.0, 6.2 Hz, 2 H), 1.79 (m, 9 H), 0.84 (t, J=7.3 Hz, 3 H).

EXAMPLE 380

N-{4-((7-chloroquinolin-4-yl)amino)cyclohexyl}-2-methylcyclohexanecarboxamide

The titled compound was prepared according to the procedure described in Example 344 by substituting 2-methyl-1-cyclohexanecarboxylic acid for 3-methyl-2-phenyl-pentanoic acid. MS (CI(+)) m/e 400 (M+H)+. ¹H NMR (500 MHz, DMSO) δ ppm 8.86 (d, J=7.2 Hz, 1 H), 8.73 (d, J=9.0 Hz, 1 H), 8.54 (d, J=7.2 Hz, 1 H), 7.95 (d, J=2.2 Hz, 1 H), 7.79 (dd, J=9.0, 2.2 Hz, 1 H), 7.47 (d, J=5.9 Hz, 1 H), 6.97 (d, J=7.5 Hz, 1 H), 3.89 (m, 1 H), 3.81 (m, 1 H), 2.41 (m, 1 H), 2.02 (m, 1 H), 1.72 (m, 11 H), 1.39 (m, 4 H), 1.23 (m, 1 H), 0.85 (d, J=7.2 Hz, 3 H).

EXAMPLE 381

N-{4-((7-chloroquinolin-4-yl)amino)cyclohexyl}-N'-phenylpentanediamide

The titled compound was prepared according to the procedure described in Example 344 by substituting glutaranilic acid for 3-methyl-2-phenyl-pentanoic acid. MS (CI(+)) m/e 465 (M)+. ¹H NMR (500 MHz, DMSO) δ ppm 9.86 (s, 1 H), 8.84 (d, J=7.2 Hz, 1 H), 8.71 (d, J=9.0 Hz, 1 H), 8.54 (d, J=7.2 Hz, 1 H), 7.93 (d, J=2.2 Hz, 1 H), 7.79 (dd, J=9.0, 2.2 Hz, 1 H), 7.71 (d, J=5.9 Hz, 1 H), 7.59 (d, J=7.5 Hz, 2 H), 7.27 (t, J=8.0 Hz, 2 H), 7.01 (t, J=7.5 Hz, 1 H), 6.97 (d, J=7.5 Hz, 1 H), 3.90 (m, 1 H), 3.80 (m, 1 H), 2.33 (t, J=7.3 Hz, 2 H), 2.19 (t, J=7.5 Hz, 2 H), 1.82 (m, 8 H), 1.65 (m, 2 H).

EXAMPLE 382

N-{4-((7-chloroquinolin-4-yl)amino)cyclohexyl}-3-phenylpropanamide

The titled compound was prepared according to the procedure described in Example 344 by substituting hydrocinnamic acid for 3-methyl-2-phenyl-pentanoic acid. MS (CI(+)) m/e 408 (M+H)+. ¹H NMR (500 MHz, DMSO) δ ppm 8.85 (d, J=6.9 Hz, 1 H), 8.72 (d, J=9.0 Hz, 1 H), 8.54 (d, J=7.2 Hz, 1 H), 7.93 (d, J=2.2 Hz, 1 H), 7.79 (dd, J=9.2, 2.0 Hz, 1 H), 7.72 (d, J=5.9 Hz, 1 H), 7.27 (t, J=7.5 Hz, 2 H), 7.21 (d, J=6.9 Hz, 2 H), 7.17 (t, J=7.2 Hz, 1 H), 6.96 (d, J=7.2 Hz, 1 H), 3.90 (m, 1 H), 3.81 (m, 1 H), 2.83 (t, J=7.8 Hz, 2 H), 2.44 (t, J=7.8 Hz, 2 H), 1.79 (m, 6 H), 1.64 (m, 2 H).

EXAMPLE 383

3-(4-chlorophenyl)-N-{4-((7-chloroquinolin-4-yl)amino)cyclohexyl}propanamide

The titled compound was prepared according to the procedure described in Example 344 by substituting 3-(4-chlorophenyl)propionic acid for 3-methyl-2-phenyl-pentanoic acid. MS (CI(+)) m/e 442 (M)$^+$. $^1$H NMR (500 MHz, DMSO) δ ppm 8.84 (d, J=6.9 Hz, 1 H), 8.72 (d, J=9.0 Hz, 1 H), 8.54 (d, J=7.2 Hz, 1 H), 7.93 (d, J=2.2 Hz, 1 H), 7.80 (dd, J=9.0, 2.2 Hz, 1 H), 7.72 (d, J=5.9 Hz, 1 H), 7.32 (d, J=8.4 Hz, 2 H), 7.24 (d, J=8.4 Hz, 2 H), 6.96 (d, J=7.2 Hz, 1 H), 3.89 (m, 1 H), 3.79 (m, 1 H), 2.83 (t, J=7.6 Hz, 2 H), 2.43 (t, J=7.6 Hz, 2 H), 1.77 (m, 6 H), 1.64 (m, 2 H).

EXAMPLE 384

4'-amino-N-{4-((7-chloroquinolin-4-yl)amino)cyclohexyl}-5-fluoro-1,1'-biphenyl-3-carboxamide The titled compound was prepared according to the method described in Example 350 by substituting 4-(4,4,5,5-Tetramethyl-1,3,2-dioxaborolan-2-yl)aniline for 5-acetyl-2-thiophene boronic acid. MS ESI(+)Q1MS m/z 489 (M+H)$^+$; $^1$H NMR (300 MHz, DMSO) δ ppm 8.85 (d, 1 H), 8.74 (d, 1 H), 8.57 (d, 1 H), 8.32 (d, 1H), 7.97 (d, 1H), 7.94 (m, 1 H), 7.79 (dd, 1H), 7.57–7.63 (m, 4 H), 7.00 (d, 1H), 6.93 (d, 2H), 4.02(m, 2H), 3.97 (s, 1H), 3.18 (s, 1H), 1.99–2.06 (m, 4H), 1.75–1.85 (m, 4H).

EXAMPLE 385

N-{4-((7-chloroquinolin-4-yl)amino)cyclohexyl}cycloheptanecarboxamide

The titled compound was prepared according to the procedure described in Example 344 by substituting cycloheptanecarboxylic acid for 3-methyl-2-phenyl-pentanoic acid. MS (CI(+)) m/e 400 (M+H)$^+$. $^1$H NMR (500 MHz, DMSO) δ ppm 8.88 (d, J=6.9 Hz, 1 H), 8.73 (d, J=9.0 Hz, 1 H), 8.54 (d, J=7.2 Hz, 1 H), 7.95 (d, J=1.9 Hz, 1 H), 7.79 (dd, J=9.0, 1.9 Hz, 1 H), 7.54 (d, J=6.2 Hz, 1 H), 6.97 (d, J=7.5 Hz, 1 H), 3.89 (m, 3 H), 3.76 (m, 1 H), 2.39 (m, 1 H), 1.70 (m, 18 H).

EXAMPLE 386

N-{4-((7-chloroquinolin-4-yl)amino)cyclohexyl}-4-oxo-4-thien-2-ylbutanamide

The titled compound was prepared according to the procedure described in Example 344 by substituting 3-(2-thenoyl)-propionic acid for 3-methyl-2-phenyl-pentanoic acid. MS (CI(+)) m/e 442 (M+H)$^+$. $^1$H NMR (500 MHz, DMSO) δ ppm 8.88 (d, J=6.9 Hz, 1 H), 8.74 (d, J=9.4 Hz, 1 H), 8.54 (d, J=7.2 Hz, 1 H), 7.97 (m, 2 H), 7.93 (d, J=1.9 Hz, 1 H), 7.80 (dd, J=9.2, 2.0 Hz, 2 H), 7.24 (dd, J=4.8, 3.9 Hz, 1 H), 6.97 (d, J=7.2 Hz, 1 H), 3.90 (m, 1 H), 3.79 (m, 1 H), 3.19 (t, J=6.9 Hz, 2 H), 2.54 (m, 2 H), 1.83 (m, 6 H), 1.65 (m, 2 H).

EXAMPLE 387

N-{4-((7-chloroquinolin-4-yl)amino)cyclohexyl}-3-methylcyclohexanecarboxamide

The titled compound was prepared according to the procedure described in Example 344 by substituting 3-methyl-1-cyclohexanecarboxylic acid for 3-methyl-2-phenyl-pentanoic acid. MS (CI(+)) m/e 400 (M+H)$^+$. $^1$H NMR (500 MHz, DMSO) δ ppm 8.87 (d, J=6.9 Hz, 1 H), 8.72 (d, J=9.0 Hz, 1 H), 8.54 (d, J=7.2 Hz, 1 H), 7.94 (d, J=2.2 Hz, 1 H), 7.79 (dd, J=9.2, 2.0 Hz, 1 H), 7.55 (d, J=6.2 Hz, 1 H), 6.97 (d, J=7.2 Hz, 1 H), 3.90 (m, 1 H), 3.77 (m, 1 H), 2.25 (m, 1 H), 1.75 (m, 11 H), 1.35 (m, 4 H), 1.03 (m, 1 H), 0.88 (d, J=6.6 Hz, 3 H).

EXAMPLE 388

N-{4-((7-chloroquinolin-4-yl)amino)cyclohexyl}-2-hydroxy-4-methoxybenzamide

The titled compound was prepared according to the methods described in Example 23, substituting 2-hydroxy-4-methoxybenzoic acid for indole-6-carboxylic acid. MS (ESI(+)Q1MS m/z 426 (M+H)$^+$); $^1$H NMR (500 MHz, DMSO-D6) δ ppm 1.73–2.02 (m, 8 H) 3.77 (s, 3 H) 3.94–4.08 (m, 2 H) 6.44 (d, J=2.50 Hz, 1 H) 6.49 (dd, J=8.89, 2.34 Hz, 1 H) 6.98 (d, J=6.86 Hz, 1 H) 7.79 (dd, J=9.05, 2.18 Hz, 1 H) 7.92 (m, 2 H) 8.27 (d, J=5.62 Hz, 1 H) 8.55 (d, J=7.18 Hz, 1 H) 8.69 (d, J=9.05 Hz, 1 H) 8.75 (br. s., 1 H).

EXAMPLE 389

N-{4-((7-chloroquinolin-4-yl)amino)cyclohexyl}cinnoline-4-carboxamide

The titled compound was prepared according to the methods described in Example 23, substituting cinnoline-4-carboxylic acid for indole-6-carboxylic acid. MS (ESI(+)Q1MS m/z 432 (M+H)$^+$); $^1$H NMR (500 MHz, DMSO-D6) δ ppm 1.82–2.11 (m, 8 H) 3.98 (m, 1 H) 4.19 (m, 1 H) 7.01 (d, J=7.49 Hz, 1 H) 7.79 (dd, J=9.05, 2.18 Hz, 1 H) 7.93 (d, J=2.18 Hz, 1 H) 7.96–8.05 (m, 2 H) 8.20 (d, J=8.42 Hz, 1 H) 8.57 (m, 2 H) 8.69 (d, J=9.05 Hz, 1 H) 8.86 (dd, J=13.73, 6.55 Hz, 2 H).

EXAMPLE 390

N-{4-((7-chloroquinolin-4-yl)amino)cyclohexyl}-4-methylcyclohexanecarboxamide

The titled compound was prepared according to the procedure described in Example 344 by substituting 4-methyl-1-cyclohexanecarboxylic acid for 3-methyl-2-phenyl-pentanoic acid. MS (CI(+)) m/e 400 (M+H)$^+$. $^1$H NMR (500 MHz, DMSO) δ ppm 8.85 (d, J=7.2 Hz, 1 H), 8.72 (d, J=9.0 Hz, 1 H), 8.54 (d, J=7.2 Hz, 1 H), 7.94 (d, J=1.9 Hz, 1 H), 7.79 (dd, J=9.2, 2.0 Hz, 1 H), 7.48 (d, J=5.9 Hz, 1 H), 6.97 (d, J=7.2 Hz, 1 H), 3.89 (m, 1 H), 3.78 (m, 1 H), 2.30 (m, 1 H), 1.75 (m, 11 H), 1.42 (m, 6 H), 0.91 (d, J=6.9 Hz, 3 H).

EXAMPLE 391

N-{4-((7-chloroquinolin-4-yl)amino)cyclohexyl}-2-(2-methylphenoxy)acetamide

The titled compound was prepared according to the procedure described in Example 344 by substituting (2-methylphenoxy)acetic acid for 3-methyl-2-phenyl-pentanoic acid. MS (CI(+)) m/e 424 (M+H)$^+$. $^1$H NMR (500 MHz, DMSO) δ ppm 8.82 (d, J=6.9 Hz, 1 H), 8.70 (d, J=9.4 Hz, 1 H), 8.56 (d, J=6.9 Hz, 1 H), 7.93 (d, J=2.2 Hz, 1 H), 7.81 (dd, J=9.0, 2.2 Hz, 1 H), 7.72 (d, J=6.6 Hz, 1 H), 7.16 (m, 2 H), 6.99 (d, J=7.2 Hz, 1 H), 6.87 (m, 2 H), 4.54 (s, 2 H), 3.92 (m, 2 H), 2.24 (s, 3 H), 1.83 (m, 6 H), 1.73 (m, 2 H).

EXAMPLE 392

N-{4-((7-chloroquinolin-4-yl)amino)cyclohexyl}-3-methylbutanamide

The titled compound was prepared according to the procedure described in Example 344 by substituting isovaleric acid for 3-methyl-2-phenyl-pentanoic acid. MS (CI(+)) m/e 360 (M+H)[+]. $^1$H NMR (500 MHz, DMSO) δ ppm 8.89 (d, J=6.9 Hz, 1 H), 8.74 (d, J=9.0 Hz, 1 H), 8.54 (d, J=7.2 Hz, 1 H), 7.95 (d, J=2.2 Hz, 1 H), 7.79 (dd, J=9.2, 2.0 Hz, 1 H), 7.67 (d, J=6.2 Hz, 1 H), 6.97 (d, J=7.2 Hz, 1 H), 3.90 (m, 1 H), 3.82 (m, 1 H), 2.01 (m, 3 H), 1.81 (m, 6 H), 1.66 (m, 2 H), 0.89 (d, J=6.6 Hz, 6 H).

EXAMPLE 393

N-{4-((7-chloroquinolin-4-yl)amino)cyclohexyl}cyclohexanecarboxamide

The titled compound was prepared according to the procedure described in Example 344 by substituting cyclohexanecarboxylic acid for 3-methyl-2-phenyl-pentanoic acid. MS (CI(+)) m/e 386 (M+H)[+]. $^1$H NMR (500 MHz, DMSO) δ ppm 8.86 (d, J=6.9 Hz, 1 H), 8.72 (d, J=9.0 Hz, 1 H), 8.54 (d, J=7.2 Hz, 1 H), 7.94 (d, J=2.2 Hz, 1 H), 7.79 (dd, J=9.2, 2.0 Hz, 1 H), 7.53 (d, J=5.9 Hz, 1 H), 6.97 (d, J=7.2 Hz, 1 H), 3.90 (m, 1 H), 3.77 (m, 1 H), 2.22 (m, 1 H), 1.84 (m, 4 H), 1.70 (m, 9 H), 1.36 (m, 2 H), 1.21 (m, 3 H).

EXAMPLE 394

N-{4-((7-chloroquinolin-4-yl)amino)cyclohexyl}-3-(2,5-dimethoxyphenyl)propanamide The titled compound was prepared according to the procedure described in Example 344 by substituting 3-(2,5-dimethoxyphenyl)propionic acid for 3-methyl-2-phenyl-pentanoic acid. MS (CI(+)) m/e 468 (M)[+]. $^1$H NMR (500 MHz, DMSO) δ ppm 8.84 (d, J=7.2 Hz, 1 H), 8.71 (d, J=9.4 Hz, 1 H), 8.54 (d, J=7.2 Hz, 1 H), 7.93 (d, J=2.2 Hz, 1 H), 7.79 (dd, J=9.0, 1.9 Hz, 1 H), 7.69 (d, J=6.2 Hz, 1 H), 6.96 (d, J=7.5 Hz, 1 H), 6.86 (d, J=8.4 Hz, 1 H), 6.73 (m, 2 H), 3.90 (m, 1 H), 3.81 (m, 1 H), 3.73 (s, 3 H), 3.66 (s, 3 H), 2.76 (t, J=7.8 Hz, 2 H), 2.38 (t, J=7.8 Hz, 2 H), 1.81 (m, 6 H), 1.81 (m, 2 H).

EXAMPLE 395

N-{4-((7-chloroquinolin-4-yl)amino)cyclohexyl}-3-methylpentanamide

The titled compound was prepared according to the procedure described in Example 344 by substituting 3-methylpentanioc acid for 3-methyl-2-phenyl-pentanoic acid. MS (CI(+)) m/e 374 (M+H)[+]. $^1$H NMR (500 MHz, DMSO) δ ppm 8.89 (d, J=7.2 Hz, 1 H), 8.74 (d, J=9.4 Hz, 1 H), 8.54 (d, J=7.2 Hz, 1 H), 7.95 (d, J=1.9 Hz, 1 H), 7.79 (dd, J=9.2, 2.0 Hz, 1 H), 7.69 (d, J=6.2 Hz, 1 H), 6.97 (d, J=7.5 Hz, 1 H), 3.90 (m, 1 H), 3.83 (m, 1 H), 2.12 (m, 1 H), 1.95 (m, 1 H), 1.83 (m, 7 H), 1.66 (m, 2 H), 1.32 (m, 1 H), 1.16 (m, 1 H), 0.86 (m, 6 H).

EXAMPLE 396

N-{4-((7-chloroquinolin-4-yl)amino)cyclohexyl}-2-hydroxy-6-methoxybenzamide

The titled compound was prepared according to the methods described in Example 23, substituting 2-hydroxy-6-methoxycarboxylic acid for indole-6-carboxylic acid. MS (ESI(+)Q1MS m/z 426 (M+H)[+]); $^1$H NMR (500 MHz, DMSO-D6) δ ppm 1.72–2.00 (m, 8 H) 3.88 (m, 1 H) 4.00 (s, 3 H) 4.20 (m, 1 H) 6.54 (d, J=8.73 Hz, 1 H) 6.64 (d, J=8.74 Hz, 1 H) 6.94 (m, 1 H) 7.35 (t, J=8.42 Hz, 1 H) 7.75 (m, 1 H) 7.89 (s, 1 H) 8.53 (d, J=7.49 Hz, 1 H) 8.61–8.67 (m, 2 H).

EXAMPLE 397

3'-acetyl-N-{4-((7-chloroquinolin-4-yl)amino)cyclohexyl}-5-fluoro-1,1'-biphenyl-3-carboxamide The titled compound was prepared according to the method described in Example 350 by substituting 3-acetylphenylboronic acid for 5-acetyl-2-thiophene boronic acid. MS ESI(+)Q1MS m/z 516 (M+H)[+]; $^1$H NMR (300 MHz, DMSO) δ ppm 8.85 (d, 1 H), 8.73 (d, 1 H), 8.57 (d, 1 H), 8.37 (d, 1 H), 8.27 (s, 1 H), 8.01–8.06 (m, 3 H), 7.97 (d, 1 H), 7.78–7.83 (m, 2 H), 7.74 (d, 1 H), 7.68 (t, 1 H), 7.01 (d, 1 H), 4.01–4.05 (m, 2 H), 2.68 (s, 3 H), 1.98–2.07 (m, 4 H), 1.76–1.85 (m, 4 H).

EXAMPLE 398

N-{4-((7-chloroquinolin-4-yl)amino)cyclohexyl}-4,4,4-trifluorobutanamide

The titled compound was prepared according to the procedure described in Example 344 by substituting 4,4,4-trifluorobutyric acid for 3-methyl-2-phenyl-pentanoic acid. MS (CI(+)) m/e 400 (M+H)[+]. $^1$H NMR (500 MHz, DMSO) δ ppm 8.90 (d, J=7.2 Hz, 1 H), 8.73 (d, J=9.0 Hz, 1 H), 8.54 (d, J=7.2 Hz, 1 H), 7.95 (d, J=1.9 Hz, 2 H), 7.79 (dd, J=9.2, 2.0 Hz, 1 H), 6.98 (d, J=7.5 Hz, 1 H), 3.90 (m, 1 H), 3.82 (m, 1 H), 2.44 (m, 4 H), 1.84 (m, 6 H), 1.67 (m, 2 H).

EXAMPLE 399

5-bromo-N-{4-((7-chloroquinolin-4-yl)amino)cyclohexyl}-2-hydroxy-3-methylbenzamide The titled compound was prepared according to the methods described in Example 23, substituting 5-bromo2-hydroxy-3-methylcarboxylic acid for indole-6-carboxylic acid. MS (ESI(+)Q1MS m/z 488 and 490 (M+H)[+]); $^1$H NMR (500 MHz, DMSO-D6) δ ppm 1.74–2.04 (m, 8 H) 2.16 (s, 3 H) 3.97–4.04 (m, 2 H) 6.97 (d, J=7.17 Hz, 1 H) 7.51 (d, J=1.56 Hz, 1 H) 7.79 (dd, J=9.20, 2.03 Hz, 1 H) 7.92 (d, J=1.87 Hz, 1 H) 8.10 (d, J=2.18 Hz, 1 H) 8.55–8.59 (m, 2 H) 8.70 (d, J=9.05 Hz, 2 H).

EXAMPLE 400

N-{4-((7-chloroquinolin-4-yl)amino)cyclohexyl}-3-(phenylsulfonyl)propanamide

The titled compound was prepared according to the procedure described in Example 344 by substituting 3-(phenylsulfonyl)propionic acid for 3-methyl-2-phenyl-pentanoic acid. MS (CI(+)) m/e 472 (M)[+]. $^1$H NMR (500 MHz, DMSO) δ ppm 8.85 (d, J=7.2 Hz, 1 H), 8.71 (d, J=9.0 Hz, 1 H), 8.54 (d, J=7.2 Hz, 1 H), 7.91 (m, 4 H), 7.78 (m, 2 H), 7.67 (m, 2H), 6.96 (d, J=7.2 Hz, 1 H), 3.87 (m, 1 H), 3.71 (m, 1 H), 3.51 (t, J=7.6 Hz, 4 H), 1.76 (m, 6 H), 1.62 (m, 2 H).

EXAMPLE 401

N-(7-chloroquinolin-4-yl)-N'-(4-methoxy-3,5-dimethylphenyl)cyclohexane-1,4-diamine The titled compound was prepared according to the methods described in Example 140, substituting 1-bromo- 4-methoxy-3,5-dimethylbenzene for 1-bromo-3,5-difluorobenzene. MS (ESI(+)Q1MS m/z 410 (M+H)$^+$); $^1$H NMR (300 MHz, DMSO-D6) δ ppm 1.72–2.00 (m, 8 H) 2.15 (s, 6 H) 2.18 (s, 3 H) 6.32–6.52 (m, 2 H) 6.99 (d, J=7.46 Hz, 1 H) 7.79–7.95 (m, 3 H) 8.56 (d, J=6.78 Hz, 1 H) 8.72 (d, J=9.16 Hz, 1 H) 8.85 (d, J=9.83 Hz, 1 H).

EXAMPLE 402

N-{4-((7-chloroquinolin-4-yl)amino)cyclohexyl}-3-phenoxypropanamide

The titled compound was prepared according to the procedure described in Example 344 by substituting 3-phenoxypropionic acid for 3-methyl-2-phenyl-pentanoic acid. MS (CI(+)) m/e 424 (M+H)$^+$. $^1$H NMR (500 MHz, DMSO) δ ppm 8.89 (d, J=6.9 Hz, 1 H), 8.73 (d, J=9.0 Hz, 1 H), 8.55 (d, J=7.2 Hz, 1 H), 7.94 (d, J=2.2 Hz, 1 H), 7.89 (d, J=5.9 Hz, 1 H), 7.80 (dd, J=9.0, 2.2 Hz, 1 H), 7.27 (t, J=8.1 Hz, 2 H), 6.98 (d, J=7.5 Hz, 1 H), 6.92 (m, 3 H), 4.19 (t, J=6.2 Hz, 2 H), 3.91 (m, 1 H), 3.84 (m, 1 H), 2.61 (t, J=6.2 Hz, 2 H), 1.84 (m, 6 H), 1.68 (m, 2 H).

EXAMPLE 403

N-{4-((7-chloroquinolin-4-yl)amino)cyclohexyl}-4-thien-2-ylbutanamide

The titled compound was prepared according to the procedure described in Example 344 by substituting 4-(2-thienyl)butyric acid for 3-methyl-2-phenyl-pentanoic acid. MS (CI(+)) m/e 428 (M)$^+$. $^1$H NMR (500 MHz, DMSO) δ ppm 8.85 (d, J=7.2 Hz, 1 H), 8.72 (d, J=9.4 Hz, 1 H), 8.54 (d, J=7.2 Hz, 1 H), 7.93 (d, J=2.2 Hz, 1 H), 7.79 (dd, J=9.2, 2.0 Hz, 1 H), 7.72 (d, J=5.9 Hz, 1 H), 7.31 (dd, J=5.0, 0.9 Hz, 1 H), 6.97 (d, J=7.5 Hz, 1 H), 6.94 (dd, J=5.0, 3.4 Hz, 1 H), 6.85 (d, J=3.4 Hz, 1 H), 3.91 (m, 1 H), 3.80 (m, 1 H), 2.80 (t, J=7.6 Hz, 2 H), 2.20 (t, J=7.5 Hz, 2 H), 1.82 (m, 8 H), 1.65 (m, 2 H).

EXAMPLE 404

3-(1,3-benzodioxol-5-yl)-N-{4-((7-chloroquinolin-4-yl)amino)cyclohexyl}-5-fluorobenzamide The titled compound was prepared according to the method described in Example 350 by substituting 3, 4 methylenedioxylbenzeneboronic acid for 5-acetyl-2-thiophene boronic acid. MS ESI(+)Q1MS m/z 516 (M+H)$^+$; $^1$H NMR (300 MHz, DMSO) δ ppm 8.83 (d, 1 H), 8.72 (d, 1 H), 8.57 (d, 1 H), 8.31 (d, 1 H), 7.95 (m, 2 H), 7.80 (dd, 1 H), 7.60–7.66 (m, 2 H), 7.41 (d, 1 H), 7.29 (dd, 1 H), 7.05 (d, 1 H), 7.00 (d, 1 H), 6.09 (s, 2 H), 4.01–4.03 (m, 2 H), 1.96–2.06 (m, 4 H), 1.75–1.85 (m, 4 H).

EXAMPLE 405

N-{4-((7-chloroquinolin-4-yl)amino)cyclohexyl}-2-(3,4-dimethylphenoxy)acetamide

The titled compound was prepared according to the procedure described in Example 344 by substituting 3,4-dimethylphenoxyacetic acid for 3-methyl-2-phenyl-pentanoic acid. MS (CI(+)) m/e 438 (M+H)$^+$. $^1$H NMR (500 MHz, DMSO) δ ppm 8.81 (d, J=7.2 Hz, 1 H), 8.70 (d, J=9.4 Hz, 1 H), 8.55 (d, J=7.2 Hz, 1 H), 7.93 (d, J=2.2 Hz, 1 H), 7.81 (dd, J=9.0, 2.2 Hz, 1 H), 7.74 (d, J=6.6 Hz, 1 H), 7.04 (d, J=8.1 Hz, 1 H), 6.98 (d, J=7.5 Hz, 1 H), 6.78 (m, 1 H), 6.68 (dd, J=8.3, 2.7 Hz, 1 H), 4.46 (s, 2 H), 3.95 (m, 1 H), 3.91 (m, 1 H), 2.18 (s, 3 H), 2.13 (s, 3 H), 1.86 (m, 6 H), 1.70 (m, 2 H).

EXAMPLE 406

2-(4-chloro-2-methylphenoxy)-N-{4-((7-chloroquinolin-4-yl)amino)cyclohexyl}acetamide The titled compound was prepared according to the procedure described in Example 344 by substituting 4-chloro-O-tolylacetic acid for 3-methyl-2-phenyl-pentanoic acid. MS (CI(+)) m/e 458 (M)$^+$. $^1$H NMR (500 MHz, DMSO) δ ppm 8.82 (d, J=6.9 Hz, 1 H), 8.71 (d, J=9.4 Hz, 1 H), 8.55 (d, J=7.2 Hz, 1 H), 7.93 (d, J=1.9 Hz, 1 H), 7.81 (dd, J=9.0, 2.2 Hz, 1 H), 7.78 (d, J=6.6 Hz, 1 H), 7.24 (d, J=2.2 Hz, 1 H), 7.19 (dd, J=8.7, 2.5 Hz, 1 H), 6.98 (d, J=7.2 Hz, 1 H), 6.87 (d, J=8.7 Hz, 1 H), 4.56 (s, 2 H), 3.91 (m, 2 H), 2.22 (s, 3 H), 1.84 (m, 6 H), 1.71 (m, 2 H).

EXAMPLE 407

N-{4-((7-chloroquinolin-4-yl)amino)cyclohexyl}-5-fluoro-2'-hydroxy-1,1'-biphenyl-3-carboxamide The titled compound was prepared according to the method described in Example 350 by substituting 2-(4,4,5,5-Tetramethyl-1,3,2-dioxaborolan-2-yl)phenol for 5-acetyl-2-thiophene boronic acid. MS ESI(+)Q1MS m/z 490 (M+H)$^+$; $^1$H NMR (300 MHz, DMSO) δ ppm 9.80 (s, 1H), 8.85 (d, 1 H), 8.72 (d, 1 H), 8.56 (d, 1 H), 8.28 (d, 1H), 7.98 (d, 1H), 7.69 (s, 1H), 7.78 (dd, 1H), 7.63 (d, 1 H), 7.55 (d, 1H), 7.38 (dd, 1H), 7.23 (t, 1H), 7.01–6.99(m, 2H), 6.92 (t, 1H), 3.97–4.04 (m, 2H), 1.96–2.05 (m, 4H), 1.74–1.83 (m, 4H).

EXAMPLE 408

4'-acetyl-N-{4-((7-chloroquinolin-4-yl)amino)cyclohexyl}-5-fluoro-1,1'-biphenyl-3-carboxamide The titled compound was prepared according to the method described in Example 350 by substituting 4-acetylphenylboronic acid for 5-acetyl-2-thiophene boronic acid. MS ESI(+)Q1MS m/z 516 (M+H)$^+$; $^1$H NMR (300 MHz, DMSO) δ ppm 8.83 (d, 1 H), 8.72 (d, 1 H), 8.57 (d, 1 H), 8.37 (d, 1 H), 8.07–8.09 (m, 3H), 7.94–7.96 (m, 3H), 7.79–7.83 (m, 2H), 7.75 (d, 1 H) 7.01 (d, 1 H), 4.01–4.05 (m, 2 H), 2.64 (s, 3 H), 1.97–2.06 (m, 4 H), 1.76–1.85 (m, 4H).

EXAMPLE 409

N-{4-((7-chloroquinolin-4-yl)amino)cyclohexyl}-6-methylnicotinamide

The titled compound was prepared according to the methods described in Example 23, substituting 6-methylnicotinic acid for indole-6-carboxylic acid. MS (ESI(+)Q1MS m/Z 395 (M+H)$^+$); $^1$H NMR (500 MHz, DMSO-D6) δ ppm 1.73–2.02 (m, 8 H) 2.69 (s, 3 H) 3.65–4.08 (br. s., 2 H) 7.00 (d, J=7.17 Hz, 1 H) 7.43 (d, J=8.11 Hz, 1 H) 7.81 (dd, J=9.05, 2.18 Hz, 1 H) 7.94 (d, J=1.87 Hz, 1 μl) 8.19 (dd, J=8.11, 2.18 Hz, 1 H) 8.29 (d, J=5.62 Hz, 1 H) 8.56 (d, J=7.17 Hz, 1 H) 8.71 (d, J=9.36 Hz, 1 H) 8.82 (d, J=6.86 Hz, 1 H) 8.95 (d, J=1.87 Hz, 1 H).

EXAMPLE 410

N-{4-((7-chloroquinolin-4-yl)amino)cyclohexyl}-4-phenylbutanamide

The titled compound was prepared according to the procedure described in Example 344 by substituting 4-phenylbutyric acid for 3-methyl-2-phenyl-pentanoic acid. MS (CI(+)) m/e 422 (M+H)+. $^1$H NMR (500 MHz, DMSO) δ ppm 8.85 (d, J=7.2 Hz, 1 H), 8.71 (d, J=9.4 Hz, 1 H), 8.54 (d, J=7.2 Hz, 1 H), 7.93 (d, J=2.2 Hz, 1 H), 7.79 (dd, J=9.0, 2.2 Hz, 1 H), 7.69 (d, J=6.2 Hz, 1 H), 7.28 (t, J=7.5 Hz, 2 H), 7.18 (m, 3 H), 6.97 (d, J=7.2 Hz, 1 H), 3.90 (m, 1 H), 3.81 (m, 1 H), 2.58 (t, J=7.8 Hz, 2 H), 2.15 (t, J=7.5 Hz, 2 H), 1.81 (m, 8 H), 1.65 (m, 2 H).

EXAMPLE 411

N-{4-((7-chloroquinolin-4-yl)amino)cyclohexyl}-3-(4-methoxyphenyl)propanamide

The titled compound was prepared according to the procedure described in Example 344 by substituting 3-(4-methoxyphenyl)propionic acid for 3-methyl-2-phenyl-pentanoic acid. MS (CI(+)) m/e 438 (M+H)+. $^1$H NMR (500 MHz, DMSO) δ ppm 8.85 (d, J=6.9 Hz, 1 H), 8.72 (d, J=9.0 Hz, 1 H), 8.54 (d, J=6.9 Hz, 1 H), 7.93 (d, J=2.2 Hz, 1 H), 7.79 (dd, J=9.0, 1.9 Hz, 1 H), 7.69 (d, J=5.9 Hz, 1 H), 7.12 (d, J=8.7 Hz, 2 H), 6.96 (d, J=7.2 Hz, 1 H), 6.83 (d, J=8.7 Hz, 2 H); 3.88 (m, 1 H), 3.80 (m, 1 H), 3.69 (s, 3 H), 2.76 (t, J=7.6 Hz, 2 H), 2.39 (t, J=7.8 Hz, 2 H), 1.79 (m, 6 H), 1.64 (m, 2 H).

EXAMPLE 412

N-{4-((7-chloroquinolin-4-yl)amino)cyclohexyl}-3-fluoro-5-pyridin-4-ylbenzamide

The titled compound was prepared according to the method described in Example 350 by substituting 4-pyridylboronic acid for 5-acetyl-2-thiophene boronic acid. MS ESI(+)Q1MS m/z 475 (M+H)+; $^1$H NMR (300 MHz, DMSO) δ ppm 8.86 (m, 3H), 8.74 (d, 1 H), 8.57 (d, 1 H), 8.42 (d, 1H), 8.18 (s, 1H), 8.05 (d, 2H), 7.95–7.97 (m, 2H), 7.85 (d, 1 H), 7.80 (dd, 1 H), 7.00 (d, 1 H), 4.01–4.06 (m, 2 H), 1.96–2.06 (m, 4 H), 1.76–1.85 (m, 4H).

EXAMPLE 413

N-{4-((7-chloroquinolin-4-yl)amino)cyclohexyl}heptanamide

The titled compound was prepared according to the procedure described in Example 344 by substituting heptanioc acid for 3-methyl-2-phenyl-pentanoic acid. MS (CI(+)) m/e 452 (M)+. $^1$H NMR (500 MHz, DMSO) δ ppm 8.88 (d, J=6.9 Hz, 1 H), 8.75 (d, J=9.0 Hz, 1 H), 8.54 (d, J=7.2 Hz, 1 H), 7.95 (d, J=1.9 Hz, 1 H), 7.79 (dd, J=9.0, 1.9 Hz, 1 H), 7.59 (d, J=6.6 Hz, 1 H), 6.96 (d, J=7.5 Hz, 1 H), 3.89 (m, 1 H), 3.83 (m, 1 H), 1.90 (m, 6 H), 1.78 (m, 4 H), 1.65 (m, 5 H), 1.59 (m, 10 H).

EXAMPLE 414

N-{4-((7-chloroquinolin-4-yl)amino)cyclohexyl}-4-(4-methoxyphenyl)-4-oxobutanamide The titled compound was prepared according to the procedure described in Example 344 by substituting 3-(4-methoxybenzoyl)propionic acid for 3-methyl-2-phenyl-pentanoic acid. MS (CI(+)) m/e 466 (M+H)+. $^1$H NMR (500 MHz, DMSO) δ ppm 8.89 (d, J=6.9 Hz, 1 H), 8.74 (d, J=9.0 Hz, 1 H), 8.54 (d, J=7.2 Hz, 1 H), 7.95 (m, 3 H), 7.79 (m, 2 H), 7.04 (d, J=9.0 Hz, 2 H), 6.97 (d, J=7.5 Hz, 1 H), 3.90 (m, 1 H), 3.84 (s, 3 H), 3.79 (m, 1 H), 3.19 (t, J=6.7 Hz, 2 H), 2.54 (m, 2 H), 1.85 (m, 6 H), 1.66 (m, 2 H).

EXAMPLE 415

2-chloro-N-{4-((7-chloroquinolin-4-yl)amino)cyclohexyl}nicotinamide

The titled compound was prepared according to the methods described in Example 23, substituting 2-chloronicotinic acid for indole-6-carboxylic acid. MS (ESI(+)Q1MS m/z 415 (M+H)+); $^1$H NMR (500 MHz, DMSO-D6) δ ppm 1.75–1.99 (m, 8 H) 3.93 (m, 1 H)4.03 (m, 1 H) 6.99 (d, J=7.49 Hz, 1 H) 7.50 (dd, J=7.49, 4.99 Hz, 1 H) 7.79 (dd, J=9.05, 2.18 Hz, 1 H) 7.88 (dd, J=7.33, 1.72 Hz, 1 H) 7.92 (d, J=2.18 Hz, 1 H) 8.47 (dd, J=4.84, 2.03 Hz, 1 H) 8.54 (t, J=7.18 Hz, 2 H) 8.73 (d, J=9.05 Hz, 1 H) 8.84 (d, J=7.17 Hz, 1 H).

EXAMPLE 416

N-{4-((7-chloroquinolin-4-yl)amino)cyclohexyl}-3-(3-methoxyphenyl)propanamide

The titled compound was prepared according to the procedure described in Example 344 by substituting 3-(3-methoxyphenyl)propionic acid for 3-methyl-2-phenyl-pentanoic acid. MS (CI(+)) m/e 438 (M+H)+. $^1$H NMR (500 MHz, DMSO) δ ppm 8.85 (d, J=7.2 Hz, 1 H), 8.71 (d, J=9.0 Hz, 1 H), 8.54 (d, J=7.2 Hz, 1 H), 7.93 (d, J=2.2 Hz, 1 H), 7.79 (dd, J=9.0, 2.2 Hz, 1 H), 7.72 (d, J=5.9 Hz, 1 H), 7.18 (t, J=8.1 Hz, 1 H), 6.97 (d, J=7.5 Hz, 1 H), 6.78 (m, 2 H), 6.73 (m, 1 H), 3.89 (m, 1 H), 3.81 (m, 1 H), 3.72 (s, 3 H), 2.80 (t, J=7.8 Hz, 2 H), 2.43 (t, J=7.8 Hz, 2 H), 1.80 (m, 6 H), 1.65 (m, 2 H).

EXAMPLE 417

2-(benzyloxy)-N-{4-((7-chloroquinolin-4-yl)amino)cyclohexyl}acetamide

The titled compound was prepared according to the procedure described in Example 344 by substituting benzyloxyacetic acid for 3-methyl-2-phenyl-pentanoic acid. MS (CI(+)) m/e 424 (M+H)+. $^1$H NMR (500 MHz, DMSO) δ ppm 8.79 (d, J=7.2 Hz, 1 H), 8.68 (d, J=9.4 Hz, 1 H), 8.55 (d, J=7.2 Hz, 1 H), 7.93 (d, J=2.2 Hz, 1 H), 7.80 (dd, J=9.0, 2.2 Hz, 1 H), 7.41 (d, J=6.9 Hz, 1 H), 7.38 (d, J=4.4 Hz, 3 H), 7.32 (m, 1 H), 6.98 (d, J=7.2 Hz, 1 H), 4.58 (s, 2 H), 3.94 (m, 4 H), 1.82 (m, 6 H), 1.69 (m, 2 H).

EXAMPLE 418

N-(7-chloroquinolin-4-yl)-N'-(5-methyl-1,1'-biphenyl-3-yl)cyclohexane-1,4-diamine To a solution of phenyl boronic acid (6.10 mg, 0.050 mmol), Pd(PPh$_3$)$_2$Cl$_2$ (~1 mol %), and cesium carbonate (19.5 mg, 0.060 mmol) in dimethoxyethane/water/ethanol (7/3/2) was added N-(3-bromo-5-methylphenyl)-N'-(7-chloroquinolin-4-yl)cyclohexane-1,4-diamine (20 mg, 0.050 mmol). The solution was heated in the microwave at 160° C. for 3 minutes, concentrated, and purified by high throughput HPLC to provide the desired compound as its trifluoroacetic acid salt. MS (ESI(+)Q1MS m/z 442 (M+H)+; $^1$H NMR (300 MHz, DMSO) δ ppm MS (ESI(+)Q1MS m/z 443 (M+H)+; $^1$H NMR (300 MHz, DMSO) δ ppm 8.92 (d, 1 H), 8.76 (d, 2 H), 8.73 (d, 1 H), 8.56 (d, 1 H), 7.92–7.96 (m, 4 H), 7.81 (dd, 1 H), 7.02 (d, 1H), 6.89 (m, 2 H), 6.67 (s, 1 H), 3.89 (m, 2 H), 2.30 (s, 3 H), 1.78–1.96 (m, 8 H).

EXAMPLE 419

6-(2-({4-((7-chloroquinolin-4-yl)amino)cyclohexyl}amino)-1,3-thiazol-4-yl)-3,4-dihydroquinolin-2(1 H)-one To a solution of phenyl boronic acid (6.10 mg, 0.050 mmol), Pd(PPh$_3$)$_2$Cl$_2$ (~1 mol %), and cesium carbonate (19.5 mg, 0.060 mmol) in dimethoxyethane/water/ethanol (7/3/2) was added N-(3-bromo-5-methylphenyl)-N'-(7-chloroquinolin-4-yl)cyclohexane-1,4-diamine (20 mg, 0.050 mmol). The solution was heated in the microwave at 160° C. for 3 minutes, concentrated, and purified by high throughput HPLC to provide the desired compound as its trifluoroacetic acid salt. MS (ESI(+)Q1MS m/z 442 (M+H)+; [1] H NMR (300 MHz, DMSO) δ ppm 8.91 (m, 1 H), 8.69 (m, 1 H), 8.54 (m, 1 H), 7.95 (m, 2 H), 7.71–7.83 (m, 5 H), 7.57 (d, 1 H), 7.43 (t, 1 H), 6.93–7.02 (m, 2 H), 6.67 (m, 1 H), 3.95 (s, 1 H), 3.57 (d, 1 H), 3.62 (d, 3H), 1.67–2.00 (m, 8 H).

EXAMPLE 419A

N-{4-((7-chloroquinolin-4-yl)amino)cyclohexyl}thiourea

Ammonium thiocyanate (320 mg, 4.2 mmol) was dissolved in 85 mL dry acetone. A solution of benzoyl chloride (590 mg, 4.2 mmol) in 10 mL dry acetone was added dropwise and heated at reflux for 30 minutes. A solution of 23A cis-N,N'-bis(7-chloroquinolin-4-yl)cyclohexane-1,4-diamine (1 g, 3.6 mmol) in 10 mL dry acetone was added dropwise to the refluxing solution. After the addition, the solution was poured into 100 mL of water. The resulting solid was filtered and heated in 30 mL of 10% sodium hydroxide until dissolved. The solution was then allowed to cool and was placed in the freezer overnight. The white solid was filtered and dried under vacumn to give 565 mg, 47% yield. MS ESI(+)Q1MS m/z 334 (M+H)+; [1] H NMR (300 MHz, DMSO) δ ppm 8.38–8.42 (m, 2 H), 8.78 (d, 1 H), 7.44 (dd, 1 H), 6.66–6.69 (m, 2 H), 6.53 (d, 1 H), 4.17 (m, 1 H), 3.61 (m, 1 H), 1.96–2.06 (m, 4H), 1.65–1.84 (m, 8 H).

EXAMPLE 419B 6-(2-({4-((7-chloroquinolin-4-yl)amino)cyclohexyl}amino)-1,3-thiazol-4-yl)-3,4-dihydroquinolin-2(1 H)-one Example 419A (20 mg, 0.06 mmol) was dissolved in 0.5 mL ethanol, followed by the addition of 6-(bromoacetyl)-2-oxo-1,2,3,4-tetrahydroquinoline (16.09 mg, 0.06 mmol). After two hours, the solution was concentrated and purified by high throughput HPLC to provide the desired compound as its trifluoroacetic acid salt. MS (ESI(+)Q1MS m/z 504 (M+H)+; [1] H NMR (300 MHz, MeOH) δ ppm 10.11 (s, 1 H), 8.94 (d, 1 H), 8.73 (d, 1 H), 8.55 (d, 1 H), 7.96 (d, 1 H), 7.83 (m, 1 H), 7.79 (dd, 1H), 7.62 (s, 1 H), 7.60 (m, 1H), 7.01 (d, 1H), 6.91 (s, 1 H), 6.86 (d, 1 H), 3.97 (m, 1 H), 3.88 (m, 1 H), 2.91 (t, 2 H), 2.47 (t, 2 H), 2.14 (m, 2 H), 1.77–1.97 (m, 6 H).

EXAMPLE 420

N-{4-((7-chloroquinolin-4-yl)amino)cyclohexyl}-2-hydroxy-5-iodobenzamide

The titled compound was prepared according to the methods described in Example 23, substituting 2-hydroxy-5iodobenzoic acid for indole-6-carboxylic acid. MS (ESI(+) Q1MS m/z 522 (M+H)+); [1] H NMR (500 MHz, DMSO-D6) δ ppm 1.76–2.02 (m, 8 H) 4.00 (m, 1 H) 4.08 (m, 1 H) 6.79 (d, J=8.74 Hz, 1 H) 7.01 (d, J=7.17 Hz, 1 H) 7.69 (dd, J=8.58, 2.34 Hz, 1 H) 7.80 (dd, J=9.05, 1.87 Hz, 1 H) 7.95 (d, J=2.18 Hz, 1 H) 8.28 (d, J=2.18 Hz, 1 H) 8.57 (m, 2 H) 8.72 (d, J=9.05 Hz, 1 H) 8.86 (d, J=7.18 Hz, 1 H).

EXAMPLE 421

N-{4-((7-chloroquinolin-4-yl)amino)cyclohexyl}butanamide

The titled compound was prepared according to the procedure described in Example 344 by substituting butyric acid for 3-methyl-2-phenyl-pentanoic acid. MS (CI(+)) m/e 346 (M+H)+. [1] H NMR (500 MHz, DMSO) δ ppm 8.88 (d, J-7.2 Hz, 1 H), 8.73 (d, J=9.0 Hz, 1 H), 8.54 (d, J=7.2 Hz, 1 H), 7.95 (d, J=2.2 Hz, 1 H), 7.79 (dd, J=9.0, 2.2 Hz, 1 H), 7.66 (d, J=5.9 Hz, 1 H), 6.97 (d, J=7.5 Hz, 1 H), 3.90 (m, 1 H), 3.80 (m, 1 H), 2.11 (t, J=7.3 Hz, 2 H), 1.82 (m, 6 H), 1.65 (m, 2 H), 1.53 (m, 2 H), 0.87 (t, J=7.5 Hz, 3 H).

EXAMPLE 422

N-{4-((7-chloroquinolin-4-yl)amino)cyclohexyl}-2-(3-phenoxyphenyl)acetamide

The titled compound was prepared according to the procedure described in Example 344 by substituting 3-phenoxyphenylacetic acid for 3-methyl-2-phenyl-pentanoic acid. MS (CI(+)) m/e 486 (M)+. [1] H NMR (500 MHz, DMSO) δ ppm 8.86 (d, J=6.9 Hz, 1 H), 8.72 (d, J=9.0 Hz, 1 H), 8.55 (d, J=7.2 Hz, 1 H), 7.99 (d, J=5.9 Hz, 1 H), 7.94 (d, J=1.9 Hz, 1 H), 7.80 (dd, J=9.2, 2.0 Hz, 1 H), 7.36 (t, J=8.0 Hz, 2 H), 7.31 (t, J=7.8 Hz, 1 H), 7.09 (t, J=7.3 Hz, 1 H), 7.04 (d, J=7.8 Hz, 1 H), 6.98 (m, 3 H), 6.94 (m, 1 H), 6.86 (dd, J=7.8, 1.9 Hz, 1 H), 3.90 (m, 1 H), 3.79 (m, 1 H), 3.47 (s, 2 H), 1.79 (m, 6 H), 1.66 (m, 2 H).

EXAMPLE 423

N-(3-bromo-5-methylphenyl)-N'-(7-chloroquinolin-4-yl)cyclohexane-1,4-diamine

A dry 250 mL 3-necked flask was charged with Pd$_2$(dba)$_3$ (266 mg, 2 mol %), BINAP, 384 mg, 4 mol %), and sodium t-butoxide (2.2 g, 0.023 mol) in 50 mL dry toluene. After 5 minutes, 23A cis-N,N'-bis(7-chloroquinolin-4-yl)cyclohexane-1,4-diamine (4.00 g, 0.0145 mol) was added in one portion followed by dibromotoluene (3.6 g, 0.0145 mol). The solution was heated at 70° C. under nitrogen overnight. The contents were filtered, concentrated and the residue was purified by flash chromatography (5% methanol in dichloromethane) to provide 1.03 g, a 16% yield. MS (ESI(+)Q1MS m/z 445 (M+2 H)+; [1] H NMR (300 MHz, MeOH) δ ppm 8.51 (d, 1 H), 8.37 (d, 1 H), 7.86 (d, 1 H), 7.69 (dd, 1 H), 6.96 (d, 1 H), 6.66 (s, 1 H), 6.61 (s, 1 H), 6.49 (s, 1 H), 3.98 (m, 1 H), 3.63 (m, 1 H), 2.22 (s, 3 H), 1.85–2.01 (m, 8 H).

EXAMPLE 424

N-{4-((7-chloroquinolin-4-yl)amino)cyclohexyl}-2-cyclopropylacetamide

The titled compound was prepared according to the procedure described in Example 344 by substituting cyclopropylacetic acid for 3-methyl-2-phenyl-pentanoic acid. MS (CI (+)) m/e 358 (M+H)+. [1] H NMR (500 MHz, DMSO) δ ppm 8.80 (d, J=7.2 Hz, 1 H), 8.72 (d, J=9.4 Hz, 1 H), 8.54 (d, J=7.2 Hz, 1 H), 7.92 (d, J=2.2 Hz, 1 H), 7.79 (dd, J=9.2, 2.0 Hz, 1 H), 7.57 (d, J=5.9 Hz, 1 H), 6.96 (d, J=7.5 Hz, 1 H), 3.89 (m, 1 H), 3.80 (m, 1 H), 2.04 (d, J=7.2 Hz, 2 H), 1.82 (m, 6 H), 1.66 (m, 2 H), 0.98 (m, 1 H), 0.43 (m, 2 H), 0.14 (m, 2 H).

EXAMPLE 425

N-{4-((7-chloroquinolin-4-yl)amino)cyclohexyl}-2,2-dimethylpropanamide

The titled compound was prepared according to the procedure described in Example 344 by substituting pivalic acid for 3-methyl-2-phenyl-pentanoic acid. MS (CI(+)) m/e 360 (M+H)⁺. ¹H NMR (500 MHz, DMSO) δ ppm 8.80 (d, J=7.2 Hz, 1 H), 8.72 (d, J=9.0 Hz, 1 H), 8.55 (d, J=7.2 Hz, 1 H), 7.96 (d, J=2.2 Hz, 1 H), 7.79 (d, J=10.9 Hz, 1 H), 6.97 (d, J=7.2 Hz, 1 H), 6.89 (d, J=6.2 Hz, 1 H), 3.94 (m, 1 H), 3.79 (m, 1 H), 1.86(m, 4 H), 1.77 (m, 2 H), 1.63 (m, 2 H), 1.14 (s, 9 H).

EXAMPLE 426

N-{4-((7-chloroquinolin-4-yl)amino)cyclohexyl}-2-fluoro-6-hydroxybenzamide

The titled compound was prepared according to the methods described in Example 23, substituting 2-fluoro-6-hydroxybenzoic acid for indole-6-carboxylic acid. MS (ESI (+)Q1MS m/z 414 (M+H)⁺; ¹H NMR (500 MHz, DMSO-D6) δ ppm 1.73–1.98 (m, 8 H) 3.95 (m, 1 H) 4.06 (m, 1 H) 6.71 (m, 2 H) 6.98 (d, J=7.49 Hz, 1 H) 7.28 (m, 1 H) 7.78 (dd, J=9.05, 2.18 Hz, 1 H) 7.92 (d, J=2.18 Hz, 1 H) 8.08 (m, 1 H) 8.55 (d, J=6.86 Hz, 1 H) 8.71 (d, J=9.05 Hz, 1 H) 8.82 (d, J=6.55 Hz, 1 H).

EXAMPLE 427

N-(7-chloroquinolin-4-yl)-N'-(3-methyl-5-pyridin-4-ylphenyl)cyclohexane-1,4-diamine The titled compound was prepared according to the method described in Example 418 by substituting 4-pyridylboronic acid for phenylboronic acid. MS (ESI(+)Q1MS m/z 443 (M+H)⁺; ¹H NMR (300 MHz, DMSO) δ ppm 8.92 (d, 1 H), 8.76 (d, 2 H), 8.73 (d, 1 H), 8.56 (d, 1 H), 7.92–7.96 (m, 4 H), 7.81 (dd, 1 H), 7.02 (d, 1 H), 6.89 (m, 2 H), 6.67 (s, 1H), 3.89 (m, 2 H), 2.30 (s, 3 H), 1.78–1.96 (m, 8 H).

EXAMPLE 428

N-{4-((7-chloroquinolin-4-yl)amino)cyclohexyl}-4-oxo-4-phenylbutanamide

The titled compound was prepared according to the procedure described in Example 344 by substituting 3-benzoylpropionic acid for 3-methyl-2-phenyl-pentanoic acid. MS (CI (+)) m/e 436 (M+H)⁺. ¹H NMR (500 MHz, DMSO) δ ppm 8.89 (d, J=6.9 Hz, 1 H), 8.74 (d, J=9.0 Hz, 1 H), 8.54 (d, J=7.2 Hz, 1 H), 7.98 (d, J=7.2 Hz, 2 H), 7.94 (d, J=2.2 Hz, 1 H), 7.80 (m, 2 H), 7.64 (t, J=7.3 Hz, 1 H), 7.53 (t, J=7.8 Hz, 2 H), 6.98 (d, J=7.2 Hz, 1 H), 3.90 (m, 1 H), 3.80 (m, 1 H), 3.25 (t, J=6.7 Hz, 2 H), 2.55 (m, 2 H), 1.85 (m, 6 H), 1.66 (m, 2 H).

EXAMPLE 429

N-{4-((7-chloroquinolin-4-yl)amino)cyclohexyl}-3-fluoro-5-thien-3-ylbenzamide

The titled compound was prepared according to the method described in Example 350 by substituting 3-thiopheneboronic acid for 5-acetyl-2-thiophene boronic acid. MS ESI(+)Q1MS m/z 480 (M+H)⁺; ¹H NMR (300 MHz, DMSO) δ ppm 8.85 (d, 1 H), 8.74 (d, 1 H), 8.57 (d, 1 H), 8.31 (d, 1 H), 8.08 (m, 1 H), 8.06 (s, 1 H), 7.98 (d, 1 H), 7.76–7.80 (m, 2 H), 7.68–7.17 (m, 2 H), 7.62 (d, 1 H), 7.01 (d, 1 H), 4.01–4.05 (m, 2 H), 1.98–2.07 (m, 4H), 1.75–1.85 (m, 4 H).

EXAMPLE 430

N-{4-((7-chloroquinolin-4-yl)amino)cyclohexyl}-3-fluoro-5-((E)-2-phenylvinyl)benzamide The titled compound was prepared according to the method described in Example 350 by substituting trans-2-phenylvinylboronic acid for 5-acetyl-2-thiophene boronic acid. MS ESI(+)Q1MS m/z 500 (M+H)⁺; ¹H NMR (300 MHz, DMSO) δ ppm 8.85 (d, 1 H), 8.73 (d, 1 H), 8.57 (d, 1 H), 8.26 (d, 1 H), 7.96 (d, 1 H),-7.94 (s, 1 H), 7.80 (dd, 1 H), 7.59–7.68 (m, 4 H), 7.44–7.40 (m, 3H), 7.31–7.34 (m, 2H), 7.01 (d, 1H), 4.01–4.04 (m, 2H), 1.97–2.05 (m, 4H), 1.75–1.84 (m, 4H).

EXAMPLE 431

N-{4-((7-chloroquinolin-4-yl)amino)cyclohexyl}-2-ethoxyacetamide

The titled compound was prepared according to the procedure described in Example 344 by substituting ethoxyacetic acid for 3-methyl-2-phenyl-pentanoic acid. MS (CI (+)) m/e 362 (M+H)⁺. ¹H NMR (500 MHz, DMSO) δ ppm 8.81 (d, J=7.2 Hz, 1 H), 8.69 (d, J=9.4 Hz, 1 H), 8.55 (d, J=7.2 Hz, 1 H), 7.95 (d, J=2.2 Hz, 1 H), 7.80 (dd, J=9.0, 2.2 Hz, 1 H), 7.32(d, J=6.9 Hz, 1 H), 6.99 (d, J=7.5 Hz, 1 H), 3.96 (m, 1 H), 3.90 (m, 1 H), 3.87 (s, 2 H), 3.54 (q, J=7.0 Hz, 2 H), 1.81 (m, 6 H), 1.70 (m, 2 H), 1.17 (t, J=6.9 Hz, 3 H.

EXAMPLE 432

N-{4-((7-chloroquinolin-4-yl)amino)cyclohexyl}-2-ethylbutanamide

The titled compound was prepared according to the procedure described in Example 344 by substituting 2-ethylbutyric acid for 3-methyl-2-phenyl-pentanoic acid. MS (CI(+)) m/e 374 (M+H)⁺. ¹H NMR (500 MHz, DMSO) δ ppm 8.89 (d, J=7.2 Hz, 1 H), 8.75 (d, J=9.0 Hz, 1 H), 8.54 (d, J=7.2 Hz, 1 H), 7.95 (d, J=1.9 Hz, 1 H), 7.79 (dd, J=9.0, 1.9 Hz, 1 H), 7.68 (d, J=6.6 Hz, 1 H), 6.97 (d, J=7.2 Hz, 1 H), 3.88 (m, 2 H), 2.10 (m, 1 H), 1.82 (m, 6 H), 1.67 (m, 2 H), 1.45 (m, 2 H), 1.35 (m, 2 H), 0.82 (t, J=7.3 Hz, 6 H).

EXAMPLE 433

N-{4-((7-chloroquinolin-4-yl)amino)cyclohexyl}-1-phenylcyclopropanecarboxamide

The titled compound was prepared according to the procedure described in Example 344 by substituting 1-phenyl-1-cyclopropanecarboxylic acid for 3-methyl-2-phenyl-pentanoic acid. MS (CI(+)) m/e 420 (M+H)⁺. ¹H NMR (500 MHz, DMSO) δ ppm 8.68 (m, 2 H), 8.53 (d, J=7.2 Hz, 1 H), 7.92 (d, J=1.9 Hz, 1 H), 7.80 (dd, J=9.0, 2.2 Hz, 1 H), 7.40 (m, 4 H), 7.33 (m, 1 H), 6.93 (d, J=7.2 Hz, 1 H), 6.15 (d, J=6.9 Hz, 1 H), 3.88 (m, 1 H), 3.82 (m, 1 H), 1.73 (m, 4 H), 1.63 (m, 2 H), 1.53 (m, 2 H), 1.37 (dd, J=6.7, 3.9 Hz, 2 H), 1.02 (dd, J=6.7, 3.9 Hz, 2 H).

EXAMPLE 434

3-chloro-N-{4-((7-chloroquinolin-4-yl)amino)cyclohexyl}-2-hydroxybenzamide

The titled compound was prepared according to the methods described in Example 23, substituting 3-chloro-2-hydroxybenzoic acid for indole-6-carboxylic acid. MS (ESI (+)Q1MS m/z 430 (M+H)⁺; ¹H NMR (500 MHz, DMSO-D6) δ ppm 1.74–2.07 (m, 8 H) 4.01–4.07 (m, 2 H) 6.93 (t, J=7.96 Hz, 1 H) 6.98 (d, J=7.18 Hz, 1 H) 7.62 (dd, J=7.96, 1.40 Hz, 1 H) 7.80 (dd, J=9.05, 1.87 Hz, 1 H) 7.93 (d, J=2.18 Hz, 1 H) 8.00 (dd, J=8.11, 1.25 Hz, 1 H) 8.57 (d, J=7.18 Hz, 1 H) 8.66 (d, J=5.62 Hz, 1 H) 8.71 (d, J=9.36 Hz, 1 H) 8.73 (d, J=6.55 Hz, 1 H).

EXAMPLE 435

N-(7-chloroquinolin-4-yl)-N'-(4',5-dimethyl-1,1'-biphenyl-3-yl)cyclohexane-1,4-diamine The titled compound was prepared according to the method described in Example 418 by substituting 4-methylboronic acid for phenylboronic acid. MS (ESI(+) Q1MS m/z 456 (M+H)+; [1] H NMR (300 MHz, DMSO) δ ppm 8.92 (d, 1 H), 8.73 (d, 1 H), 8.57 (d, 1H), 7.93 (d, 1H), 7.81 (dd, 1 H), 7.69–7.74 (m, 1H), 7.45 (d, 2H), 7.24 (m, 2H), 7.01 (m, 1H), 6.70 (s, 1H), 6.63 (s, 1H), 6.46 (s, 1H), 3.64 (m, 1H), 3.47 (m, 1H), 2.33 (s, 3H), 2.26 (s, 3H), 1.72–1.99 (m, 8 H).

EXAMPLE 436

N-(7-chloroquinolin-4-yl)-N'-(3',5-dimethyl-1,1'-biphenyl-3-yl)cyclohexane-1,4-diamine The titled compound was prepared according to the method described in Example 418 by substituting 3-methylboronic acid for phenylboronic acid. MS (ESI(+) Q1MS m/z 456 (M+H)+; [1] H NMR (300 MHz, DMSO) δ ppm 8.92 (d, 1 H), 8.73 (d, 1 H), 8.56 (d, 1H), 7.92 (d, 1H), 7.80 (dd, 1 H), 7.56–7.62 (m, 1H), 7.13–7.38 (m, 3H), 7.14 (d, 1H), 7.02 (d, 1H), 6.72 (s, 1H), 6.64 (s, 1H), 6.48 (s, 1H), 3.96–4.00 (m, 1H), 3.64 (m, 1H), 2.36 (s, 3H), 2.26 (s, 3H), 1.77–1.98 (m, 8 H).

EXAMPLE 437

N-{4-((7-chloroquinolin-4-yl)amino)cyclohexyl}-3-fluoro-5-thien-2-ylbenzamide

The titled compound was prepared according to the method described in Example 350 by substituting 2-thiopheneboronic acid for 5-acetyl-2-thiophene boronic acid. MS ESI(+)Q1MS m/z 480 (M+H)+; [1] H NMR (300 MHz, DMSO) δ ppm 8.82 (d, 1 H), 8.73 (d, 1 H), 8.57 (d, 1 H), 8.34 (d, 1 H), 7.95 (m, 2 H), 7.80 (dd, 1 H), 7.54–7.73 (m, 4 H), 7.20 (dd, 1H), 7.00 (d, 1H), 4.00–4.03 (m, 2H), 1.97–2.05 (m, 4H), 1.75–1.85 (m, 4H).

EXAMPLE 438

N-(7-chloroquinolin-4-yl)-N'-(4-(3,4-dihydro-2 H-1,5-benzodioxepin-7-yl)-1,3-thiazol-2-yl)cyclohexane-1,4-diamine The titled compound was prepared according to the method described in Example 419 by substituting 3,4-(trimethylenedioxy)phenacyl bromide for 6-(bromoacetyl)-2-oxo-1,2,3,4-tetrahydroquinoline. MS (ESI(+)Q1MS m/z 507 (M+H)+; [1] H NMR (300 MHz, MeOH) δ ppm 8.93 (d, 1 H), 8.72 (d, 1 H), 8.55 (d, 1H), 7.94 (d, 1H), 7.80 (dd, 1 H), 7.68 (br s, 1H), 7.43 (d, 1 H), 7.40 (dd, 1H), 7.01 (d, 1H), 6.95 (t, 2H), 4.13 (m, 4H), 3.97 (m, 1H), 3.89 (m, 1H), 2.09–2.15 (m, 4H), 1.88–1.93 (m, 2H), 1.76–1.82 (m, 4H).

EXAMPLE 439

N-(7-chloroquinolin-4-yl)-N'-(4-methyl-5-phenyl-1,3-thiazol-2-yl)cyclohexane-1,4-diamine The titled compound was prepared according to the method described in Example 419 by substituting 2-bromopropiophenone for 6-(bromoacetyl)-2-oxo-1,2,3,4-tetrahydroquinoline. MS (ESI(+)Q1MS m/z 449 (M+H)+; [1] H NMR (300 MHz, MeOH) δ ppm 8.54 (d, 1 H), 8.40 (d, 1 H), 7.88 (d, 1H), 7.71 (dd, 1H), 7.52 (m, 5 H), 6.98 (d, 1H), 4.03 (m, 1H), 3.92 (m, 1H),2.32 (s, 3H), 1.95–2.14 (m, 8H).

EXAMPLE 440

N-{4-((7-chloroquinolin-4-yl)amino)cyclohexyl}-2-(4-(methylsulfonyl)phenyl)acetamide The titled compound was prepared according to the procedure described in Example 344 by substituting 4-methylsulfonylphenylacetic acid for 3-methyl-2-phenylpentanoic acid. MS (CI(+)) m/e 472 (M)+. [1] H NMR (500 MHz, DMSO) δ ppm 8.88 (d, J=7.2 Hz, 1 H), 8.74 (d, J=9.4 Hz, 1 H), 8.55 (d, J=6.9 Hz, 1 H), 8.12 (d, J=5.9 Hz, 1 H), 7.94 (d, J=1.9 Hz, 1 H), 7.87 (d, J=8.1 Hz, 2 H), 7.81 (dd, J=9.2, 2.0 Hz, 1 H), 7.54 (d, J=8.4 Hz, 2 H), 6.98 (d, J=7.2 Hz, 1 H), 3.91 (m, 1 H), 3.81 (m, 1 H), 3.63 (s, 2 H), 3.19 (s, 3 H), 1.83 (m, 6 H), 1.68 (m, 2 H).

EXAMPLE 441

N-{4-((7-chloroquinolin-4-yl)amino)cyclohexyl}-8-hydroxyquinoline-7-carboxamide

The titled compound was prepared according to the methods described in Example 23, substituting 8-hydroxyquinoline-7-carboxylic acid for indole-6-carboxylic acid. MS (ESI(+)Q1MS m/z 447 (M+H)+); [1] H NMR (500 MHz, DMSO-D6) δ ppm 1.81–2.07 (m, 8 H) 4.03 (m, 1 H) 4.18 (m, 1 H) 7.46 (m, 2 H) 7.70 (dd, J=8.42, 4.37 Hz, 1 H) 7.80 (dd, J=9.05, 2.18 Hz, 1 H) 7.94 (d, J=1.87 Hz, 1 H) 8.11 (d, J=8.73 Hz, 1 H) 8.42 (m, 1 H) 8.57 (d, J=7.17 Hz, 1 H) 8.72 (d, J=9.05 Hz, 1 H) 8.76 (d, J=5.93 Hz, 1 H) 8.87 (d, J=7.18 Hz, 1 H) 8.94 (dd, J=4.06, 1.56 Hz, 1 H).

EXAMPLE 442

N-{4-((7-chloroquinolin-4-yl)amino)cyclohexyl}-2-(pyrimidin-2-ylthio)acetamide

The titled compound was prepared according to the procedure described in Example 344 by substituting 2-(carboxymethylthio)pyrimidine for 3-methyl-2-phenylpentanoic acid. MS (CI(+)) m/e 428 (M+H)+. [1] H NMR (500 MHz, DMSO) δ ppm 8.87 (d, J=6.9 Hz, 1 H), 8.73 (d, J=9.0 Hz, 1 H), 8.63 (d, J=5.0 Hz, 2 H), 8.55 (d, J=7.2 Hz, 1 H), 8.06 (d, J=6.2 Hz, 1 H), 7.94 (d, J=1.9 Hz, 1 H), 7.81 (dd, J=9.2, 2.0 Hz, 1 H), 7.23 (t, J=4.8 Hz, 1 H), 6.98 (d, J=7.5 Hz, 1 H), 3.93 (s, 2 H), 3.83 (m, 2 H), 1.82 (m, 6 H), 1.68 (m, 2 H).

EXAMPLE 443

N-{4-((7-chloroquinolin-4-yl)amino)cyclohexyl}-2-hydroxy-1-naphthamide

The titled compound was prepared according to the methods described in Example 23, substituting 2-hydroxy-1-naphtoic acid for indole-6-carboxylic acid. MS (ESI(+) Q1MS m/z 446 (M+H)+); [1] H NMR (500 MHz, DMSO-D6) δ ppm 1.79–2.04 (m, 8 H) 3.95 (m, 1 H) 4.15 (m, 1 H) 6.98 (d, J=7.17 Hz, 1 H) 7.19 (d, J=9.05 Hz, 1 H) 7.30 (t, J=7.49 Hz, 1 H) 7.44 (t, J=7.64 Hz, 1 H) 7.70 (d, J=8.42 Hz, 1 H) 7.75 (dd, J=9.05, 2.18 Hz, 1 H) 7.80 (t, J=8.27 Hz, 2 H) 7.91 (d, J=1.87 Hz, 1 H) 8.14 (d, J=6.55 Hz, 1 H) 8.55 (d, J=7.18 Hz, 1 H) 8.68 (d, J=9.36 Hz, 1 H) 8.82 (d, J=6.55 Hz, 1 H).

EXAMPLE 444

N-{4-((7-chloroquinolin-4-yl)amino)cyclohexyl}-3,3-dimethylbutanamide

The titled compound was prepared according to the procedure described in Example 344 by substituting tertbutylacetic acid for 3-methyl-2-phenyl-pentanoic acid. MS (CI(+)) m/e 374 (M+H)+. $^1$H NMR (500 MHz, DMSO) δ ppm 8.87 (d, J=6.9 Hz, 1 H), 8.74 (d, J=9.4 Hz, 1 H), 8.54 (d, J=7.2 Hz, 1 H), 7.94 (d, J=1.9 Hz, 1 H), 7.79 (dd, J=9.0, 2.2 Hz, 1 H), 7.61 (d, J=6.2 Hz, 1 H), 6.97 (d, J=7.2 Hz, 1 H), 3.90 (m, 1 H), 3.83 (m, 1 H), 2.03 (s, 2 H), 1.82 (m, 6 H), 1.66 (m, 2 H), 0.98 (s, 9 H).

EXAMPLE 445

N-{4-((7-chloroquinolin-4-yl)amino)cyclohexyl}adamantane-1-carboxamide

The titled compound was prepared according to the procedure described in Example 344 by substituting 1-adamantanecarboxylic acid for 3-methyl-2-phenyl-pentanoic acid. MS (CI(+)) m/e 438 (M)+. $^1$H NMR (500 MHz, DMSO) δ ppm 8.79 (d, J=7.2 Hz, 1 H), 8.71 (d, J=9.0 Hz, 1 H), 8.55 (d, J=7.2 Hz, 1 H), 7.94 (d, J=2.2 Hz, 1 H), 7.80 (dd, J=9.2, 2.0 Hz, 1 H), 6.97 (d, J=7.5 Hz, 1 H), 6.77 (d, J=6.2 Hz, 1 H), 3.94 (m, 1 H), 3.79 (m, 1 H), 1.82 (m, 23 H).

EXAMPLE 446

N-(7-chloroquinolin-4-yl)-N'-(5-phenylpyridin-3-yl)cyclohexane-1,4-diamine

A mixture of example 370 (30 mg, 0.07 mmol), Pd(dppf)Cl$_2$ (3 mg), sodium methoxide (7.5 mg, 0.14 mmol) and phenylboronic acid (9.7 mg, 0.07 mmol) in 1 ml THF was heated for 15 Hours at 65° C., concentrated. Residue was purified with high throughput reverse phase HPLC system to provide the desired compound. MS (ESI(+)Q1MS m/z 429 (M+H)+); $^1$H NMR (300 MHz, DMSO-D6) δ ppm 1.75–2.01 (m, 8 H) 3.84 (m, 1 H) 4.04 (m, 1 H) 7.52–7.60 (m, 3 H) 7.74–7.84 (m, 4 H) 7.94 (d, J=2.03 Hz, 1 H) 8.13 (d, J=2.37 Hz, 1 H) 8.33 (s, 1 H) 8.58 (d, J=7.12 Hz, 1 H) 8.73 (d, J=9.15 Hz, 1 H) 8.94 (d, J=6.78 Hz, 1 H).

EXAMPLE 447

(2R)-N-{4-((7-chloroquinolin-4-yl)amino)cyclohexyl}-2-hydroxy-4-phenylbutanamide The titled compound was prepared according to the procedure described in Example 344 by substituting (R)-2-hydroxy-4-phenylbutyric acid for 3-methyl-2-phenyl-pentanoic acid. MS (CI(+)) m/e 438 (M+H)+. $^1$H NMR (500 MHz, DMSO) δ ppm 8.78 (d, J=8.4 Hz, 1 H), 8.64 (d, J=9.0 Hz, 1 H), 8.55 (d, J=7.2 Hz, 1 H), 7.92 (d, J=2.2 Hz, 1 H), 7.80 (dd, J=9.0, 2.2 Hz, 1 H), 7.41 (d, J=7.8 Hz, 1 H), 7.28 (m, 2 H), 7.18 (m, 2 H), 6.99 (d, J=7.2 Hz, 1 H), 5.74 (m, 1 H), 3.93 (m, 3 H), 3.93 (m, 2 H), 1.94 (m, 1 H), 1.76 (m, 9 H).

EXAMPLE 448

3'-({4-((7-chloroquinolin-4-yl)amino)cyclohexyl}amino)-5'-methyl-1,1'-biphenyl-4-ol The titled compound was prepared according to the method described in Example 418 by substituting 4-hydroxyboronic acid for phenylboronic acid. MS (ESI(+) Q1MS m/z 458 (M+H)+; $^1$H NMR (300 MHz, DMSO) δ ppm 9.45 (br s, 1 H), 8.92 (d, 1 H), 8.73 (d, 1 H), 8.56 (d, 1H), 7.92 (d, 1H), 7.81 (dd, 1 H), 7.38 (m, 2H), 7.01 (d, 1H), 6.81 (m, 2 H), 6.65 (s, 1H), 6.58 (s, 1H), 6.42 (s, 1H), 3.61–3.96 (m, 2H), 2.24 (s, 3H), 1.72–1.99 (m, 8H).

EXAMPLE 449

N-{4-((7-chloroquinolin-4-yl)amino)cyclohexyl}-2-methylpentanamide

The titled compound was prepared according to the procedure described in Example 344 by substituting 2-methylvaleric acid for 3-methyl-2-phenyl-pentanoic acid. MS (CI(+)) m/e 374 (M+H)+. $^1$H NMR (500 MHz, DMSO) δ ppm 8.85 (d, J=6.9 Hz, 1 H), 8.73 (d, J=9.0 Hz, 1 H), 8.54 (d, J=7.2 Hz, 1 H), 7.93 (d, J=1.9 Hz, 1 H), 7.80 (dd, J=9.0, 2.2 Hz, 1 H), 7.62 (d, J=5.9 Hz, 1 H), 6.97 (d, J=7.2 Hz, 1 H), 3.90 (m, 1 H), 3.79 (m, 1 H), 2.37 (m, 1 H), 1.81 (m, 6 H), 1.66 (m, 2 H), 1.48 (m, 1 H), 1.23 (m, 3 H), 0.99 (d, J=6.9 Hz, 3 H), 0.86 (t, J=7.0 Hz, 3 H).

EXAMPLE 451

N-{4-((7-chloroquinolin-4-yl)amino)cyclohexyl}-1-methylcyclohexanecarboxamide

The titled compound was prepared according to the procedure described in Example 344 by substituting 1-methyl-1-cyclohexanecarboxylic acid for 3-methyl-2-phenyl-pentanoic acid. MS (CI(+)) m/e 400 (M+H)+. $^1$H NMR (500 MHz, DMSO) δ ppm 8.78 (d, J=6.9 Hz, 1 H), 8.72 (d, J=9.0 Hz, 1 H), 8.55 (d, J=7.2 Hz, 1 H), 7.95 (d, J=1.9 Hz, 1 H), 7.80 (dd, J=9.0, 2.2 Hz, 1 H), 6.97 (d, J=7.2 Hz, 1 H), 6.91 (d, J=6.2 Hz, 1 H), 3.94 (m, 1 H), 3.83 (m, 1 H), 1.99 (m, 2 H), 1.86 (m, 4 H), 1.78 (m, 2 H), 1.64 (m, 2 H), 1.32 (m, 8 H), 1.08 (s, 3 H).

EXAMPLE 452

N-{4-((7-chloroquinolin-4-yl)amino)cyclohexyl}-2-hydroxy-3-isopropylbenzamide

The titled compound was prepared according to the methods described in Example 23, substituting 2-hydroxy-3-isopropylbenzoic acid for indole-6-carboxylic acid. MS (ESI(+)Q1MS m/z 438 (M+H)+); $^1$H NMR (500 MHz, DMSO-D6) δ ppm 1.18 (d, J=6.86 Hz, 6 H) 1.73–2.05 (m, 8 H) 4.02 (m, 2 H) 6.86 (t, J=7.64 Hz, 1 H) 6.96 (d, J=7.17 Hz, 1 H) 7.36 (d, J=7.18 Hz, 1 H) 7.78–7.83 (m, 2 H) 7.92 (d, J=2.18 Hz, 1 H) 8.42 (d, J=6.24 Hz, 1 H) 8.64 (m, 1 H) 8.69 (d, J=9.05 Hz, 1 H).

EXAMPLE 453

N-{4-((7-chloroquinolin-4-yl)amino)cyclohexyl}-3-hydroxy-2-naphthamide

The titled compound was prepared according to the methods described in Example 23, substituting 3-hydroxy-2-naphtoic acid for indole-6-carboxylic acid. MS (ESI(+) Q1MS m/z 446 (M+H)+); $^1$H NMR (500 MHz, DMSO-D6) δ ppm 1.81–2.07 (m, 8 H) 4.00 (m, 1 H) 4.15 (m, 1 H) 7.01 (d, J=7.49 Hz, 1 H) 7.30 (s, 1 H) 7.36 (t, J=7.64 Hz, 1 H) 7.51 (t, J=7.49 Hz, 1 H) 7.75 (d, J=8.73 Hz, 1 H) 7.80 (dd, J=9.05, 2.18 Hz, 1 H) 7.89 (d, J=8.42 Hz, 1 H) 7.92 (d, J=1.87 Hz, 1 H) 8.57 (d, J=7.17 Hz, 1 H) 8.59 (s, 1 H) 8.70 (d, J=9.05 Hz, 1 H) 8.78 (m, 2 H).

EXAMPLE 454

N-{4-((7-chloroquinolin-4-yl)amino)cyclohexyl}tetrahydrofuran-2-carboxamide

The titled compound was prepared according to the procedure described in Example 344 by substituting tetrahydrofuran-2-carboxylic acid for 3-methyl-2-phenyl-pentanoic acid. MS (CI(+)) m/e 374 (M+H)+. $^1$H NMR (500 MHz, DMSO) δ ppm 8.80 (d, J=7.5 Hz, 1 H), 8.68 (d, J=9.0 Hz, 1 H), 8.55 (d, J=7.2 Hz, 1 H), 7.95 (d, J=1.9 Hz, 1 H), 7.80 (dd, J=9.2, 2.0 Hz, 1 H), 7.32 (d, J=7.2 Hz, 1 H), 6.99 (d, J=7.5 Hz, 1 H), 4.25 (m, 1 H), 3.94 (m, 3 H), 3.81 (m, 1 H), 2.12 (m, 1 H), 1.82 (m, 9 H), 1.68 (m, 2 H).

EXAMPLE 455

N-{4-((7-chloroquinolin-4-yl)amino)cyclohexyl}-2-(4-methylphenoxy)acetamide

The titled compound was prepared according to the procedure described in Example 344 by substituting 4-methylphenoxyacetic aicd for 3-methyl-2-phenylpentanoic acid. MS (CI(+)) m/e 424 (M+H)$^+$. $^1$H NMR (500 MHz, DMSO) δ ppm 8.81 (d, J=6.9 Hz, 1 H), 8.71 (d, J=9.0 Hz, 1 H), 8.55 (d, J=7.2 Hz, 1 H), 7.94 (d, J=2.2 Hz, 1 H), 7.81 (dd, J=9.0, 2.2 Hz, 1 H), 7.76 (d, J=6.6 Hz, 1 H), 7.10 (d, J=8.4 Hz, 2 H), 6.98 (d, J=7.5 Hz, 1 H), 6.86 (d, J=8.7 Hz, 2 H), 4.48 (s, 2 H), 3.95 (m, 1 H), 3.90 (m, 1 H), 2.22 (s, 3 H), 1.83 (m, 6 H), 1.69 (m, 2 H).

EXAMPLE 456

N-(7-chloroquinolin-4-yl)-N'-(4-(4-methoxyphenyl)-1,3-thiazol-2-yl)cyclohexane-1,4-diamine The titled compound was prepared according to the method described in Example 419 by substituting 2-bromo-4'-methoxyacetophenone for 6-(bromoacetyl)-2-oxo-1,2,3,4-tetrahydroquinoline. MS (ESI(+)Q1MS m/z 465 (M+H)$^+$; $^1$H NMR (300 MHz, DMSO) δ ppm 8.93 (d, 1 H), 8.72 (d, 1 H), 8.55 (d, 1H), 7.94 (m, 1H), 7.80 (dd, 1 H), 7.72 (s, 1H), 7.76 (m, 2H), 7.01 (d, 1H), 6.95 (d, 2H), 6.89 (s, 1H), 3.97 (m, 1H), 3.88 (m, 1H), 3.78 (s, 3H), 1.77–2.16 (m, 8H).

EXAMPLE 457

3'-(({4-((7-chloroquinolin-4-yl)amino)cyclohexyl}amino)carbonyl)-5'-fluoro-1,1'-biphenyl-3-carboxylic acid The titled compound was prepared according to the method described in Example 350 by substituting 3-carboxyphenylboronic acid for 5-acetyl-2-thiophene boronic acid. MS ESI(+)Q1MS m/z 518 (M+H)$^+$; $^1$H NMR (300 MHz, DMSO) δ ppm 13.12 (br.s, 1H), 8.84 (d, 1 H), 8.72 (d, 1 H), 8.57 (d, 1 H), 8.39 (d, 1 H), 8.27 (m, 1 H), 8.00–8.04 (m, 3H), 7.95 (d, 1H), 7.80 (dd, 1 H), 7.72–7.77 (m, 2H), 7.66 (t, 1H), 7.00 (d, 1H), 4.01–4.04 (m, 2H), 1.97–2.06 (m, 4 H), 1.76–1.85 (m, 4 H).

EXAMPLE 458

3'-(({4-((7-chloroquinolin-4-yl)amino)cyclohexyl}amino)carbonyl)-5'-fluoro-1,1'-biphenyl-4-carboxylic acid The titled compound was prepared according to the method described in Example 350 by substituting 4-carboxyphenylboronic acid for 5-acetyl-2-thiophene boronic acid. MS ESI(+)Q1MS m/z 518 (M+H)$^+$; $^1$H NMR (300 MHz, DMSO) δ ppm 13.07 (br.s, 1H), 8.83 (d, 1 H), 8.72 (d, 1 H), 8.57 (d, 1 H), 8.36 (d, 1H), 8.08(d, 2H), 8.06 (s, 1H), 7.91–7.95 (m, 3H), 7.80 (dd, 2 H), 7.74 (d, 1H), 7.00 (d, 1H), 4.03–4.04 (m, 2H), 1.96–2.06 (m, 4H), 1.76–1.83 (m, 4H).

EXAMPLE 459

N-(7-chloroquinolin-4-y)-N'-(4,5-dimethyl-1,3-thiazol-2-yl)cyclohexane-1,4-diamine The titled compound was prepared according to the method described in Example 419 by substituting 3-bromo-2-butanone for 6-(bromoacetyl)-2-oxo-1,2,3,4-tetrahydroquinoline. MS (ESI(+)Q1MS m/z 387 (M+H)$^+$; $^1$H NMR (300 MHz, MeOH) δ ppm 8.53 (d, 1 H), 8.41 (d, 1 H), 7.88 (d, 1H), 7.71 (dd, 1H), 6.98 (d, 1H), 4.04 (m, 1H), 3.84 (m, 1H), 2.22 (s, 3H), 2.20 (s, 3 H), 1.92–2.10 (m, 8 H).

EXAMPLE 460

7-chloro-N-{4-((7-chloroquinolin-4-yl)amino)cyclohexyl}-4-hydroxyquinoline-3-carboxamide The titled compound was prepared according to the methods described in Example 23, substituting 4-hydroxyquinoline-2-carboxylic acid for indole-6-carboxylic acid. MS (ESI(+)Q1MS m/z 481 (M+H)$^+$); $^1$H NMR (300 MHz, DMSO-D6) δ ppm 1.179–1.97 (m, 8 H) 3.98 (m, 1 H) 4.22 (m, 1 H) 7.05 (d, J=7.46 Hz, 1 H) 7.53 (dd, J=8.81, 2.03 Hz, 1 H) 7.79 (m, 2 H) 7.92 (d, J=2.37 Hz, 1 H) 8.27 (d, J=8.81 Hz, 1 H) 8.56 (d, J=7.12 Hz, 1 H) 8.72 (d, J=9.15 Hz, 1 H) 8.82 (m, 1 H) 9.05 (d, J=8.48 Hz, 1 H) 10.37 (d, J=7.12 Hz, 1 H).

What is claimed is:

1. A compound of formula (I),

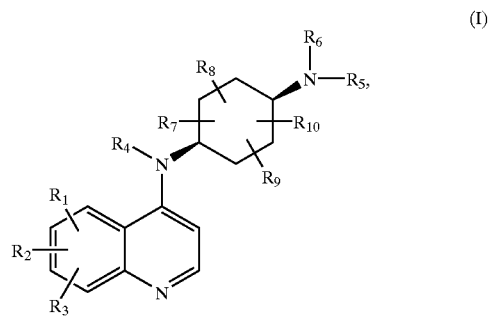

(I)

or a therapeutically suitable salt or prodrug thereof, wherein $R_1$, $R_2$ and $R_3$ are each independently a member selected from the group consisting of hydrogen, alkyl, alkoxy, halo, haloalkyl, haloalkoxy, hydroxy and $R_A R_B N$— wherein $R_A$ and $R_B$ are each independently a member selected from the group consisting of hydrogen and alkyl, alkylcarbonyl, alkylsulfonyl, arylcarbonyl, arylsulfonyl and $R_C R_D$Ncarbonyl, wherein $R_C$ and $R_D$ are each independently a member selected from the group consisting of hydrogen, alkyl and aryl;

$R_4$ is a member selected from the group consisting of hydrogen and alkyl;

$R_5$ is —$(CH_2)_m$—Y-A-B;

m is from 0–6;

A is absent or is a member selected from the group consisting of alkoxyalkylene, alkylene and hydroxyalkylene;

B is a member selected from the group consisting of aryl, arylC(O)—, arylS(O)$_2$—, arylalkenyl, aryloxyalkyl, biaryl, biarylalkyl, cycloalkyl, heterocycle, heterocycleC(O)—, heterocycleS(O)$_2$—, haloalkyl, $R_E R_F N$—, $R_E R_F NC(O)$—, $R_G S$— and $R_G O$—, wherein the heterocycles may be substituted or unsubstituted and can be selected from the group consisting of azetidinyl, azepanyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridinyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl (thiomorpholine sulfone), thiopyranyl, triazinyl, triazolyl, trithianyl, benzimidazolyl, benzodioxinyl, benzothiazolyl, benzothienyl, benzotriazolyl, benzoxazolyl, benzofuranyl, benzopyranyl, benzothiopyranyl, cinnolinyl, indazolyl, indolyl, 2,3-dihydroindolyl, indolizinyl, naphthyridinyl, isobenzofuranyl, isobenzothienyl, isoindolyl, isoquinolinyl, phthalazinyl, 4H-pyrido(1.2-a)pyrimidin-4-one, pyranopyridinyl, quinolizinyl, quinoxalinyl, acridinyl, carbazolyl, carbolinyl, dibenzo(b,d)furanyl, dibenzo(b, d)thienyl, naphtho(2,3-b)furan, naphtho(2,3-b)thienyl, phenazinyl, phenothiazinyl, phenoxazinyl, thianthrenyl, thioxanthenyl and xanthenyl;

$R_E$ and $R_F$ are independently a member selected from the group consisting of hydrogen, alkyl, alkylC(O)—, aryl, arylalkyl, heterocycle, heterocyclealkyl, arylC(O)— and arylS(O)$_2$—;

$R_G$ is a member selected from the group consisting of hydrogen, alkyl, aryl, arylalkyl and heterocycle;

Y is a member selected from the group consisting of —C(O)—, —S—, —S(O)— and —S(O)$_2$—, or is absent;

$R_6$ is a member selected from the group consisting of hydrogen, alkyl and arylcarboxyalkyl; and $R_7$, $R_8$, $R_9$, and $R_{10}$ are each independently a member selected from the group consisting of hydrogen, alkyl, alkoxy, halo, haloalkyl, haloalkoxy and hydroxy or $R_7$ and $R_8$ taken together with the carbon atom that they are attached form oxo;

with the following provisos $P_1$–$P_5$:

$P_1$ if Y is absent, m is 0 and if A is absent or is a member selected from the group consisting of alkoxyalkylene, alkylene and hydroxyalkylene, then B is a member selected from the group consisting of hydrogen, alkyl, arylC(O)—, arylS(O)$_2$—, arylalkenyl, aryloxyalkyl, biarylalkyl, cycloalkyl, heterocycle, heterocycleC(O)—, heterocycleS(O)$_2$—, haloalkyl, $R_E R_F N$—, $R_E R_F NC(O)$—, $R_G S$— and $R_G(O)$—; or $P_2$ if Y is —C(O)—, m is 0 and A is absent, then B is a member selected from the group consisting of hydrogen, alkyl, arylalkenyl, aryloxyalkyl, cycloalkyl, heterocycle, haloalkyl, and $R_E R_F NC(O)$—; or $P_3$ if Y is —C(O)—, A is absent and B is aryl or heterocycle, then m is 1–6; or $P_4$ if Y is —C(O)— and B is a member selected from the group consisting of arylC(O)—, arylS(O)$_2$—, heterocycleC(O)—, heterocycleS(O)$_2$—, then A is a member selected from the group consisting of alkoxyalkylene, alkylene and hydroxyalkylene; or $P_5$ if Y is absent, m is 2, and A is absent, then B is not aryl.

2. A compound of formula (Ia),

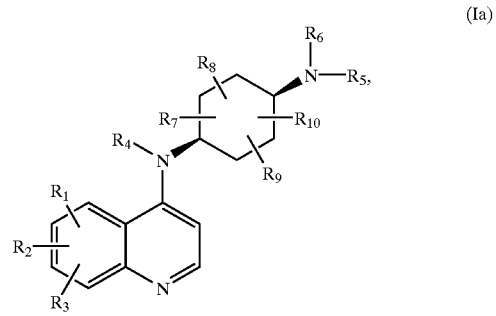

(Ia)

or a therapeutically suitable salts, or prodrug thereof, wherein $R_1$, $R_2$ and $R_3$ are each independently a member selected from the group consisting of hydrogen, alkyl, alkoxy, halo, haloalkyl, haloalkoxy, hydroxy and $R_A R_B N$— wherein $R_A$ and $R_B$ are each independently a member selected from the group consisting of hydrogen and alkyl, alkylcarbonyl, alkylsulfonyl, arylcarbonyl, arylsulfonyl and $R_C R_D N$carbonyl, wherein $R_C$ and $R_D$ are independently a member selected from the group consisting of hydrogen, alkyl and aryl;

$R_4$ is a member selected from the group consisting of hydrogen and alkyl;

$R_5$ is B;

B is a substituted or unsubstituted heterocycle wherein the heterocycle is selected from the group consisting of azetidinyl, azepanyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridinyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl (thiomorpholine sulfone), thiopyranyl, triazinyl, triazolyl, trithianyl, benzimidazolyl, benzodioxinyl, benzothiazolyl, benzothienyl, benzotriazolyl, benzoxazolyl, benzofuranyl, benzopyranyl, benzothiopyranyl, cinnolinyl, indazolyl, indolyl, 2,3-dihydroindolyl, indolizinyl, naphthyridinyl, isobenzofuranyl, isobenzothienyl, isoindolyl, isoquinolinyl, phthalazinyl, 4H-pyrido(1,2-a)nyrhnidin-4-one, pyranopyridinyl, quinolizinyl, quinoxalinyl, acridinyl, carbazolyl, carbolinyl, dibenzo(b,d)furanyl, dibenzo(b, d)thienyl, naphtho(2,3-b)furan, naphtho(2,3-b)thienyl, phenazinyl, phenothiazinyl, phenoxazinyl, thianthrenyl, thioxanthenyl and xanthenyl;

$R_6$ is a member selected from the group consisting of hydrogen, alkyl and arylcarboxyalkyl; and $R_7$, $R_8$, $R_9$, and $R_{10}$ are each independently a member selected from the group consisting of hydrogen, alkyl, alkoxy, halo, haloalkyl, haloalkoxy and hydroxy or $R_7$ and $R_8$ taken together with the carbon atom that they are attached form oxo.

3. A compound that is cis-N-(7-chloroquinolin-4-yl)-N'-(3,5-dimethylphenyl)cyclohexane-1,4-diamine.

4. A compound of formula (Ib),

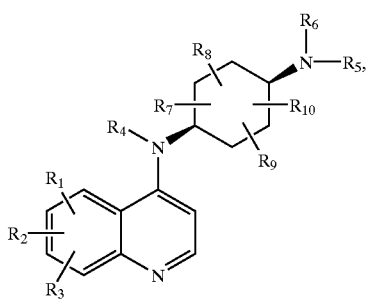

or a therapeutically suitable salts, prodrug thereof, wherein $R_1$, $R_2$ and $R_3$ are each independently a member selected from the group consisting of hydrogen, alkyl, alkoxy, halo, haloalkyl, haloalkoxy, hydroxy and $R_A R_B N$— wherein $R_A$ and $R_B$ are each independently a member selected from the group consisting of hydrogen and alkyl, alkylcarbonyl, alkylsulfonyl, arylcarbonyl, arylsulfonyl and $R_C R_D$Ncarbonyl, wherein $R_C$ and $R_D$ are each independently a member selected from the group consisting of hydrogen, alkyl and aryl;

$R_4$ is a member selected from the group consisting of hydrogen and alkyl;

$R_5$ is -A-B;

A is a member selected from the group consisting of alkoxyalkylene, alkylene and hydroxyalkylene;

B is a substituted or unsubstituted heterocycle wherein the heterocycle is selected from the group consisting of azetidinyl, azepanyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridinyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl (thiomorpholine sulfone), thiopyranyl, triazinyl, triazolyl, trithianyl, benzimidazolyl, benzodioxinyl, benzothiazolyl, benzothienyl, benzotriazolyl, benzoxazolyl, benzofuranyl, benzopyranyl, benzothiopyranyl, cinnolinyl, indazolyl, indolyl, 2,3-dihydroindolyl, indolizinyl, naphthpyridinyl, isobenzofuranyl, isobenzothienyl, isoindolyl, isocininolinyl, phthalazinyl, 4H-pyrido(1,2-a)pyrimidin-4-one, pyranopyridinyl, quinolizinyl, quinoxalinyl, acridinyl, carbazolyl, carbolinyl, dibenzo(b,d)furanyl, dibenzo(b,d)thienyl, naphtho(2,3-b)furan, naphtho(2,3-b)thienyl, phenazinyl, phenothiazinyl, phenoxazinyl, thianthrenyl, thioxanthenyl, and xanthenyl;

$R_6$ is a member selected from the group consisting of hydrogen, alkyl and arylcarboxyalkyl; and $R_7$, $R_8$, $R_9$, and $R_{10}$ are each independently a member selected from the group consisting of hydrogen, alkyl, alkoxy, halo, haloalkyl, haloalkoxy and hydroxy or $R_7$ and $R_8$ taken together with the carbon atom that they are attached form oxo.

5. The compound selected from the group consisting of
cis-N-(2,8-bis(trifluoromethyl)quinolin-4-yl)-N'-(7-chloroquinolin-4-yl)cyclohexane-1,4-diamine;
cis-N-(7-chloroquinolin-4-yl)-N'-(3,5-difluoronhenvl)cyclohexane-1,4-diamine;
cis-N-(7-chloroquinolin-4-yl)-N'-phenylcyclohexane-1,4-diamine;
cis-N-(7-chloroquinolin-4-yl)-N'-(2-fluorophenyl)cyclohexane-1,4-diamine;
cis-N-(7-chloroquinolin-4-yl)-N'-(3-fluorophenyl)cvciohexane-1,4-diamine;
cis-N-(7-chloroquinolin-4-yl)-N'-2-naphthylcyclohexane-1,4-diamine;
cis-N-(7-chloroquinolin-4-yl)-N'-(3-fluoro-4-methvlvhenvl)cyclohexane-1,4-diamine;
cis-N-(7-chloroquinolin-4-yl)-N'-1-naphthylcyclohexane-1,4-diamine;
cis-N-(7-chloroquinolin-4-yl)-N'-(3,5-dichlorophenyl)cyclohexane-1,4-diamine;
cis-N-(7-chloroquinolin-4-yl)-N'-(3-methylphenyl)cyclohexane-1,4-diamine;
cis-N-(3,5-bis(trifluoromethyl)phenyl)-N'-(7-chloroquinolin-4-yl)cyclohexane-1,4-diamine;
cis-N-1,1'-biphenyl-3-yl-N'-(7-chloroquinolin-4-yl)cyclohexane-1,4-diamine;
cis-N-(7-chloroquinolin-4-yl)-N'-(3-(trifluoromethyl)phenyl)cyclohexane-1,4-diamine;
cis-4-{(4-((7-chloroquinolin-4-yl)amino)cyclohexvl}amino)-2H-chromen-2-one;
cis-N,N'-bis(7-chloro-4-aminoquinolin-4-cyclohexane-1,4-diamine;
cis-N-1,1'-biphenyl-3-yl-N'-(7-chloroquinolin-4-yl)cyclohexane-1,4-diamine;
cis-N-(7-chloroquinazolin-4-yl)-N'-(7-chloroquinolin-4-yl)cyclohexane-1,4-diamine;
cis-4-({4-((7-chloroquinolin-4-yl)amino)cyclohexyl}amino)-2H-chromen-2-one;
cis-N-(7-chloroquinolin-4-yl)-N'-pyridin-2-ylcyclohexane-1,4-diamine;
cis-N-(7-chloroquinolin-4-yl)-N'-isoquinolin-4-ylcyclohexane-1,4-diamine;
cis-N-(7-chloroquinolin-4-yl)-N'-quinolin-3-ylcyclohexane-1,4-diamine;
(1S,2R,4S,5R)-N,N'-bis(7-chloroquinolin-4-yl)-2,5-dimethylcyclohexane-1,4-diamine;
(1S,2R,4S,5R)-N-(7-chloroquinolin-4-yl)-N'-(3,5-dimethylphenyl)-2,5-dimethylcyclohexane-1,4-diamine;
N-((1S,2R,4S,5R)-4-((7-chloroquinolin-4-yl)amino)-2,5-dimethylcyclohexyl)-3,5-difluorobenzamide;
5-bromo-N-{4-((7-chloroquinolin-4-yl)amino)cyclohexyl}-2-hydroxybenzamide;
(1S,2R,4S,5R)-N,N'-bis(7-chloroquinolin-4-yl)-2,5-dimethylcyclohexane-1,4-diamine; 4-({4-((7-chloroquinolin-4-yl)amino)cyclohexyl}amino)-6-methyl-2H-chromen-2-one;
N-(7-chloroquinolin-4-yl)-N'-(2',5-dimethyl-1,1'-biphenyl-3-yl)cyclohexane-1,4-diamine;

N-(5-bromopyridin-3-yl)-N'-(7-chloroquinolin-4-yl)cyclohexane-1,4-diamine;

N-(7-chloroquinolin-4-yl)-N'-(4-methoxy-3,5-dimethylphenyl)cyclohexane-1,4-diamine;

N-(7-chloroquinolin-4-yl)-N'-(5-methvl-1,1'-biphenyl-3-yl)cyclohexane-1,4-diamine;

6-(2-({4-((7-chloroquinolin-4-yl)amino)cyclohexyl}amino)-1,3-thiazol-4-yl)-3,4-dihydroquinolin-2(1H)-one;

N-(3-bromo-5-methylphenyl)-N'-(7-chloroquinolin-4-yl)cyclohexane-1,4-diamine;

N-(7-chloroquinolin-4-yl)-N'-(3-methyl-5-pyridin-4-ylphenyl)cyclohexane-1,4-diamine;

N-(7-chloroquinolin-4-yl)-N'-(4',5-dimethyl-1,1'-biphenyl-3-yl)cyclohexane-1,4-diamine;

N-(7-chloroquinolin-4-yl)-N'-(3',5-dimethyl-1,1'-biyhenyl-3-yl)cyclohexane-1,4-diamine;

N-(7-chloroquinolin-4-yl)-N'-(4-(3,4-dihydro-2H-1,5-benzodioxepin-7-yl)-1,3-thiazol-2-yl)cyclohexane-1,4-diamine;

N-(7-chloroquinolin-4-yl)-N'-(4-methyl-5-phenyl-1,3-thiazoi-2-yl)cyclohexane-1,4-diamine;

N-(7-chloroquinolin-4-yl)-N'-(5-phenylpyridin-3-yl)cyclohexane-1,4-diamine;

3'-({4-((7-chloroquinolin-4-yl)amino)cvclohexyl}amino)-5'-methyl-1,1'-biphenyl-4-ol;

N'-{4-((2-N-methylamino-7-chloroquinolin-4-yl)amino)cyclohexyl}-7-chloro-N-methylquinoline-2,4-diamine;

N-(7-chloroquinolin-4-yl)-N'-(4-(4-methoxyphenyl)-1,3-thiazol-2-yl)cyclohexane-1,4-diamine;

N-(7-chloroquinolin-4-yl)-N'-(4,5-dimethyl-1,3-thiazol-2-yl)cyclohexane-1,4-diamine;

cis-N-(4-bromobenzyl)-N'-(7-chloroquinolin-4-yl)cyclohexane-1,4-diamine;

cis-N-(7-chloroquinolin-4-yl)-N'-{(4-(dimethylamino)-1-naphthyl)methyl}cyclohexane-1,4-diamine;

cis-N-(7-chloroquinolin-4-yl)-N'-(4-pyridin-2-ylbenzyl)cyclohexane-1,4-diamine;

cis-N-(7-chloroquinolin-4-yl)-N'-(1H-indol-6-ylmethyl)cyclohexane-1,4-diamine;

cis-N-(4,4-bis(4-fluorophenyl)butyl)-N'-(7-chloroquinolin-4-yl)cyclohexane-1,4-diamine;

cis-N-(7-chloroquinolin-4-yl)-N'-(4-phenylbutyl)cyclohexane-1,4-diamine;

cis-N-(7-chloroquinolin-4-yl)-N'-(5-phenylpentyl)cyclohexane-1,4-diamine;

cis-N-(7-chloroquinolin-4-yl)-N'-(3,5-difluorobenzyl)cyclohexane-1,4-diamine;

cis-N-(7-chloroquinolin-4-yl)-N'-(3-fluorobenzyl)cyclohexane-1,4-diamine; and cis-7-chloro-N~4~-(4-{(3-(trifluoromethyl)benzyl)amino}cyclohexyl)quinoline-2,4-diamine.

6. A compound according to formula (Ic)

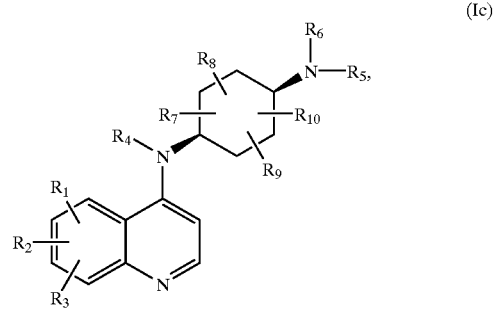

(Ic)

or a therapeutically suitable salts, or prodrug thereof, wherein $R_1$, $R_2$ and $R_3$ are each independently a member selected from the group consisting of hydrogen, alkyl, alkoxy, halo, haloalkyl, haloalkoxy, hydroxy and $R_A R_B N$— wherein $R_A$ and $R_B$ are each independently a member selected from the group consisting of hydrogen and alkyl, alkylcarbonyl, alkylsulfonyl, arylcarbonyl, arylsulfonyl and $R_C R_D$Ncarbonyl, wherein $R_C$ and $R_D$ are each independently a member selected from the group consisting of hydrogen, alkyl and aryl;

$R_4$ is a member selected from the group consisting of hydrogen and alkyl;

$R_5$ is —$(CH_2)_m$—C(O)-A-B, m is from 0–6;

A is absent or is a member selected from the group consisting of alkoxyalkylene, alkylene and hydroxyalkylene;

B is a member selected from the group consisting of hydrogen, alkyl, aryl, arylC(O)—, arylS(O)$_2$—, arylalkenyl, aryloxyalkyl, biaryl, biarylalkyl, cycloalkyl, heterocycle, heterocycleC(O)—, heterocycleS(O)$_2$—, haloalkyl, $R_E R_F N$—, $R_E R_F NC(O)$—, $R_G S$— and $R_G O$—;

$R_E$ and $R_F$ are each independently a member selected from the group consisting of hydrogen, alkyl, alkylC(O)—, aryl, arylalkyl, heterocycle, heterocyclealkyl, arylC(O)— and arylS(O)$_2$—;

$R_G$ is a member selected from the group consisting of hydrogen, alkyl, aryl, arylalkyl and heterocycle;

$R_6$ is a member selected from the group consisting of hydrogen, alkyl and arylcarboxyalkyl; and $R_7$, $R_8$, $R_9$, and $R_{10}$ are each independently a member selected from the group consisting of hydrogen, alkyl, alkoxy, halo, haloalkyl, haloalkoxy and hydroxy or $R_7$ and $R_8$ taken together with the carbon atom that they are attached form oxo.

7. The compound according to claim 6, wherein m is 0; and

A is absent.

8. The compound according to claim 6, wherein m is 0;

A is absent; and

B is a member selected from the group consisting of aryl, arylalkenyl, aryloxyalkyl, biaryl and heterocycle.

9. The compound according to claim 8 selected from the group consisting of cis-N-{4-((7-chloroquinolin-4-yl)amino)cyclohexyl}-1H-indole-6-carboxamide;

cis-N-{4-((7-chloroquinolin-4-yl)amino)cyclohexyl}-3-methylbenzamide;
cis-N-{4-((7-chloroquinolin-4-yl)amino)cyclohexyl}-4-methylbenzamide;
cis-2-amino-N-{4-((7-chloroquinolin-4-yl)amino)cyclohexyl}benzamide;
cis-N-{4-((7-chloroquinolin-4-yl)amino)cyclohexyl}-2-hydroxybenzamide;
cis-N-{4-((7-chloroquinolin-4-yl)amino)cyclohexyl}-3-hydroxybenzamide;
cis-N-{4-((7-chloroquinolin-4-yl)amino)cyclohexyl}-3-methoxybenzamide;
cis-N-{4-((7-chloroquinolin-4-yl)amino)cyclohexyl}-4-methoxybenzamide;
cis-N-{4-((7-chloroquinolin-4-yl)amino)cyclohexyl}-3-fluorobenzamide;
cis-N-{4-((7-chloroquinolin-4-yl)amino)cyclohexyl}-4-fluorobenzamide;
cis-4-chloro-N-{4-((7-chloroquinolin-4-yl)amino)cyclohexyl}benzamide;
cis-2-bromo-N-{4-((7-chloroquinolin-4-yl)amino)cyclohexyl}benzamide;
cis-3-bromo-N-{4-((7-chloroquinolin-4-yl)amino)cyclohexyl}benzaxnide;
cis-4-bromo-N-{4-((7-chloroquinolin-4-yl)amino)cyclohexyl}benzamide;
cis-N-{4-((7-chloroquinolin-4-yl)amino)cyclohexyl}-4-cyanobenzamide;
cis-N-{4-((7-chloroquinolin-4-yl)amino)cyclohexyl}-3-(dimethylamino)benzamide;
cis-N-{4-((7-chloroquinolin-4-yl)amino)cyclohexyl}-3-cyanobenzamide;
cis-N-{4-((7-chloroquinolin-4-yl)amino)cyclohexyl}-4-(dimethylamino)benzamide;
cis-N-{4-((7-chloroquinolin-4-yl)amino)cyclohexyl}-3-(trifluoromethyl)benzamide;
cis-N-{4-((7-chloroquinolin-4-yl)amino)cyclohexyl}-4-(trifluoromethyl)benzamide;
cis-N-{4-((7-chloroquinolin-4-yl)amino)cyclohexyl}-2,3-dimethylbenzamide;
cis-N-{4-((7-chloroquinolin-4-yl)amino)cyclohexyl}-2,4-dimethylbenzamnide;
cis-N-{4-((7-chloroquinolin-4-yl)amino)cyclohexyl}-3-(trifluoromethoxy)benzamide;
cis-N-{4-((7-chloroquinolin-4-yl)amino)cyclohexyl}-2,5-dimethylbenzamide;
cis-N-{4-((7-chloroquinolin-4-yl)amino)cyclohexyl}-3,4-dimethylbenzamide;
cis-N-{4-((7-chloroquinolin-4-yl)amino)cyclohexyl}-2,4-dimethoxybenzamide;
cis-N-{4-((7-chloroquinolin-4-yl)amino)cyclohexyl}-3,4-dimethoxybenzamide;
cis-N-{4-((7-chloroquinolin-4-yl)amino)cyclohexyl}-3,5-dimethoxybenzamide;
cis-N-{4-((7-chloroquinolin-4-yl)amino)cyclohexyl}-1,3-benzodioxole-5-carboxamide;
cis-N-{4-((7-chloroquinolin-4-yl)amino)cyclohexyl}-3,4,5-trimethoxybenzamide;
cis-2,4-dichloro-N-{4-((7-chloroquinolin-4-yl)amino)cyclohexyl}benzamide;
cis-3,4-dichloro-N-{4-((7-chloroquinolin-4-yl)amino)cyclohexyl}benzamide;
cis-N-{4-((7-chloroquinolin-4-yl)amino)cyclohexyl}-2-furamide;
cis-N-{4-((7-chloroquinolin-4-yl)amino)cyclohexyl}-3-furamide;
cis-N-{4-((7-chloroquinolin-4-yl)amino)cyclohexyl}-2,5-dimethyl-3-furamide;
cis-N-{4-((7-chloroquinolin-4-yl)amino)cyclohexyl}thiophene-2-carboxamide;
cis-N-{4-((7-chloroquinolin-4-yl)amino)cyclohexyl}thiophene-3-carboxamide;
cis-N-{4-((7-chloroquinolin-4-yl)amino)cyclohexyl}-3-methylthiophene-2-carboxamide;
cis-N-{4-((7-chloroquinolin-4-yl)axnino)cyclohexyl}-1H-pyrrole-2-carboxainide;
cis-N-{4-((7-chloroquinolin-4-yl)amino)cyclohexyl}-3,5-dimethylbenzamide;
cis-N-{4-((7-chloroquinolin-4-yl)amino)cyclohexyl}-5-methylthiophene-2-carboxamide;
cis-N-{4-((7-chloroquinolin-4-yl)amino)cyclohexyl}-2,5-dimethyl-1H-pyrrole-3-carboxamide;
cis-N-{4-((7-chloroquinolin-4-yl)amino)cyclohexyl}-1,2,5-trimethyl-1H-pyrrole-3-carboxamide;
cis-N-{4-((7-chloroquinolin-4-yl)amino)cyclohexyl}-1,3-thiazole-2-carboxamide;
cis-N-{4-((7-chloroquinolin-4-yl)amino)cyclohexyl}-1-methyl-1H-pyrrole-2-carboxamide;
cis-N-{4-((7-chloroquinolin-4-yl)amino)cyclohexyl}-1,3-thiazole-4-carboxamide;
cis-N-{4-((7-chloroquinolin-4-yl)amino)cyclohexyl}-1,3-thiazole-5-carboxamide;
cis-N-{4-((7-chloroquinolin-4-yl)amino)cyclohexyl}isoxazole-5-carboxamide;
cis-N-{4-((7-chloroquinolin-4-yl)amino)cyclohexyl}-5-methyl-3-phenylisoxazole-4-carboxamide;
cis-N-{4-((7-chloroquinolin-4-yl)amino)cyclohexyl}pyridine-2-carboxamide;
cis-N-{4-((7-chloroquinolin-4-yl)amino)cyclohexyl}-3-hydroxypyridine-2-carboxamide;
cis-N-{4-((7-chloroquinolin-4-yl)amino)cyclohexyl}-2-hydroxynicotinamide;
cis-N-{4-((7-chloroquinolin-4-yl)amino)cyclohexyl}-5-methylpyrazine-2-carboxamide;
cis-N-{4-((7-chloroquinolin-4-yl)amino)cyclohexyl}-1H-indole-3-carboxamide;
cis-N-{4-((7-chloroquinoiin-4-yl)amino)cyclohexyl}-8-methyl-4-oxo-4H-pyrido(1,2-a)pyrimidine-3-carboxamide;
cis-N-{4-((7-chloroquinolin-4-yl)amino)cyclohexyl}-5-methyl-1-phenyl-1H-pyrazole-4-carboxamide;
cis-N-{4-((7-chloroquinolin-4-yl)amino)cyclohexyl}-4-oxo-4,5,6,7-tetrahydro-1-benzofuran-3-carboxamide;
cis-6-chloro-N-{4-((7-chloroquinolin-4-yl)amino)cyclohexyl}-2H-chromene-3-carboxamide;
cis-N-{4-((7-chloroquinolin-4-yl)amino)cyclohexyl}-4-ethylbenzamide;
cis-N-{4-((7-chloroquinolin-4-yl)amino)cyclohexyl}-2-hydroxy-4-methylbenzamide;
cis-N-{4-((7-chloroquinolin-4-yl)amino)cyclohexyl}-3-hydroxy-4-methylbenzamide;
cis-N-{4-((7-chloroquinolin-4-yl)amino)cyclohexyl}-5-fluoro-2-methylbenzamide;
cis-N-{4-((7-chloroquinolin-4-yl)amino)cyclohexyl}-3-fluoro-4-methylbenzamide;

cis-N-{4-((7-chloroquinolin-4-yl)amino)cyclohexyl}-2,3-difluorobenzamide;
cis-N-{4-((7-chloroquinolin-4-yl)amino)cyclohexyl}-2,4-difluorobenzamide;
cis-N-{4-((7-chloroquinolin-4-yl)amino)cyclohexyl}-2,5-difluorobenzamide;
cis-N-{4-((7-chloroquinolin-4-yl)amino)cyclohexyl}-3,5-difluorobenzamide;
cis-4-acetyl-N-{4-((7-chloroquinolin-4-yl)amino)cyclohexyl}benzamide;
cis-N-{4-((7-chloroquinolin-4-yl)amino)cyclohexyl}-3-methoxy-4-methylbenzamide;
cis-N-{4-((7-chloroquinolin-4-yl)amino)cyclohexyl}-2-ethoxybenzamide;
cis-N-{4-((7-chloroquinolin-4-yl)amino)cyclohexyl}-4-(methylthio)benzamide;
cis-N-{4-((7-chloroquinolin-4-yl)amino)cyclohexyl}-3-fluoro-4-methoxybenzamide;
cis-N-{4-((7-chloroquinolin-4-yl)amino)cyclohexyl}-2-naphthamide;
cis-N-{4-((7-chloroquinolin-4-yl)amino)cyclohexyl}-1-naphthamide;
cis-5-chloro-N-{4-((7-chloroquinolin-4-yl)amino)cyclohexyl}-2-hydroxybenzamide;
cis-2-(acetylamino)-N-{4-((7-chloroquinolin-4-yl)amino)cyclohexyl}benzamide;
cis-4-(acetylamino)-N-{4-((7-chloroquinolin-4-yl)amino)cyclohexyl}benzamide;
cis-N-{4-((7-chloroquinolin-4-yl)amino)cyclohexyl}-4-isopropoxybenzamide;
cis-5-chloro-N-{4-((7-chloroquinolin-4-yl)amino)cyclohexyl}-2-metboxybenzamide;
cis-N-{4-((7-chloroquinolin-4-yl)amino)cyclohexyl}-4-fluoro-1-naphthamide;
cis-N-{4-((7-chloroquinolin-4-yl)amino)cyclohexyl}-3,4-diethoxybenzamide;
cis-2-benzyl-N-{4-((7-chloroquinolin-4-yl)amino)cyclohexyl}benzamide;
cis-N-{4-((7-chloroquinolin-4-yl)amino)cyclohexyl}-2-(2-phenylethyl)benzamide;
cis-2-bromo-N-{4-((7-chloroquinolin-4-yl)amino)cyclohexyl}-5-methoxybenzamide;
cis-N-{4-((7-chloroquinolin-4-yl)amino)cyclohexyl}-2-(4-methylbenzoyl)benzamide;
cis-N-{4-((7-chloroquinolin-4-yl)amino)cyclohexyl}-2-iodobenzamide;
cis-N-{4-((7-chloroquinolin-4-yl)amino)cyclohexyl}-3-iodobenzamide;
cis-N-{4-((7-chloroquinolin-4-yl)amino)cyclohexyl}-4-iodobenzamide;
cis-2-chloro-N-{4-((7-chloroquinolin-4-yl)amino)cyclohexyl}isonicotinamide;
cis-2-chloro-N-{4-((7-chloroquinolin-4-yl)amino)cyclohexyl}-6-methylisonicotinamide;
cis-2,6-dichloro-N-{4-((7-chloroquinolin-4-yl)amino)cyclohexyl}isonicotinamide;
cis-N-{4-((7-chloroquinolin-4-yl)amino)cyclohexyl}-4-phenoxybutanamide;;
cis-N-{4-((7-chloroquinolin-4-yl)amino)cyclohexyl}-3-(3-methyl-1H-indol-1-yl)propanamide;
cis-N-{4-((7-chloroquinolin-4-yl)amino)cyclohexyl}-3-(1-methyl-1H-benzimidazol-2-yl)propanamide;
cis-1-benzoyl-N-{4-((7-chloroquinolin-4-yl)amino)cyclobexyl}piperidine-4-carboxamide;
cis-N-{4-((7-chloroquinolin-4-yl)amino)cyclohexyl}-N'-(4-propoxyphenyl)urea;
cis-N-(5-tert-butyl-2-methoxyphenyl)-N'-{4-((7-chloroquinolin-4-yl)amino)cyclohexyl}urea;
cis-3,5-difluoro-N-(4-{(6-fluoro-2-(trifluoromethyl)quinolin-4-yl)amino}cyclohexyl)benzamide;
cis-3 ,5-difluoro-N-(4-{(8-(trifluoromethoxy)-2-(trifluoromethyl)quinolin-4-yl)amino}cyclohexyl)benzamide;
cis-N-(4-{(5,7-dichloro-2-(trifluoromethyl)quinolin-4-yl)amino}cyclohexyl)-3,5-difluorobenzamide;
cis-3,5-difluoro-N-(4-{(6-methyl-2-(trifluoromethyl)quinolin-4-yl)amino}cyclohexyl)benzamide;
cis-N-{4-((2-amino-7-chloroquinolin-4-yl)amino)cyclohexyl}-3,5-difluorobenzamide;
cis-N-{4-((2-amino-7-chloroquinolin-4-yl)amino)cyclohexyl}-3,5-dichlorobenzamide;
cis-N-{4-((2-amino-7-chloroquinolin-4-yl)amino)cyclohexyl}-4-phenoxybutanamide;
3-bromo-N-{4-((7-chloroquinolin-4-yl)amino)cyclohexyl}-5-fluorobenzamide;
N-{4-((7-chloroquinolin-4-yl)amino)cyclohexyl}-2-hydroxy-5-methylbenzamide;
N-{4-((7-chloroquinolin-4-yl)amino)cyclohexyl}-2,2-diphenylacetamide;
N-{4-((7-chloroquinolin-4-yl)amino)cyclohexyl}-5-fluoro-2-hydroxybenzamide;
N-{(1S,2R,4S,5R)-4-((7-chloroquinolin-4-yl)amino)-2,5-dimethylcyclohexyl}-3,5-difluorobenzamide;
3-(5-acetylthien-2-yl)-N-{4-((7-chloroquinolin-4-yl)amino)cyclohexyl}-5-fluorobenzamide;
N-{4-((7-chloroquinolin-4-yl)amino)cyclohexyl}-2-hydroxy-5-methoxybenzamide;
4-chloro-N-{4-((7-chloroquinolin-4-yl)amino)cyclohexyl}-2-hydroxybenzamide;
N-{4-((7-chloroquinolin-4-yl)amino)cyclohexyl}quinoline-3-carboxamide;
N-{4-((7-chloroquinolin-4-yl)amino)cyclohexyl}-2-hydroxy-3-methylbenzamide;
N-{4-((7-chloroquinolin-4-yl)amino)cyclohexyl}-2,6-dimethoxynicotinamide;
3-chloro-N-{4-((7-chloroquinolin-4-yl)amino)cyclohexyl}-5-fluorobenzamide;
3'-amino-N-{4-((7-chloroquinolin-4-yl)amino)cyclohexyl}-5-fluoro-1,1'-biphenyl-3-carboxamide;
N-{4-((7-chloroquinolin-4-yl)amino)cyclohexyl}-5-fluoro-3'-hydroxy-1,1'-biphenyl-3-carboxamide;
N-{4-((7-chloroquinolin-4-yl)amino)cyclohexyl}-5-fluoro-3'-(hydroxymethyl)-1,1'-biphenyl-3-carboxamide;
N-{4-((7-chloroquinolin-4-yl)amino)cyclohexyl}-5-fluoro-4'-hydroxy-1,1'-biphenyl-3-carboxamide;

N-(4-((7-chloroquinolin-4-yl)amino)cyclohexyl)-1H-indole-4-carboxamide;
N-{4-((7-chloroquinolin-4-yl)amino)cyclohexyl}quinoxaline-2-carboxamide;
4'-amino-N-{4-((7-chloroquinolin-4-yl)amino)cyclohexyl}-5-fluoro-1,1'-biphenyl-3-carboxamide;
N-{4-((7-chloroquinolin-4-yl)amino)cyclohexyl}-2-hydroxy-4-methoxybenzamide;
N-{4-((7-chloroquinolin-4-yl)amino)cyclohexyl}cinnoline-4-carboxamide;
N-{4-((7-chloroquinolin-4-yl)amino)cyclohexyl}-2-hydroxy-6-methoxybenzamide;
3'-acetyl-N-{4-((7-chloroquinolin-4-yl)amino)cyclohexyl}-5-fluoro-1,1'-biphenyl-3-carboxamide;
5-bromo-N-{4-((7-chloroquinolin-4-yl)amino)cyclohexyl}-2-hydroxy-3-methylbenzamide;
3-(1,3-benzodioxol-5-yl)-N-{4-((7-chloroquinolin-4-yl)amino)cyclohexyl}-5-fluorobenzamide;
N-{4-((7-chloroquinolin-4-yl)amino)cyclohexyl}-5-fluoro-2'-hydroxy-1,1'-biphenyl-3-carboxamide;
4'-acetyl-N-{4-((7-chloroquinolin-4-yl)amino)cyclohexyl}-5-fluoro-1,1'-biphenyl-3-carboxamnide;
N-{4-((7-chloroquinolin-4-yl)amino)cyclohexyl}-6-methylnicotinamide;
N-{4-((7-chloroquinolin-4-yl)amino)cyclohexyl}-3-fluoro-5-pyridin-4-ylbenzamide;
2-chloro-N-{4-((7-chloroquinolin-4-yl)amino)cyclohexyl}nicotinamide;
N-{4-((7-chloroquinolin-4-yl)amino)cyclohexyl}-2-hydroxy-5-iodobenzamide;
N-{4-((7-chloroquinolin-4-yl)amino)cyclohexyl}-2-fluoro-6-hydroxybenzamide;
N-{4-((7-chloroquinolin-4-yl)amino)cyclohexyl}-3-fluoro-5-thien-3-ylbenzamide;
N-{4-((7-chloroquinolin-4-yl)amino)cyclohexyl}-3-fluoro-5-((E)-2-phenylvinyl)benzamide;
3-chloro-N-{4-((7-chloroquinolin-4-yl)amino)cyclohexyl}-2-hydroxybenzamide;
N-{4-((7-chloroquinolin-4-yl)amino)cyclohexyl}-3-fluoro-5-thien-2-ylbenzamide;
N-{4-((7-chloroquinolin-4-yl)amino)cyclohexyl}-8-hydroxyquinoline-7-carboxamide;
N-{4-((7-chloroquinolin-4-yl)amino)cyclohexyl}-2-hydroxy-1-naphthamide;
N-{4-((7-chloroquinolin-4-yl)amino)cyclohexyl}-2-hydroxy-3-isopropylbenzamide;
N-{4-((7-chloroquinolin-4-yl)amino)cyclohexyl}-3-hydroxy-2-naphthamide;
N-{4-((7-chloroquinolin-4-yl)amino)cyclohexyl}tetrahydrofuran-2-carboxamide;
3'-(({4-((7-chloroquinolin-4-yl)amino)cyclohexyl}amino)carbonyl)-5'-fluoro-1,1'-biphenyl-3-carboxylic acid;
3'-(({4-((7-chloroquinolin-4-yl)amino)cyclohexyl}amino)carbonyl)-5'-fluoro-1,1'-biphenyl-4-carboxylic acid; and
7-chloro-N-{4-((7-chloroquinolin-4-yl)amino)cyclohexyl}-4-hydroxyquinoline-3-carboxamide.

10. A compound of formula (Id),

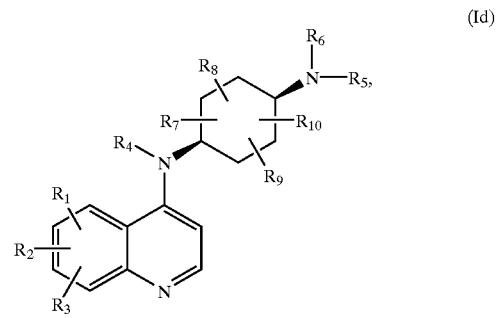

or a therapeutically suitable salts, or prodrug thereof, wherein $R_1$, $R_2$ and $R_3$ are each independently a member selected from the group consisting of hydrogen, alkyl, alkoxy, halo, haloalkyl, haloalkoxy, hydroxy and $R_A R_B N$— wherein $R_A$ and $R_B$ are each independently a member selected from the group consisting of hydrogen and alkyl, alkylcarbonyl, alkylsulfonyl, arylcarbonyl, arylsulfonyl and $R_C R_D N$carbonyl, wherein $R_C$ and $R_D$ are each independently a member selected from the group consisting of hydrogen, alkyl and aryl;

$R_4$ is a member selected from the group consisting of hydrogen and alkyl;

$R_5$ is —$(CH_2)_m$—C(O)-A-B;

m is 0;

A is a member selected from the group consisting of alkoxyalkylene, alkylene and hydroxyalkylene;

B is a member selected from the group consisting of arylC(O)—, arylNC(O)—, arylS(O)$_2$—, heterocycleC(O)—, heterocycleNC(O)— and heterocycleS(O)$_2$—;

$R_6$ is a member selected from the group consisting of hydrogen, alkyl and arylcarboxyalkyl; and $R_7$, $R_8$, $R_9$, and $R_{10}$ are each independently a member selected from the group consisting of hydrogen, alkyl, alkoxy, halo, haloallcyl, haloalkoxy and hydroxy or $R_7$ and $R_8$ taken together with the carbon atom that they are attached form oxo.

11. The compound according to claim 10 selected from the group consisting of

N-{4-((7-chloroquinolin-4-yl)amino)cyclohexyl}-4-oxo-4-thien-2-ylbutanamide;

N-{4-((7-chloroquinolin-4-yl)amino)cyclohexyl}-3-(phenylsulfonyl)propanamide;

N-{4-((7-chloroquinolin-4-yl)amino)cyclohexyl}-4-(4-methoxyphenyl)-4-oxobutanamide; and N-{4-((7-chloroquinolin-4-yl)amino)cyclohexyl}-4-oxo-4-phenylbutanamide.

12. A compound of formula (Ie),

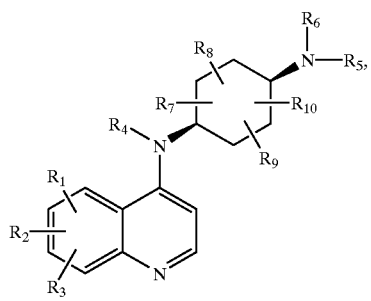

or a therapeutically suitable salts, or prodrug thereof, wherein $R_1$, $R_2$ and $R_3$ are each independently a member selected from the group consisting of hydrogen, alkyl, alkoxy, halo, haloalkyl, haloalkoxy, hydroxy and $R_AR_BN$—wherein $R_A$ and $R_B$ are each independently a member selected from the group consisting of hydrogen and alkyl, alkylcarbonyl, alkylsulfonyl, arylcarbonyl, arylsulfonyl and $R_CR_D$Ncarbonyl, wherein $R_C$ and $R_D$ are each independently a member selected from the group consisting of hydrogen, alkyl and aryl;

$R_4$ is a member selected from the group consisting of hydrogen and alkyl;

$R_5$ is —$(CH_2)_m$—C(O)-A-B;

m is from 1–6;

A is absent;

B is a member selected from the group consisting of aryl and heterocycle;

$R_6$ is a member selected from the group consisting of hydrogen, alkyl and arylcarboxyalkyl; and $R_7$, $R_8$, $R_9$, and $R_{10}$ are each independently a member selected from the group consisting of hydrogen, alkyl, alkoxy, halo, haloalkyl, haloalkoxy and hydroxy or $R_7$ and $R_8$ taken together with the carbon atom that they are attached form oxo.

13. The compound according to claim 12 selected from the group consisting of cis-2-(N-{4-((7-chloroquinolin-4-yl)amino)cyclohexyl}glycyl)benzaldehyde;

cis-di-3-({4-((7-chloroquinolin-4-yl)amino)cyclohexyl}amino)-1-(4-fluorophenyl)propan-1-one; and cis-5-({4-((7-chloroquinolin-4-yl)amino)cyclohexyl}amino)-1-(4-fluorophenyl)pentan-1-one.

14. A compound of formula (If),

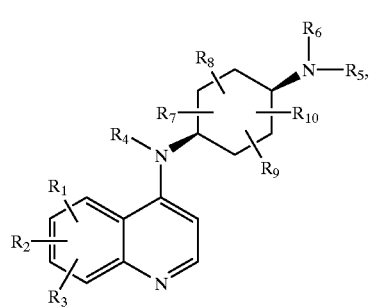

or a therapeutically suitable salts, or prodrug thereof, wherein $R_1$, $R_2$ and $R_3$ are each independently a member selected from the group consisting of hydrogen, alkyl, alkoxy, halo, haloalkyl, haloalkoxy, hydroxy and $R_AR_BN$—wherein $R_A$ and $R_B$ are each independently a member selected from the group consisting of hydrogen and alkyl, alkylcarbonyl, alkylsulfonyl, arylcarbonyl, arylsulfonyl and $R_CR_D$Ncarbonyl, wherein $R_C$ and $R_D$ are each independently a member selected from the group consisting of hydrogen, alkyl and aryl;

$R_4$ is a member selected from the group consisting of hydrogen and alkyl;

$R_5$ is —$(CH_2)_m$—C(O)-A-B;

m is 0;

A is absent or is a member selected from the group consisting of alkoxyalkylene, alkylene and hydroxyalkylene;

B is a member selected from the group consisting of aryl and heterocycle;

$R_6$ is a member selected from the group consisting of hydrogen, alkyl and arylcarboxyalkyl; and $R_7$, $R_8$, $R_9$, and $R_{10}$ are each independently a member selected from the group consisting of hydrogen, alkyl, alkoxy, halo, haloalkyl, haloalkoxy and hydroxy or $R_7$ and $R_8$ taken together with the carbon atom that they are attached form oxo.

15. The compound selected from the group consisting of cis-N-{4-((7-chloroquinolin-4-yl)amino)cyclohexyl}-2-(4-fluorophenyl)acetamide;

cis-N-{4-((7-chloroquinolin-4-yl)amino)cyclohexyl}-5-phenylpentanamide;

cis-N-{4-((7--chloroquinolin-4-yl)amino)cyclohexyl}-2-(6-methoxy-3-oxo-2,3-dihydro-1H-inden-1-yl)acetamide;

cis-N-{4-((7-chloroquinolin-4-yl)amino)cyclohexyl}-2-(3-fluorophenyl)acetamide;

cis-N-{4-((7-chloroquinolin-4-yl)amino)cyclohexyl}-2-(3-(trifluoromethyl)phenyl)acetamide;

cis-N-{4-((7-chloroquinolin-4-yl)amino)cyclohexyl}-2-(4-(trifluoroniethyl)phenyl)acetamide;

N-{4-((7-chloroquinolin-4-yl)amino)cyclohexyl}-3-methyl-2-phenylpentanamide;

(2R)-N-{4-((7-chloroquinolin-4-yl)amino)cyclohexyl}-2-methoxy-2-phenylacetamide;

(2S)-N-{4-((7-chloroquinolin-4-yl)amino)cyclohexyl}-2-methoxy-2-phenylacetamide;

N-{4-((7-chloroquinolin-4-yl)amino)cyclohexyl}-2-(3,5-difluorophenyl)acetamide;

3-(2-chlorophenyl)-N-{4-((7-chloroquinolin-4-yl)amino)cyclohexyl}propanamide;

(2S)-N-{4-((7-chloroquinolin-4-yl)amino)cyclohexyl}-2-phenylbutanamide;

N-{4-((7-chloroquinolin-4-yl)amino)cyclohexyl}-3-phenylpropanamide;

3-(4-chlorophenyl)-N-{4-((7-chloroquinolin-4-yl)amino)cyclohexyl}propanamide;

N-{4-((7-chloroquinolin-4-yl)amino)cyclohexyl}-3-(2,5-dimethoxyphenyl)propanamide;

N-{4-((7-chloroquinolin-4-yl)amino)cyclohexyl}-4-thien-2-ylbutanamide;

N-{4-((7-chloroquinolin-4-yl)amino)cyclohexyl}-4-phenylbutanamide;

N-{4-((7-chloroquinolin-4-yl)amino)cyclohexyl}-3-(4-methoxyphenyl)propanamide;

N-{4-((7-chloroquinolin-4-yl)amino)cyclohexyl}-3-(3-methoxyphenyl)propanamide;

N-{4-((7-chloroquinolin-4-yl)amino)cyclohexyl}-2-(3-phenoxyphenyl)acetamide;

N-{4-((7-chloroquinolin-4-yl)amino)cyclohexyl}-2-(4-(methylsulfonyl)phenyl)acetamide; and (2R)-N-{4-((7-chloroquinolin-4-yl)amino)cyclohexyl}-2-hydroxy-4-phenylbutanamide.

16. A compound of formula (Ig),

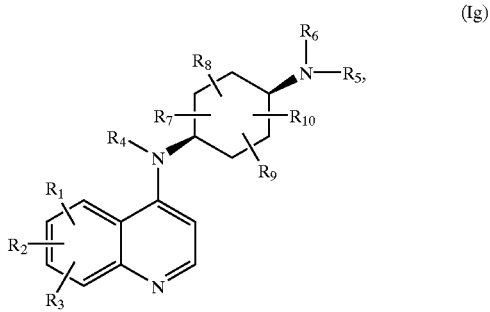

(Ig)

or a therapeutically suitable salts, or prodrug thereof, wherein $R_1$, $R_2$ and $R_3$ are each independently a member selected from the group consisting of hydrogen, alkyl, alkoxy, halo, haloalkyl, haloalkoxy, hydroxy and $R_AR_BN$— wherein $R_A$ and $R_B$ are each independently a member selected from the group consisting of hydrogen and alkyl, alkylcarbonyl, alkylsulfonyl, arylcarbonyl, arylsulfonyl and $R_CR_DN$carbonyl, wherein $R_C$ and $R_D$ are each independently a member selected from the group consisting of hydrogen, alkyl and aryl;

$R_4$ is a member selected from the group consisting of hydrogen and alkyl;

$R_5$ is —$(CH_2)_mC(O)$-A-B;

m is from 0–6;

A is absent or is a member selected from the group consisting of alkoxyalkylene, alkylene and hydroxyalkylene;

B is $R_ER_FN$—;

$R_E$ and $R_F$ are independently a member selected from the group consisting of hydrogen, alkyl, alkylC(O)—, aryl, arylalkyl, heterocycle, heterocyclealkyl, arylC(O)— and arylS(O)$_2$—;

$R_6$ is a member selected from the group consisting of hydrogen, alkyl and arylcarboxyalkyl; and $R_7$, $R_8$, $R_9$, and $R_{10}$ are each independently a member selected from the group consisting of hydrogen, alkyl, alkoxy, halo, haloalkyl, haloalkoxy and hydroxy or $R_7$ and $R_8$ taken together with the carbon atom that they are attached form oxo.

17. The compound according to claim 16 wherein $R_E$ is a member selected from the group consisting of alkylC(O)—, arylC(O)— and arylS(O)$_2$—;

m is 0; and

A is alkylene.

18. The compound according to claim 17 selected from the group consisting of cis-$N^2$-benzoyl-$N^1$-{4-((7-chloroquinolin-4-yl)amino)cyclohexyl}glycinamide cis-$N^1$-{4-((7-chloroquinolin-4-yl)amino)cyclohexyl}-$N^3$-(4-nitrobenzoyl)-β-alaninamide;

cis-$N^3$-benzoyl-$N^1$-{4-((7-chloroquinolin-4-yl)amino)cyclohexyl}-β-alaninamide;

N-(2-({4-((7-chloroquinolin-4-yl)amino)cyclohexyl}amino)-2-oxo-1-ethyl)-2-hydroxybenzamide;

N~2~-acetyl-N~1~-{4-((7-chloroquinolin-4-yl)amino)cyclohexyl}-L-leucinamide; and N~1~-{4-((7-chloroquinolin-4-yl)amino)cyclohexyl}-N~2~-((4-methylphenyl)sulfonyl)glycinamide.

19. The compound according to claim 16, wherein

B is $R_ER_FN$—;

$R_E$ is a member selected from the group consisting of aryl, arylalkyl, heterocycle and heterocyclealkyl;

m is 0; and

A is absent.

20. The compound according to claim 19 selected from the group consisting of cis-N-{4-((7-chloroquinolin-4-yl)amino)cyclohexyl}-N'-(3-(methylthio)phenyl)urea;

cis-N-(2-chlorophenyl)-N'-{4-((7-chloroquinolin-4-yl)amino)cyclohexyl}urea;

cis-N-{4-((7-chloroquinolin-4-yl)amino)cyclohexyl}-N'-(2-(trifluoromethyl)phenyl)urea;

cis-N-{4-((7-chloroquinolin-4-yl)amino)cyclohexyl}-N'-(3-(trifluoromethyl)phenyl)urea;

cis-N-{4-((7-chloroquinolin-4-yl)amino)cyclohexyl}-N'-(4-(trifluoromethyl)phenyl)urea;

cis-N-{4-((7-chloroquinolin-4-yl)amino)cyclohexyl}-N'-(4-(trifluoromethoxy)phenyl)urea;

cis-N-1,3-benzodioxol-5-yl-N'-{4-((7-chloroquinolin-4-yl)amino)cyclohexyl}urea;

cis-N-{4-((7-chloroquinolin-4-yl)amino)cyclohexyl}-N'-{3-((trifluoromethyl)thio)phenyl}urea;

cis-N-(3-bromophenyl)-N'-{4-((7-chloroquinolin-4-yl)amino)cyclohexyl}urea;

cis-N-(4-bromophenyl)-N'-{4-((7-chloroquinolin-4-yl)amino)cyclohexyl}urea;

cis-N-{4-((7-chloroquinolin-4-yl)amino)cyclohexyl}-N'-(3,4-dichlorophenyl)urea;

cis-N-{4-((7-chloroquinolin-4-yl)amino)cyclohexyl}-N'-(2,4-dichlorophenyl)urea;
cis-N-{4-((7-chloroquinolin-4-yl)amino)cyclohexyl}-N'-(3,5-dichlorophenyl)urea;
cis-N-{4-((7-chloroquinolin-4-yl)amino)cyclohexyl}-N'-1-naphthylurea;
cis-N-{4-((7-chloroquinolin-4-yl)amino)cyclohexyl}-N'-2-naphthylurea;
cis-N-benzyl-N'-{4-((7-chloroquinolin-4-yl)amino)cyclohexyl}urea;
cis-N-(3-chlorophenyl)-N'-{4-((7-chloroquinolin-4-yl)amino)cyclohexyl}urea;
cis-N-{4-((7-chloroquinolin-4-yl)amino)cyclohexyl}-N'-(2-furylmethyl)urea; and
cis-N-{4-((7-chloroquinolin-4-yl)amino)cyclohexyl}-N'-(3-fiirylmethyl)urea.

21. A compound of formula (Ih),

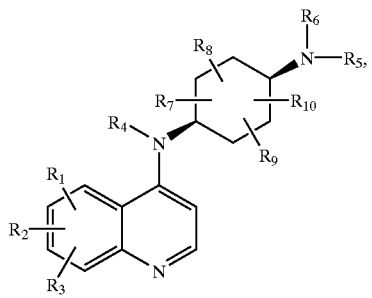

(Ih)

or a therapeutically suitable salts, or prodrug thereof, wherein $R_1$, $R_2$ and $R_3$ are each independently a member selected from the group consisting of hydrogen, alkyl, alkoxy, halo, haloalkyl, haloalkoxy, hydroxy and $R_A R_B N$— wherein $R_A$ and $R_B$ are each independently a member selected from the group consisting of hydrogen and alkyl, alkylcarbonyl, alkylsulfonyl, arylcarbonyl, arylsulfonyl and $R_C R_D N$carbonyl, wherein $R_C$ and $R_D$ are each independently a member selected from the group consisting of hydrogen, alkyl and aryl;

$R_4$ is a member selected from the group consisting of hydrogen and alkyl;

$R_5$ is —$(CH_2)_m$—C(O)-A-B;

m is from 0–6;

A is absent or is a member selected from the group consisting of alkoxyalkylene, alkylene and hydroxyalkylene;

B is $R_E R_F NC(O)$—;

$R_E$ and $R_F$ are independently a member selected from the group consisting of hydrogen, alkyl, alkylC(O)—, aryl, arylalkyl, heterocycle, heterocyclealkyl, arylC(O)— and arylS(O)$_2$—;

$R_6$ is a member selected from the group consisting of hydrogen, alkyl and arylcarboxyalkyl; and $R_7$, $R_8$, $R_9$, and $R_{10}$ are each independently a member selected from the group consisting of hydrogen, alkyl, alkoxy, halo, haloalkyl, haloalkoxy and hydroxy or $R_7$ and $R_8$ taken together with the carbon atom that they are attached form oxo.

22. The compound according to claim 21, wherein $R_E$ is a member selected from the group consisting of aryl, arylalkyl, heterocycle and heterocyclealkyl;

m is 0; and

A is alkylene.

23. The compound according to claim 22 that is N-{4-((7-chloroquinolin-4-yl)amino)cyclohexyl}-N'-phenylpentanediamide.

24. A compound of formula (Ij),

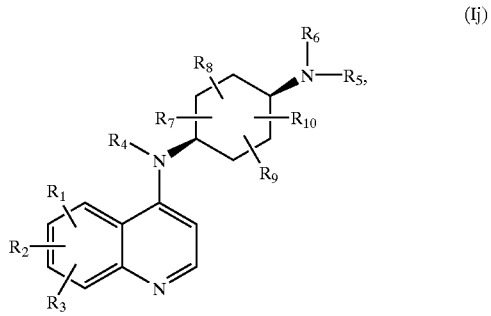

(Ij)

or a therapeutically suitable salts, or prodrug thereof, wherein $R_1$, $R_2$ and $R_3$ are each independently a member selected from the group consisting of hydrogen, alkyl, alkoxy, halo, haloalkyl, haloalkoxy, hydroxy and $R_A R_B N$— wherein $R_A$ and $R_B$ are each independently a member selected from the group consisting of hydrogen and alkyl, alkylcarbonyl, alkylsulfonyl, arylcarbonyl, arylsulfonyl and $R_C R_D N$carbonyl, wherein $R_C$ and $R_D$ are each independently a member selected from the group consisting of hydrogen, alkyl and aryl;

$R_4$ is a member selected from the group consisting of hydrogen and alkyl;

$R_5$ is —$(CH_2)_m$—C(O)-A-B;

m is from 0–6;

A is absent or is a member selected from the group consisting of alkoxyalkylene, alkylene and hydroxyalkylene;

B is a member selected from the group consisting of $R_G S$— and $R_G O$—;

$R_G$ is a member selected from the group consisting of hydrogen, alkyl, aryl, arylalkyl, heterocycle and heterocyclealkyl;

$R_6$ is a member selected from the group consisting of hydrogen, alkyl and arylcarboxyalkyl; and $R_7$, $R_8$, $R_9$, and $R_{10}$ are each independently a member selected from the group consisting of hydrogen, alkyl, alkoxy, halo, haloalkyl, haloalkoxy and hydroxy or $R_7$ and $R_8$ taken together with the carbon atom that they are attached form oxo.

25. The compound according to claim 24 wherein $R_G$ member selected from the group consisting of alkyl, aryl, arylalkyl, heterocycle and heterocyclealkyl;

m is 0; and

A is alkylene.

26. The compound according to claim 25 from the group consisting of

N-{4-((7-chloroquinolin-4-yl)amino)cyclohexyl}-2-((4-methylpyrimidin-2-yl)thio)acetamide;

N-{4-((7-chloroquinolin-4-yl)amino)cyclohexyl}-2-(3-methoxyphenoxy)acetamide;

N-{4-((7-chloroquinolin-4-yl)amino)cyclohexyl}-2-(3-niethylphenoxy)acetamide;

N-{4-((7-chloroquinolin-4-yl)amino)cyclohexyl}-2-(2-methylphenoxy)acetamide;

N-{4-((7-chloroquinolin-4-yl)amino)cyclohexyl}-3-phenoxypropanamide;

N-{4-((7-chloroquinolin-4-yl)amino)cyclohexyl}-2-(3,4-dimethylphenoxy)acetamide;

2-(4-chloro-2-methylphenoxy)-N-{4-((7-chloroquinolin-4-yl)amino)cyclohexyl}acetamide;

2-(benzyloxy)-N-{4-((7-chloroquinolin-4-yl)amino)cyclohexyl}acetamide;

N-{4-((7-chloroquinolin-4-yl)amino)cyclohexyl}-2-ethoxyacetamide;

N-{4-((7-chloroquinolin-4-yl)amino)cyclohexyl}-2-(pyrimidin-2-ylthio)acetamide; and N-{4-((7-chloroquinolin-4-yl)amino)cyclohexyl}-2-(4-methylphenoxy)acetamide.

27. A compound of formula (Ik),

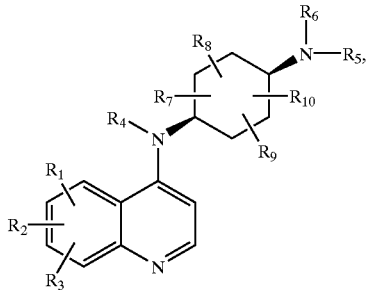

or a therapeutically suitable salts, or prodrug thereof, wherein $R_1$, $R_2$ and $R_3$ are each independently a member selected from the group consisting of hydrogen, alkyl, alkoxy, halo, haloalkyl, haloalkoxy, hydroxy and $R_AR_BN-$ wherein $R_A$ and $R_B$ are each independently a member selected from the group consisting of hydrogen and alkyl, alkylcarbonyl, alkylsulfonyl, arylcarbonyl, arylsulfonyl and $R_CR_DN$carbonyl, wherein $R_C$ and $R_D$ are each independently a member selected from the group consisting of hydrogen, alkyl and aryl;

$R_4$ is a member selected from the group consisting of hydrogen and alkyl;

$R_5$ is $-(CH_2)_m-C(O)$-A-B;

m is 0;

A is absent or is a member selected from the group consisting of alkoxyalkylene, alkylene and hydroxyalkylene;

B is a member selected from the group consisting of alkyl, cycloalkyl and haloalkyl;

$R_6$ is a member selected from the group consisting of hydrogen, alkyl and arylcarboxyalkyl; and $R_7$, $R_8$, $R_9$, and $R_{10}$ are independently a member selected from the group consisting of hydrogen, alkyl, alkoxy, halo, haloalkyl, haloalkoxy and hydroxy or $R_7$ and $R_8$ taken together with the carbon atom that they are attached form oxo.

28. The compound according to claim 27 selected from the group consisting of cis-N-{4-((7-chloroquinolin-4-yl)amino)cyclohexyl}-2-cyclohexylacetamide;

cis-N-{4-((7-chloroquinolin-4-yl)amino)cyclohexyl}-2-cycloheptylacetamide;

cis-2-((1R,4S)-bicyclo(2.2.1)hept-2-yl)-N-{4-((7-chloroquinolin-4-yl)amino)cyclohexyl}acetamide;

cis-2-(1-adamantyl)-N-{4-((7-chloroquinolin-4-yl)amino)cyclohexyl}acetamide;

N-{4-((7-chloroquinolin-4-yl)amino)cyclohexyl}-4-methylpentanamide;

N-{4-((7-chloroquinolin-4-yl)amino)cyclohexyl}pentanamide;

N-{4-((7-chloroquinolin-4-yl)amino)cyclohexyl}hexanamide;

N-{4-((7-chloroquinolin-4-yl)amino)cyclohexyl}cyclopentanecarboxamide;

N-{4-((7-chloroquinolin-4-yl)amino)cyclohexyl}-2-cyclopentylacetamide;

N-{4-((7-chloroquinolin-4-yl)amino)cyclohexyl}-2-methylcyclohexanecarboxamide;

N-{4-((7-chloroquinolin-4-yl)amino)cyclohexyl}cycloheptanecarboxamide;

N-{4-((7-chloroquinolin-4-yl)amino)cyclohexyl}-3-methylcyclohexanecarboxamide;

N-{4-((7-chloroquinolin-4-yl)amino)cyclohexyl}-4-methylcyclohexanecarboxamide;

N-{4-((7-chloroquinolin-4-yl)amino)cyclohexyl}-3-methylbutanamide;

N-{4-((7-chloroquinolin-4-yl)amino)cyclohexyl}cyclohexanecarboxamide;

N-{4-((7-chloroquinolin-4-yl)amino)cyclohexyl}-3-methylpentanamide;

N-{4-((7-chloroquinolin-4-yl)amino)cyclohexyl}-4,4,4-trifluorobutanamide;

N-{4-((7-chloroquinolin-4-yl)amino)cyclohexyl}heptanamide;

N-{4-((7-chloroquinolin-4-yl)amino)cyclohexyl}butanamide;

N-{4-((7-chloroquinolin-4-yl)amino)cyclohexyl}-2-cyclopropylacetamide;

N-{4-((7-chloroquinolin-4-yl)amino)cyclohexyl}-2,2-dimethylpropanamide;

N-{4-((7-chloroquinolin-4-yl)amino)cyclohexyl}-2-ethylbutanamide;

N-{4-((7-chloroquinolin-4-yl)amino)cyclohexyl}-1-phenylcyclopropanecarboxamide;

N-{4-((7-chloroquinolin-4-yl)amino)cyclohexyl}-3,3-dimethylbutanamide;

N-{4-((7-chloroquinolin-4-yl)amino)cyclohexyl}adamantane-1-carboxamide;

N-{4-((7-chloroquinolin-4-yl)amino)cyclohexyl}-2-methylpentanamide; and

N-{4-((7-chloroquinolin-4-yl)amino)cyclohexyl}-1-methylcyclohexanecarboxamide.

29. A compound of formula (Im),

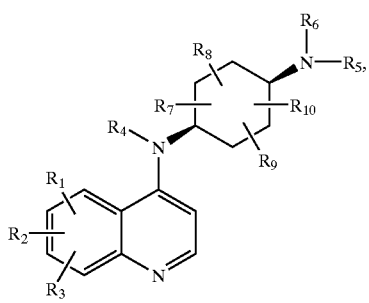

or a therapeutically suitable salts, or prodrug thereof, wherein $R_1$, $R_2$ and $R_3$ are each independently a member selected from the group consisting of hydrogen, alkyl, alkoxy, halo, haloalkyl, haloalkoxy, hydroxy and $R_AR_BN$— wherein $R_A$ and $R_B$ are each independently a member selected from the group consisting of hydrogen and alkyl, alkylcarbonyl, alkylsulfonyl, arylcarbonyl, arylsulfonyl and $R_CR_DN$carbonyl, wherein $R_C$ and $R_D$ are each independently a member selected from the group consisting of hydrogen, alkyl and aryl;

$R_4$ is a member selected from the group consisting of hydrogen and alkyl;

$R_5$ is —$(CH_2)_m$—$S(O)_2$-A-B;

m is from 0–6;

A is absent or is a member selected from the group consisting of alkoxyalkylene, alkylene and hydroxyalkylene;

B is a member selected from the group consisting of alkyl, aryl, arylalkenyl, cycloalkyl and heterocycle;

$R_6$ is a member selected from the group consisting of hydrogen, alkyl and arylcarboxyalkyl; and $R_7$, $R_8$, $R_9$, and $R_{10}$ are each independently a member selected from the group consisting of hydrogen, alkyl, alkoxy, halo, haloalkyl, haloalkoxy and hydroxy or $R_7$ and $R_8$ taken together with the carbon atom that they are attached form oxo.

30. The compound according to claim 29, wherein m is 0;

A is absent; and

B is a member selected from the group consisting of aryl and heterocycle.

31. The compound according to claim 30 selected from the group consisting of cis-4-chloro-N-{4-((7-chloroquinolin-4-yl)amino)cyclohexyl}benzenesulfonamide;

cis-N-{4-((7-chloroquinolin-4-yl)amino)cyclohexyl}benzenesulfonamide;

cis-2-chloro-N-{4-((7-chloroquinolin-4-yl)amino)cyclohexyl}-4-fluorobenzenesulfonamide;

cis-N-{4-((7-chloroquinolin-4-yl)amino)cyclohexyl}thiophene-2-sulfonamide;

cis-N-{4-((7-chloroquinolin-4-yl)amino)cyclohexyl}-2-(trifluoromethoxy)benzenesulfonamide;

cis-N-{4-((7-chloroquinolin-4-yl)amino)cyclohexyl}-3-methylbenzenesulfonamide;

cis-N-{4-((7-chloroquinolin-4-yl)amino)cyclohexyl}-4-methylbenzenesulfonamide;

cis-N-{4-((7-chloroquinolin-4-yl)amino)cyclohexyl}-2-fluorobenzenesulfonamide;

cis-N-{4-((7-chloroquinolin-4-yl)amino)cyclohexyl}-3-fluorobenzenesulfonamide;

cis-N-{4-((7-chloroquinolin-4-yl)amino)cyclohexyl}-4-fluorobenzenesulfonamide;

cis-N-{4-((7-chloroquinolin-4-yl)amino)cyclohexyl}-2-cyanobenzenesulfonamide;

cis-N-{4-((7-chloroquinolin-4-yl)amino)cyclohexyl}-3-cyanobenzenesulfonamide;

cis-N-{4-((7-chloroquinolin-4-yl)amino)cyclohexyl}-4-cyanobenzenesulfonamide;

cis-N-{4-((7-chloroquinolin-4-yl)amino)cyclohexyl}-2,5-dimetbylbenzenesulfonamide;

cis-N-{4-((7-chloroquinolin-4-yl)amino)cyclohexyl}-3-methoxybenzenesulfonamide;

cis-N-{4-((7-chloroquinolin-4-yl)amino)cyclohexyl}-4-methoxybenzenesulfonamide;

cis-2-chloro-N-{4-((7-chloroquinolin-4-yl)amino)cyclohexyl}benzenesulfonaxnide;

cis-3-chloro-N-{4-((7-chloroquinolin-4-yl)amino)cyclohexyl}benzenesulfonamide;

cis-4-(2-chloro-6-nitrophenoxy)-N-{4-((7-chloroquinolin-4-yl)amino)cyclohexyl}benzenesulfonamide;

cis-N-{4-((7-chloroquinolin-4-yl)amino)cyclohexyl}-2,4-difluorobenzenesulfonamide;

cis-N-{4-((7-chloroquinolin-4-yl)amino)cyclohexyl}-3,4-difluorobenzenesulfonamide;

cis-N-{4-((7-chloroquinolin-4-yl)amino)cyclohexyl}-4-propylbenzenesulfonamide;

cis-N-{4-((7-chloroquinolin-4-yl)amino)cyclohexyl}-4-isopropylbenzenesulfonamide;

cis-4-chloro-N-({5-(({4-((7-chloroquinolin-4-yl)amino)cyclohexyl}amino)sulfonyl)thien-2-yl}methyl)benzamide;

cis-5-bromo-6-chloro-N-{4-((7-chloroquinolin-4-yl)amino)cyclohexyl}pyridine-3-sulfonamide;

cis-4-tert-butyl-N-{4-((7-chloroquinolin-4-yl)amino)cyclohexyl}benzenesulfonamide;

cis-3-chloro-N-{4-((7-chloroquinolin-4-yl)amino)cyclohexyl}-4-fluorobenzenesulfonamide;

cis-N-{4-(({4-((7-chloroquinolin-4-yl)amino)cyclohexyl}amino)sulfonyl)phenyl}acetamide;

cis-N-{4-((7-chloroquinolin-4-yl)amino)cyclohexyl}-2,5-dimethoxybenzenesulfonamide;

cis-N-{4-((7-chloroquinolin-4-yl)amino)cyclohexyl}-3,4-dimethoxybenzenesulfonamide;

cis-N-{4-((7-chloroquinolin-4-yl)amino)cyclohexyl}-3-(trifluoromethyl)benzenesulfonamide;

cis-N-{4-((7-chloroquinolin-4-yl)amino)cyclohexyl}-4-(trifluoromethyl)benzenesulfonamide;

cis-2,3-dichloro-N-{4-((7-cbloroquinolin-4-yl)amino)cyclohexyl}benzenesulfonamide;

cis-2,4-dichloro-N-{4-((7-chloroquinolin-4-yl)amino)cyclohexyl}benzenesulfonamide;

cis-2,5-dichloro-N-{4-((7-chloroquinolin-4-yl)amino)cyclohexyl}benzenesulfonamide;

cis-3,4-dichloro-N-{4-((7-chloroquinolin-4-yl)amino)cyclohexyl}benzenesulfonamide;

cis-3,5-dichloro-N-{4-((7-chloroquinolin-4-yl)amino)eyclohexyl}benzenesulfonamide;

cis-N-{4-((7-chloroquinolin-4-yl)amino)cyclohexyl}-1,1'-biphenyl-4-sulfonamide;
cis-2-bromo-N-{4-((7-chloroquinolin-4-yl)amino)cyclohexyl}benzenesulfonamide;
cis-3-bromo-N-{4-((7-chloroquinolin-4-yl)amino)cyclohexyl}benzenesulfonamide;
cis-4-bromo-N-{4-((7-chloroquinolin-4-yl)amino)cyclohexyl}benzenesulfonamide;
cis-N-{4-((7-chloroquinolin-4-yl)amino)cyclohexyl}-4-(trifluoromethoxy)benzenesulfonamide;
cis-N-{4-((7-chloroquinolin-4-yl)amino)cyclohexyl}-3,5-dimethylisoxazole-4-sulfonamide;
cis-(E)-N-{4-((7-chloroquinolin-4-yl)amino)cyclohexyl}-2-phenylethylenesulfonamide;
cis-N-{4-((7-chloroquinolin-4-yl)amino)cyclohexyl}-4-vinylbenzenesulfonamide;
cis-5-chloro-N-{4-((7-chloroquinolin-4-yl)amino)cyclohexyl}thiophene-2-sulfonamide;
cis-N-{4-((7-chloroquinolin-4-yl)amino)cyclohexyl}-2,1,3-benzoxadiazole-4-sulfonamide;
cis-N-{4-((7-chloroquinolin-4-yl)amino)cyclohexyl}-3-nitrobenzenesulfonamide;
cis-N-{4-((7-chloroquinolin-4-yl)amino)cyclohexyl}-4-nitrobenzenesulfonamide;
cis-3-chloro-N-{4-((7-chloroquinolin-4-yl)amino)cyclohexyl}-4-methylbenzenesulfonamide;
cis-N-{4-((7-chloroquinolin-4-yl)amino)cyclohexyl}quinoline-8-sulfonamide;
cis-5-chloro-N-{4-((7-chloroquinolin-4-yl)amino)cyclohexyl}-1,3-dimethyl-1H-pyrazole-4-sulfonamide;
cis-N-{4-((7-chloroquinolin-4-yl)amino)cyclohexyl}-2,1,3-benzothiadiazole-4-sulfonamide;
cis-N-{4-((7-chloroquinolin-4-yl)amino)cyclohexyl}-2-methyl-5-nitrobenzenesulfonamide;
cis-methyl 3-(({4-((7-chloroquinolin-4-yl)amino)cyclohexyl}amino)sulfonyl)thiophene-2-carboxylate;
cis-N-{4-((7-chloroquinolin-4-yl)amino)cyclohexyl}-4-(1,1-dimethylpropyl)benzenesulfonamide;
cis-4-butoxy-N-{4-((7-chloroquinolin-4-yl)amino)cyclohexyl}benzenesulfonamide;
cis-N-{4-((7-chloroquinolin-4-yl)amino)cyclohexyl}-5-isoxazol-3-ylthiophene-2-sulfonamide;
cis-2,5-dichloro-N-{4-((7-chloroquinolin-4-yl)amino)cyclohexyl}thiophene-3-sulfonamide;
cis-4,5-dichloro-N-{4-((7-chloroquinolin-4-yl)amino)cyclohexyl}thiophene-2-sulfonamide;
cis-7-chloro-N-{4-((7-chloroquinolin-4-yl)amino)cyclohexyl}-2,1,3-benzoxadiazole-4-sulfonamide;
cis-N-{4-((7-chloroquinolin-4-yl)amino)cyclohexyl}-4-(methylsulfonyl)benzenesulfonamide;
cis-4-chloro-N-{4-((7-chloroquinolin-4-yl)amino)cyclohexyl}-3-nitrobenzenesulfonamide;
cis-6-chloro-N-{4-((7-chloroquinolin-4-yl)amino)cyclohexyl}-3H-1lambda~4~-imidazo(2,1-b)(1,3)thiazole-5-sulfonamide;
cis-N-{4-((7-chloroquinolin-4-yl)amino)cyclohexyl}-2-(trifluoroacetyl)-1,2,3,4-tetrahydroisoquinoline-7-sulfonamide;
cis-N-{4-((7-chloroquinolin-4-yl)amino)cyclohexyl}-5-fluoro-2-methylbeazenesulfonamide;
cis-4-chloro-N-{4-((7-chloroquinolin-4-yl)amino)cyclohexyl}-3-(trifluoromethyl)benzenesulfonamide;
cis-2,4,5-trichloro-N-{4-((7-chloroquinolin-4-yl)amino)cyclohexyl}benzenesulfonamide;
cis-2,4,6-trichloro-N-{4-((7-chloroquinolin-4-yl)amino)cyclohexyl}benzenesulfonamide;
cis-2,3,4-trichloro-N-{4-((7-chloroquinolin-4-yl)amino)cyclohexyl}benzenesulfonamide;
cis-5-chloro-N-{4-((7-chloroquinolin-4-yl)amino)cyclohexyl}-3-methyl-1-benzothiophene-2-sulfonamide;
cis-5-bromo-N-{4-((7-chloroquinolin-4-yl)amino)cyclohexyl}-2-methoxybenzenesulfonamide;
cis-N-{4-((7-chloroquinolin-4-yl)amino)cyclohexyl}-2-nitro4-(trifluoromethyl)benzenesulfonamide;
cis-N-({5-(({4-((7-chloroquinolin-4-yl)amino)cyclohexyl}amino)sulfonyl)thien-2-yl}methyl)benzamide;
cis-N-{4-((7-chloroquinolin-4-yl)amino)cyclohexyl}-5-(2-(methylthio)pyrimidin-4-yl)thiophene-2-sulfonamide;
cis-N-{4-((7-chloroquinolin-4-yl)amino)cyclohexyl}-3,5-bis(trifluoromethyl)benzenesulfonamide;
cis-2,6-dichloro-N-{4-((7-chloroquinolin-4-yl)amino)cyclohexyl}-4-(trifluoromethyl)benzenesulfonamide;
cis-2-butoxy-N-{4-((7-chloroquinolin-4-yl)amino)cyclohexyl}-5-(1,1-dimethylpropyl)benzenesulfonamide;
cis-N-{4-((7-chloroquinolin-4-yl)amino)cyclohexyl}-5-(phenylsulfonyl)thiophene-2-sulfonamide;
cis-4-(3-chloro-2-cyano-phenoxy)-N-{4-((7-chloroquinolin-4-yl)amino)cyclohexyl}benzenesulfonamide;
cis-N-{4-((7-chloroquinolin-4-yl)amino)cyclohexyl}-4-ethylbenzenesulfonamide;
cis-4-bromo-2,5-dichloro-N-{4-((7-chloroquinolin-4-yl)amino)cyclohexyl}thiophene-3-sulfonamide;
cis-N-{4-((7-chloroquinolin-4-yl)amino)cyclohexyl}-2-methoxy-5-methylbenzenesulfonamide; and
cis-N-{4-((7-chloroquinolin-4-yl)amino)cyclo)iexyl}-2-nitrobenzenesulfonamide.

32. The compound according to claim 29 wherein
m is 0;
A is alkylene; and
B is a member selected from the group consisting of aryl and heterocycle.

33. The compound according to claim 32 selected from the group consisting of
cis-N-{4-((7-chloroquinolin-4-yl)amino)cyclohexyl}-1-(3,4-dichlorophenyl)methanesulfonamide; and
cis-N-{4-((7-chloroquinolin-4-yl)amino)cyclohexyl}-1-(3,5-dichlorophenyl)methanesulfonamide.

34. The compound according to claim 29, wherein
m is 0;
A is alkylene; and
B is a member selected from the group consisting of alkyl and cycloalkyl.

35. The compound according to claim 34 selected from the group consisting of
cis-N-{4-((7-chloroquinolin-4-yl)amino)cyclohexyl}propane-1-sulfonamide;
cis-N-{4-((7-chloroquinolin-4-yl)amino)cyclohexyl}butane-1-sulfonamide; and
cis-N-{4-((7-chloroquinolin-4-yl)amino)cyclohexyl}-1-((1S,4R)-7,7-dimethyl-2-oxobicyclo(2.2.1)hept-1-yl)methanesulfonamide.

* * * * *

UNITED STATES PATENT AND TRADEMARK OFFICE
CERTIFICATE OF CORRECTION

PATENT NO. : 6,818,772 B2
DATED : November 16, 2004
INVENTOR(S) : Phillip R. Kym et al.

It is certified that error appears in the above-identified patent and that said Letters Patent is hereby corrected as shown below:

Column 138,
Line 16, replace "salts" with -- salt --.
Line 53, replace "nyrhnidin" with -- pyrimidin --.

Column 139,
Line 16, replace "salts" with -- salt --.
Line 54, replace "isocininolinyl" with -- isoquinolinyl --.

Column 141,
Line 28, replace "thiazoi" with -- thiazol --.
Line 33, replace "cvclohexyl" with -- cyclohexyl --.

Column 142,
Line 17, replace "salts" with -- salt --.

Column 143,
Line 26, replace "benzaxnide" with -- benzamide --.

Column 146,
Line 15, replace "3 ,5" with -- 3,5 --.

Column 148,
Line 19, replace "salts" with -- salt --.
Line 51, replace "haloallcyl" with -- haloalkyl --.

Column 149,
Line 21, replace "salts" with -- salt --.

Column 150,
Line 20, replace "salts" with -- salt --.
Line 29, replace "7--chloroquinolin" with -- 7-chloroquinolin --.

Column 151,
Line 49, replace "salts" with -- salt --.

Column 153,
Line 33, replace "salts" with -- salt --.

Column 154,
Line 22, replace "salts" with -- salt --.
Line 65, replace "niethylphenoxy" with -- methylphenoxy --.

UNITED STATES PATENT AND TRADEMARK OFFICE
CERTIFICATE OF CORRECTION

PATENT NO.     : 6,818,772 B2
DATED          : November 16, 2004
INVENTOR(S)    : Phillip R. Kym et al.

It is certified that error appears in the above-identified patent and that said Letters Patent is hereby corrected as shown below:

<u>Column 155,</u>
Line 33, replace "salts" with -- salt --.

<u>Column 157,</u>
Line 16, replace "salts" with -- salt --.

<u>Column 158,</u>
Line 67, replace "eyclohexyl" with -- cyclohexyl --.

<u>Column 160,</u>
Line 28, replace "cyano-phenoxy" with -- cyanophenoxy --.

Signed and Sealed this

Fourth Day of April, 2006

JON W. DUDAS
*Director of the United States Patent and Trademark Office*